(12) United States Patent
Vechorkin et al.

(10) Patent No.: US 10,800,761 B2
(45) Date of Patent: Oct. 13, 2020

(54) CARBOXAMIDE COMPOUNDS AND USES THEREOF

(71) Applicant: Incyte Corporation, Wilmington, DE (US)

(72) Inventors: Oleg Vechorkin, Wilmington, DE (US); Jun Pan, Media, PA (US); Alexander Sokolsky, Philadelphia, PA (US); Evan Styduhar, Claymont, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 16/278,865

(22) Filed: Feb. 19, 2019

(65) Prior Publication Data

US 2019/0382380 A1    Dec. 19, 2019

Related U.S. Application Data

(60) Provisional application No. 62/750,371, filed on Oct. 25, 2018, provisional application No. 62/672,772, filed on May 17, 2018, provisional application No. 62/632,702, filed on Feb. 20, 2018.

(51) Int. Cl.
| | |
|---|---|
| C07D 403/14 | (2006.01) |
| C07D 239/26 | (2006.01) |
| C07D 401/12 | (2006.01) |
| C07D 401/14 | (2006.01) |
| C07D 403/12 | (2006.01) |
| C07D 413/12 | (2006.01) |
| C07D 413/14 | (2006.01) |
| C07D 487/04 | (2006.01) |
| C07D 487/08 | (2006.01) |

(52) U.S. Cl.
CPC ......... *C07D 403/14* (2013.01); *C07D 239/26* (2013.01); *C07D 401/12* (2013.01); *C07D 401/14* (2013.01); *C07D 403/12* (2013.01); *C07D 413/12* (2013.01); *C07D 413/14* (2013.01); *C07D 487/04* (2013.01); *C07D 487/08* (2013.01)

(58) Field of Classification Search
None
See application file for complete search history.

(56) References Cited

U.S. PATENT DOCUMENTS

| | | | |
|---|---|---|---|
| 5,250,534 A | 10/1993 | Bell et al. | |
| 6,200,980 B1 | 3/2001 | Piazza et al. | |
| 6,333,330 B1 | 12/2001 | Bunnage et al. | |
| 6,458,951 B1 | 10/2002 | Bunnage et al. | |
| 6,512,002 B2 | 1/2003 | Lee et al. | |
| 6,670,366 B1 | 12/2003 | Bunnage et al. | |
| 6,743,799 B2 | 6/2004 | Westbrook et al. | |
| 6,756,373 B1 | 6/2004 | Allerton et al. | |
| 6,770,645 B2 | 8/2004 | Denton et al. | |
| 6,784,185 B2 | 8/2004 | Allerton et al. | |
| 6,916,927 B2 | 7/2005 | Bunnage et al. | |
| 7,105,532 B2 | 9/2006 | Rawlings | |
| 7,166,293 B2 | 1/2007 | Teng et al. | |
| 7,259,165 B2 | 8/2007 | Bernotas et al. | |
| 7,345,178 B2 | 3/2008 | Nunes et al. | |
| 7,576,087 B2 | 8/2009 | Bernotas et al. | |
| 7,919,487 B2 | 4/2011 | Sun et al. | |
| 7,968,719 B2 | 6/2011 | Zoller et al. | |
| 8,106,190 B2 | 1/2012 | Kuramochi et al. | |
| 8,450,335 B2 | 5/2013 | Singh et al. | |

(Continued)

FOREIGN PATENT DOCUMENTS

| | | |
|---|---|---|
| CN | 102206172 | 10/2011 |
| CN | 102503959 | 6/2012 |

(Continued)

OTHER PUBLICATIONS

Alzabin et al., "Hematopoietic progenitor kinase 1 is a critical component of prostaglandin E2-mediated suppression of the anti-tumor immune response," Cancer Immunol Immunother, 2010, 59(3):419-429.
Alzabin et al., "Hematopoietic progenitor kinase 1 is a negative regulator of dendritic cell activation," J Immunol, 2009, 182(10):6187-6194.
Antoine et al., "Efficient synthesis of novel disubstituted pyrido[3,4-b]pyrazines for the design of protein kinase inhibitors," Med Chem Common., 2016, 6:224-229.
Antunes et al., "In silico prediction of novel phosphodiesterase type-5 inhibitors derived from Sildenafil, Vardenafil and Tadalafil," Bioorg Med Chem., Aug. 15, 2008, 16(16):7599-7606.
Atzrodt et al., "The Renaissance of H/D Exchange," Angew. Chem. Int. Ed., 2007, 7744-7765.

(Continued)

*Primary Examiner* — Zinna Northington Davis
(74) *Attorney, Agent, or Firm* — Fish & Richardson P.C.

(57) ABSTRACT

Disclosed are compounds of Formula (I') methods of using the compounds for inhibiting HPK1 activity and pharmaceutical compositions comprising such compounds. The compounds are useful in treating, preventing or ameliorating diseases or disorders associated with HPK1 activity such as cancer.

12 Claims, No Drawings

(56) References Cited

U.S. PATENT DOCUMENTS

| | | |
|---|---|---|
| 8,546,403 B2 | 10/2013 | Whitten et al. |
| 8,637,507 B2 | 1/2014 | Zhou et al. |
| 8,722,691 B2 | 3/2014 | He et al. |
| 8,987,273 B2 | 3/2015 | Rehwinkel et al. |
| 9,090,593 B2 | 7/2015 | Wang et al. |
| 9,260,425 B2 | 2/2016 | Do et al. |
| 9,284,319 B2 | 3/2016 | Eis et al. |
| 9,320,737 B2 | 4/2016 | Eis et al. |
| 9,718,818 B2 | 8/2017 | DeMong et al. |
| 9,730,929 B2 | 8/2017 | Eis et al. |
| 10,266,530 B2 | 4/2019 | Vechorkin et al. |
| 10,280,164 B2 | 5/2019 | Ye et al. |
| 10,435,405 B2 | 10/2019 | Vechorkin et al. |
| 2002/0013327 A1 | 1/2002 | Lee et al. |
| 2003/0162782 A1 | 8/2003 | Grossman et al. |
| 2003/0186996 A1 | 10/2003 | Teng et al. |
| 2004/0063730 A1 | 4/2004 | Eggenweiler et al. |
| 2004/0077681 A1 | 4/2004 | Rawlings et al. |
| 2004/0147546 A1 | 7/2004 | Tanaka et al. |
| 2004/0157866 A1 | 8/2004 | Takasugi et al. |
| 2004/0167030 A1 | 8/2004 | Bernotas et al. |
| 2004/0204417 A1 | 10/2004 | Perez et al. |
| 2005/0070557 A1 | 3/2005 | Fryburg et al. |
| 2005/0075795 A1 | 4/2005 | Pandit |
| 2005/0119278 A1 | 6/2005 | Teng et al. |
| 2005/0137226 A1 | 6/2005 | Ji et al. |
| 2005/0208582 A1 | 9/2005 | Ohi et al. |
| 2005/0261339 A1 | 11/2005 | Ohi et al. |
| 2006/0106032 A1 | 5/2006 | Kuo et al. |
| 2007/0087988 A1 | 4/2007 | Sawasdikosol et al. |
| 2007/0161673 A1 | 7/2007 | Barker et al. |
| 2007/0185152 A1 | 8/2007 | Yamashita et al. |
| 2007/0270412 A1 | 11/2007 | Bell et al. |
| 2008/0280891 A1 | 11/2008 | Kelly et al. |
| 2010/0035891 A1 | 2/2010 | Bunnage et al. |
| 2010/0087464 A1 | 4/2010 | Mi et al. |
| 2010/0216798 A1 | 8/2010 | Nakai et al. |
| 2012/0129852 A1 | 5/2012 | Duan et al. |
| 2012/0225869 A1 | 9/2012 | Liu et al. |
| 2012/0295884 A1 | 11/2012 | Altmann et al. |
| 2013/0039906 A1 | 2/2013 | Do et al. |
| 2013/0040949 A1 | 2/2013 | Gray et al. |
| 2013/0281433 A1 | 10/2013 | Babaoglu et al. |
| 2014/0225073 A1 | 8/2014 | Lee et al. |
| 2014/0249135 A1* | 9/2014 | Burger ............... C07D 405/14 514/211.15 |
| 2014/0288045 A1 | 9/2014 | Ren et al. |
| 2014/0288069 A1 | 9/2014 | Eis et al. |
| 2014/0350017 A1 | 11/2014 | Williams et al. |
| 2014/0364605 A1 | 12/2014 | Li et al. |
| 2015/0038485 A1 | 2/2015 | Eis et al. |
| 2015/0191462 A1 | 7/2015 | Hommel et al. |
| 2015/0239868 A1 | 8/2015 | Pais et al. |
| 2015/0239889 A1 | 8/2015 | Nakajima et al. |
| 2015/0243908 A1 | 8/2015 | Lee et al. |
| 2015/0274639 A1 | 10/2015 | Williams et al. |
| 2015/0328188 A1 | 11/2015 | Orlemans et al. |
| 2016/0013427 A1 | 1/2016 | Kim et al. |
| 2016/0046648 A1 | 2/2016 | Petrukhin et al. |
| 2016/0068529 A1 | 3/2016 | Kc et al. |
| 2016/0068547 A1 | 3/2016 | Kc et al. |
| 2016/0068548 A1 | 3/2016 | Kc et al. |
| 2016/0068551 A1 | 3/2016 | Kc et al. |
| 2016/0200722 A1 | 7/2016 | DeMong et al. |
| 2018/0072718 A1 | 3/2018 | Liu et al. |
| 2018/0072719 A1 | 3/2018 | Ye et al. |
| 2018/0072720 A1 | 3/2018 | Vechorkin et al. |
| 2018/0072741 A1 | 3/2018 | Vechorkin et al. |
| 2018/0228786 A1 | 8/2018 | Sokolsky |
| 2019/0076401 A1 | 3/2019 | Vechorkin et al. |
| 2019/0106419 A1 | 4/2019 | Vechorkin et al. |
| 2019/0256500 A1 | 8/2019 | Vechorkin et al. |
| 2019/0256520 A1 | 8/2019 | Sokolsky |
| 2019/0315717 A1 | 10/2019 | Hummel et al. |
| 2019/0315743 A1 | 10/2019 | Liu et al. |
| 2019/0343814 A1 | 11/2019 | Sokolsky |
| 2020/0048241 A1 | 2/2020 | Hummel et al. |

FOREIGN PATENT DOCUMENTS

| | | |
|---|---|---|
| CN | 102516263 | 6/2012 |
| CN | 103570709 | 2/2014 |
| DE | 10 2004 054 666 | 5/2006 |
| EP | 2543372 | 1/2013 |
| EP | 2824099 | 1/2015 |
| IN | 187433 | 4/2002 |
| JP | H03287584 | 12/1991 |
| JP | 2000-038350 | 2/2000 |
| JP | 2007-055940 | 3/2007 |
| JP | 2010-111624 | 5/2010 |
| JP | 2011-246389 | 12/2011 |
| KR | 963644 | 2/1996 |
| KR | 10 2014 0019055 | 2/2014 |
| MX | 9910322 | 7/2003 |
| MY | 146643 | 9/2012 |
| WO | WO 1989/008263 | 9/1989 |
| WO | WO 2000/43394 | 7/2000 |
| WO | WO 2001/19827 | 3/2001 |
| WO | WO 2001/19828 | 3/2001 |
| WO | WO 2001/021576 | 3/2001 |
| WO | WO 2001/046124 | 6/2001 |
| WO | WO 2002/000196 | 1/2002 |
| WO | WO 2002/16348 | 2/2002 |
| WO | WO 2002/19975 | 3/2002 |
| WO | WO 2002/50073 | 6/2002 |
| WO | WO 2002/090347 | 11/2002 |
| WO | WO 2003/037432 | 5/2003 |
| WO | WO 2003/049681 | 6/2003 |
| WO | WO 2004/072069 | 8/2004 |
| WO | WO 2004/096810 | 11/2004 |
| WO | WO 2004/108133 | 12/2004 |
| WO | WO 2005/004799 | 1/2005 |
| WO | WO 2005/011681 | 2/2005 |
| WO | WO 2005/028475 | 3/2005 |
| WO | WO 2005/051906 | 6/2005 |
| WO | WO 2005/066167 | 7/2005 |
| WO | WO 2005/073199 | 8/2005 |
| WO | WO 2005/073232 | 8/2005 |
| WO | WO 2003/101968 | 9/2005 |
| WO | WO 2005/085227 | 9/2005 |
| WO | WO 2005/085248 | 9/2005 |
| WO | WO 2005/085249 | 9/2005 |
| WO | WO 2006/013095 | 2/2006 |
| WO | WO 2006/028958 | 3/2006 |
| WO | WO 2006/038001 | 4/2006 |
| WO | WO 2006/045010 | 4/2006 |
| WO | WO 2006/050097 | 5/2006 |
| WO | WO 2006/053109 | 5/2006 |
| WO | WO 2006/053121 | 5/2006 |
| WO | WO 2006/053227 | 5/2006 |
| WO | WO 2006/074428 | 7/2006 |
| WO | WO 2006/105289 | 10/2006 |
| WO | WO 2006/128172 | 11/2006 |
| WO | WO 2007/019344 | 2/2007 |
| WO | WO 2007/019345 | 2/2007 |
| WO | WO 2007/019346 | 2/2007 |
| WO | WO 2007/019417 | 2/2007 |
| WO | WO 2007/020050 | 2/2007 |
| WO | WO 2007/023110 | 3/2007 |
| WO | WO 2007/023111 | 3/2007 |
| WO | WO 2007/023114 | 3/2007 |
| WO | WO 2007/030582 | 3/2007 |
| WO | WO 2007/056280 | 5/2007 |
| WO | WO 2007/063925 | 6/2007 |
| WO | WO 2007/065924 | 6/2007 |
| WO | WO 2007/080382 | 7/2007 |
| WO | WO 2007/093402 | 8/2007 |
| WO | WO 2007/112093 | 10/2007 |
| WO | WO 2007/114848 | 10/2007 |
| WO | WO 2007/137030 | 11/2007 |
| WO | WO 2008/008059 | 1/2008 |
| WO | WO 2008/008539 | 1/2008 |
| WO | WO 2008/012027 | 1/2008 |

(56) References Cited

FOREIGN PATENT DOCUMENTS

| | | |
|---|---|---|
| WO | WO 2008/045627 | 4/2008 |
| WO | WO 2008/070313 | 6/2008 |
| WO | WO 2008/089307 | 7/2008 |
| WO | WO 2008/089310 | 7/2008 |
| WO | WO 2008/113856 | 9/2008 |
| WO | WO 2009/019167 | 2/2009 |
| WO | WO 2009/024341 | 2/2009 |
| WO | WO 2009/032651 | 3/2009 |
| WO | WO 2009/038784 | 3/2009 |
| WO | WO 2009/100130 | 8/2009 |
| WO | WO 2009/139834 | 11/2009 |
| WO | WO 2009/152356 | 12/2009 |
| WO | WO 2010/029300 | 3/2010 |
| WO | WO 2010/035217 | 4/2010 |
| WO | WO 2010/035219 | 4/2010 |
| WO | WO 2010/035221 | 4/2010 |
| WO | WO 2010/046780 | 4/2010 |
| WO | WO 2010/080503 | 7/2010 |
| WO | WO 2010/104306 | 9/2010 |
| WO | WO 2010/107765 | 9/2010 |
| WO | WO 2010/107768 | 9/2010 |
| WO | WO 2010/111624 | 9/2010 |
| WO | WO 2010/118367 | 10/2010 |
| WO | WO 2011/019780 | 2/2011 |
| WO | WO 2011/031628 | 3/2011 |
| WO | WO 2011/050245 | 4/2011 |
| WO | WO 2011/051535 | 5/2011 |
| WO | WO 2011/062253 | 5/2011 |
| WO | WO 2011/078143 | 6/2011 |
| WO | WO 2011/082400 | 7/2011 |
| WO | WO 2011/082488 | 7/2011 |
| WO | WO 2011/107186 | 9/2011 |
| WO | WO 2011/133920 | 10/2011 |
| WO | WO 2011/139489 | 11/2011 |
| WO | WO 2011/141756 | 11/2011 |
| WO | WO 2011/147765 | 12/2011 |
| WO | WO 2011/153553 | 12/2011 |
| WO | WO 2011/157653 | 12/2011 |
| WO | WO 2011/158108 | 12/2011 |
| WO | WO 2012/048058 | 4/2012 |
| WO | WO 2012/049277 | 4/2012 |
| WO | WO 2012/078777 | 6/2012 |
| WO | WO 2012/080376 | 6/2012 |
| WO | WO 2012/109263 | 8/2012 |
| WO | WO 2012/130780 | 10/2012 |
| WO | WO 2012/141487 | 10/2012 |
| WO | WO 2012/143144 | 10/2012 |
| WO | WO 2012/158810 | 11/2012 |
| WO | WO 2012/163959 | 12/2012 |
| WO | WO 2013/007708 | 1/2013 |
| WO | WO 2013/021276 | 2/2013 |
| WO | WO 2013/024002 | 2/2013 |
| WO | WO 2013/024011 | 2/2013 |
| WO | WO 2013/042137 | 3/2013 |
| WO | WO 2013/064445 | 5/2013 |
| WO | WO 2013/123215 | 8/2013 |
| WO | WO 2013/130890 | 9/2013 |
| WO | WO 2013/146942 | 10/2013 |
| WO | WO 2014/003405 | 1/2014 |
| WO | WO 2014/024125 | 2/2014 |
| WO | WO 2014/047616 | 3/2014 |
| WO | WO 2014/055955 | 4/2014 |
| WO | WO 2014/151616 | 9/2014 |
| WO | WO 2015/026683 | 2/2015 |
| WO | WO 2015/037965 | 3/2015 |
| WO | WO 2015/038503 | 3/2015 |
| WO | WO 2015/058163 | 4/2015 |
| WO | WO 2015/061247 | 4/2015 |
| WO | WO 2015/089327 | 6/2015 |
| WO | WO 2015/089479 | 6/2015 |
| WO | WO 2015/090235 | 6/2015 |
| WO | WO 2015/091426 | 6/2015 |
| WO | WO 2015/104662 | 7/2015 |
| WO | WO 2015/117718 | 8/2015 |
| WO | WO 2015/164956 | 11/2015 |
| WO | WO 2015/192939 | 12/2015 |
| WO | WO 2015/193506 | 12/2015 |
| WO | WO 2015/193846 | 12/2015 |
| WO | WO 2015/200682 | 12/2015 |
| WO | WO 2016/040180 | 3/2016 |
| WO | WO 2016/040181 | 3/2016 |
| WO | WO 2016/041618 | 3/2016 |
| WO | WO 2016/057500 | 4/2016 |
| WO | WO 2016/083433 | 6/2016 |
| WO | WO 2016/090300 | 6/2016 |
| WO | WO 2016/124304 | 8/2016 |
| WO | WO 2016/144351 | 9/2016 |
| WO | WO 2016/144702 | 9/2016 |
| WO | WO 2016/164285 | 10/2016 |
| WO | WO 2016/174183 | 11/2016 |
| WO | WO 2016/205942 | 12/2016 |
| WO | WO 2017/009798 | 1/2017 |
| WO | WO 2017/009806 | 1/2017 |
| WO | WO 2017/023894 | 2/2017 |
| WO | WO 2017/023972 | 2/2017 |
| WO | WO 2017/027400 | 2/2017 |
| WO | WO 2017/045955 | 3/2017 |
| WO | WO 2017/058915 | 4/2017 |
| WO | WO 2017/108744 | 6/2017 |
| ZA | 2003005330 | 7/2003 |

OTHER PUBLICATIONS

Balog et al., "The synthesis and evaluation of [2.2.1]-bicycloazahydantoins as androgen receptor antagonists," Bioorg. Med. Chem. Lett., Dec. 20, 2004, 14(24):6107-6111.

Batliwalla et al., "Microarray analyses of peripheral blood cells identifies unique gene expression signature in psoriatic arthritis," Mol Med, 2005, 11(1-12):21-29.

Berge et al., "Pharmaceutical Salsts," J. Pharm. Sci., 1977, 66(1):1-19.

Blom et al., "Optimizing Preparative LC-MS Configurations and Methods for Parallel Synthesis Purification,"J. Combi. Chem., 2003, 5:670.

Blom et al., "Preparative LC-MS Purification: Improved Compound Specific Method Optimization," J. Combi. Chem., 2004, 6:874-883.

Blom et al., "Two-Pump At Column Dilution Configuration for Preparative LC-MS," J. Combi. Chem., 2002, 4: 295.

Chessari et al., "Fragment-Based Drug Discovery Targeting Inhibitor of Apoptosis Proteins: Discovery of a Non-Alanine Lead Series with Dual Activity Against cIAP1 and XIAP," J. Med. Chem., Jul. 18, 2015, 58(16):6574-6588.

Chinchilla and Najera, "Recent advances in Sonogashira reactions," Chem. Soc. Rev., 2011, 40: 5084-5121.

Choi et al., "In vitro metabolism of a novel phosphodiesterase-5 inhibitor DA-8159 in rat liver preparations using liquid chromatography/electrospray mass spectrometry," Biomed Chromatogr., Sep. 2002, 16(6):395-399.

Cordovilla et al., "The Stille Reaction, 38 Years Later," ACS Catalysis, 2015, 5: 3040-3053.

Devegowda et al., "Novel 6-N-arylcarboxamidopyrazolo[4,3-d]pyrimidin-7-one derivatives as potential anti-cancer agents," Bioorg Med Chem Lett., Mar. 1, 2010, 20(5):1630-1633.

Di Bartolo et al., "A novel pathway down-modulating T cell activation involves HPK-1-dependent recruitment of 14-3-3 proteins on SLP-76," J. Exp. Med., Mar. 2007, 204(3): 681-691.

Dumestre-Toulet et al., "Last performance with VIAGRA: postmortem identification of sildenafil and its metabolites in biological specimens including hair sample," Forensic Sci Int., Mar. 28, 2002, 126(1):71-76.

Edmondson et al., "Aminopiperidine-fused imidazoles as dipeptidyl peptidase-IV inhibitors," Bioorg Med Chem Lett., Aug. 2009, 19(15):4097-4101.

Elgemeie et al., "Novel Nucleoside Analogues: First Synthesis of Pyridine-4-Thioglycosides and Their Cytotoxic Evaluation," Nucleosides, Nucleotides and Nucleic Acids, Jun. 27, 2015, 34:659-673.

Elgemeie et al., "Synthesis of Novel Derivatives of 4-Methylthio-N-Aryl-2-Pyridone and Deazapurine Analogues: The Reaction of

(56) References Cited

OTHER PUBLICATIONS

Ketene Dithioacetals with Substituted Acetanilides," Phosphorus, Sulfur and Silicon, 2000, 164:189-197.
Erian, "2-Aryl-1,1-dicyano-3-phenylsulfonylpropenes in heterocyclic synthesis. A synthetic strategy towards heterocyclic sulfone," Monatshefte fuer Chemie, Oct. 1998, 129(10):1049-1056.
Figueiredo et al., "A chemometric study of phosphodiesterase 5 inhibitors," J Mol Graph Model., Jan. 2006, 24(4):227-232.
Gao, "Slidenafil" Handbook of Metabolic Pathways of Xenobiotics, 2014, 5:2151-2154.
Goodarzi et al., "Feature Selection and Linear/Nonlinear Regression Methods for the Accurate Prediction of Glycogen Synthase Kinase-3β Inhibitory Activities," J. Chem. Inf. Model, 2009, 49(4):824-832.
Haas et al., "Recent Developments in Negishi Cross-Coupling Reactions," ACS Catalysis, 2016, 6: 1540-1552.
Haring et al., "Comparison of different heterocyclic scaffolds as substrate analog PDE5 inhibitors," Sep. 1, 2005, 15(17):3900-3907.
Hanson, "Diterpenoids of Terrestrial Origin", National Product Reports, 2016, 33:1227-1238.
Hu et al., "Human HPK1, a novel human hematopoietic progenitor kinase that activates the JNK/SAPK kinase cascade," Genes Dev, 1996, 10(18): p. 2251-2264.
Ho et al., "Discovery of 4-phenyl-2-phenylaminopyridine based TNIK inhibitors," Boorg Med Chem Lett, 2013, 23(2):569-573.
Howard et al., "Identification of potent phosphodiesterase inhibitors that demonstrate cyclic nucleotide-dependent functions in apicomplexan parasites," ACS Chem Biol, Apr. 17, 2015, 10(4):1145-1154.
Ikegami et al., "The expression of prostaglandin E receptors EP2 and EP4 and their different regulation by lipopolysaccharide in C3H/HeN peritoneal macrophages," J. Immunol., Apr. 2001, 166(7): 4689-4696.
International Search Report and Written Opinion in International Application No. PCT/US2017/048880, dated Nov. 2, 2017, 15 pages.
International Search Report and Written Opinion in International Application No. PCT/US2017/050669, dated Nov. 6, 2017, 16 pages.
International Search Report and Written Opinion in International Application No. PCT/US2017/050727, dated Nov. 2, 2017, 16 pages.
International Search Report and Written Opinion in International Application No. PCT/US2017/050737, dated Nov. 2, 2017, 16 pages.
International Search Report and Written Opinion in International Application No. PCT/US2017/050757, dated Nov. 10, 2017, 20 pages.
International Search Report and Written Opinion in International Application No. PCT/US2018/018205, dated Apr. 30, 2018, 16 pages.
International Search Report and Written Opinion in International Application No. PCT/US2018/049908, dated Nov. 7, 2018.
International Search Report and Written Opinion in International Application No. PCT/US2019/018609, dated May 13, 2019, 12 pages.
International Search Report and Written Opinion in International Application No. PCT/US2019/018608, dated Apr. 16, 2019, 14 pages.
International Preliminary Report on Patentability in International Application No. PCT/US2017/050669, dated Mar. 12, 2019, 8 pages.
International Preliminary Report on Patentability in International Application No. PCT/US2017/050737, dated Mar. 12, 2019, 8 pages.
International Preliminary Report on Patentability in International Application No. PCT/US2017/050727, dated Mar. 12, 2019, 8 pages.
International Preliminary Report on Patentability in International Application No. PCT/US2017/050757, dated Mar. 12, 2019, 10 pages.
International Preliminary Report on Patentability in International Application No. PCT/US2018/018205, dated Aug. 20, 2019, 10 pages.
Ivon et al., "Synthesis of a 2,5-Diazabicyclo[2.2.1]heptane-Derived α,β-Diamino Acid," Synthesis, 2015, 47(8):1123-1130.
Karaman "Analyzing the efficiency in intramolecular amide hydrolysis of Kirby's N-alkylmaleamic acids—A computational approach," Computational and Theoretical Chemistry, 2011, 974(1-3):133-142.
Katritzky et al., "QSAR modeling of the inhibition of Glycogen Synthase Kinase-3," Bioorganic & Medicinal Chemistry, 2006, 14(14):4987-5002.
Kerekes et al., "Aurora kinase inhibitors based on the imidazo[1,2-a]pyrazine core: fluorine and deuterium incorporation improve oral absorption and exposure," J. Med. Chem., Jan. 2011, 54(1): 201-210.
Kiefer et al., "HPK1, a hematopoietic protein kinase activating the SAPK/JNK pathway," EMBO. J., Dec. 1996, 154(24): 7013-7025.
Kim et al., "Reliable screening and confirmation of 156 multi-class illegal adulterants in dietary supplements based on extracted common ion chromatograms by ultra-high-performance liquid chromatography-quadrupole/time of flight-mass spectrometry," J Chromatogr A., Mar. 31, 2017, 1491:43-56.
Kotha et al., "Recent applications of the Suzuki—Miyaura cross-coupling reaction in organic synthesis," Tetrahedron, 2002, 58: 9633-9695.
Kumar et al., "3-(1H-Indol-2-yl)-1H-pyrazolo[4,3-b]pyridines as Wnt pathway modulators and their preparation," retrieved from STN Database Accession No. 2017: 232331, Feb. 9, 2017, Chemical Abstracts Service, Columbus, Ohio, US, XP002775032.
Kumar et al., "3-(1H-Indol-2-yl)-1H-pyrazolo[4,3-b]pyridines as Wnt pathway modulators and their preparation," retrieved from STN Database Accession No. 2017: 232415, Feb. 9, 2017, Chemical Abstracts Service, Columbus, Ohio, US, XP002775031.
Kumar et al., "3-(1H-Indol-2-yl)-1H-pyrazolo[4,3-b]pyridines as Wnt pathway modulators and their preparation," retrieved from STN Database Accession No. 2017: 232564, Feb. 9, 2017, Chemical Abstracts Service, Columbus, Ohio, US, XP002775030.
Kumar et al., "3-(1H-Indol-2-yl)-1H-pyrazolo[4,3-b]pyridines as Wnt pathway modulators and their preparation," retrieved from STN Database Accession No. 2017: 233013, Feb. 9, 2017, Chemical Abstracts Service, Columbus, Ohio, US, XP002775029.
Kumar et al., "3-(1H-Indol-2-yl)-1H-pyrazolo[4,3-b]pyridines as Wnt pathway modulators and their preparation," retrieved from STN Database Accession No. 2017: 233418, Feb. 9, 2017, Chemical Abstracts Service, Columbus, Ohio, US, XP002775028.
Kumar et al., "3-(1H-Indol-2-yl)-1H-pyrazolo[4,3-b]pyridines as Wnt pathway modulators and their preparation," retrieved from STN Database Accession No. 2017: 233427, Feb. 9, 2017, Chemical Abstracts Service, Columbus, Ohio, US, XP002775027.
Kumar et al., "3-(1H-Indol-2-yl)-1H-pyrazolo[4,3-b]pyridines as Wnt pathway modulators and their preparation," retrieved from STN Database Accession No. 2017: 233436, Feb. 9, 2017, Chemical Abstracts Service, Columbus, Ohio, US, XP002775026.
Lebel et al., "A rapid, quantitative liquid chromatography-mass spectrometry screening method for 71 active and 11 natural erectile dysfunction ingredients present in potentially adulterated or counterfeit products," J Chromatogr A., May 23, 2014, 1343:143-151.
Lee et al., "Comparative metabolism of sildenafil in liver microsomes of different species by using LC/MS-based multivariate analysis," J of Chromato., Oct. 15, 2011, 879(28):3005-3011.
Li et al., "Metabolism of aildenafil in vivo in rats and in vitro in mouse, rat, dog, and human liver microsomes," Drug Test Anal., Jun. 2014., 6(6):552-562.
Lim et al., "Discovery of 1-(1 H-Pyrazolo [4,3-c]pyridin-6-yl)urea Inhibitors of Extracellular Signal-Regulated Kinase (ERK) for the Treatment of Cancers," Journal of Medicinal Chemistry, Jul. 2016, 59(13): 6501-6511.
Lin et al., "2,3,4-Trisbustituted pyridines as selective AKT inhibitors. Part II: Improved drug-like properties and kinase selectivity from azaindazoles," Bioorganic & Medicinal Chemistry Letters, 2010, 20: 679-683.
Liou et al., "HPK1 is activated by lymphocyte antigen receptors and negatively regulates AP-1," Immunity, Apr. 2000, 12(4): 399-408.

(56) References Cited

OTHER PUBLICATIONS

Liu et al., "Synthesis and SAR of 1,9-dihydro-9-hydroxypyrazolo[3,4-b]quinolin-4-ones as novel, selective c-Jun N-terminal kinase inhibitors," Bioorg Med Chem Lett., May 15, 2006, 16(10):2590-2594.
Michelotti et al., "Two Classes of p38a MAP kinase inhibitors having a common core but exhibiting devergent binding modes," 2005, 15:5274-5279.
Miyazaki et al., "Design and effective synthesis of novel templates, 3,7-diphenyl-4-amino-thieno and furo-[3,2-c]pyridines as protein kinase inhibitors and in vitro evaluation targeting angiogenetic kinases," Bioorg Med Chem Lett., Jan. 1, 2007, 17(1):250-254.
Mulvihill et al., "Novel 2-phenylquinolin-7-yl-derived imidazo[1,5-a]pyrazines as potent insulin-like growth factor-I receptor (IGF-IR) inhibitors," Bioorg Med Chem Lett, Feb. 2008, 16(3):1359-1375.
Patel et al., "Selectivity criterion for pyrazolo[3,4-b]pyrid[az]ine derivatives as GSK-3 inhibitors: CoMFA and molecular docking studies," European Journal of Medicinal Chemistry, 2008, 43: 949-957.
Peturssion et al., "Protecting Groups in Carbohydrate Chemistry," J. Chem. Educ., 1997, 74(11), 1297.
Piersanti et al., "Synthesis of Benzo[1,2-d;3,4']diimidazole and 1H-Pyrazolo[4,3-b]pyridine as Putative A2A Receptor Antagonists," Organic a& Biomolecular Chemistry, Jul. 13, 2007, 5:2567-2571.
Pitt et al., "Heteroaromatic rings of the future," J Med Chem., May 14, 2009, 52(9):2952-2963.
Pozharskii et al., Heterocycles in Life and Society Wiley, 1997, pp. 1-6.
Remington's Pharmaceutical Sciences, 17th Ed., (Mack Publishing Company, Easton, 1985), p. 1418.
Sawasdikosol et al., "HPK1 as a novel target for cancer immunotherapy," Immunologic Research, Apr. 4, 2012, 54(1-3): 262-265.
Sawasdikosol, S. et al., The journal of immunology, 2012. 188(supplement 1): p. 163.
Shaughnessy et al., "Copper-Catalyzed Amination of Aryl and Alkenyl Electrophiles," Organic Reactions, Chapter 1, 2014, 85: 1-668.
Shou et al., "Simple means to alleviate sensitivity loss by trifluoroacetic acid (TFA) mobile phases in the hydrophilic interaction chromatography-electrospray tandem mass spectrometric (HILIC-ESI/MS/MS) bioanalysis of basic compounds," J Chromatogr B Analyt Technol Biomed Life Sci., Oct. 25, 2008, 825:186-192.
Shui et al., "Hematopoietic progenitor kinase 1 negatively regulates T cell receptor signaling and T cell-mediated immune responses," Nat. Immunol., Jan. 2007, 8(1): 84-91.
Smyth et al., "Synthesis and reactivity of 3-amino-1H-pyrazolo[4,3-c]pyridin-4(5H)-ones: development of a novel kinase-focussed library," Tetrahedron, Apr. 2010, 66(15): 2843-2854.
Subramanyam et al., "6-(4-Pyridinyl)-1H-1,2,3-triazolo[4,5-d]-pyrimidin-4(5H)-one: A Structurally Novel Competitive AMPA Receptor Antagonist," J Med Chem., 1995, 38(4):587-589.
Surry and Buchwald, "Dialkylbiaryl Phosphines in Pd-Catalyzed Amination: A User's Guide," Chem. Sci., 2011, 2(1): 27-50.
Taha et al., "Pharmacophore Modeling, Quantitative Structure-Activity Relationship Analysis, and in silico Screening Reveal Potent Glycogen Synthase Kinase-3β Inhibitory Activities for Cimetidine, Hydroxychloroquine, and Gemifloxacin," J. Med. Chem., 2008, 51(7):2062-2077.
Terrett et al., "Sildenafil (VIAGRATM), a potent and selective inhibitor of type 5 cGMP phosphodiesterase with utility for the treatment of male erectile dysfunction," Bioorg & Med Chem Lett., Aug. 6, 1996, 6(15):1819-1824.
Vaclavik et al., "Single-Laboratory Validation Study of a Method for Screening and Identification of Phosphodiesterase Type 5 Inhibitors in Dietary Ingredients and Supplements Using Liquid Chromatography/Quadrupole-Orbital Ion Trap Mass Spectrometry: First Action 2015. 12," J AOAC Int., Jan.-Feb. 2016, 99(1):55-72.
Vymetalova et al., "5-Substituted 3-isopropyl-7-[4-(2-pyridyl)benzyl]amino-1(2)H-pyrazolo[4,3-d]pyrimidines with anti-proliferative activity as potent and selective inhibitors of cyclin-dependent kinases," Eur J Med Chem., Mar. 3, 2016, 110:391-301.
Wang et al., "Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction," J. Biol. Chem., Sep. 1997, 272(36): 22771-22775.
Wang et al., "Down-regulation of B cell receptor signaling by hematopoietic progenitor kinase 1 (HPK-1)-mediated phosphorylation and ubiquitination of activated B cell linker protein (BLNK)," J. Biol. Chem., Mar. 2012, 297(14): 11037-11048.
Wang et al., "Fragment-based identification and optimization of a class of potent pyrrolo[2,1-][1,2,4]triazine MAP4K4 inhibitors," Boorg Med Chem Lett., 24(18):4546-4552, (2014).
Wang et al., "Synthesis and evaluation of human phosphodiesterases (PDE) 5 inhibitor analogs as trypanosomal PDE inhibitors. Part 1. Sildenafil analogs," Bioorg Med Chem Lett., Apr. 1, 2012, 22(7):2579-2581.
Weinmann et al., "Identification of lorazepam and sildenafil as examples for the application of LC/ionspray-MS and MS-MS with mass spectra library searching in forensic toxicology," Forensic Sci Int., Sep. 11, 2000, 113(1-3):339-344.
Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1577-1580.
Witherington et al., "5-Aryl-pyrazolo[3,4-b]pyridazines: Potent Inhibitors of Glycogen Synthase Kinase-3 (GSK-3)," Bioorganic & Medicinal Letters, 2003, 13: 1581-1584.
Wislicenus "Adolph Strecker's Short Textbook of Organic Chemistry," 1881, Spottiswood, London, pp. 38-39.
Xu et al., "Design, synthesis and biological evaluation of euterated nintedanib for improving pharmacokinetic properties," J. Labelled Comp. Radiopharm., Jun. 2015, 58(7): 308-312.
Yang et al., "Highly efficient synthesis of fused bicyclic 2,3-diaryl-pyrimidin-4(3H)-ones via Lewis acid assisted cyclization reaction," Tetrahedron Letters, Mar. 10, 2008, 49(11):1725-1728.
Yeo et al., "New metabolites of hongdenafil, homosildenafil and hydroxyhomosildenafil," J Pharm Biomed Anal., Feb. 5, 2018, 149:586-590.
Zhang et al., "Anti-angiogenic effects of novel cyclin-dependent kinase inhibitors with a pyrazolo[4,3-d]pyrimidine scaffold," Br J Pharmacol., Sep. 2016, 173(17):2645-2656.
Zhou et al., "Hematopoietic progenitor kinase 1 is a component of transforming growth factor beta-induced c-Jun N-terminal kinase signaling cascade," J. Biol. Chem., May 1999, 274(19): 13133-13138.
Zhu et al., "Design and Synthesis of Pyridine-pyrazolopyridine based inhibitors of protein kinase B/Akt," Bioorganic and Medicinal Chemistry, Jan. 17, 2007, 15: 2441-2452.
Zhu et al., "Characterization of TPN729 metabolites in humans using ultra-performance liquid chromatography/quadrupole time-of-flight mass spectrometry," J Pharm Biomed Anal., Jan. 5, 2016, 117:217-226.
Literature and Patent Chemical Structure Search, Science IP, The CAS Search Service, Jul. 1, 2016, 441 pages.
Literature and Patent Chemical Structure Search, Science IP, The CAS Search Service, Jun. 30, 2016, 200 pages.
Structure 4: Substance Search Patent and Non-Patent Databases, Science IP, The CAS Search Service, Jun. 8, 2016, 820 pages.
Structure 3: Substance Search Patent and Non-Patent Databases, Science IP, The CAS Search Service, Jun. 7, 2016, 512 pages.
Structure 2: Substance Search Patent and Non-Patent Databases, Science IP, The CAS Search Service, Jun. 7, 2016, 833 pages.
Structure 1: Substance Search Patent and Non-Patent Databases, Science IP, The CAS Search Service, Jun. 6, 2016, 583 pages.
STN Search Report dated Aug. 17, 2016, 157 pages.
STN Search Report dated Aug. 25, 2016, 25 pages.
STN Search Report dated Aug. 30, 2016, 31 pages.
STN Search Report dated Aug. 31, 2016, 32 pages.
STN Search Report dated Jan. 27, 2017, 94 pages.
STN Search Report dated on Jan. 23, 2018, 26 pages.
STN Search Report dated on Apr. 25, 2018, 19 pages.
STN Search Report dated on May 9, 2018, 16 pages.

(56) References Cited

OTHER PUBLICATIONS

Anonymous, "Crystalline ethyl 1-(4-methoxyphenyl)-6-(4-nitrophenyl)-7-oxo-,5,6,7-tetmhydro-1H-pyrazolo[3,4-c]pyridine-3-carboxylate," IP.com #IPCOM000233229D, Dec. 3, 2019, 4 pages.

Anonymous, "Crystalline APX," IP.com #IPCOM000233879, Dec. 25, 2013, 3 pages.

Ballell et al., "Fueling Open-Source Drug Discovery: 177 Small-Molecule Leads against Tuberculosis," ChemMedChem., 2013, 8(2):313-321.

Brioche et al., "Chiral Phosphoric Acid-Catalyzed Enantioselective Three-Component Aza-Diels—Alder Reactions of Aminopyrroles and Aminopyrazoles," Advanced Synthesis & Catalysis, 2014, 356(8):1719-1724.

Cheung et al., "A Parallel Synthesis Approach to the Identification of Novel Diheteroalylamide-Based Compounds Blocking HIV Replication: Potential Inhibitors of HIV-1 Pre-mRNA Alternative Splicing," J Med Chem., Mar. 10, 2016, 59(5):1869-1879.

Dong et al., "Pharmacophore identification, virtual screening and biological evaluation of prenylated flavonoids derivatives as PKB/Akt1 inhibitors," Eur J Med Chem., Dec. 2011, 46(12):5949-5958.

Dong et al., "QSAR study of Akt/protein kinase B (PKB) inhibitors using support vector machine," Eur J Med Chem., Oct. 2009, 44(10):4090-4097

Dornow et al., "Syntheses of nitrogen-containing heterocycles. XXXVIII. Preparation and reaction of several substituted 3-nitropyridines," Chemische Berichte, 1996, 99(1):244-252 (Machine Translation).

El-Aziz et al., "Synthesis and in vitro anti-breast cancer activity of some novel 1,4-dihydropyridine derivatives," Int J of Pharm Pharma. Sci., 2013, 5(Suppl. 3):183-189.

El Sayed et al., "New route for the preparation of pyrazolo[4,3-c]pyridines," Bulletin of the Chemical Society of Japan (1973), 46(6), 1801-1803.

Elgemeie et al., "A new general method for substituted 4-alkylthio-N-arylsulfonylamino-2-pyridones: Reaction of ketene-S,S-acetals with arylsulfonylhydrazides," Phosphorus, Sulfur and Silicon and the Related Elements, 2001, 170:171-179.

Elgemeie et al., "Novel N-Substituted Amino-4-methylsulfanyl-2-pyridones and Deazapurine Analogues from Ketene Dithioacetals," J Chem Res., 1998, 3:164-165.

Elgemeie et al., "Novel synthesis of N-aroylaminated pyridones via reaction of ketene dithioacetals with cyanoaceto-N-aroylhydrazides," Synth Comm., 2003, 33(2):253-258.

He et al., "Predicting the Genotoxicity of Polycyclic Aromatic Compounds from Molecular Structure with Different Classifiers," Chemical Research in Toxicology (2003), 16(12):1567-1580.

Hu et al., "Discovery of 3,5-substituted-6-azaindazoles as potent pan-Pim inhibitors," Bioorg Med Chem Lett., 2015, 25(22):5258-5264.

Li et al., "A highly effective one-pot synthesis of quinolines from o-nitroarylcarbaldehydes," Organic & Biomolecular Chemistry, 2007, 5(1):61-64.

Li et al., "One-pot Friedlander quinoline synthesis: scope and limitations," Synthesis, 2010, 10:1678-1686.

Lin et al., "Tetrasubstituted pyridines as potent and selective AKT inhibitors: Reduced CYP450 and hERG inhibition of aminopyridines," Bioorg Med Chem Lett. Jan. 15, 2010;20(2):684-688.

Muddassar et al., "Elucidation of binding mode and three dimensional quantitative structure-activity relationship studies of a novel series of protein kinase B/Akt inhibitors," J Mol Model., Feb. 2009, 15(2):183-192.

Waddell et al., "Benzothiazolylthio Carbapenems: Potent Anti-MRSA Agents," Biorg & Med Chem Lett., 1995, 5(13):1427-1432.

Zhu et al., "Syntheses of potent, selective, and orally bioavailable indazole-pyridine series of protein kinase B/Akt inhibitors with reduced hypotension," J Med Chem., Jun. 28, 2007, 50(13):2990-3003.

STN Search Report dated Jan. 22, 2018, 9 pages.
STN Search Report dated Sep. 5, 2017, 26 pages.
STN Search Report dated Sep. 5, 2017, 5 pages.
STN Search Report dated Apr. 9, 2018, 7 pages.

* cited by examiner

CARBOXAMIDE COMPOUNDS AND USES THEREOF

FIELD OF THE INVENTION

The disclosure provides compounds as well as their compositions and methods of use. The compounds modulate hematopoietic progenitor kinase 1 (HPK1) activity and are useful in the treatment of various diseases including cancer.

BACKGROUND OF THE INVENTION

Hematopoietic progenitor kinase 1 (HPK1) originally cloned from hematopoietic progenitor cells is a member of MAP kinase kinase kinase kinases (MAP4Ks) family, which includes MAP4K1/HPK1, MAP4K2/GCK, MAP4K3/GLK, MAP4K4/HGK, MAP4K5/KHS, and MAP4K6/MINK (Hu, M. C., et al., Genes Dev, 1996. 10(18): p. 2251-64). HPK1 is of particular interest because it is predominantly expressed in hematopoietic cells such as T cells, B cells, macrophages, dendritic cells, neutrophils, and mast cells (Hu, M. C., et al., Genes Dev, 1996. 10(18): p. 2251-64; Kiefer, F., et al., EMBO J, 1996. 15(24): p. 7013-25). HPK1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-βR) (Wang, W., et al., J Biol Chem, 1997. 272(36): p. 22771-5; Zhou, G., et al., J Biol Chem, 1999. 274(19): p. 13133-8), or Gs-coupled $PGE_2$ receptors (EP2 and EP4) (Ikegami, R., et al., J Immunol, 2001. 166(7): p. 4689-96). As such, HPK1 regulates diverse functions of various immune cells.

HPK1 is important in regulating the functions of various immune cells and it has been implicated in autoimmune diseases and anti-tumor immunity (Shui, J. W., et al., Nat Immunol, 2007. 8(1): p. 84-91; Wang, X., et al., J Biol Chem, 2012. 287(14): p. 11037-48). HPK1 knockout mice were more susceptible to the induction of experimental autoimmune encephalomyelitis (EAE) (Shui, J. W., et al., Nat Immunol, 2007. 8(1): p. 84-91). In human, HPK1 was downregulated in peripheral blood mononuclear cells of psoriatic arthritis patients or T cells of systemic lupus erythematosus (SLE) patients (Batliwalla, F. M., et al., Mol Med, 2005. 11(1-12): p. 21-9). Those observations suggested that attenuation of HPK1 activity may contribute to autoimmunity in patients. Furthermore, HPK1 may also control anti-tumor immunity via T cell-dependent mechanisms. In the PGE2-producing Lewis lung carcinoma tumor model, the tumors developed more slowly in HPK1 knockout mice as compared to wild-type mice (see US 2007/0087988). In addition, it was shown that adoptive transfer of HPK1 deficient T cells was more effective in controlling tumor growth and metastasis than wild-type T cells (Alzabin, S., et al., Cancer Immunol Immunother, 2010. 59(3): p. 419-29). Similarly, BMDCs from HPK1 knockout mice were more efficient to mount a T cell response to eradicate Lewis lung carcinoma as compared to wild-type BMDCs (Alzabin, S., et al., J Immunol, 2009. 182(10): p. 6187-94). These data, in conjunction with the restricted expression of HPK1 in hematopoietic cells and lack of effect on the normal development of immune cells, suggest that HPK1 is a drug target for enhancing antitumor immunity. Accordingly, there is a need for new compounds that modulate HPK1 activity.

SUMMARY

The present disclosure provides, inter alia, a compound of Formula (I'):

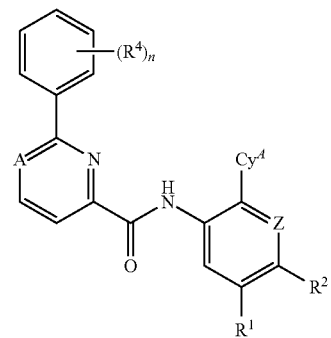

I' or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting HPK1 activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

The present disclosure provides a compound of Formula (I'):

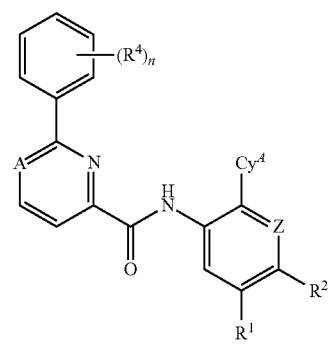

I' or a pharmaceutically acceptable salt thereof, wherein:

$Cy^A$ is $C_{3-12}$ cycloalkyl or 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of the 4-12 membered heterocycloalkyl is optionally substituted by oxo to form a carbonyl group; and wherein the $C_{3-12}$ cycloalkyl and 4-12 membered heterocycloalkyl are each optionally substituted with 1, 2, 3 or 4 substituents independently selected from $R^4$;

A is N or $CR^{16}$;

$R^{16}$ is selected from H, D, $C_{1-6}$ alkyl, $C_{2-6}$ alkenyl, $C_{2-6}$ alkynyl, $C_{1-6}$ haloalkyl, halo, CN, $NO_2$, $OR^{a16}$, $SR^{a16}$, $C(O)R^{b16}$, $C(O)NR^{c16}R^{d16}$, $C(O)OR^{a16}$, $OC(O)R^{b16}$, $OC(O)NR^{c16}R^{d16}$, $NR^{c16}R^{d16}$, $NR^{c16}C(O)R^{b16}$, $NR^{c16}C(O)OR^{a16}$, $NR^{c16}C(O)NR^{c16}R^{d16}$, $NR^{c16}S(O)R^{b16}$, $NR^{c16}S(O)_2R^{b16}$, $NR^{c16}S(O)_2NR^{c16}R^{d16}$, $S(O)R^{b16}$, $S(O)NR^{c16}R^{d16}$, $S(O)_2R^{b16}$, $S(O)_2NR^{c16}R^{d16}$ and $BR^{h16}R^{i16}$; wherein said $C_{1-6}$ alkyl, $C_{2-6}$ alkenyl and $C_{2-6}$ alkynyl are each optionally substituted with 1, 2, 3, or 4 substituents independently selected from $R^g$;

$R^1$ is selected from H, D, halo, CN, $C_{1-6}$ alkyl, $OR^{a15}$ and $NR^{c15}R^{d15}$; wherein the $C_{1-6}$ alkyl is optionally substituted with 1, 2, or 3 substituents independently selected from $R^g$;

$R^2$ is selected from H, D, $Cy^2$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$ and $BR^hR^i$; wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$Cy^2$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

Z is N or $CR^3$;

$R^3$ is selected from H, D, $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$ and $BR^{h4}R^{i4}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$Cy^3$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{13}$;

each $R^4$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NOR^{a8})R^{b8}$, $C(=NR^{e8})NR^{c8}R^{d8}$, $NR^{c8}C(=NR^e)NR^{c8}R^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$ and $BR^{h8}R^{i8}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^5$;

each $R^5$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$ and $BR^{h9}R^{i9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^6$;

each $R^6$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR_{c10}S(O)R^{b10}$, $NR_{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

each $R^4$ is selected from H, D, $Cy^1$, $C_{1-6}$ alkyl, $C_{2-6}$ alkenyl, $C_{2-6}$ alkynyl, $C_{1-6}$ haloalkyl, halo, CN, $NO_2$, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NOR^{a11})R^{b11}$, $C(=NR^{e11})NR^{c11}R^{d11}$, $NR^{c11}C(=NR^{e11})NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$ and $BR^{h11}R^{i11}$; wherein said $C_{1-6}$ alkyl, $C_{2-6}$ alkenyl and $C_{2-6}$ alkynyl are each optionally substituted with 1, 2, 3, or 4 substituents independently selected from $R^7$;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^7$;

each $R^7$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NOR^{a12})R^{b12}$, $C(=NR^{e12})NR^{c12}R^{d12}$, $NR^{c12}C(=NR^{e12})NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c2}R^{d12}$ and $BR^{h12}R^{i12}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^8$;

each $R^8$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a13}$, $SR^{a13}$, $C(O)R^{b13}$, $C(O)NR^{c13}R^{d13}$, $C(O)OR^{a13}$, $NR^{c13}R^{d13}$, $NR^{c13}C(O)R^{b13}$, $NR^{c13}C(O)OR^{a13}$, $NR^{c13}S(O)R^{b13}$, $NR^{c13}S(O)_2R^{b13}$, $NR^{c13}S(O)_2NR^{c13}R^{d13}$, $S(O)R^{b13}$, $S(O)NR^{c13}R^{d13}$, $S(O)_2R^{b13}S(O)_2NR^{c13}R^{d13}$ and $BR^{h13}R^{i13}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^9$;

each $R^9$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a14}$, $SR^{a14}$, $C(O)R^{b14}$, $C(O)NR^{c14}R^{d14}$, $C(O)OR^{a14}$, $NR^{c14}R^{d14}$, $NR^{c14}C(O)R^{b14}$, $NR^{c14}C(O)OR^{a14}$, $NR^{c14}S(O)R^{b14}$, $NR^{c14}S(O)_2R^{b14}$, $NR^{c14}S(O)_2R^{c14}R^{d14}$, $S(O)R^{b14}$, $S(O)NR^{c14}R^{d14}$, $S(O)_2R^{b14}$ and $S(O)_2NR^{c14}R^{d14}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and $BR^{h1}R^{i1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ $S(O)_2NR^{c2}R^{d2}$ and $BR^{h2}R^{i2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c13}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, $S(O)_2NR^{c5}R^{d5}$ and $BR^{h5}R^{i5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{14}$;

each $R^{14}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$ $S(O)_2NR^{c6}R^{d6}$ and $BR^{h6}R^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{15}$;

each $R^{15}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^a$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

or any $R^c$ and $R^d$ attached to the same N atom, together with the N atom to which they are attached, form a 4-, 5-, 6- or 7-membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH and $C_{1-6}$ alkoxy;

or any $R^h$ and $R^i$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl; each $R^{h1}$ and $R^{i1}$ is independently selected from OH and $C_{1-6}$ alkoxy;

or any $R^{h1}$ and $R^{i1}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl; each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{12}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3 or 4 substituents independently selected from $R^{12}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{12}$;

each $R^{h2}$ and $R^{i2}$ is independently selected from OH and $C_{1-6}$ alkoxy;

or any $R^{h2}$ and $R^{i2}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl; each $R^{a3}$, $R^{c3}$ and $R^{d3}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b3}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3 or 4 substituents independently selected from $R^{13}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{e4}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH and $C_{1-6}$ alkoxy;

or any $R^{h4}$ and $R^{i4}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a5}$, $R^{c5}$ and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3 or 4 substituents independently selected from $R^{14}$;

each $R^{b5}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

each $R^{e5}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH and $C_{1-6}$ alkoxy;

or any $R^{h5}$ and $R^{i5}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

or any $R^{c6}$ and $R^{d6}$ attached to the same N atom, together with the N atom to which they are attached, form a 4-, 5-, 6- or 7-membered heterocycloalkyl group optionally substituted with 1, 2, 3 or 4 substituents independently selected from $R^{15}$;

each $R^{b6}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

each $R^{h6}$ and $R^{i6}$ is independently selected from OH and $C_{1-6}$ alkoxy;

or any $R^{h6}$ and $R^{i6}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a7}$, $R^{c7}$ and $R^{d7}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b7}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a8}$, $R^{c8}$ and $R^{d8}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^5$;

or any $R^{c8}$ and $R^{d8}$ attached to the same N atom, together with the N atom to which they are attached, form a 4-, 5-, 6- or 7-membered heterocycloalkyl group optionally substituted with 1, 2, 3 or 4 substituents independently selected from $R^5$;

each $R^{b8}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^5$;

each $R^{e8}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h8}$ and $R^{i8}$ is independently selected from OH and $C_{1-6}$ alkoxy;

or any $R^{h8}$ and $R^{i8}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a9}$, $R^{c9}$ and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^6$;

or any $R^{c9}$ and $R^{d9}$ attached to the same N atom, together with the N atom to which they are attached, form a 4-, 5-, 6- or 7-membered heterocycloalkyl group optionally substituted with 1, 2, 3 or 4 substituents independently selected from $R^6$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^6$;

each $R^{h9}$ and $R^{i9}$ is independently selected from OH and $C_{1-6}$ alkoxy;

or any $R^{h9}$ and $R^{i9}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a10}$, $R^{c10}$ and $R^{d10}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b10}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a11}$, $R^{c11}$ and $R^{d11}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^7$;

or any $R^{c11}$ and $R^{d11}$ attached to the same N atom, together with the N atom to which they are attached, form a 4-, 5-, 6- or 7-membered heterocycloalkyl group optionally substituted with 1, 2, 3 or 4 substituents independently selected from $R^7$;

each $R^{b11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^7$;

each $R^{e11}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h11}$ and $R^{i11}$ is independently selected from OH and $C_{1-6}$ alkoxy;

or any $R^{h11}$ and $R^{i11}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a12}$, $R^{c12}$ and $R^{d12}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any $R^{c12}$ and $R^{d12}$ attached to the same N atom, together with the N atom to which they are attached, form a 4-, 5-, 6- or 7-membered heterocycloalkyl group optionally substituted with 1, 2, 3 or 4 substituents independently selected from $R^8$;

each $R^{b12}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each $R^{e12}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h12}$ and $R^{i12}$ is independently selected from OH and $C_{1-6}$ alkoxy;

or any $R^{h12}$ and $R^{i12}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a13}$, $R^{c13}$ and $R^{d13}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

or any $R^{c13}$ and $R^{d13}$ attached to the same N atom, together with the N atom to which they are attached, form a 4-, 5-, 6- or 7-membered heterocycloalkyl group optionally substituted with 1, 2, 3 or 4 substituents independently selected from $R^9$;

each $R^{b13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

each $R^{h13}$ and $R^{i13}$ is independently selected from OH and $C_{1-6}$ alkoxy;

or any $R^{h13}$ and $R^{i13}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a14}$, $R^{c14}$ and $R^{d14}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b14}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a15}$, $R^{c15}$ and $R^{d15}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a16}$, $R^{c16}$ and $R^{d16}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b16}$ is independently selected from $C_{1-6}$ alkyl, $C_{2-6}$ alkenyl, $C_{2-6}$ alkynyl and $C_{1-6}$ haloalkyl; wherein said $C_{1-6}$ alkyl $C_{2-6}$ alkenyl and $C_{2-6}$ alkynyl are each optionally substituted with 1, 2, 3, or 4 substituents independently selected from $R^g$;

each $R^{h16}$ and $R^{i6}$ is independently selected from OH and $C_{1-6}$ alkoxy;

or any $R^{h16}$ and $R^{i16}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl; and each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3 or 4.

The present disclosure provides a compound of Formula (I') or a pharmaceutically acceptable salt thereof, wherein:

$Cy^A$ is $C_{3-12}$ cycloalkyl or 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of the 4-12 membered heterocycloalkyl is optionally substituted by oxo to form a carbonyl group; and wherein the $C_{3-12}$ cycloalkyl and 4-12 membered heterocycloalkyl are each optionally substituted with 1, 2, 3 or 4 substituents independently selected from $R^A$;

A is N or $CR^{16}$;

$R^{16}$ is selected from H, D, $C_{1-6}$ alkyl, $C_{2-6}$ alkenyl, $C_{2-6}$ alkynyl, $C_{1-6}$ haloalkyl, halo, CN, $NO_2$, $OR^{a16}$, $SR^{a16}$, $C(O)R^{b16}$, $C(O)NR^{c16}R^{d16}$, $C(O)OR^{a16}$, $OC(O)R^{b16}$, $OC(O)NR^{c16}R^{d16}$, $NR^{c16}R^{d16}$, $NR^{c16}C(O)R^{b16}$, $NR^{c16}C(O)OR^{a16}$, $NR^{c16}C(O)NR^{c16}R^{d16}$, $NR^{c16}S(O)R^{b16}$, $NR^{c16}S(O)_2R^{b16}$, $NR^{c16}S(O)_2NR^{c16}R^{d16}$, $S(O)R^{b16}$, $S(O)NR^{c16}R^{d16}$, $S(O)_2R^{b16}$, $S(O)_2NR^{c16}R^{d16}$ and $BR^{h16}R^{i16}$; wherein said $C_{1-6}$ alkyl, $C_{2-6}$ alkenyl and $C_{2-6}$ alkynyl are each optionally substituted with 1, 2, 3 or 4 substituents independently selected from $R^g$;

$R^1$ is selected from H, D, halo, CN, $C_{1-6}$ alkyl and $OR^{a15}$; wherein the $C_{1-6}$ alkyl is optionally substituted with 1, 2, or 3 substituents independently selected from $R^g$;

$R^2$ is selected from H, D, $Cy^2$, $C_{1-6}$ alkyl, $C_{2-6}$ alkenyl, $C_{2-6}$ alkynyl, $C_{1-6}$ haloalkyl, halo, CN, and $NO_2$; wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$Cy^2$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl and 5-10 membered heteroaryl are each optionally substituted with 1, 2, 3 or 4 substituents independently selected from $R^{10}$;

Z is N or $CR^3$;

$R^3$ is selected from H, D, $Cy^3$, halo and CN;

$Cy^3$ is 6-10 membered heteroaryl; wherein the 6-10 membered heteroaryl each has at least one ring-forming carbon atom and 1, 2, 3, or 4 ring-forming heteroatoms independently selected from N, O, and S;

each $R^4$ is independently selected from $C_{1-6}$ alkyl, $C_{1-6}$ haloalkyl, halo, D, CN and $OR^{a8}$;

$R^4$ is selected from H, D, $Cy^1$, $C_{1-6}$ alkyl, $C_{1-6}$ haloalkyl, halo, CN, $OR^{a11}$, $C(O)NR^{c11}R^{d11}$, and $NR^{c11}R^{d11}$; wherein said $C_{1-6}$ alkyl, is optionally substituted with 1, 2, 3, or 4 substituents independently selected from $R^7$;

$Cy^1$ is selected from $C_{3-10}$ cycloalkyl and 5-10 membered heteroaryl; wherein the 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the $C_{3-10}$ cycloalkyl and 5-10 membered heteroaryl are each optionally substituted with 1, 2, 3 or 4 substituents independently selected from $R^7$;

each $R^7$ is independently selected from $C_{1-6}$ alkyl, halo, D, CN, $OR^{a12}$ and $NR^{c12}R^{d12}$;

each $R^{10}$ is independently selected from $C_{1-6}$ alkyl, $C_{1-6}$ haloalkyl, 4-10 membered heterocycloalkyl, halo, D, CN, $OR^{a1}$, $C(O)NR^{c1}R^{d1}$ and $NR^{c1}R^{d1}$; wherein said $C_{1-6}$ alkyl, and 4-10 membered heterocycloalkyl are each optionally substituted with 1, 2, 3, or 4 substituents independently selected from $R^{11}$;

each $R^{11}$ is independently selected from $C_{1-6}$ alkyl, $C_{1-6}$ haloalkyl, halo, D, CN and $OR^{a2}$;

each $R^{a1}$, $R^{c1}$ and $R^{d1}$ is independently selected from H, $C_{1-6}$ alkyl, $C_{1-6}$ haloalkyl and $C_{3-10}$ cycloalkyl; wherein said $C_{1-6}$ alkyl and $C_{3-10}$ cycloalkyl are each optionally substituted with 1, 2, 3, or 4 substituents independently selected from $R^{11}$;

each $R^{a2}$, $R^{c2}$ and $R^{d2}$ is independently selected from H, $C_{1-6}$ alkyl and $C_{1-6}$ haloalkyl;

each $R^{a8}$, $R^{c8}$ and $R^{d8}$ is independently selected from H, $C_{1-6}$ alkyl and $C_{1-6}$ haloalkyl;

each $R^{a11}$, $R^{c11}$ and $R^{d11}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^7$;

each $R^{a12}$, $R^{c12}$ and $R^{d12}$ is independently selected from H, $C_{1-6}$ alkyl and $C_{1-6}$ haloalkyl;

each $R^{a15}$, $R^{c15}$ and $R^{d15}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^g$;

$R^{a16}$ is independently selected from H and $C_{1-6}$ alkyl;

each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylthio, $C_{1-6}$ alkylsulfonyl; and n is 0, 1, 2 or 3.

The present disclosure provides a compound of Formula (I') or a pharmaceutically acceptable salt thereof, wherein:

$Cy^4$ is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein a ring-forming carbon atom of the 4-12 membered heterocycloalkyl is optionally substituted by oxo to form a carbonyl group; and wherein the 4-12 membered heterocycloalkyl are each optionally substituted with 1, 2, 3 or 4 substituents independently selected from $R^4$;

A is N or $CR^{16}$;

$R^{16}$ is selected from H, D, $C_{1-6}$ alkyl, halo, CN and $OR^{a16}$;

$R^1$ is selected from H, D, halo, CN, $C_{1-6}$ alkyl and $OR^{a15}$; wherein the $C_{1-6}$ alkyl is optionally substituted with 1, 2, or 3 substituents independently selected from $R^g$;

$R^2$ is selected from H, D, $Cy^2$, $C_{1-6}$ alkyl, $C_{1-6}$ haloalkyl, halo, CN; wherein said $C_{1-6}$ alkyl, is optionally substituted with 1, 2, 3, or 4 substituents independently selected from $R^{10}$;

$Cy^2$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl and 5-10 membered heteroaryl are each optionally substituted with 1, 2, 3 or 4 substituents independently selected from $R^{10}$;

Z is N or $CR^3$;

$R^3$ is selected from H, D, $Cy^3$, halo and CN;

$Cy^3$ is 6-10 membered heteroaryl; wherein the 6-10 membered heteroaryl each has at least one ring-forming carbon atom and 1, 2, 3, or 4 ring-forming heteroatoms independently selected from N, O, and S;

each $R^4$ is independently selected from $C_{1-6}$ alkyl, $C_{1-6}$ haloalkyl, halo, D, CN and $OR^{a8}$;

$R^A$ is selected from H, D, $Cy^1$, $C_{1-6}$ alkyl, $C_{1-6}$ haloalkyl, halo, CN, $OR^{a11}$, $C(O)NR^{c11}R^{d11}$, and $NR^{c11}R^{d11}$; wherein said $C_{1-6}$ alkyl, is optionally substituted with 1, 2, 3, or 4 substituents independently selected from $R^7$;

$Cy^1$ is selected from $C_{3-10}$ cycloalkyl and 5-10 membered heteroaryl; wherein the 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the $C_{3-10}$ cycloalkyl and 5-10 membered heteroaryl are each optionally substituted with 1, 2, 3 or 4 substituents independently selected from $R^7$;

each $R^7$ is independently selected from $C_{1-6}$ alkyl, halo, D, CN, $OR^{a12}$ and $NR^{c12}R^{d12}$;

each $R^{10}$ is independently selected from $C_{1-6}$ alkyl, $C_{1-6}$ haloalkyl, 4-10 membered heterocycloalkyl, halo, D, CN, $OR^{a1}$, $C(O)NR^{c1}R^{d1}$ and $NR^{c1}R^{d1}$; wherein said $C_{1-6}$ alkyl, and 4-10 membered heterocycloalkyl are each optionally substituted with 1, 2, 3, or 4 substituents independently selected from $R^{11}$;

each $R^{11}$ is independently selected from $C_{1-6}$ alkyl, $C_{1-6}$ haloalkyl, halo, D, CN and $OR^{a2}$;

each $R^{a1}$, $R^{c1}$ and $R^{d1}$ is independently selected from H, $C_{1-6}$ alkyl, $C_{1-6}$ haloalkyl and $C_{3-10}$ cycloalkyl; wherein said $C_{1-6}$ alkyl and $C_{3-10}$ cycloalkyl are each optionally substituted with 1, 2, 3, or 4 substituents independently selected from $R^{11}$;

each $R^{a2}$, $R^{c2}$ and $R^{d2}$ is independently selected from H, $C_{1-6}$ alkyl and $C_{1-6}$ haloalkyl;

each $R^{a8}$, $R^{c8}$ and $R^{d8}$ is independently selected from H, $C_{1-6}$ alkyl and $C_{1-6}$ haloalkyl;

each $R^{a11}$, $R^{c11}$ and $R^{d11}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^7$;

each $R^{a12}$, $R^{c12}$ and $R^{d12}$ is independently selected from H, $C_{1-6}$ alkyl and $C_{1-6}$ haloalkyl;

each $R^{a15}$, $R^{c15}$ and $R^{d15}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^g$;

$R^{a16}$ is independently selected from H and $C_{1-6}$ alkyl;

each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylthio, $C_{1-6}$ alkylsulfonyl; and n is 0, 1, 2 or 3.

The present disclosure provides a compound of Formula (I):

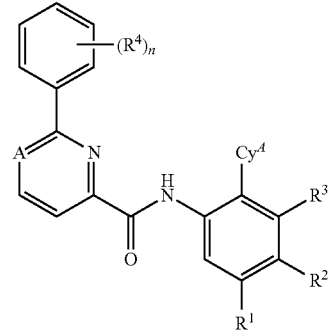

or a pharmaceutically acceptable salt thereof, wherein:

$Cy^4$ is $C_{3-12}$ cycloalkyl or 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of the 4-12 membered heterocycloalkyl is optionally substituted by oxo to form a carbonyl group; and wherein the $C_{3-12}$ cycloalkyl and 4-12 membered heterocycloalkyl are each optionally substituted with 1, 2, 3 or 4 substituents independently selected from $R^4$;

A is N or CF;

$R^1$ is selected from H, D, halo, CN, $C_{1-6}$ alkyl, $OR^{a15}$ and $NR^{c15}R^{d15}$; wherein the $C_{1-6}$ alkyl is optionally substituted with 1, 2, or 3 substituents independently selected from $R^g$;

$R^2$ is selected from H, D, $Cy^2$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$ and $BR^hR^i$; wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$Cy^2$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, D, $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$ and $BR^{h4}R^{i4}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$Cy^3$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{13}$;

each $R^4$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $C(=NR_{e8})R^{b8}$, $C(=NOR^{a8})R^{b8}$, $C(=NR^{e8})NR^{c8}R^{d8}$, $NR^{c8}C(=NR^{e8})NR^{c8}R^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$ and $BR^{h8}R^{i8}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^5$;

each $R^5$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$ and $BR^{h9}R^{i9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^6$;

each $R^6$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

$R^A$ is selected from H, D, $Cy^1$, $C_{1-6}$ alkyl, $C_{2-6}$ alkenyl, $C_{2-6}$ alkynyl, $C_{1-6}$ haloalkyl, halo, CN, $NO_2$, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NOR^{a11})R^{b11}$, $C(=NR^{e11})NR^{c11}R^{d11}$, $NR^{c1}C(=NR^{e11})NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$ and $BR^{h11}R^{i11}$; wherein said $C_{1-6}$ alkyl, $C_{2-6}$ alkenyl and $C_{2-6}$ alkynyl are each optionally substituted with 1, 2, 3, or 4 substituents independently selected from $R^7$;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^7$;

each $R^7$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a12}$, $SR^{a12}$, $C(O)R^{b12}$, $C(O)NR^{c12}R^{d12}$, $C(O)OR^{a12}$, $OC(O)R^{b12}$, $OC(O)NR^{c12}R^{d12}$, $NR^{c12}R^{d12}$, $NR^{c12}C(O)R^{b12}$, $NR^{c12}C(O)OR^{a12}$, $NR^{c12}C(O)NR^{c12}R^{d12}$, $C(=NR^{e12})R^{b12}$, $C(=NOR^{a12})R^{b12}$, $C(=NR^{e12})NR^{c12}R^{d12}$, $NR^{c12}C(=NR^{e12})NR^{c12}R^{d12}$, $NR^{c12}S(O)R^{b12}$, $NR^{c12}S(O)_2R^{b12}$, $NR^{c12}S(O)_2NR^{c12}R^{d12}$, $S(O)R^{b12}$, $S(O)NR^{c12}R^{d12}$, $S(O)_2R^{b12}$, $S(O)_2NR^{c12}R^{d12}$ and $BR^{h12}R^{i12}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally selected from $R^8$;

each $R^8$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a13}$, $SR^{a13}$, $C(O)R^{b3}$, $C(O)NR^{c13}R^{d13}$, $C(O)OR^{a13}$, $NR^{c13}R^{d13}$, $NR^{c13}C(O)R^{b13}$, $NR^{c13}C(O)OR^{a13}$, $NR^{c13}S(O)R^{b13}$, $NR^{c13}S(O)_2R^{b13}$, $NR^{c13}S(O)_2NR^{c13}R^{d13}$, $S(O)R^{b13}$, $S(O)NR^{c13}R^{d13}$, $S(O)_2R^{b13}S(O)_2NR^{c13}R^{d13}$ and $BR^{h13}R^{i13}$; wherein said $C_{1-6}$ alkyl, $C_{2-6}$ alkenyl, $C_{2-6}$ alkynyl, $C_{3-6}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^9$;

each $R^9$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a14}$, $SR^{a14}$, $C(O)R^{b14}$, $C(O)NR^{c14}R^{d14}$, $C(O)OR^{a14}$, $NR^{c14}R^{d14}$, $NR^{c14}C(O)R^{b14}$, $NR^{c14}C(O)OR^{a14}$, $NR^{c14}S(O)R^{b14}$, $NR^{c14}S(O)_2R^{b14}$, $NR^{c14}S(O)_2NR^{c14}R^{d14}$, $S(O)R^{b14}$, $S(O)NR^{c14}R^{d14}$, $S(O)_2R^{b14}$ and $S(O)_2NR^{c14}R^{d14}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NOR^{a1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$ and $BR^{h1}R^{i1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{11}$;

each $R^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a2}$, $SR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, $NR^{c2}C(O)OR^{a2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ $S(O)_2NR^{c2}R^{d2}$ and $BR^{h2}R^{i2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{12}$;

each $R^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c13}C(O)R^{b3}$, $NR^{c3}C(O)OR^{a3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$ and $S(O)_2NR^{c3}R^{d3}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a5}$, $SR^{a8}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $C(=NR^{e5})R^{b5}$, $C(=NOR^{a5})R^{b5}$, $C(=NR^{e5})NR^{c5}R^{d5}$, $NR^{c5}C(=NR^{e5})NR^{c5}R^{d5}$, $NR^{c5}S(O)R^{b5}$, $NR^{c5}S(O)_2R^{b5}$, $NR^{c5}S(O)_2NR^{c5}SR^{d5}$, $S(O)R^{b5}$, $S(O)NR^{c5}R^{d5}$, $S(O)_2R^{b5}$, $S(O)_2NR^{c5}R^{d5}$ and $BR^{h5}R^{i5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{14}$;

each $R^{14}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a6}$, $SR^{a6}$, $C(O)R^{b6}$, $C(O)NR^{c6}R^{d6}$, $C(O)OR^{a6}$, $NR^{c6}R^{d6}$, $NR^{c6}C(O)R^{b6}$, $NR^{c6}C(O)OR^{a6}$, $NR^{c6}S(O)R^{b6}$, $NR^{c6}S(O)_2R^{b6}$, $NR^{c6}S(O)_2NR^{c6}R^{d6}$, $S(O)R^{b6}$, $S(O)NR^{c6}R^{d6}$, $S(O)_2R^{b6}$ $S(O)_2NR^{c6}R^{d6}$ and $BR^{h6}R^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^{15}$;

each $R^{15}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^a$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

or any $R^c$ and $R^d$ attached to the same N atom, together with the N atom to which they are attached, form a 4-, 5-, 6- or 7-membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH and $C_{1-6}$ alkoxy;

or any $R^h$ and $R^i$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h1}$ and $R^{i1}$ is independently selected from OH and $C_{1-6}$ alkoxy;

or any $R^{h1}$ and $R^{i1}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{12}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3 or 4 substituents independently selected from $R^{12}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{12}$;

each $R^{h2}$ and $R^{i2}$ is independently selected from OH and $C_{1-6}$ alkoxy;

or any $R^{h2}$ and $R^{i2}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a3}$, $R^{c3}$ and $R^{d3}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b3}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3 or 4 substituents independently selected from $R^{13}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{e4}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH and $C_{1-6}$ alkoxy;

or any $R^{h4}$ and $R^{i4}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a5}$, $R^{c5}$ and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3 or 4 substituents independently selected from $R^{14}$;

each $R^{b5}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

each $R^{e5}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH and $C_{1-6}$ alkoxy;

or any $R^{h5}$ and $R^{i5}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

or any $R^{c6}$ and $R^{d6}$ attached to the same N atom, together with the N atom to which they are attached, form a 4-, 5-, 6- or 7-membered heterocycloalkyl group optionally substituted with 1, 2, 3 or 4 substituents independently selected from $R^{15}$;

each $R^{b6}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

each $R^{h6}$ and $R^{i6}$ is independently selected from OH and $C_{1-6}$ alkoxy;

or any $R^{h6}$ and $R^{i6}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a7}$, $R^{c7}$ and $R^{d7}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b7}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a8}$, $R^{c8}$ and $R^{d8}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^5$;

or any $R^{c8}$ and $R^{d8}$ attached to the same N atom, together with the N atom to which they are attached, form a 4-, 5-, 6- or 7-membered heterocycloalkyl group optionally substituted with 1, 2, 3 or 4 substituents independently selected from $R^5$;

each $R^{b8}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^5$;

each $R^{e8}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h8}$ and $R^{i8}$ is independently selected from OH and $C_{1-6}$ alkoxy;

or any $R^{h8}$ and $R^{i8}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a9}$, $R^{c9}$ and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^6$;

or any $R^{c9}$ and $R^{d9}$ attached to the same N atom, together with the N atom to which they are attached, form a 4-, 5-, 6- or 7-membered heterocycloalkyl group optionally substituted with 1, 2, 3 or 4 substituents independently selected from $R^6$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^6$;

each $R^{h9}$ and $R^{i9}$ is independently selected from OH and $C_{1-6}$ alkoxy;

or any $R^{h9}$ and $R^{i9}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a10}$, $R^{c10}$ and $R^{d10}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b10}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a11}$, $R^{c11}$ and $R^{d11}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^7$;

or any $R^{c11}$ and $R^{d11}$ attached to the same N atom, together with the N atom to which they are attached, form a 4-, 5-, 6- or 7-membered heterocycloalkyl group optionally substituted with 1, 2, 3 or 4 substituents independently selected from $R^7$;

each $R^{b11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^7$;

each $R^{e11}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h11}$ and $R^{i11}$ is independently selected from OH and $C_{1-6}$ alkoxy;

or any $R^{h11}$ and $R^{i11}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a12}$, $R^{c12}$ and $R^{d12}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any $R^{c12}$ and $R^{d12}$ attached to the same N atom, together with the N atom to which they are attached, form a 4-, 5-, 6- or 7-membered heterocycloalkyl group optionally substituted with 1, 2, 3 or 4 substituents independently selected from $R^8$;

each $R^{b12}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each $R^{e12}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h12}$ and $R^{i12}$ is independently selected from OH and $C_{1-6}$ alkoxy;

or any $R^{h12}$ and $R^{i12}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a13}$, $R^{c13}$ and $R^{d13}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

or any $R^{c13}$ and $R^{d13}$ attached to the same N atom, together with the N atom to which they are attached, form a 4-, 5-, 6- or 7-membered heterocycloalkyl group optionally substituted with 1, 2, 3 or 4 substituents independently selected from $R^9$;

each $R^{b13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

each $R^{h13}$ and $R^{i13}$ is independently selected from OH and $C_{1-6}$ alkoxy;

or any $R^{h13}$ and $R^{i13}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a14}$, $R^{c14}$ and $R^{d14}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b14}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a15}$, $R^{c15}$ and $R^{d15}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3 or 4;

provided that $R^4$ is other than unsubstituted or substituted 4-morpholinyl, 4-thiomorpholinyl, 1-oxido-4-thiomorpholinyl and 1,1-dioxido-4-thiomorpholinyl.

In some embodiments, provided herein is a compound of Formula (I), or a pharmaceutically acceptable salt thereof, wherein:

$Cy^A$ is $C_{3-12}$ cycloalkyl or 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of the 4-12 membered heterocycloalkyl is optionally substituted by oxo to form a carbonyl group; and wherein the $C_{3-12}$ cycloalkyl and 4-12 membered heterocycloalkyl are each optionally substituted with 1, 2, 3 or 4 substituents independently selected from $R^A$;

A is N or CF;

$R^1$ is selected from H, D, halo, CN, $C_{1-6}$ alkyl, $OR^{a15}$ and $NR^{c15}R^{d15}$; wherein the $C_{1-6}$ alkyl is optionally substituted with 1, 2, or 3 substituents independently selected from $R^g$;

$R^2$ is selected from H, D, $Cy^2$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NOR^a)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$ and $BR^{h}R^i$; wherein said $C_{1-6}$ alkyl, $C_{2-6}$ alkenyl and $C_{2-6}$ alkynyl are each optionally substituted with 1, 2, 3, or 4 substituents independently selected from $R^{10}$;

$Cy^2$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, D, $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NOR^{a4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$ and $BR^{h4}R^{i4}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$;

$Cy^3$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{13}$;

each $R^4$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NOR^{a8})R^{b8}$, $C(=NR^{e8})NR^{c8}R^{d8}$, $NR^{c8}C(=NR^{e8})NR^{c8}R^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$ and $BR^{h8}R^{i8}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^5$;

each $R^5$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, $OR^{a9}$, $SR^{a9}$, $C(O)R^{b9}$, $C(O)NR^{c9}R^{d9}$, $C(O)OR^{a9}$, $NR^{c9}R^{d9}$, $NR^{c9}C(O)R^{b9}$, $NR^{c9}C(O)OR^{a9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$ and $BR^{h9}R^{i9}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^6$;

each $R^6$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a10}$, $SR^{a10}$, $C(O)R^{b10}$, $C(O)NR^{c10}R^{d10}$, $C(O)OR^{a10}$, $NR^{c10}R^{d10}$, $NR^{c10}C(O)R^{b10}$, $NR^{c10}C(O)OR^{a10}$, $NR^{c10}S(O)R^{b10}$, $NR^{c10}S(O)_2R^{b10}$, $NR^{c10}S(O)_2NR^{c10}R^{d10}$, $S(O)R^{b10}$, $S(O)NR^{c10}R^{d10}$, $S(O)_2R^{b10}$, and $S(O)_2NR^{c10}R^{d10}$; wherein said $C_{1-6}$ alkyl, $C_{2-6}$ alkenyl, $C_{2-6}$ alkynyl, $C_{3-6}$ cycloalkyl, phenyl, 5-6 membered heteroaryl and 4-7 membered heterocycloalkyl are each optionally substituted with 1, 2, 3, or 4 substituents independently selected from $R^g$;

$R^A$ is selected from H, D, $Cy^1$, $C_{1-6}$ alkyl, $C_{2-6}$ alkenyl, $C_{2-6}$ alkynyl, $C_{1-6}$ haloalkyl, halo, CN, $NO_2$, $OR^{a11}$, $SR^{a11}$, $C(O)R^{b11}$, $C(O)NR^{c11}R^{d11}$, $C(O)OR^{a11}$, $OC(O)R^{b11}$, $OC(O)NR^{c11}R^{d11}$, $NR^{c11}R^{d11}$, $NR^{c11}C(O)R^{b11}$, $NR^{c11}C(O)OR^{a11}$, $NR^{c11}C(O)NR^{c11}R^{d11}$, $C(=NR^{e11})R^{b11}$, $C(=NOR^{a11})R^{b11}$, $C(=NR^{e11})NR^{c11}R^{d11}$, $NR^{c11}C(=NR^{e11})NR^{c11}R^{d11}$, $NR^{c11}S(O)R^{b11}$, $NR^{c11}S(O)_2R^{b11}$, $NR^{c11}S(O)_2NR^{c11}R^{d11}$, $S(O)R^{b11}$, $S(O)NR^{c11}R^{d11}$, $S(O)_2R^{b11}$, $S(O)_2NR^{c11}R^{d11}$ and $BR^{h11}R^{i11}$; wherein said $C_{1-6}$ alkyl, $C_{2-6}$ alkenyl and $C_{2-6}$ alkynyl are each optionally substituted with 1, 2, 3, or 4 substituents independently selected from $R^7$;

$Cy^1$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^7$;

each $R^7$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a12}$, SR$^{a12}$, C(O)R$^{b12}$, C(O)NR$^{c12}$R$^{d12}$, C(O)OR$^{a12}$, OC(O)R$^{b12}$, OC(O)NR$^{c12}$R$^{d12}$, NR$^{c12}$R$^{d12}$, NR$^{c12}$C(O) R$^{b12}$, NR$^{c12}$C(O)OR$^{a12}$, NR$^{c12}$C(O)NR$^{c12}$R$^{d12}$, C(=NR$^{e12}$)R$^{b12}$, C(=NOR$^{a12}$)R$^{b12}$, C(=NR$^{e12}$) NR$^{c12}$R$^{d12}$, NR$^{c12}$C(=NR$^{e12}$)NR$^{c12}$R$^{d12}$, NR$^{c12}$S(O)R$^{b12}$, NR$^{c12}$S(O)$_2$R$^{b12}$, NR$^{c12}$S(O)$_2$NR$^{c12}$R$^{d12}$, S(O)R$^{b12}$, S(O) NR$^{c12}$R$^{d12}$, S(O)$_2$R$^{b12}$, S(O)$_2$NR$^{c12}$R$^{d12}$ and BR$^{h12}$R$^{i12}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^8$;

each R$^8$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, OR$^{a13}$, SR$^{a13}$, C(O)R$^{b13}$, C(O)NR$^{c13}$R$^{d13}$, C(O)OR$^{a13}$, NR$^{c13}$R$^{d13}$, NR$^{c13}$C(O)R$^{b13}$, NR$^{c13}$C(O)OR$^{a13}$, NR$^{c13}$S(O)R$^{b13}$, NR$^{c13}$S(O)$_2$R$^{b13}$, NR$^{c13}$S(O)$_2$NR$^{c13}$R$^{d13}$, S(O)R$^{b13}$, S(O) NR$^{c13}$R$^{d13}$, S(O)$_2$R$^{b13}$S(O)$_2$NR$^{c13}$R$^{d13}$ and BR$^{h13}$R$^{i13}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^9$;

each R$^9$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, OR$^{a14}$, SR$^{a14}$, C(O)R$^{b14}$, C(O) NR$^{c14}$R$^{d14}$, C(O)OR$^{a14}$, NR$^{c14}$R$^{d14}$, NR$^{c14}$C(O)R$^{b14}$, NR$^{c14}$C(O)OR$^{a14}$, NR$^{c14}$S(O)R$^{b14}$, NR$^{c14}$S(O)$_2$R$^{b14}$, NR$^{c14}$S(O)$_2$R$^{c14}$R$^{d14}$, S(O)R$^{b14}$, S(O)NR$^{c14}$R$^{d14}$, S(O)$_2$ R$^{b14}$ and S(O)$_2$NR$^{c14}$R$^{d14}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from R$^g$;

each R$^{10}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a1}$, SR$^{a1}$, C(O)R$^{b1}$, C(O)NR$^{c1}$R$^{d1}$, C(O)OR$^{a1}$, OC(O) R$^{b1}$, OC(O)NR$^{c1}$R$^{d1}$, NR$^{c1}$R$^{d1}$, NR$^{c1}$C(O)R$^{b1}$, NR$^{c1}$C(O) OR$^{a1}$, NR$^{c1}$C(O)NR$^{c1}$R$^{d1}$, C(=NR$^{e1}$)R$^{b1}$, C(=NOR$^{a1}$) R$^{b1}$, C(=NR$^{e1}$)NR$^{c1}$R$^{d1}$, NR$^{c1}$C(=NR$^{e1}$)NR$^{c1}$R$^{d1}$, NR$^{c1}$S (O)R$^{b1}$, NR$^{c1}$S(O)$_2$R$^{b1}$, NR$^{c1}$S(O)$_2$NR$^{c1}$R$^{d1}$, S(O)R$^{b1}$, S(O) NR$^{c1}$R$^{d1}$, S(O)$_2$R$^{b1}$, S(O)$_2$NR$^{c1}$R$^{d1}$ and BR$^{h1}$R$^{i1}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{11}$;

each R$^{11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, OR$^{a2}$, SR$^{a2}$, C(O)R$^{b2}$, C(O)NR$^{c2}$R$^{d2}$, C(O)OR$^{a2}$, NR$^{c2}$R$^{d2}$, NR$^{c2}$C (O)R$^{b2}$, NR$^{c2}$C(O)OR$^{a2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$ S(O)$_2$NR$^{c2}$R$^{d2}$ and BR$^{h2}$R$^{i2}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{12}$;

each R$^{12}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, OR$^{a3}$, SR$^{a3}$, C(O)R$^{b3}$, C(O)NR$^{c3}$R$^{d3}$, C(O)OR$^{a3}$, NR$^{c3}$R$^{d3}$, NR$^{c13}$C(O)R$^{b3}$, NR$^{c3}$C(O)OR$^{a3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O) R$^{b3}$, S(O)NR$^{c3}$R$^{d3}$, S(O)$_2$R$^{b3}$ and S(O)$_2$NR$^{c3}$R$^{d3}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from R$^g$;

each R$^{13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, NO$_2$, OR$^{a5}$, SR$^{a5}$, C(O)R$^{b5}$, C(O)NR$^{c5}$R$^{d5}$, C(O)OR$^{a5}$, OC(O) R$^{b5}$, OC(O)NR$^{c5}$R$^{d5}$, NR$^{c5}$R$^{d5}$, NR$^{c5}$C(O)R$^{b5}$, NR$^{c5}$C(O) OR$^{a5}$, NR$^{c5}$C(O)NR$^{c5}$R$^{d5}$, C(=NR$^{e5}$)R$^{b5}$, C(=NOR$^{a5}$) R$^{b5}$, C(=NR$^{e5}$)NR$^{c5}$R$^{d5}$, NR$^{c5}$C(=NR$^{e5}$)NR$^{c5}$R$^{d5}$, NR$^{c5}$S (O)R$^{b5}$, NR$^{c5}$S(O)$_2$R$^{b5}$, NR$^{c5}$S(O)$_2$NR$^{c5}$R$^{d5}$, S(O)R$^{b5}$, S(O) NR$^{c5}$R$^{d5}$, S(O)$_2$R$^{b5}$, S(O)$_2$NR$^{c5}$R$^{d5}$ and BR$^{h5}$R$^{i5}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{14}$;

each R$^{14}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene, 5-10 membered heteroaryl-$C_{1-3}$ alkylene, halo, D, CN, OR$^{a6}$, SR$^{a6}$, C(O)R$^{b6}$, C(O)NR$^{c6}$R$^{d6}$, C(O)OR$^{a6}$, NR$^{c6}$R$^{d6}$, NR$^{c6}$C (O)R$^{b6}$, NR$^{c6}$C(O)OR$^{a6}$, NR$^{c6}$S(O)R$^{b6}$, NR$^{c6}$S(O)$_2$R$^{b6}$, NR$^{c6}$S(O)$_2$NR$^{c6}$R$^{d6}$, S(O)R$^{b6}$, S(O)NR$^{c6}$R$^{d6}$, S(O)$_2$R$^{b6}$ S(O)$_2$NR$^{c6}$R$^{d6}$ and BR$^{h6}$R$^{i6}$; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{3-10}$ cycloalkyl-$C_{1-3}$ alkylene, 4-10 membered heterocycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from R$^{15}$;

each R$^{15}$ is independently selected from $C_{1-6}$ alkyl, $C_{2-6}$ alkenyl, $C_{2-6}$ alkynyl, $C_{1-6}$ haloalkyl, $C_{3-6}$ cycloalkyl, phenyl, 5-6 membered heteroaryl, 4-7 membered heterocycloalkyl, halo, D, CN, $OR^{a7}$, $SR^{a7}$, $C(O)R^{b7}$, $C(O)NR^{c7}R^{d7}$, $C(O)OR^{a7}$, $NR^{c7}R^{d7}$, $NR^{c7}C(O)R^{b7}$, $NR^{c7}C(O)OR^{a7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$ and $S(O)_2NR^{c7}R^{d7}$; wherein said $C_{1-6}$ alkyl, $C_{2-6}$ alkenyl, $C_{2-6}$ alkynyl, $C_{3-6}$ cycloalkyl, $C_{6-10}$ aryl, 5-10 membered heteroaryl and 4-7 membered heterocycloalkyl are each optionally substituted with 1, 2, 3, or 4 substituents independently selected from $R^g$;

each $R^a$, $R^c$ and $R^d$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

or any $R^c$ and $R^d$ attached to the same N atom, together with the N atom to which they are attached, form a 4-, 5-, 6- or 7-membered heterocycloalkyl group optionally substituted with 1, 2, 3 or 4 substituents independently selected from $R^{10}$;

each $R^b$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{10}$;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^h$ and $R^i$ is independently selected from OH and $C_{1-6}$ alkoxy;

or any $R^h$ and $R^i$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a1}$, $R^{c1}$ and $R^{d1}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

or any $R^{c1}$ and $R^{d1}$ attached to the same N atom, together with the N atom to which they are attached, form a 4-, 5-, 6- or 7-membered heterocycloalkyl group optionally substituted with 1, 2, 3 or 4 substituents independently selected from $R^{11}$;

each $R^{b1}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{11}$;

each $R^{e1}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h1}$ and $R^{i1}$ is independently selected from OH and $C_{1-6}$ alkoxy;

or any $R^{h1}$ and $R^{i1}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a2}$, $R^{c2}$ and $R^{d2}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{12}$;

or any $R^{c2}$ and $R^{d2}$ attached to the same N atom, together with the N atom to which they are attached, form a 4-, 5-, 6- or 7-membered heterocycloalkyl group optionally substituted with 1, 2, 3 or 4 substituents independently selected from $R^{12}$;

each $R^{b2}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{12}$;

each $R^{h2}$ and $R^{i2}$ is independently selected from OH and $C_{1-6}$ alkoxy;

or any $R^{h2}$ and $R^{i2}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a3}$, $R^{c3}$ and $R^{d3}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b3}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a4}$, $R^{c4}$ and $R^{d4}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

or any $R^{c4}$ and $R^{d4}$ attached to the same N atom, together with the N atom to which they are attached, form a 4-, 5-, 6- or 7-membered heterocycloalkyl group optionally substituted with 1, 2, 3 or 4 substituents independently selected from $R^{13}$;

each $R^{b4}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{13}$;

each $R^{e4}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h4}$ and $R^{i4}$ is independently selected from OH and $C_{1-6}$ alkoxy;

or any $R^{h4}$ and $R^{i4}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a5}$, $R^{c5}$ and $R^{d5}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

or any $R^{c5}$ and $R^{d5}$ attached to the same N atom, together with the N atom to which they are attached, form a 4-, 5-, 6- or 7-membered heterocycloalkyl group optionally substituted with 1, 2, 3 or 4 substituents independently selected from $R^{14}$;

each $R^{b5}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{14}$;

each $R^{e5}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h5}$ and $R^{i5}$ is independently selected from OH and $C_{1-6}$ alkoxy;

or any $R^{h5}$ and $R^{i5}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a6}$, $R^{c6}$ and $R^{d6}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

or any $R^{c6}$ and $R^{d6}$ attached to the same N atom, together with the N atom to which they are attached, form a 4-, 5-, 6- or 7-membered heterocycloalkyl group optionally substituted with 1, 2, 3 or 4 substituents independently selected from $R^{15}$;

each $R^{b6}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^{15}$;

each $R^{h6}$ and $R^{i6}$ is independently selected from OH and $C_{1-6}$ alkoxy;

or any $R^{h6}$ and $R^{i6}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a7}$, $R^{c7}$ and $R^{d7}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b7}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a8}$, $R^{c8}$ and $R^{d8}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^5$;

or any $R^{c8}$ and $R^{d8}$ attached to the same N atom, together with the N atom to which they are attached, form a 4-, 5-, 6- or 7-membered heterocycloalkyl group optionally substituted with 1, 2, 3 or 4 substituents independently selected from $R^5$;

each $R^{b8}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^5$;

each $R^{e8}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h8}$ and $R^{i8}$ is independently selected from OH and $C_{1-6}$ alkoxy;

or any $R^{h8}$ and $R^{i8}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a9}$, $R^{c9}$ and $R^{d9}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^6$;

or any $R^{c9}$ and $R^{d9}$ attached to the same N atom, together with the N atom to which they are attached, form a 4-, 5-, 6- or 7-membered heterocycloalkyl group optionally substituted with 1, 2, 3 or 4 substituents independently selected from $R^6$;

each $R^{b9}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^6$;

each $R^{h9}$ and $R^{i9}$ is independently selected from OH and $C_{1-6}$ alkoxy;

or any $R^{h9}$ and $R^{i9}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a10}$, $R^{c10}$ and $R^{d10}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b10}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a11}$, $R^{c11}$ and $R^{d11}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^7$;

or any $R^{c11}$ and $R^{d11}$ attached to the same N atom, together with the N atom to which they are attached, form a 4-, 5-, 6- or 7-membered heterocycloalkyl group optionally substituted with 1, 2, 3 or 4 substituents independently selected from R;

each $R^{b11}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^7$;

each $R^{e11}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h11}$ and $R^{i11}$ is independently selected from OH and $C_{1-6}$ alkoxy;

or any $R^{h11}$ and $R^{i11}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a12}$, $R^{c12}$ and $R^{d12}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

or any $R^{c12}$ and $R^{d12}$ attached to the same N atom, together with the N atom to which they are attached, form a 4-, 5-, 6- or 7-membered heterocycloalkyl group optionally substituted with 1, 2, 3 or 4 substituents independently selected from $R^8$;

each $R^{b12}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^8$;

each $R^{e12}$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl and di($C_{1-6}$ alkyl)aminosulfonyl;

each $R^{h12}$ and $R^{i12}$ is independently selected from OH and $C_{1-6}$ alkoxy;

or any $R^{h12}$ and $R^{i12}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a13}$, $R^{c13}$ and $R^{d13}$ is independently selected from H, $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

or any $R^{c13}$ and $R^{d13}$ attached to the same N atom, together with the N atom to which they are attached, form a 4-, 5-, 6- or 7-membered heterocycloalkyl group optionally substituted with 1, 2, 3 or 4 substituents independently selected from $R^9$;

each $R^{b13}$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, 4-10 membered heterocycloalkyl, $C_{6-10}$ aryl and 5-10 membered heteroaryl; wherein said $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl and 5-10 membered heteroaryl are each optionally substituted with 1, 2, 3, or 4 substituents independently selected from $R^9$;

each $R^{h13}$ and $R^{i13}$ is independently selected from OH and $C_{1-6}$ alkoxy;

or any $R^{h13}$ and $R^{i13}$ attached to the same B atom are $C_{2-3}$ dialkoxy and together with the B atom to which they are attached, form a 5- or 6-membered heterocycloalkyl group optionally substituted with 1, 2, 3 or 4 substituents independently selected from $C_{1-6}$ alkyl;

each $R^{a14}$, $R^{c14}$ and $R^{d14}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{b14}$ is independently selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^{a15}$, $R^{c15}$ and $R^{d15}$ is independently selected from H, $C_{1-6}$ alkyl, $C_{2-6}$ alkenyl, $C_{2-6}$ alkynyl and $C_{1-6}$ haloalkyl; wherein said $C_{1-6}$ alkyl, $C_{2-6}$ alkenyl and $C_{2-6}$ alkynyl are each optionally substituted with 1, 2, 3, or 4 substituents independently selected from $R^g$;

each $R^g$ is independently selected from OH, $NO_2$, CN, halo, $C_{1-6}$ alkyl, $C_{2-6}$ alkenyl, $C_{2-6}$ alkynyl, $C_{1-6}$ haloalkyl, $C_{3-6}$ cycloalkyl, $C_{3-6}$ cycloalkyl-$C_{1-2}$ alkylene, $C_{1-6}$ alkoxy, $C_{1-6}$ haloalkoxy, $C_{1-3}$ alkoxy-$C_{1-3}$ alkyl, $C_{1-3}$ alkoxy-$C_{1-3}$ alkoxy, HO—$C_{1-3}$ alkoxy, HO—$C_{1-3}$ alkyl, cyano-$C_{1-3}$ alkyl, $H_2N$—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3 or 4.

In some embodiments, provided herein is a compound of Formula (I), or a pharmaceutically acceptable salt thereof, wherein $Cy^A$ is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein a ring-forming carbon atom of the 4-12 membered heterocycloalkyl is optionally substituted by oxo to form a carbonyl group; and wherein the 4-12 membered heterocycloalkyl are each optionally substituted with 1, 2, 3 or 4 substituents independently selected from $R^A$;

A is N;

$R^1$ is selected from H, D, halo, CN, $C_{1-6}$ alkyl and $OR^{a15}$; wherein the $C_{1-6}$ alkyl is optionally substituted with 1, 2, or 3 substituents independently selected from $R^g$;

$R^2$ is selected from H, D, $Cy^2$, $C_{1-6}$ alkyl, $C_{1-6}$ haloalkyl, halo, CN; wherein said $C_{1-6}$ alkyl, is optionally substituted with 1, 2, 3, or 4 substituents independently selected from $R^{10}$;

$Cy^2$ is selected from 4-10 membered heterocycloalkyl, and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl and 5-10 membered heteroaryl are each optionally substituted with 1, 2, 3 or 4 substituents independently selected from $R^{10}$;

$R^3$ is selected from H, D, $Cy^3$, halo and CN;

$Cy^3$ is 5-10 membered heteroaryl; wherein the 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the 5-10 membered heteroaryl is optionally substituted with 1, 2, 3 or 4 substituents independently selected from $R^{13}$;

each $R^4$ is independently selected from $C_{1-6}$ alkyl, $C_{1-6}$ haloalkyl, halo, D, CN and $OR^{a8}$; wherein said $C_{1-6}$ alkyl is optionally substituted with 1, 2, 3, or 4 substituents independently selected from $R^5$;

each $R^5$ is independently selected from $C_{1-6}$ alkyl, $C_{1-6}$ haloalkyl, halo, D, CN, $OR^{a9}$ and $NR^{c9}R^{d9}$;

$R^A$ is selected from H, D, $Cy^1$, $C_{1-6}$ alkyl, $C_{1-6}$ haloalkyl, halo, CN, $OR^{a11}$, $C(O)NR^{c11}R^{d11}$, and $NR^{c}R^{d11}$; wherein said $C_{1-6}$ alkyl, is optionally substituted with 1, 2, 3, or 4 substituents independently selected from $R^7$;

$Cy^1$ is 5-10 membered heteroaryl; wherein the 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the 5-10 membered heteroaryl are each optionally substituted with 1, 2, 3 or 4 substituents independently selected from $R^7$;

each $R^7$ is independently selected from $C_{1-6}$ alkyl, halo, D, CN, $OR^{a12}$ and $NR^{c12}R^{d12}$;

each $R^{10}$ is independently selected from $C_{1-6}$ alkyl, $C_{1-6}$ haloalkyl, 4-10 membered heterocycloalkyl, halo, D, CN, $OR^{a1}$, $C(O)NR^{c1}R^{d1}$ and $NR^{c1}R^{d1}$; wherein said $C_{1-6}$ alkyl, and 4-10 membered heterocycloalkyl are each optionally substituted with 1, 2, 3, or 4 substituents independently selected from $R^{11}$;

each $R^{11}$ is independently selected from $C_{1-6}$ alkyl, $C_{1-6}$ haloalkyl, halo, D, CN and $OR^{a2}$;

each $R^{13}$ is independently selected from $C_{1-6}$ alkyl and $C_{1-6}$ haloalkyl;

each $R^{a1}$, $R^{c1}$ and $R^{d1}$ is independently selected from H, $C_{1-6}$ alkyl, $C_{1-6}$ haloalkyl and $C_{3-10}$ cycloalkyl; wherein said $C_{1-6}$ alkyl and $C_{3-10}$ cycloalkyl are each optionally substituted with 1, 2, 3, or 4 substituents independently selected from $R^{11}$;

each $R^{a2}$, $R^{c2}$ and $R^{d2}$ is independently selected from H, $C_{1-6}$ alkyl and $C_{1-6}$ haloalkyl;

each $R^{a5}$, $R^{c8}$ and $R^{d8}$ is independently selected from H, $C_{1-6}$ alkyl and $C_{1-6}$ haloalkyl;

each $R^{a9}$, $R^{c9}$ and $R^{d9}$ is independently selected from H, $C_{1-6}$ alkyl and $C_{1-6}$ haloalkyl;

each $R^{a11}$, $R^{c11}$ and $R^{d11}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^7$;

each $R^{a12}$, $R^{c12}$ and $R^{d12}$ is independently selected from H, $C_{1-6}$ alkyl and $C_{1-6}$ haloalkyl;

each $R^{a15}$, $R^{c15}$ and $R^{d15}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^g$;

each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylthio, $C_{1-6}$ alkylsulfonyl; and n is 0, 1, 2 or 3.

In some embodiments, provided herein is a compound of Formula (I), or a pharmaceutically acceptable salt thereof, wherein:

$Cy^A$ is $C_{3-12}$ cycloalkyl or 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein the N and S are optionally oxidized; wherein a ring-forming carbon atom of the 4-12 membered heterocycloalkyl is optionally substituted by oxo to form a carbonyl group; and wherein the $C_{3-12}$ cycloalkyl and 4-12 membered heterocycloalkyl are each optionally substituted with 1, 2, 3 or 4 substituents independently selected from $R^A$;

A is N or $CR^{16}$;

$R^{16}$ is selected from H, D, $C_{1-6}$ alkyl, halo, CN and $OR^{a16}$;

$R^1$ is selected from H, D, halo, CN, $C_{1-6}$ alkyl and $OR^{a15}$; wherein the $C_{1-6}$ alkyl is optionally substituted with 1, 2, or 3 substituents independently selected from $R^g$;

$R^2$ is selected from H, D, $Cy^2$, $C_{1-6}$ alkyl, $C_{1-6}$ haloalkyl, halo, CN and $S(O)_2R^b$; wherein said $C_{1-6}$ alkyl, is optionally substituted with 1, 2, 3, or 4 substituents independently selected from $R^{10}$;

$Cy^2$ is selected from $C_{3-10}$ cycloalkyl, 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 5-10 membered heteroaryl are each optionally substituted with 1, 2, 3 or 4 substituents independently selected from $R^{10}$;

$R^3$ is selected from H, D, $Cy^3$, halo and CN;

$Cy^3$ is 6-10 membered heteroaryl; wherein the 6-10 membered heteroaryl each has at least one ring-forming carbon atom and 1, 2, 3, or 4 ring-forming heteroatoms independently selected from N, O, and S;

each $R^4$ is independently selected from $C_{1-6}$ alkyl, $C_{1-6}$ haloalkyl, $C_{3-10}$ cycloalkyl, halo, D, CN and $OR^{a8}$;

each $R^5$ is independently selected from halo, D and CN;

$R^A$ is selected from H, D, $Cy^1$, $C_{1-6}$ alkyl, $C_{1-6}$ haloalkyl, halo, CN, $OR^{a11}$, $C(O)NR^{c11}R^{d11}$, and $NR^{c11}R^{d11}$; wherein said $C_{1-6}$ alkyl, is optionally substituted with 1, 2, 3, or 4 substituents independently selected from $R^7$;

$Cy^1$ is selected from $C_{3-10}$ cycloalkyl and 5-10 membered heteroaryl; wherein the 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the $C_{3-10}$ cycloalkyl and 5-10 membered heteroaryl are each optionally substituted with 1, 2, 3 or 4 substituents independently selected from $R^7$;

each $R^7$ is independently selected from $C_{1-6}$ alkyl, halo, D, CN, $OR^{a12}$ and $NR^{c12}R^{d12}$;

each $R^{10}$ is independently selected from $C_{1-6}$ alkyl, $C_{1-6}$ haloalkyl, 4-10 membered heterocycloalkyl, halo, D, CN, $OR^{a1}$, $C(O)NR^{c1}R^{d1}$ and $NR^{c1}R^{d1}$; wherein said $C_{1-6}$ alkyl, and 4-10 membered heterocycloalkyl are each optionally substituted with 1, 2, 3, or 4 substituents independently selected from $R^{11}$;

each $R^{11}$ is independently selected from $C_{1-6}$ alkyl, $C_{1-6}$ haloalkyl, halo, D, CN and $OR^{a2}$;

each $R^{13}$ is independently selected from $C_{1-6}$ alkyl;

each $R^b$ is independently $C_{1-6}$ alkyl;

each $R^{a1}$, $R^{c1}$ and $R^{d1}$ is independently selected from H, $C_{1-6}$ alkyl, $C_{1-6}$ haloalkyl and $C_{3-10}$ cycloalkyl; wherein said $C_{1-6}$ alkyl and $C_{3-10}$ cycloalkyl are each optionally substituted with 1, 2, 3, or 4 substituents independently selected from $R^{11}$;

each $R^{a2}$, $R^{c2}$ and $R^{d2}$ is independently selected from H, $C_{1-6}$ alkyl and $C_{1-6}$ haloalkyl;

each $R^{a8}$, $R^{c8}$ and $R^{d8}$ is independently selected from H, $C_{1-6}$ alkyl and $C_{1-6}$ haloalkyl;

each $R^{a11}$, $R^{c11}$ and $R^{d11}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^7$;

each $R^{a12}$, $R^{c12}$ and $R^{d12}$ is independently selected from H, $C_{1-6}$ alkyl and $C_{1-6}$ haloalkyl;

each $R^{a15}$, $R^{c15}$ and $R^{d15}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^g$;

$R^{a16}$ is independently selected from H and $C_{1-6}$ alkyl;

each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylthio, $C_{1-6}$ alkylsulfonyl; and n is 0, 1, 2 or 3.

In some embodiments, $Cy^A$ is 4-12 membered heterocycloalkyl; wherein the 4-12 membered heterocycloalkyl has at least one ring-forming carbon atom and 1, 2, 3, or 4 ring-forming heteroatoms independently selected from N, O, and S; wherein a ring-forming carbon atom of the 4-12 membered heterocycloalkyl is optionally substituted by oxo to form a carbonyl group; and wherein the 4-12 membered heterocycloalkyl are each optionally substituted with 1, 2, 3 or 4 substituents independently selected from $R^4$.

In some embodiments, $Cy^A$ is selected from 2,5-diazabicyclo[2.2.1]heptan-2-yl; 3-aminopyrrolidin-1-yl; 2-(aminomethyl)pyrrolidin-1-yl; 2-(hydroxymethyl)pyrrolidin-1-yl; 2-(methoxymethyl)pyrrolidin-1-yl; 4-amino-2-(hydroxymethyl)pyrrolidin-1-yl; 4-hydroxy-2-methylpyrrolidin-1-yl; 2-(pyridin-2-yl)pyrrolidin-1-yl; hexahydropyrrolo[3,4-b]pyrrol-1(2H)-yl; 2-methylpiperazin-1-yl; 2-(hydroxymethyl)piperazin-1-yl; 3-(hydroxymethyl)morpholino; 5-ethyl-2,5-diazabicyclo[2.2.1]heptan-2-yl; (2-hydroxyethyl)-2,5-diazabicyclo[2.2.1]heptan-2-yl); 5-(propylcarbamoyl)-2,5-diazabicyclo[2.2.1]heptan-2-yl; 4-hydroxy-2-(hydroxymethyl)pyrrolidin-1-yl; 2-(hydroxymethyl)-5-methylpiperazin-1-yl; 6-(hydroxymethyl)-4,7-diazaspiro[2.5]octan-7-yl; 4-amino-2-(1-hydroxycyclopropyl)pyrrolidin-1-yl; 4-amino-2-(2-hydroxypropan-2-yl)pyrrolidin-1-yl; 4-amino-2-(hydroxymethyl-d2)pyrrolidin-1-yl; 3-(hydroxymethyl)-2,5-diazabicyclo[2.2.1]heptan-2-yl; 4-amino-2-methylpiperidin-1-yl; piperidin-4-yl; 4-(dimethylamino)-2-(hydroxymethyl)pyrrolidin-1-yl; 2-(hydroxymethyl)-4-(isopropylamino)pyrrolidin-1-yl; 4-(hydroxymethyl)-5-methyl-2,5-diazabicyclo[2.2.1]heptan-2-yl; 2-(hydroxymethyl)morpholino; 2-(2-((dimethylamino)methyl)morpholino; 2-(cyanomethyl)morpholino; 3-oxotetrahydro-3H-oxazolo[3,4-a]pyrazin-7(1H)-yl; 3-(hydroxymethyl)piperazin-1-yl; 3-(methoxymethyl)azetidin-1-yl; 2-(hydroxymethyl)azetidin-1-yl; 2-((dimethylamino)methyl)azetidin-1-yl; 4-methylpiperazin-1-yl; and 4-(2-hydroxyethyl)piperazin-1-yl.

In some embodiments, $Cy^A$ is selected from 2,5-diazabicyclo[2.2.1]heptan-2-yl; 3-aminopyrrolidin-1-yl; 2-(aminomethyl)pyrrolidin-1-yl; 2-(hydroxymethyl)pyrrolidin-1-yl; 2-(methoxymethyl)pyrrolidin-1-yl; 4-amino-2-(hydroxymethyl)pyrrolidin-1-yl; 4-hydroxy-2-methylpyrrolidin-1-yl; 2-(pyridin-2-yl)pyrrolidin-1-yl; hexahydropyrrolo[3,4-b]pyrrol-1(2H)-yl; 2-methylpiperazin-1-yl; 2-(hydroxymethyl)piperazin-1-yl; 3-(hydroxymethyl)morpholino; 5-ethyl-2,5-diazabicyclo[2.2.1]heptan-2-yl; (2-hydroxyethyl)-2,5-diazabicyclo[2.2.1]heptan-2-yl); 5-(propylcarbamoyl)-2,5-diazabicyclo[2.2.1]heptan-2-yl; 4-hydroxy-2-(hydroxymethyl)pyrrolidin-1-yl; 2-(hydroxymethyl)-5-methylpiperazin-1-yl; 6-(hydroxymethyl)-4,7-diazaspiro[2.5]octan-7-yl; 4-amino-2-(1-hydroxycyclopropyl)pyrrolidin-1-yl; 4-amino-2-(2-hydroxypropan-2-yl)pyrrolidin-1-yl; 4-amino-2-(hydroxymethyl-d2)pyrrolidin-1-yl; 3-(hydroxymethyl)-2,5-diazabicyclo[2.2.1]heptan-2-yl; and 4-amino-2-methylpiperidin-1-yl.

In some embodiments, $Cy^A$ is selected from 2,5-diazabicyclo[2.2.1]heptan-2-yl; 3-aminopyrrolidin-1-yl; 2-(aminomethyl)pyrrolidin-1-yl; 2-(hydroxymethyl)pyrrolidin-1-yl; 2-(methoxymethyl)pyrrolidin-1-yl; 4-amino-2-(hydroxymethyl)pyrrolidin-1-yl; 4-hydroxy-2-methylpyrrolidin-1-yl; 2-(pyridin-2-yl)pyrrolidin-1-yl; hexahydropyrrolo[3,4-b]pyrrol-1(2H)-yl; 2-methylpiperazin-1-yl; 2-(hydroxymethyl)piperazin-1-yl; 3-(hydroxymethyl)morpholino; 5-ethyl-2,5-diazabicyclo[2.2.1]heptan-2-yl; (2-hydroxyethyl)-2,5-diazabicyclo[2.2.1]heptan-2-yl); and 5-(propylcarbamoyl)-2,5-diazabicyclo[2.2.1]heptan-2-yl.

In some embodiments, $Cy^4$ is selected from 4-hydroxy-2-(hydroxymethyl)pyrrolidin-1-yl; 2-(hydroxymethyl)-5-methylpiperazin-1-yl; 6-(hydroxymethyl)-4,7-diazaspiro[2.5]octan-7-yl; 4-amino-2-(1-hydroxycyclopropyl)pyrrolidin-1-yl; 4-amino-2-(2-hydroxypropan-2-yl)pyrrolidin-1-yl; 4-amino-2-(hydroxymethyl-d2)pyrrolidin-1-yl; 3-(hydroxymethyl)-2,5-diazabicyclo[2.2.1]heptan-2-yl; and 4-amino-2-methylpiperidin-1-yl.

In some embodiments, $Cy^4$ is 4-amino-2-(hydroxymethyl)pyrrolidin-1-yl.

In some embodiments, $Cy^4$ is a 5-membered heterocycloalkyl.

In some embodiments, $Cy^4$ is selected from 2,5-diazabicyclo[2.2.1]heptanyl, pyrrolidinyl, hexahydropyrrolo[3,4-b]pyrrol-1(2H)-yl, and piperazinyl, each of which is optionally substituted with 1, 2, 3 or 4 substituents independently selected from $R^4$.

In some embodiments, $Cy^4$ is $C_{3-10}$ cycloalkyl, wherein the $C_{3-10}$ cycloalkyl is optionally substituted with 1, 2, or 3 substituents independently selected from $R^4$. In some embodiments, $Cy^4$ is selected from cyclopentyl and cyclohexyl, wherein the cyclopentyl and cyclohexyl are optionally substituted with $NH_2$.

In some embodiments, A is N.
In some embodiments, A is CF.
In some embodiments, A is $CR^{16}$.
In some embodiments, $R^{16}$ is H, CN, or $OR^{a16}$.
In some embodiments, $R^{a16}$ is independently selected from H and $C_{1-6}$ alkyl. In some embodiments, $R^{a16}$ is methyl.

In some embodiments, $R^1$ is selected from H, D, halo, CN, $C_{1-6}$ alkyl and $OR^{a15}$; wherein the $C_{1-6}$ alkyl is optionally substituted with 1, 2, or 3 substituents independently selected from $R^g$.

In some embodiments, $R^1$ is selected from H, D, F, CN, methyl, hydroxymethyl and methoxy.

In some embodiments, $R^1$ is H or D. In some embodiments, $R^1$ is H. In some embodiments, $R^1$ is D.

In some embodiments, $R^1$ is halo.
In some embodiments, $R^1$ is F.
In some embodiments, $R^1$ is $OR^{a15}$.
In some embodiments, $R^1$ is methoxy.
In some embodiments, $R^1$ is $C_{1-6}$ alkyl; wherein the $C_{1-6}$ alkyl is optionally substituted with 1, 2, or 3 substituents independently selected from $R^g$.
In some embodiments, $R^1$ is hydroxymethyl.
In some embodiments, $R^1$ is CN.
In come embodiments, $R^1$ is methyl.

In some embodiments, $R^2$ is selected from H, D, $Cy^2$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $NR^cR^d$, $NR^cC(O)R^b$, $NR^cC(O)OR^a$, and $S(O)_2R^b$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^2$ is selected from H, D, $Cy^2$, $C_{1-6}$ alkyl, $C_{2-6}$ alkenyl, $C_{2-6}$ alkynyl, $C_{1-6}$ haloalkyl, halo, CN, $NO_2$, $OR^a$, $SR^a$, $C(O)R^b$, $C(O)NR^cR^d$, $C(O)OR^a$, $NR^cR^d$ $NR^cC(O)R^b$, and $NR^cC(O)OR^a$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^2$ is selected from H, D, $Cy^2$, $C_{1-6}$ alkyl, $C_{2-6}$ alkenyl, $C_{2-6}$ alkynyl, $C_{1-6}$ haloalkyl, halo, CN, and $OR^a$; wherein said $C_{1-6}$ alkyl, $C_{2-6}$ alkenyl and $C_{2-6}$ alkynyl are each optionally substituted with 1, 2, 3, or 4 substituents independently selected from $R^{10}$.

In some embodiments, $R^2$ is selected from H, D, $Cy^2$, $C_{1-6}$ alkyl, $C_{1-6}$ haloalkyl, halo, CN; wherein said $C_{1-6}$ alkyl, is optionally substituted with 1, 2, 3, or 4 substituents independently selected from $R^{10}$.

In some embodiments, $R^2$ is selected from H, D, $Cy^2$, $C_{1-6}$ alkyl, halo, and $S(O)_2R^b$; wherein said $C_{1-6}$ alkyl is optionally substituted with 1, 2, 3, or 4 substituents independently selected from $R^{10}$.

In some embodiments, $R^2$ is selected from H, D, $Cy^2$, $C_{1-6}$ alkyl, and halo; wherein said $C_{1-6}$ alkyl is optionally substituted with 1, 2, 3, or 4 substituents independently selected from $R^{10}$.

In some embodiments, $R^2$ is H or D. In some embodiments, $R^2$ is H. In some embodiments, $R^2$ is D.

In some embodiments, $R^2$ is $C_{1-6}$ alkyl; wherein said $C_{1-6}$ alkyl is optionally substituted with 1, 2, 3, or 4 substituents independently selected from $R^{10}$.

In some embodiments, $R^2$ is selected from isopropyl, F, Cl, Br, and $S(O)_2CH_3$.

In some embodiments, $R^2$ is isopropyl.
In some embodiments, $R^2$ is halo.
In some embodiments, $R^2$ is selected from Br, Cl, and F.
In some embodiments, $R^2$ is Br.
In some embodiments, $R^2$ is $S(O)_2CH_3$.
In some embodiments, $R^2$ is $Cy^2$.

In some embodiments, $Cy^2$ is selected from 4-10 membered heterocycloalkyl, $C_{6-10}$ aryl and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl and 4-10 membered heterocycloalkyl is optionally substituted by oxo to form a carbonyl group; and wherein the 4-10 membered heterocycloalkyl, $C_{6-10}$ aryl and 5-10 membered heteroaryl are each optionally substituted with 1, 2, 3 or 4 substituents independently selected from $R^{10}$.

In some embodiments, $Cy^2$ is selected from 4-10 membered heterocycloalkyl, and 5-10 membered heteroaryl; wherein the 4-10 membered heterocycloalkyl and 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl and 4-10 membered heterocycloalkyl is optionally substituted by oxo to form a carbonyl group; and wherein the 4-10 membered heterocycloalkyl and 5-10 membered heteroaryl are each optionally substituted with 1, 2, 3 or 4 substituents independently selected from $R^{10}$.

In some embodiments, $Cy^2$ is $C_{6-10}$ aryl optionally substituted with 1, 2, 3 or 4 substituents independently selected from $R^{10}$.

$Cy^2$ is selected from 1-methyl-1H-pyrazol-4-yl; 6-(hydroxymethyl)pyridin-3-yl; 6-(methylcarbamoyl)pyridin-3-yl; 1-methyl-6-oxo-1,6-dihydropyridin-3-yl; 2-methylpyridin-3-yl; 4-methoxypyridin-3-yl; 4-cyanopyridin-3-yl; 1,3,5-trimethyl-1H-pyrazol-4-yl; morpholino; azetidin-1-yl; 2-(methoxymethyl)azetidin-1-yl); 3-cyanopyridin-4-yl; 3-methoxypyridin-4-yl; 2-cyano-6-fluorophenyl; 3-cyanopyridin-2-yl; 4-cyano-1-methyl-1H-pyrazol-5-yl; tetrahydro-2H-pyran-4-yl; 5-cyano-2-(pyrrolidin-1-yl)pyridin-4-yl; and 1-cyanocyclopropyl. In some embodiments, $Cy^2$ is selected from 1-methyl-1H-pyrazol-4-yl; 6-(hydroxymethyl)pyridin-3-yl; 6-(methylcarbamoyl)pyridin-3-yl; 1-methyl-6-oxo-1,6-dihydropyridin-3-yl; 2-methylpyridin-3-yl; 4-methoxypyridin-3-yl; 4-cyanopyridin-3-yl; 1,3,5- trimethyl-1H-pyrazol-4-yl; morpholino; azetidin-1-yl; 2-(methoxymethyl)azetidin-1-yl); 3-cyanopyridin-4-yl; 3-methoxypyridin-4-yl; 2-cyano-6-fluorophenyl; 3-cyano-pyridin-2-yl; and 4-cyano-1-methyl-1H-pyrazol-5-yl.

In some embodiments, $Cy^2$ is selected from 1-methyl-1H-pyrazol-4-yl; 6-(hydroxymethyl)pyridin-3-yl; 6-(methylcarbamoyl)pyridin-3-yl; 1-methyl-6-oxo-1,6-dihydropyridin-3-yl; 2-methylpyridin-3-yl; 4-methoxypyridin-3-yl; 4-cyanopyridin-3-yl; 1,3,5-trimethyl-1H-pyrazol-4-yl; morpholino; and azetidin-1-yl.

In some embodiments, $Cy^2$ is selected from 2-(methoxymethyl)azetidin-1-yl); 3-cyanopyridin-4-yl; 3-methoxypyridin-4-yl; 2-cyano-6-fluorophenyl; 3-cyano-pyridin-2-yl; and 4-cyano-1-methyl-1H-pyrazol-5-yl.

In some embodiments, $Cy^2$ is selected from 3-cyanopyridin-4-yl; 4-cyanopyridin-3-yl; and 3-cyanopyridin-2-yl. In some embodiments, $Cy^2$ is 4-cyanopyridin-3-yl.

In some embodiments, Z is N.

In some embodiments, Z is $CR^3$.

In some embodiments, $R^3$ is selected from H, D, $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a4}$, $SR^{a4}$, $C(O)R^{b4}$, $C(O)NR^{c4}R^{d4}$, $C(O)OR^{a4}$ $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2 R^{b4}$, $S(O)_2NR^{c4}R^{d4}$ and $BR^{h4}R^{i4}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

In some embodiments, $R^3$ is selected from H, D, $Cy^3$, $C_{1-6}$ alkyl, $C_{2-6}$ alkenyl, $C_{2-6}$ alkynyl, $C_{1-6}$ haloalkyl, halo, CN, $NO_2$, $OR^{a4}$, $SR^{a4}$, $C(O)R^{b4}$, $NR^{c4}R^{d4}$, and $NR^{c4}C(O)R^{b4}$; wherein said $C_{1-6}$ alkyl, $C_{2-6}$ alkenyl and $C_{2-6}$ alkynyl are each optionally substituted with 1, 2, 3, or 4 substituents independently selected from $R^{13}$.

In some embodiments, $R^3$ is selected from H, D, $Cy^3$, halo and CN. In some embodiments $R^3$ is selected from H, D, F, Br, and CN.

In some embodiments, $R^3$ is H or D. In some embodiments, $R^3$ is H. In some embodiments, $R^3$ is D.

In some embodiments, $R^3$ is halo.

In some embodiments, $R^3$ is Br.

In some embodiments, $R^3$ is F.

In some embodiments, $R^3$ is CN.

In some embodiments, $R^3$ is $Cy^3$.

In some embodiments, $Cy^3$ is 5-10 membered heteroaryl; wherein the 5-10 membered heteroaryl each has at least one ring-forming carbon atom and 1, 2, 3, or 4 ring-forming heteroatoms independently selected from N, O, and S; wherein a ring-forming carbon atom of 5-10 membered heteroaryl is optionally substituted by oxo to form a carbonyl group; and wherein the 5-10 membered heteroaryl is optionally substituted with 1, 2, 3 or 4 substituents independently selected from $R^{13}$.

In some embodiments, $Cy^3$ is 6-10 membered heteroaryl; wherein the 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl is optionally substituted by oxo to form a carbonyl group; and wherein the 6-10 membered heteroaryl is optionally substituted with 1, 2, 3 or 4 substituents independently selected from $R^{13}$.

In some embodiments, $Cy^3$ is selected from pyridin-3-yl and 1-methyl-1H-pyrazol-4-yl.

In some embodiments, $R^4$ is independently selected from $C_{1-6}$ alkyl, $C_{2-6}$ alkenyl, $C_{2-6}$ alkynyl, $C_{1-6}$ haloalkyl, $C_{3-10}$ cycloalkyl, $C_{6-10}$ aryl, 5-10 membered heteroaryl, $C_{3-10}$ cycloalkyl-$C_{1-3}$ alkylene, $C_{6-10}$ aryl-$C_{1-3}$ alkylene, 5-10 membered heteroaryl-$C_{1-3}$ alkylene, halo, D, CN, $NO_2$, $OR^{a8}$, $SR^{a8}$, $C(O)R^{b8}$, $C(O)NR^{c8}R^{d8}$, $C(O)OR^{a8}$, $OC(O)R^{b8}$, $OC(O)NR^{c8}R^{d8}$, $NR^{c8}R^{d8}$, $NR^{c8}C(O)R^{b8}$, $NR^{c8}C(O)OR^{a8}$, $NR^{c8}C(O)NR^{c8}R^{d8}$, $C(=NR^{e8})R^{b8}$, $C(=NOR^{a8})R^{b8}$, $C(=NR^{e8})NR^{c8}R^{d8}$, $NR^{c8}C(=NR^{e8})NR)CR^{d8}$, $NR^{c8}S(O)R^{b8}$, $NR^{c8}S(O)_2R^{b8}$, $NR^{c8}S(O)_2NR^{c8}R^{d8}$, $S(O)R^{b8}$, $S(O)NR^{c8}R^{d8}$, $S(O)_2R^{b8}$, $S(O)_2NR^{c8}R^{d8}$ and $BR^{h8}R^{i8}$; wherein said $C_{1-6}$ alkyl, $C_{2-6}$ alkenyl, $C_{2-6}$ alkynyl, $C_{3-10}$ cycloalkyl, $C_{6-10}$ aryl, 5-10 membered heteroaryl, $C_{3-10}$ cycloalkyl-$C_{1-3}$ alkylene, $C_{6-10}$ aryl-$C_{1-3}$ alkylene and 5-10 membered heteroaryl-$C_{1-3}$ alkylene are each optionally substituted with 1, 2, 3, or 4 substituents independently selected from $R^5$.

In some embodiments, $R^4$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a8}$, $SR^{a8}$, $C(O)R^{b8}$, $C(O)NR^{c8}R^{d8}$, $C(O)OR^{a8}$, $NR^{c8}R^{d8}$, $NR^{c8}C(O)R^{b8}$, $NR^{c8}C(O)OR^{a8}$, $S(O)R^{b8}$, $S(O)NR^{c8}R^{d8}$, $S(O)_2R^{b8}$, and $S(O)_2NR^{c8}R^{d8}$; wherein said $C_{1-6}$ alkyl, $C_{2-6}$ alkenyl, and $C_{2-6}$ alkynyl are each optionally substituted with 1 or 2 substituents independently selected from $R^5$.

In some embodiments, $R^4$ is independently selected from $C_{1-6}$ alkyl, $C_{1-6}$ haloalkyl, $C_{3-10}$ cycloalkyl, halo, D, CN and $OR^{a8}$; wherein said $C_{1-6}$ alkyl, is optionally substituted with 1, 2, 3, or 4 substituents independently selected from $R^5$.

In some embodiments, each $R^4$ is independently selected from $C_{1-6}$ alkyl, $C_{1-6}$ haloalkyl, halo, D, CN and $OR^{a8}$; wherein said $C_{1-6}$ alkyl is optionally substituted with 1, 2, 3, or 4 substituents independently selected from $R^5$.

In some embodiments, each $R^4$ is independently selected from $C_{1-6}$ alkyl, $C_{1-6}$ haloalkyl, halo, D, CN, and $OR^{a5}$.

In some embodiments, each $R^4$ is independently selected from D, methyl, F, Cl, CN, methoxy, methoxy-d3, ethoxy, difluoromethoxy, and cyclopropyl.

In some embodiments, each $R^4$ is independently selected from halo and $OR^{a5}$.

In some embodiments, each $R^4$ is independently selected from F and methoxy.

In some embodiments, each $R^4$ is independently selected from halo.

In some embodiments, each $R^4$ is independently selected from F and Cl.

In some embodiments, each $R^4$ is independently selected from F and methyl.

In some embodiments, each $R^4$ is F.

In some embodiments, $R^4$ is not unsubstituted or substituted 4-morpholinyl, unsubstituted or substituted 4-thiomorpholinyl, unsubstituted or substituted 1-oxido-4-thiomorpholinyl, or unsubstituted or substituted 1,1-dioxido-4-thiomorpholinyl.

In some embodiments, each $R^5$ is independently selected from $C_{1-6}$ alkyl, $C_{1-6}$ haloalkyl, halo, D, CN, $OR^{a9}$ and $NR^{c9}R^{d9}$.

In some embodiments, each $R^5$ is independently selected from F and D.

In some embodiments, each $R^A$ is selected from H, D, $Cy^1$, $C_{1-6}$ alkyl, $C_{2-6}$ alkenyl, $C_{2-6}$ alkynyl, $C_{1-6}$ haloalkyl, halo, CN, $NO_2$, $OR^{a11}$, $SR^{a11}$, $C(O)R^{b11}$, $C(O)NR^{c11}R^{d11}$, $C(O)OR^{a11}$, and $NR^{c11}R^{d11}$; wherein said $C_{1-6}$ alkyl, $C_{2-6}$ alkenyl and $C_{2-6}$ alkynyl are each optionally substituted with 1, 2, 3, or 4 substituents independently selected from $R^7$.

In some embodiments, $R^A$ is selected from H, D, $Cy^1$, $C_{1-6}$ alkyl, $C_{1-6}$ haloalkyl, halo, CN, $OR^{a11}$, $C(O)NR^{c11}R^{d11}$, and $NR^{c11}R^{d11}$; wherein said $C_{1-6}$ alkyl, is optionally substituted with 1, 2, 3, or 4 substituents independently selected from $R^7$.

In some embodiments, $R^A$ is selected from $Cy^1$, $C_{1-6}$ alkyl, $OR^{a11}$, $C(O)NR^{c11}R^{d11}$, and $NR^{c11}R^{d11}$; wherein said $C_{1-6}$ alkyl, is optionally substituted with 1, 2, 3, or 4 substituents independently selected from $R^7$.

In some embodiments, $R^A$ is $C_{1-6}$ alkyl; wherein said $C_{1-6}$ alkyl, is optionally substituted with 1, 2, 3, or 4 substituents independently selected from $R^7$.

In some embodiments, $R^A$ is selected from methyl and ethyl; wherein said methyl and ethyl are each optionally substituted with 1, 2, or 3 substituents independently selected from $R^7$.

In some embodiments, $R^A$ is $Cy^1$.

In some embodiments, $R^A$ is selected from OH, $NH_2$, aminomethyl, hydroxymethyl, methoxymethyl, OH, pyridinyl, ethyl, hydroxyethyl, and propylcarbamoyl.

In some embodiments, $Cy^1$ is selected from $C_{3-10}$ cycloalkyl and 5-10 membered heteroaryl; wherein the 5-10 membered heteroaryl each has at least one ring-forming carbon atom and 1, 2, 3, or 4 ring-forming heteroatoms independently selected from N, O, and S; wherein the N and S are optionally oxidized; wherein a ring-forming carbon atom of 5-10 membered heteroaryl is optionally substituted by oxo to form a carbonyl group; and wherein the $C_{3-10}$ cycloalkyl and 5-10 membered heteroaryl are each optionally substituted with 1, 2, 3 or 4 substituents independently selected from $R^7$.

In some embodiments, $Cy^1$ is 5-10 membered heteroaryl; wherein the 5-10 membered heteroaryl has at least one ring-forming carbon atom and 1, 2, 3, or 4 ring-forming heteroatoms independently selected from N, O, and S; and wherein the 5-10 membered heteroaryl is optionally substituted with 1, 2, 3 or 4 substituents independently selected from $R^7$.

In some embodiments, $Cy^1$ is selected from $C_{3-10}$ cycloalkyl optionally substituted with 1, 2, 3 or 4 substituents independently selected from $R^7$.

In some embodiments, $Cy^1$ is pyridinyl. In some embodiments, $Cy^1$ is cyclopropyl.

In some embodiments, each $R^7$ is independently selected from $C_{1-6}$ alkyl, $C_{2-6}$ alkenyl, $C_{2-6}$ alkynyl, $C_{1-6}$ haloalkyl, halo, D, CN, $NO_2$, $OR^{a12}$, $SR^{a12}$, $C(O)R^{b12}$, $C(O)NR^{c12}R^{d12}$, $C(O)OR^{a12}$, $OC(O)R^{b12}$, and $NR^{c12}R^{d12}$; wherein said $C_{1-6}$ alkyl, $C_{2-6}$ alkenyl, and $C_{2-6}$ alkynyl are each optionally substituted with 1, 2, 3, or 4 substituents independently selected from $R^8$.

In some embodiments, each $R^7$ is independently selected from $C_{1-6}$ alkyl, halo, D, CN, $OR^{a2}$ and $NR^{c12}R^{d12}$.

In some embodiments, each $R^7$ is independently selected from CN, $OR^{a12}$, $NR^{c12}R^{d12}$, and D.

In some embodiments, each $R^7$ is independently selected from $OR^{a12}$, D, and $NR^{c12}R^{d12}$.

In some embodiments, each $R^7$ is independently selected from D, CN, $NH_2$, and methoxy.

In some embodiments, each $R^7$ is independently selected from OH, D, $NH_2$, and methoxy.

In some embodiments, each $R^{10}$ is independently selected from $C_{1-6}$ alkyl, $C_{1-6}$ haloalkyl, 4-10 membered heterocycloalkyl, halo, D, CN, $OR^{a1}$, $C(O)NR^{c1}R^{d1}$ and $NR^{c1}R^{d1}$; wherein said $C_{1-6}$ alkyl, and 4-10 membered heterocycloalkyl are each optionally substituted with 1, 2, 3, or 4 substituents independently selected from $R^1$.

In some embodiments, each $R^{10}$ is independently selected from $C_{1-6}$ alkyl, $C_{2-6}$ alkenyl, $C_{2-6}$ alkynyl, $C_{1-6}$ haloalkyl, 4-10 membered heterocycloalkyl, halo, D, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, and $NR^{c1}C(O)NR^{c1}R^{d1}$; wherein said $C_{1-6}$ alkyl, $C_{2-6}$ alkenyl, $C_{2-6}$ alkynyl, and 4-10 membered heterocycloalkyl are each optionally substituted with 1, 2, 3, or 4 substituents independently selected from $R^{11}$.

In some embodiments, each $R^{10}$ is independently selected from $C_{1-6}$ alkyl, 4-10 membered heterocycloalkyl, CN, OH, $OR^{a1}$, $C(O)NR^{c1}R^{d1}$ and $NR^{c1}R^{d1}$; wherein said $C_{1-6}$ alkyl, and 4-10 membered heterocycloalkyl are each optionally substituted with 1, 2, 3, or 4 substituents independently selected from $R^{11}$.

In some embodiments, each $R^{10}$ is independently selected from $C_{1-6}$ alkyl, 4-10 membered heterocycloalkyl, halo, CN, OH, $OR^{a1}$, $C(O)NR^{c1}R^{d1}$ and $NR^{c1}R^{d1}$; wherein said $C_{1-6}$ alkyl, and 4-10 membered heterocycloalkyl are each optionally substituted with 1, 2, 3, or 4 substituents independently selected from $R^1$.

In some embodiments, each $R^{10}$ is independently selected from OH, CN, methyl, hydroxymethyl, methylcarbamoyl, methoxy, morpholino, and cyclobutylamino.

In some embodiments, each $R^{10}$ is independently selected from OH, F, CN, methyl, hydroxymethyl, methylcarbamoyl, methoxy, morpholino, and cyclobutylamino.

In some embodiments, each $R^{11}$ is independently selected from $C_{1-6}$ alkyl, $C_{1-6}$ haloalkyl, halo, D, CN and $OR^{a2}$.

In some embodiments, each $R^{11}$ is $OR^{a2}$. In some embodiments, each $R^{11}$ is OH.

In some embodiments, each $R^{13}$ is independently selected from $C_{1-6}$ alkyl and $C_{1-6}$ haloalkyl.

In some embodiments, each $R^{13}$ is independently $C_{1-6}$ alkyl.

In some embodiments, $R^{13}$ is methyl.

In some embodiments, each $R^{a1}$, $R^{c1}$ and $R^{d1}$ is independently selected from H, $C_{1-6}$ alkyl, $C_{1-6}$ haloalkyl and $C_{3-10}$ cycloalkyl; wherein said $C_{1-6}$ alkyl and $C_{3-10}$ cycloalkyl are each optionally substituted with 1, 2, 3, or 4 substituents independently selected from $R^{11}$.

In some embodiments, each $R^{a1}$, $R^{c1}$ and $R^{d1}$ is independently selected from H, $C_{1-6}$ alkyl, and $C_{3-10}$ cycloalkyl; wherein said $C_{1-6}$ alkyl and $C_{3-10}$ cycloalkyl are each optionally substituted with 1, 2, 3, or 4 substituents independently selected from $R^{11}$.

In some embodiments, each $R^{a2}$, $R^{c2}$ and $R^{d2}$ is independently selected from H, $C_{1-6}$ alkyl and $C_{1-6}$ haloalkyl. In some embodiments, each $R^{a2}$, $R^{c2}$ and $R^{d2}$ is independently H.

In some embodiments, each $R^{a5}$, $R^{c8}$ and $R^{d8}$ is independently selected from H, $C_{1-6}$ alkyl and $C_{1-6}$ haloalkyl. In some embodiments, each $R^{a5}$, $R^{c8}$ and $R^{d8}$ is independently selected from H and $C_{1-6}$ alkyl.

In some embodiments, each $R^{a9}$, $R^{c9}$ and $R^{d9}$ is independently selected from H, $C_{1-6}$ alkyl and $C_{1-6}$ haloalkyl. In some embodiments, each $R^{a9}$, $R^{c9}$ and $R^{d9}$ is independently selected from H and $C_{1-6}$ alkyl.

In some embodiments, each $R^{a11}$, $R^{c11}$ and $R^{d11}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^7$. In some embodiments, each $R^{a11}$, $R^{c11}$ and $R^{d11}$ is independently selected from H and $C_{1-6}$ alkyl; wherein said $C_{1-6}$ alkyl is optionally substituted with 1, 2, 3, or 4 substituents independently selected from $R^7$.

In some embodiments, each $R^{a12}$, $R^{c12}$ and $R^{d12}$ is independently selected from H, $C_{1-6}$ alkyl and $C_{1-6}$ haloalkyl.

In some embodiments, $R^{a12}$ is H.

In some embodiments, $R^{c12}$ and $R^{d12}$ are each H.

In some embodiments, each $R^{a15}$, $R^{c15}$ and $R^{d15}$ is independently selected from H, $C_{1-6}$ alkyl and $C_{1-6}$ haloalkyl; wherein said $C_{1-6}$ alkyl is optionally substituted with 1, 2, 3, or 4 substituents independently selected from $R^g$. In some embodiments, each $R^{a15}$, $R^{c15}$ and $R^{d15}$ is independently selected from H and $C_{1-6}$ alkyl; wherein said $C_{1-6}$ alkyl is optionally substituted with 1, 2, 3, or 4 substituents independently selected from $R^g$.

In some embodiments, each $R^g$ is independently selected from OH, CN, halo, $C_{1-6}$ alkyl, $C_{1-6}$ haloalkyl, $C_{1-6}$ alkoxy, $C_{1-6}$ haloalkoxy, amino, $C_{1-6}$ alkylthio, $C_{1-6}$ alkylsulfonyl. In some embodiments, each $R^g$ is OH.

In some embodiments, n is 0, 1, 2, 3 or 4. In some embodiments, n is 0, 1, 2, or 3. In some embodiments, n is 0. In some embodiments, n is 1. In some embodiments, n is 2. In some embodiments, n is 3. In some embodiments, n is 4.

In some embodiments, provided herein is a compound having Formula IA:

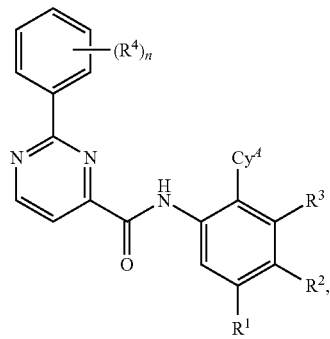

IA or a pharmaceutically acceptable salt thereof.

In some embodiments, provided herein is a compound having Formula IB:

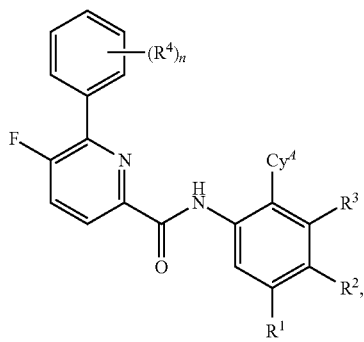

IB or a pharmaceutically acceptable salt thereof.

In some embodiments, provided herein is a compound having Formula IC:

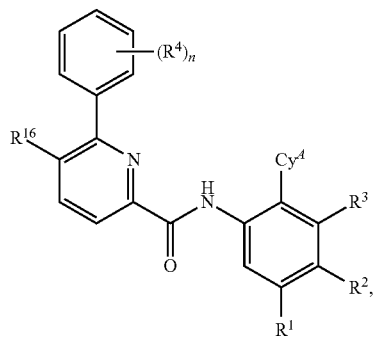

IC or a pharmaceutically acceptable salt thereof.

In some embodiments, provided herein is a compound having Formula IIA:

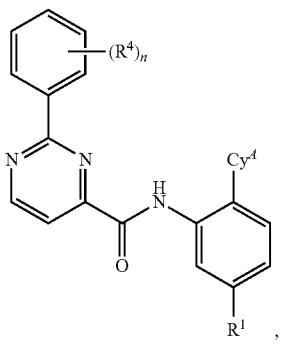

IIA or a pharmaceutically acceptable salt thereof.

In some embodiments, provided herein is a compound having Formula IIB:

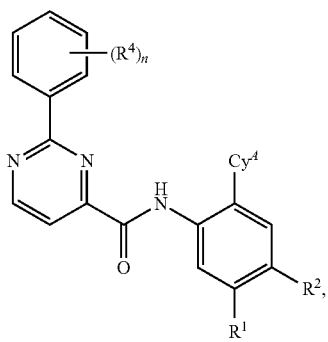

IIB or a pharmaceutically acceptable salt thereof.

In some embodiments, provided herein is a compound having Formula IIC:

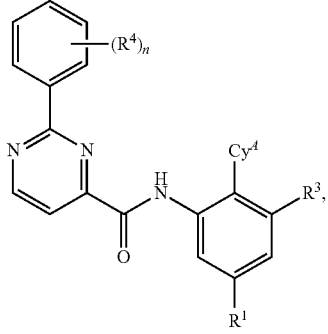

IIC or a pharmaceutically acceptable salt thereof.

In some embodiments, provided herein is a compound having Formula IID:

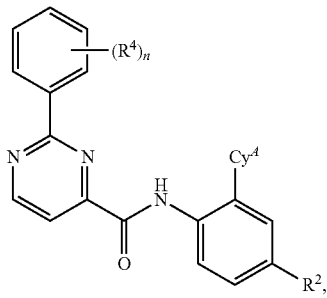

IID or a pharmaceutically acceptable salt thereof.

In some embodiments, provided herein is a compound having Formula III:

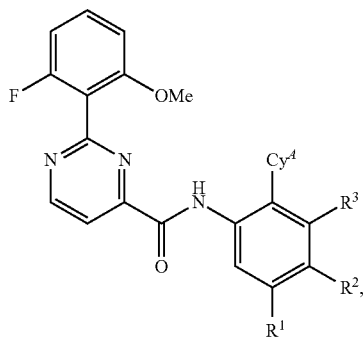

III or a pharmaceutically acceptable salt thereof.

In some embodiments, provided herein is a compound having Formula IV:

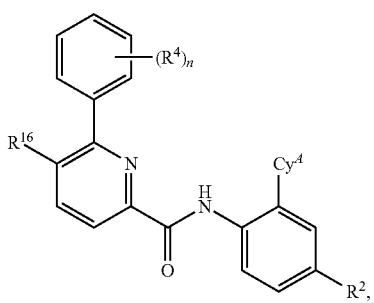

IV or a pharmaceutically acceptable salt thereof.

In some embodiments, provided herein is a compound having Formula V:

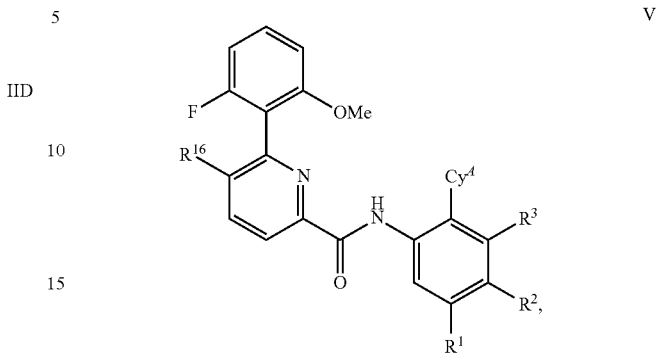

V or a pharmaceutically acceptable salt thereof.

In some embodiments, provided herein is a compound having Formula VI:

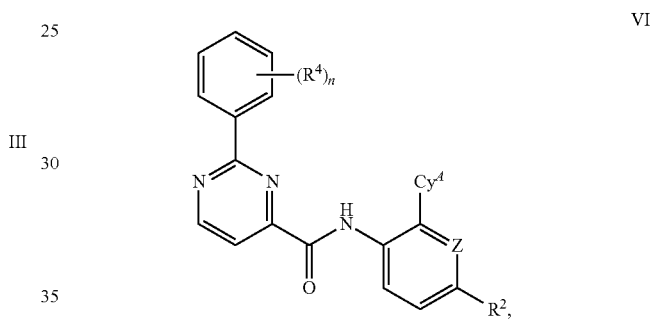

VI or a pharmaceutically acceptable salt thereof.

In some embodiments, provided herein is a compound selected from:
N-(2-((1R,4R)-2,5-diazabicyclo[2.2.1]heptan-2-yl)-5-fluorophenyl)-2-(2-fluoro-6-methoxyphenyl)pyrimidine-4-carboxamide;
(S)—N-(2-(3-aminopyrrolidin-1-yl)-5-fluorophenyl)-2-(2-fluoro-6-methoxyphenyl)pyrimidine-4-carboxamide;
(R)—N-(2-(2-(aminomethyl)pyrrolidin-1-yl)-5-fluorophenyl)-2-(2-fluoro-6-methoxyphenyl)pyrimidine-4-carboxamide;
(R)—N-(5-fluoro-2-(2-(hydroxymethyl)pyrrolidin-1-yl)phenyl)-2-(2-fluoro-6-methoxyphenyl)pyrimidine-4-carboxamide;
(R)—N-(5-fluoro-2-(2-(methoxymethyl)pyrrolidin-1-yl)phenyl)-2-(2-fluoro-6-methoxyphenyl)pyrimidine-4-carboxamide;
N-(2-((2S,4S)-4-amino-2-(hydroxymethyl)pyrrolidin-1-yl)-5-fluorophenyl)-2-(2-fluoro-6-methoxyphenyl)pyrimidine-4-carboxamide;
N-(5-fluoro-2-((2S,4S)-4-hydroxy-2-methylpyrrolidin-1-yl)phenyl)-2-(2-fluoro-6-methoxyphenyl)pyrimidine-4-carboxamide;
N-(5-fluoro-2-(2-(pyridin-2-yl)pyrrolidin-1-yl)phenyl)-2-(2-fluoro-6-methoxyphenyl)pyrimidine-4-carboxamide;
N-(5-fluoro-2-(hexahydropyrrolo[3,4-b]pyrrol-1(2N)-yl)phenyl)-2-(2-fluoro-6-methoxyphenyl)pyrimidine-4-carboxamide;
(R)—N-(5-fluoro-2-(2-methylpiperazin-1-yl)phenyl)-2-(2-fluoro-6-methoxyphenyl)pyrimidine-4-carboxamide;

(R)—N-(5-fluoro-2-(2-(hydroxymethyl)piperazin-1-yl)phenyl)-2-(2-fluoro-6-methoxyphenyl)pyrimidine-4-carboxamide;

N-(5-fluoro-2-(3-(hydroxymethyl)morpholino)phenyl)-2-(2-fluoro-6-methoxyphenyl)pyrimidine-4-carboxamide;

N-(2-((1R,4R)-2,5-diazabicyclo[2.2.1]heptan-2-yl)-3-bromo-5-fluorophenyl)-2-(2-fluoro-6-methoxyphenyl)pyrimidine-4-carboxamide;

N-(2-((1R,4R)-2,5-diazabicyclo[2.2.1]heptan-2-yl)-3-cyanophenyl)-2-(2-fluoro-6-methoxyphenyl)pyrimidine-4-carboxamide;

N-(2-((1R,4R)-2,5-diazabicyclo[2.2.1]heptan-2-yl)-5-fluoro-3-(pyridin-3-yl)phenyl)-2-(2-fluoro-6-methoxyphenyl)pyrimidine-4-carboxamide;

N-(2-((1R,4R)-2,5-diazabicyclo[2.2.1]heptan-2-yl)-5-fluoro-3-(1-methyl-1H-pyrazol-4-yl)phenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-(hydroxymethyl)phenyl)-2-(2-fluoro-6-methoxyphenyl)pyrimidine-4-carboxamide;

N-(2-((1S,4S)-2,5-diazabicyclo[2.2.1]heptan-2-yl)-4-bromo-5-fluorophenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-(1-methyl-1H-pyrazol-4-yl)phenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-(6-(hydroxymethyl)pyridin-3-yl)phenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-(6-(methylcarbamoyl)pyridin-3-yl)phenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-(1-methyl-6-oxo-1,6-dihydropyridin-3-yl)phenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-(2-methylpyridin-3-yl)phenyl)-2-(2-fluoro-6-methoxyphenyl)pyrimidine-4-carboxamide;

N-(2-((1S,4S)-2,5-diazabicyclo[2.2.1]heptan-2-yl)-4-(2-methylpyridin-3-yl)phenyl)-2-(2-fluoro-6-methoxyphenyl)pyrimidine-4-carboxamide;

N-(2-((1S,4S)-2,5-diazabicyclo[2.2.1]heptan-2-yl)-4-(4-methoxypyridin-3-yl)phenyl)-2-(2-fluoro-6-methoxyphenyl)pyrimidine-4-carboxamide;

N-(2-((1S,4S)-2,5-diazabicyclo[2.2.1]heptan-2-yl)-4-(4-cyanopyridin-3-yl)phenyl)-2-(2-fluoro-6-methoxyphenyl)pyrimidine-4-carboxamide;

N-(2-((1S,4S)-2,5-diazabicyclo[2.2.1]heptan-2-yl)-4-(1,3,5-trimethyl-1H-pyrazol-4-yl)phenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-morpholinophenyl)-2-(2-fluoro-6-methoxyphenyl)pyrimidine-4-carboxamide;

N-(4-(azetidin-1-yl)-2-((1S,4S)-2,5-diazabicyclo[2.2.1]heptan-2-yl)-5-fluorophenyl)-2-(2-fluoro-6-methoxyphenyl)pyrimidine-4-carboxamide;

N-(2-((1S,4S)-2,5-diazabicyclo[2.2.1]heptan-2-yl)-5-fluoro-4-(morpholinomethyl)phenyl)-2-(2-fluoro-6-methoxyphenyl)pyrimidine-4-carboxamide;

N-(2-((1S,4S)-2,5-diazabicyclo[2.2.1]heptan-2-yl)-4-((cyclobutylamino)methyl)-5-fluorophenyl)-2-(2-fluoro-6-methoxyphenyl)pyrimidine-4-carboxamide;

N-(2-((1R,4R)-5-ethyl-2,5-diazabicyclo[2.2.1]heptan-2-yl)-5-fluorophenyl)-2-(2-fluoro-6-methoxyphenyl)pyrimidine-4-carboxamide;

N-(5-fluoro-2-((1R,4R)-5-(2-hydroxyethyl)-2,5-diazabicyclo[2.2.1]heptan-2-yl)phenyl)-2-(2-fluoro-6-methoxyphenyl)pyrimidine-4-carboxamide;

(1R,4R)-5-(4-fluoro-2-(2-(2-fluoro-6-methoxyphenyl)pyrimidine-4-carboxamido)phenyl)-N-propyl-2,5-diazabicyclo[2.2.1]heptane-2-carboxamide;

N-(2-((1R,4R)-2,5-diazabicyclo[2.2.1]heptan-2-yl)-5-methoxyphenyl)-2-(2-fluoro-6-methoxyphenyl)pyrimidine-4-carboxamide;

N-(2-((1R,4R)-2,5-diazabicyclo[2.2.1]heptan-2-yl)-5-(hydroxymethyl)phenyl)-2-(2-fluoro-6-methoxyphenyl)pyrimidine-4-carboxamide; and N-(2-((1R,4R)-2,5-diazabicyclo[2.2.1]heptan-2-yl)-5-cyanophenyl)-2-(2-fluoro-6-methoxyphenyl)pyrimidine-4-carboxamide;

or a pharmaceutically acceptable salt thereof.

In some embodiments, provided herein is a compound selected from:

N-(4-(azetidin-1-yl)-2-((1S,4S)-2,5-diazabicyclo[2.2.1]heptan-2-yl)phenyl)-2-(2-fluoro-6-methoxyphenyl)pyrimidine-4-carboxamide;

N-(2-((1S,4S)-2,5-diazabicyclo[2.2.1]heptan-2-yl)-4-((S)-2-(methoxymethyl)azetidin-1-yl)phenyl)-2-(2-fluoro-6-methoxyphenyl)pyrimidine-4-carboxamide;

N-(2-((1S,4S)-2,5-diazabicyclo[2.2.1]heptan-2-yl)-4-(3-cyanopyridin-4-yl)-3-fluorophenyl)-2-(2-fluoro-6-methoxyphenyl)pyrimidine-4-carboxamide;

N-(2-((2S,4S)-4-amino-2-(hydroxymethyl)pyrrolidin-1-yl)-4-(3-cyanopyridin-4-yl)phenyl)-2-(2-fluoro-6-methoxyphenyl)pyrimidine-4-carboxamide;

N-(2-((2S,4S)-4-amino-2-(hydroxymethyl)pyrrolidin-1-yl)-4-(4-cyanopyridin-3-yl)phenyl)-2-(2-fluoro-6-methoxyphenyl)pyrimidine-4-carboxamide;

N-(2-((2S,4S)-4-amino-2-(hydroxymethyl)pyrrolidin-1-yl)-4-(2-methylpyridin-3-yl)phenyl)-2-(2-fluoro-6-methoxyphenyl)pyrimidine-4-carboxamide;

N-(2-((2S,4S)-4-amino-2-(hydroxymethyl)pyrrolidin-1-yl)-4-(3-methoxypyridin-4-yl)phenyl)-2-(2-fluoro-6-methoxyphenyl)pyrimidine-4-carboxamide;

N-(3-((2S,4S)-4-amino-2-(hydroxymethyl)pyrrolidin-1-yl)-2'-cyano-6'-fluorobiphenyl-4-yl)-2-(2-fluoro-6-methoxyphenyl)pyrimidine-4-carboxamide;

N-(2-((2S,4S)-4-amino-2-(hydroxymethyl)pyrrolidin-1-yl)-4-(3-cyanopyridin-2-yl)phenyl)-2-(2-fluoro-6-methoxyphenyl)pyrimidine-4-carboxamide;

N-(2-((2S,4S)-4-amino-2-(hydroxymethyl)pyrrolidin-1-yl)-4-(4-cyano-1-methyl-1H-pyrazol-5-yl)phenyl)-2-(2-fluoro-6-methoxyphenyl)pyrimidine-4-carboxamide;

N-(2-((2S,4S)-4-amino-2-(hydroxymethyl)pyrrolidin-1-yl)-4-isopropylphenyl)-2-(2-fluoro-6-methoxyphenyl)pyrimidine-4-carboxamide;

N-(4-(3-cyanopyridin-4-yl)-2-((2S,4S)-4-hydroxy-2-(hydroxymethyl)pyrrolidin-1-yl)phenyl)-2-(2-fluoro-6-methoxyphenyl)pyrimidine-4-carboxamide;

N-(4-(4-cyanopyridin-3-yl)-2-((2S,5R)-2-(hydroxymethyl)-5-methylpiperazin-1-yl)phenyl)-2-(2-fluoro-6-methoxyphenyl)pyrimidine-4-carboxamide;

N-(4-(4-cyanopyridin-3-yl)-2-((2S,5S)-2-(hydroxymethyl)-5-methylpiperazin-1-yl)phenyl)-2-(2-fluoro-6-methoxyphenyl)pyrimidine-4-carboxamide;

(S)—N-(4-(4-cyanopyridin-3-yl)-2-(6-(hydroxymethyl)-4,7-diazaspiro[2.5]octan-7-yl)phenyl)-2-(2-fluoro-6-methoxyphenyl)pyrimidine-4-carboxamide;

N-(2-((2S,4S)-4-amino-2-(1-hydroxycyclopropyl)pyrrolidin-1-yl)-4-(4-cyanopyridin-3-yl)phenyl)-2-(2-fluoro-6-methoxyphenyl)pyrimidine-4-carboxamide;

N-(2-((2S,4S)-4-amino-2-(2-hydroxypropan-2-yl)pyrrolidin-1-yl)-4-(4-cyanopyridin-3-yl)phenyl)-2-(2-fluoro-6-methoxyphenyl)pyrimidine-4-carboxamide;

N-(2-((2S,4S)-4-amino-2-(hydroxymethyl-d2)pyrrolidin-1-yl)-4-(4-cyanopyridin-3-yl)phenyl)-2-(2-fluoro-6-methoxyphenyl)pyrimidine-4-carboxamide;

N-(4-(4-cyanopyridin-3-yl)-2-((1S,3R,4S)-3-(hydroxymethyl)-2,5-diazabicyclo[2.2.1]heptan-2-yl)phenyl)-2-(2-fluoro-6-methoxyphenyl)pyrimidine-4-carboxamide;

N-(4-(4-cyanopyridin-3-yl)-2-((1S,4S)-1-(hydroxymethyl)-2,5-diazabicyclo[2.2.1]heptan-2-yl)phenyl)-2-(2-fluoro-6-methoxyphenyl)pyrimidine-4-carboxamide;

N-(2-((2S,4S)-4-amino-2-methylpiperidin-1-yl)-4-(4-cyanopyridin-3-yl)phenyl)-2-(2-fluoro-6-methoxyphenyl)pyrimidine-4-carboxamide;

N-(2-((2S,4S)-4-amino-2-(hydroxymethyl)pyrrolidin-1-yl)-4-(4-cyanopyridin-3-yl)phenyl)-6-(2-fluoro-6-methoxyphenyl)picolinamide;

N-(2-((2S,4S)-4-amino-2-(hydroxymethyl)pyrrolidin-1-yl)-4-(4-cyanopyridin-3-yl)phenyl)-5-cyano-6-(2-fluoro-6-methoxyphenyl)picolinamide;

N-(2-((2S,4S)-4-amino-2-(hydroxymethyl)pyrrolidin-1-yl)-4-(4-cyanopyridin-3-yl)phenyl)-6-(2-fluoro-6-methoxyphenyl)-5-methoxypicolinamide;

N-(2-((2S,4S)-4-amino-2-(hydroxymethyl)pyrrolidin-1-yl)-4-(4-cyanopyridin-3-yl)phenyl)-2-(2,6-difluorophenyl)pyrimidine-4-carboxamide;

N-(2-((2S,4S)-4-amino-2-(hydroxymethyl)pyrrolidin-1-yl)-4-(4-cyanopyridin-3-yl)phenyl)-2-(2-fluoro-6-methylphenyl)pyrimidine-4-carboxamide;

N-(2-((2S,4S)-4-amino-2-(hydroxymethyl)pyrrolidin-1-yl)-4-(4-cyanopyridin-3-yl)phenyl)-2-(2-chloro-6-fluorophenyl)pyrimidine-4-carboxamide;

N-(2-((2S,4S)-4-Amino-2-(hydroxymethyl)pyrrolidin-1-yl)-6-(1,3,5-trimethyl-1H-pyrazol-4-yl)pyridin-3-yl)-2-(2-fluoro-6-methoxyphenyl)pyrimidine-4-carboxamide;

N-(2-((2S,4S)-4-Amino-2-(hydroxymethyl)pyrrolidin-1-yl)-5-fluorophenyl)-2-(2,6-difluorophenyl)pyrimidine-4-carboxamide;

N-(2-((2S,4S)-4-Amino-2-(hydroxymethyl)pyrrolidin-1-yl)-5-fluorophenyl)-2-(3-cyano-2-fluoro-6-methoxyphenyl)pyrimidine-4-carboxamide;

N-(2-((2S,4S)-4-Amino-2-(hydroxymethyl)pyrrolidin-1-yl)-5-fluorophenyl)-2-(2,3-difluoro-6-methoxyphenyl)pyrimidine-4-carboxamide;

N-(2-((2S,4S)-4-Amino-2-(hydroxymethyl)pyrrolidin-1-yl)-5-fluorophenyl)-2-(2-fluoro-6-(methoxy-d3)-3-methylphenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2-fluoro-6-methoxy-4-methylphenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(3,6-difluoro-2-methylphenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2,3-difluoro-6-methoxyphenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(3,6-difluoro-2-methoxyphenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(3-cyano-2-fluoro-6-(methoxy-d₃)phenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(3,6-difluoro-2-(methoxy-d₃)phenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2,3-difluoro-6-(methoxy-d₃)phenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2-fluoro-6-(methoxy-d₃)phenyl-5-d)pyrimidine-4-carboxamide;

2-(2-Fluoro-6-methoxyphenyl)-N-(2-(piperidin-4-yl)phenyl)pyrimidine-4-carboxamide;

N-(2-(cis)4-Aminocyclohexyl)phenyl)-2-(2-fluoro-6-methoxyphenyl)pyrimidine-4-carboxamide;

N-(2-(trans)4-Aminocyclohexyl)phenyl)-2-(2-fluoro-6-methoxyphenyl)pyrimidine-4-carboxamide;

N-(2-(3-Aminocyclohexyl)phenyl)-2-(2-fluoro-6-methoxyphenyl)pyrimidine-4-carboxamide;

N-(2-(3-aminocyclopentyl)phenyl)-2-(2-fluoro-6-methoxyphenyl)pyrimidine-4-carboxamide;

N-(2-((cis)-4-Aminocyclohexyl)-4-(4-cyanopyridin-3-yl)phenyl)-2-(2-fluoro-6-methoxyphenyl)pyrimidine-4-carboxamide;

N-(2-((trans)-4-Aminocyclohexyl)-4-(4-cyanopyridin-3-yl)phenyl)-2-(2-fluoro-6-methoxyphenyl)pyrimidine-4-carboxamide;

N-(2-((cis)-4-Aminocyclohexyl)-4-(4-cyano-1-methyl-1H-pyrazol-5-yl)phenyl)-2-(2-fluoro-6-methoxyphenyl)pyrimidine-4-carboxamide;

N-(2-((trans)-4-aminocyclohexyl)-4-(4-cyano-1-methyl-1H-pyrazol-5-yl)phenyl)-2-(2-fluoro-6-methoxyphenyl)pyrimidine-4-carboxamide;

N-(2-((cis)-4-Aminocyclohexyl)-4-(1,3,5-trimethyl-1H-pyrazol-4-yl)phenyl)-2-(2-fluoro-6-methoxyphenyl)pyrimidine-4-carboxamide;

N-(2-((2S,4S)-4-Amino-2-(hydroxymethyl)pyrrolidin-1-yl)-4-(methylsulfonyl)phenyl)-2-(2-fluoro-6-methoxyphenyl)pyrimidine-4-carboxamide;

N-(2-((2S,4S)-4-Amino-2-(hydroxymethyl)pyrrolidin-1-yl)phenyl)-2-(2-fluoro-6-methoxyphenyl)pyrimidine-4-carboxamide;

N-(2-((2S,4S)-4-Amino-2-(hydroxymethyl)pyrrolidin-1-yl)-5-methylphenyl)-2-(2-fluoro-6-methoxyphenyl)pyrimidine-4-carboxamide;

N-(2-((2S,4S)-4-(Dimethylamino)-2-(hydroxymethyl)pyrrolidin-1-yl)-5-fluorophenyl)-2-(2-fluoro-6-methoxyphenyl)pyrimidine-4-carboxamide;

N-(5-Fluoro-2-((2S,4S)-2-(hydroxymethyl)-4-(isopropylamino)pyrrolidin-1-yl)phenyl)-2-(2-fluoro-6-methoxyphenyl)pyrimidine-4-carboxamide;

N-(2-((2S,4S)-4-Amino-2-(hydroxymethyl)pyrrolidin-1-yl)-4-(tetrahydro-2H-pyran-4-yl)phenyl)-2-(2-fluoro-6-methoxyphenyl)pyrimidine-4-carboxamide;

N-(2-((2S,4S)-4-Amino-2-(hydroxymethyl)pyrrolidin-1-yl)-4-chlorophenyl)-2-(2-fluoro-6-methoxyphenyl)pyrimidine-4-carboxamide;

N-(2-((2S,4S)-4-Amino-2-(hydroxymethyl)pyrrolidin-1-yl)-4-fluorophenyl)-2-(2-fluoro-6-methoxyphenyl)pyrimidine-4-carboxamide;

N-(2-((2S,4S)-4-Amino-2-(hydroxymethyl)pyrrolidin-1-yl)-4-(5-cyano-2-(pyrrolidin-1-yl)pyridin-4-yl)phenyl)-2-(2,6-difluorophenyl)pyrimidine-4-carboxamide;

N-(2-((2S,4S)-4-Amino-2-(hydroxymethyl)pyrrolidin-1-yl)-4-(1-cyanocyclopropyl)phenyl)-2-(2,6-difluorophenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2-(difluoromethoxy)-6-fluorophenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2-fluoro-6-(methoxy-d₃)phenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2-cyclopropyl-6-fluorophenyl)pyrimidine-4-carboxamide;

N-(2-((2S,4S)-4-Amino-2-(hydroxymethyl)pyrrolidin-1-yl)-4-(4-cyanopyridin-3-yl)phenyl)-2-(2-ethoxy-6-fluorophenyl)pyrimidine-4-carboxamide;

N-(4-(4-Cyanopyridin-3-yl)-2-((1S,4S)-4-(hydroxymethyl)-5-methyl-2,5-diazabicyclo[2.2.1]heptan-2-yl)phenyl)-2-(2-fluoro-6-methoxyphenyl)pyrimidine-4-carboxamide;

(S)—N-(4-(4-Cyanopyridin-3-yl)-2-(2-(hydroxymethyl)morpholino)phenyl)-2-(2-fluoro-6-methoxyphenyl)pyrimidine-4-carboxamide;

(S)—N-(4-(4-Cyanopyridin-3-yl)-2-(2-((dimethylamino)methyl)morpholino)phenyl)-2-(2-fluoro-6-methoxyphenyl)pyrimidine-4-carboxamide;

(R)—N-(2-(2-(Cyanomethyl)morpholino)-4-(4-cyanopyridin-3-yl)phenyl)-2-(2-fluoro-6-methoxyphenyl)pyrimidine-4-carboxamide;

(R)—N-(4-(4-Cyanopyridin-3-yl)-2-(3-oxotetrahydro-3H-oxazolo[3,4-a]pyrazin-7(1H)-yl)phenyl)-2-(2-fluoro-6-methoxyphenyl)pyrimidine-4-carboxamide;

(S)—N-(5-Fluoro-2-(3-(hydroxymethyl)piperazin-1-yl)phenyl)-2-(2-fluoro-6-methoxyphenyl)pyrimidine-4-carboxamide;

N-(4-(4-Cyanopyridin-3-yl)-2-(3-(methoxymethyl)azetidin-1-yl)phenyl)-2-(2-fluoro-6-methoxyphenyl)pyrimidine-4-carboxamide;

(S)—N-(4-(4-Cyanopyridin-3-yl)-2-(2-(hydroxymethyl)azetidin-1-yl)phenyl)-2-(2-fluoro-6-methoxyphenyl)pyrimidine-4-carboxamide;

(R)—N-(4-(4-Cyanopyridin-3-yl)-2-(2-((dimethylamino)methyl)azetidin-1-yl)phenyl)-2-(2-fluoro-6-methoxyphenyl)pyrimidine-4-carboxamide;

N-(4-(4-Cyanopyridin-3-yl)-2-(4-methylpiperazin-1-yl)phenyl)-2-(2-fluoro-6-methoxyphenyl)pyrimidine-4-carboxamide;

N-(4-(4-Cyanopyridin-3-yl)-2-(4-(2-hydroxyethyl)piperazin-1-yl)phenyl)-2-(2-fluoro-6-methoxyphenyl)pyrimidine-4-carboxamide; and (S)—N-(5-Fluoro-2-(3-(hydroxymethyl)piperazin-1-yl)-4-isopropylphenyl)-2-(2-fluoro-6-methoxyphenyl)pyrimidine-4-carboxamide;

or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula (I) and (I') can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene", employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include —$OCH_2CH_2O$— and $OCH_2CH_2CH_2O$—. In some embodiments, the two O atoms of a $C_{n-m}$ dialkoxy group may be attached to the same B atom to form a 5- or 6-membered heterocycloalkyl group.

The term "amino" refers to a group of formula —$NH_2$.

The term "carbonyl", employed alone or in combination with other terms, refers to a —C(=O)— group, which also may be written as C(O).

The term "cyano" or "nitrile" refers to a group of formula—C≡N, which also may be written as —CN.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized π (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments aryl groups have 6 carbon atoms. In some embodiments aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_3$-7). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazobicyclo[2.2.1]heptanyl; pyrrolidinyl; hexahydropyrrolo[3,4-b]pyrrol-1(2H)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, e.g., 1H— and 3H-imidazole, 1H—, 2H—and 4H—1,2,4-triazole, 1H—and 2H-isoindole and 1H—and 2H—pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, *Protecting Groups*, (Thieme, 2007); Robertson, *Protecting Group Chemistry*, (Oxford University Press, 2000); Smith et al., *Mar.'s Advanced Organic Chemistry: Reactions, Mechanisms, and Structure*, 6$^{th}$ Ed. (Wiley, 2007); Peturssion et al., "Protecting Groups in Carbohydrate Chemistry," *J. Chem. Educ.*, 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry or by chromatographic methods such as high performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Compounds of Formula (I) and (I') can be prepared, e.g., using a process as illustrated in the schemes below.

Compounds of Formula (I) and (I') can be prepared using a process as illustrated in Scheme 1. In the process depicted in Scheme 1, the halo substituent of compounds of Formula 1-1 can be used to install a $Cy^A$ substituent by a number of methods, e.g., by nucleophilic displacement with an appropriate amine nucleophile with a suitable base (e.g., triethylamine or DIPEA) in a suitable solvent (e.g., DMF, DMSO, dioxane), or by a suitable cross-coupling reaction, to give compounds of Formula 1-2. Suitable cross-coupling reactions include but are not limited to a Buchwald coupling (e.g., in the presence of a palladacycle precatalyst, such as RuPhod Pd G2), and a Negishi or Suzuki coupling (e.g., in the presence of a palladacycle precatalyst, such as Xphos Pd G2). Examples of different cross-coupling procedures include Stille (ACS Catalysis 2015, 5, 3040-3053), Suzuki (Tetrahedron 2002, 58, 9633-9695), Sonogashira (Chem. Soc. Rev. 2011, 40, 5084-5121), Negishi (ACS Catalysis 2016, 6, 1540-1552), Buchwald-Hartwig amination (Chem. Sci. 2011, 2, 27-50), and Cu-catalyzed amination (Org. React. 2014, 85, 1-688), among others.

Reduction of the nitro group with an appropriate reducing agent (e.g., iron in the presence of ammonium chloride or hydrogen gas in the presence of Pd/C catalyst) provides compounds of Formula 1-3. Amide bond formation with acids of Formula 1-5 (e.g., using HATU and a base such as Hunig's base) provides compounds of the desired Formula (I) or (I').

Scheme 1

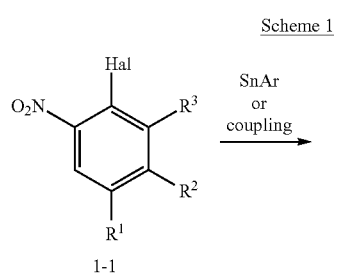

1-1

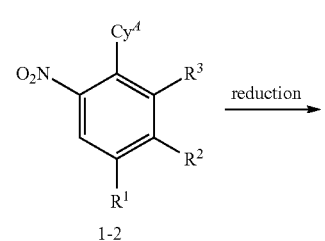

1-2

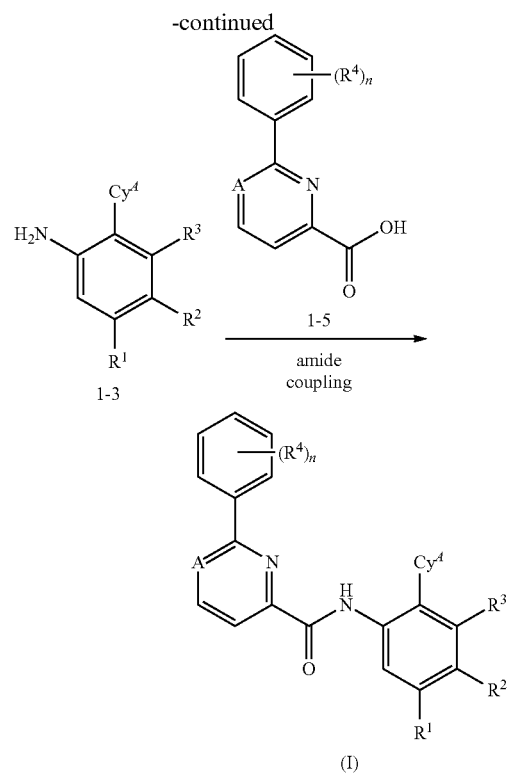

The acids of Formula 1-5 can be prepared from the compounds of Formula 1-4 using a cross coupling, such as Suzuki (e.g., in the presence of a palladacycle precatalyst, such as Xphos Pd G2) or Stille (e.g., in the precense of a palladium catalyst such as $(PPh_3)_2PdCl_2$ and base such as triethylamine).

Scheme 2

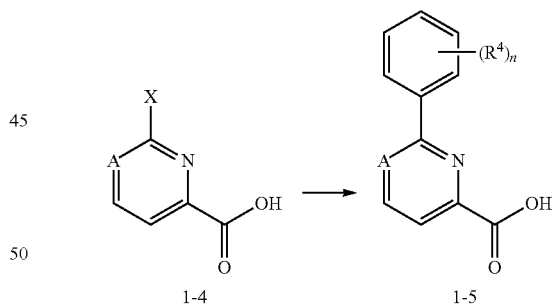

HPK1 Kinase

Studies have established that HPK1 is a negative regulator of T cell and B cell activation (Hu, M. C., et al., Genes Dev, 1996. 10(18): p. 2251-64; Kiefer, F., et al., EMBO J, 1996. 15(24): p. 7013-25). HPK1-deficient mouse T cells showed dramatically increased activation of TCR proximal signaling, enhanced IL-2 production, and hyper-proliferation in vitro upon anti-CD3 stimulation (Shui, J. W., et al., Nat Immunol, 2007. 8(1): p. 84-91). Similar to T cells, HPK1 knockout B cells produced much higher levels of IgM and IgG isoforms after KLH immunization and displayed hyper-proliferation potentially as a result of enhanced BCR signaling. Wang, X., et al., J Biol Chem, 2012. 287(14): p. 11037-48. Mechanistically, during TCR or BCR signaling, HPK1 is activated by LCK/ZAP70 (T cells) or SYK/LYN (B cells) mediated-Tyr379 phosphorylation and its subsequent binding to adaptor protein SLP-76 (T cells) or BLNK (B cells) (Wang, X., et al., J Biol Chem, 2012. 287(14): p. 11037-48). Activated HPK1 phosphorylates SLP-76 on Ser376 or BLNK on Thr152, leading to the recruitment of signaling molecule 14-3-3 and ultimate ubiquitination-mediated degradation of SLP-76 or BLNK (Liou, J., et al., Immunity, 2000. 12(4): p. 399-408; Di Bartolo, V., et al., J Exp Med, 2007. 204(3): p. 681-91). As SLP-76 and BLNK are essential for TCR/BCR-mediated signaling activation (e.g. ERK, phospholipase Cγ1, calcium flux, and NFAT activation), HPK1-mediated downregulation of these adaptor proteins provide a negative feedback mechanism to attenuate signaling intensity during T cell or B cell activation (Wang, X., et al., J Biol Chem, 2012. 287(14): p. 11037-48). The bone marrow-derived dendritic cells (BDMCs) from HPK1 knockout mice showed higher expression of co-stimulatory molecules (e.g. CD80/CD86) and enhanced production of proinflammatory cytokines (IL-12, TNF-α etc), and demonstrated superior ability to stimulate T cell proliferation in vitro and in vivo as compared to wild-type DCs (Alzabin, S., et al., J Immunol, 2009. 182 (10): p. 6187-94). These data suggest that HPK1 is also an important negative regulator of dendritic cell activation (Alzabin, S., et al., J Immunol, 2009. 182(10): p. 6187-94). However, the signaling mechanisms underlying HPK-1 mediated negative regulation of DC activation remains to be elucidated.

In contrast, HPK1 appears to be a positive regulator of suppressive functions of regulatory T cells (Treg) (Sawasdikosol, S. et al., The journal of immunology, 2012. 188 (supplement 1): p. 163). HPK1 deficient mouse Foxp3+ Tregs were defective in suppressing TCR-induced effector T cell proliferation, and paradoxically gained the ability to produce IL-2 following TCR engagement (Sawasdikosol, S. et al., The Journal of Immunology, 2012. 188(supplement 1): p. 163). These data suggest that HPK1 is an important regulator of Treg functions and peripheral self-tolerance.

HPK1 was also involved in PGE2-mediated inhibition of CD4+ T cell activation (Ikegami, R., et al., J Immunol, 2001. 166(7): p. 4689-96). Studies published in US 2007/0087988 indicated that HPK1 kinase activity was increased by exposure to physiological concentrations of PGE2 in CD4+ T cells and this effect was mediated by PEG2-induced PKA activation. The proliferation of HPK1 deficient T cells was resistant to the suppressive effects of PGE2 (see US 2007/0087988). Therefore, PGE2-mediated activation of HPK1 may represent a novel regulatory pathway of modulating immune response.

The present disclosure provides methods of modulating (e.g., inhibiting) HPK1 activity, by contacting HPK1 with a compound of the invention, or a pharmaceutically acceptable salt thereof. In some embodiments, the contacting can be administering to a patient a compound provided herein, or a pharmaceutically acceptable salt thereof. In certain embodiments, the compounds of the present disclosure, or pharmaceutically acceptable salts thereof, are useful for therapeutic administration to enhance, stimulate and/or increase immunity in cancer. For example, a method of treating a disease or disorder associated with inhibition of HPK1 interaction can include administering to a patient in need thereof a therapeutically effective amount of a compound provided herein, or a pharmaceutically acceptable salt thereof. The compounds of the present disclosure can be used alone, in combination with other agents or therapies or as an adjuvant or neoadjuvant for the treatment of diseases or disorders, including cancers. For the uses described herein, any of the compounds of the disclosure, including any of the embodiments thereof, may be used.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer,T-cell lymphoma, environmentally induced cancers including those induced by asbestos, and combinations of said cancers.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, HPK1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

As used herein, the term "contacting" refers to the bringing together of the indicated moieties in an in vitro system or an in vivo system such that they are in sufficient physical proximity to interact.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

I. Immune-Checkpoint Therapies

In some embodiments, the HPK1 inhibitors provided herein can be used in combination with one or more immune checkpoint inhibitors for the treatment of cancer as described herein. Compounds of the present disclosure can be used in combination with one or more immune checkpoint inhibitors. Exemplary immune checkpoint inhibitors include inhibitors against immune checkpoint molecules such as CD20, CD28, CD39, CD40, CD122, CD96, CD73, CD47, GITR, CSF1R, JAK, PI3K delta, PI3K gamma, TAM, arginase, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab).

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of CSF1R, e.g., an anti-CSF1R antibody. In some embodiments, the anti-CSF1R antibody is IMC-CS4 or RG7155.

In some embodiments, the inhibitor of an immune checkpoint molecule is an inhibitor of LAG3, e.g., an anti-LAG3 antibody. In some embodiments, the anti-LAG3 antibody is BMS-986016, LAG525, IMP321, GSK2831781, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is INCAGN01949, MEDI0562, MEDI6469, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. An example of an arginase inhibitor is CB-1158.

As provided throughout, the additional compounds, inhibitors, agents, etc. can be combined with the present compound in a single or continuous dosage form, or they can be administered simultaneously or sequentially as separate dosage forms.

II. Cancer Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions.

Examples of agents that may be combined with compounds of the present disclosure include inhibitors of the PI3K-AKT-mTOR pathway, inhibitors of the Raf-MAPK pathway, inhibitors of JAK-STAT pathway, inhibitors of beta catenin pathway, inhibitors of notch pathway, inhibitors of hedgehog pathway, inhibitors of Pim kinases, and inhibitors of protein chaperones and cell cycle progression. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors for the treatment of diseases, such as cancer. Examples of cancers include solid tumors and liquid tumors, such as blood cancers. For example, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf.

In some embodiments, the compounds of the present disclosure can be combined with one or more of the following inhibitors for the treatment of cancer. Non-limiting examples of inhibitors that can be combined with the compounds of the present disclosure for treatment of cancers include an FGFR inhibitor (FGFR1, FGFR2, FGFR3 or FGFR4, e.g., AZD4547, BAY1187982, ARQ087, BGJ398, BIBF1120, TKI258, lucitanib, dovitinib, TAS-120, JNJ-42756493, Debio1347, INCB54828, INCB62079 and INCB63904), a JAK inhibitor (JAK1 and/or JAK2, e.g., ruxolitinib, baricitinib or INCB39110), an IDO inhibitor (e.g., epacadostat and NLG919), an LSD1 inhibitor (e.g., GSK2979552, INCB59872 and INCB60003), a TDO inhibitor, a PI3K-delta inhibitor (e.g., INCB50797 and INCB50465), a PI3K-gamma inhibitor such as a PI3K-gamma selective inhibitor, a CSF1R inhibitor (e.g., PLX3397 and LY3022855), a TAM receptor tyrosine kinases (Tyro-3, Axl, and Mer), an angiogenesis inhibitor, an interleukin receptor inhibitor, bromo and extra terminal family members inhibitors (for example, bromodomain inhibitors or BET inhibitors such as OTX015, CPI-0610, INCB54329 and INCB57643) and an adenosine receptor antagonist or combinations thereof. Inhibitors of HDAC such as panobinostat and vorinostat. Inhibitors of c-Met such as onartumzumab, tivantnib, and INC-280. Inhibitors of BTK such as ibrutinib. Inhibitors of mTOR such as rapamycin, sirolimus, temsirolimus, and everolimus. Inhibitors of Raf, such as vemurafenib and dabrafenib. Inhibitors of MEK such as trametinib, selumetinib and GDC-0973. Inhibitors of Hsp90 (e.g., tanespimycin), cyclin dependent kinases (e.g., palbociclib), PARP (e.g., olaparib) and Pim kinases (LGH447, INCB053914 and SGI-1776) can also be combined with compounds of the present disclosure.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include bendamustine, nitrogen mustards, ethylenimine derivatives, alkyl sulfonates, nitrosoureas and triazenes, uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, CAR (Chimeric antigen receptor) T cell treatment as a booster for T cell activation, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, abiraterone, afatinib, aflibercept, aldesleukin, alemtuzumab, alitretinoin, allopurinol, altretamine, amsacrine, anastrozole, aphidicolon, arsenic trioxide, asparaginase, axitinib, azacitidine, bevacizumab, bexarotene, baricitinib, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mithramycin, mitomycin C, mitotane, mitoxantrone, nandrolone phenpropionate, navelbene, necitumumab, nelarabine, neratinib, nilotinib, nilutamide, nofetumomab, oserelin, oxaliplatin, paclitaxel, pamidronate, panitumumab, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, ruxolitinib, sorafenib, streptozocin, sunitinib, sunitinib maleate, tamoxifen, tegafur, temozolomide, teniposide, testolactone, thalidomide, thioguanine, thiotepa, topotecan, toremifene, tositumomab, trastuzumab, tretinoin, triptorelin, uracil mustard, valrubicin, vandetanib, vinblastine, vincristine, vindesine, vinorelbine, vorinostat and zoledronate.

Other anti-cancer agent(s) include antibody therapeutics such as trastuzumab (Herceptin), antibodies to costimulatory molecules such as CTLA-4 (e.g., ipilimumab or tremelimumab), 4-1BB, antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

The compounds of the present disclosure can further be used in combination with one or more anti-inflammatory agents, steroids, immunosuppressants or therapeutic antibodies. The steroids include but are not limited to 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

The compounds of the present disclosure can also be used in combination with lonafarnib (SCH6636), tipifarnib (R115777), L778123, BMS 214662, tezacitabine (MDL 101731), Sml1, triapine, didox, trimidox and amidox.

The compounds of Formula (I), (I'), or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I), (I') or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I), (I'), or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

When more than one pharmaceutical agent is administered to a patient, they can be administered simultaneously, separately, sequentially, or in combination (e.g., for more than two agents).

In some embodiments, the compounds of the disclosure can be used in combination with INCB086550.

Formulation, Dosage Forms and Administration

When employed as pharmaceuticals, the compounds of the present disclosure can be administered in the form of pharmaceutical compositions. Thus the present disclosure provides a composition comprising a compound of Formula (I), (I'), or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating HPK1 protein in tissue samples, including human, and for identifying HPK1 ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes HPK1 binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}$H (also written as D for deuterium), $^{3}$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. For example, one or more hydrogen atoms in a compound of the present disclosure can be replaced by deuterium atoms (e.g., one or more hydrogen atoms of a $C_{1-6}$ alkyl group of Formula (I) or (I') can be optionally substituted with deuterium atoms, such as —$CD_3$ being substituted for —$CH_3$). In some embodiments, alkyl groups in Formula (I) or (I') can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^3H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from the group consisting of $^3H$, $^{14}C$, $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a HPK1 protein by monitoring its concentration variation when contacting with the HPK1, through tracking of the labeling. For example, a test compound (labeled) can be evaluated for its ability to reduce binding of another compound which is known to bind to a HPK1 protein (i.e., standard compound). Accordingly, the ability of a test compound to compete with the standard compound for binding to the HPK1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of HPK1, such as cancer or infections, which include one or more containers containing a pharmaceutical composition comprising a therapeutically effective amount of a compound of Formula (I), (I'), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of HPK1 according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ C18 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ C18 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge C18 5 μm particle size, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute."

The following abbreviations may be used herein: AcOH (acetic acid); Ac$_2$O (acetic anhydride); aq. (aqueous); atm. (atmosphere(s)); Boc (t-butoxycarbonyl); BOP ((benzotri-azol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N, N'-diisopropyl azidodicarboxylate); DIEA (N,N-diisopropylethylamine); DIPEA (N, N-diisopropylethylamine); DIBAL (diisobutylaluminium hydride); DMF (N, N-dimethylformamide); Et (ethyl); EtOAc (ethyl acetate); FCC (flash column chromatography); g (gram(s)); h (hour(s)); HATU (N, N, N', N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); nM (nanomolar); NMP (N-methylpyrrolidinone); NMR (nuclear magnetic resonance spectroscopy); OTf (trifluoromethanesulfonate); Ph (phenyl); pM (picomolar); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent). Brine is saturated aqueous sodium chloride. In vacuo is under vacuum.

Example 1. N-(2-((1R,4R)-2,5-Diazabicyclo[2.2.1]heptan-2-yl)-5-fluorophenyl)-2-(2-fluoro-6-methoxyphenyl)pyrimidine-4-carboxamide

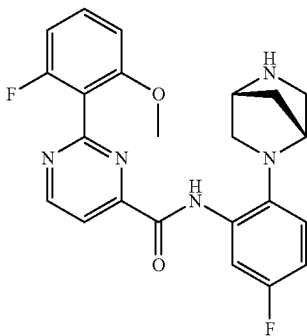 [SMILES: COc1cccc(F)c1-c1nccc(C(=O)Nc2cc(F)ccc2N2C[C@H]3C[C@@H]2CN3)n1]

Step 1. 2-(2-Fluoro-6-methoxyphenyl)pyrimidine-4-carboxylic acid

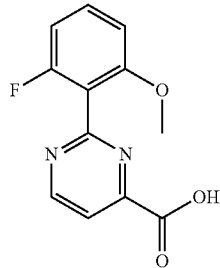 [SMILES: COc1cccc(F)c1-c1nccc(C(=O)O)n1]

A mixture of 2-chloropyrimidine-4-carboxylic acid (9.0 g, 56.8 mmol), (2-fluoro-6-methoxyphenyl)boronic acid (11.58 g, 68.1 mmol), XPhosPd G2 (1.340 g, 1.703 mmol) and potassium phosphate, tribasic (24.10 g, 114 mmol) were combined with 1,4-dioxane (100 mL) and water (20.00 mL). The reaction flask was evacuated, back filled with nitrogen, and then heated to 80° C. for 2 h. The reaction mixture was then cooled to room temperature, treated with water and diluted with ethyl acetate. The aqueous phase was separated and acidified with 1 N HCl. The resulting solid was collected by filtration and washed with water. After air drying, it was used in Step 4 without further purification. LCMS calculated for $C_{12}H_{10}FN_2O_3$ (M+H)$^+$: m/z=249.2; found 249.2.

Step 2. (1R,4R)-tert-Butyl 5-(4-fluoro-2-nitrophenyl)-2,5-diazabicyclo[2.2.1]heptane-2-carboxylate

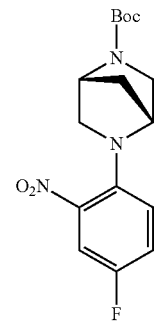 [SMILES: CC(C)(C)OC(=O)N1C[C@H]2C[C@@H]1CN2c1ccc(F)cc1N]

A solution of 1,4-difluoro-2-nitrobenzene (257 mg, 1.6 mmol) and tert-butyl (1R,4R)-2,5-diazabicyclo[2.2.1]heptane-2-carboxylate (320 mg, 1.6 mmol) in DMSO (2.5 mL) was treated with triethylamine (338 μl, 2.4 mmol). The reaction mixture was heated to 80° C. for 3 h. After cooling to room temperature, the reaction mixture was diluted with dichloromethane and washed with brine. The separated organic phase was dried over sodium sulfate and concentrated. The crude product was used in the next step without further purification. LCMS calculated for $C_{12}H_{13}FN_3O_4$ (M+H−$C_4H_8$)$^+$: m/z=282.1; found 282.1.

Step 3. (1R,4R)-tert-Butyl 5-(2-amino-4-fluorophenyl)-2,5-diazabicyclo[2.2.1]heptane-2-carboxylate

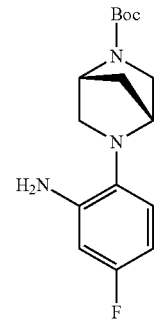

A mixture of tert-butyl (1R,4R)-5-(4-fluoro-2-nitrophenyl)-2,5-diazabicyclo[2.2.1]heptane-2-carboxylate (545 mg, 1.6 mmol), iron (451 mg, 8.1 mmol) and ammonium chloride (518 mg, 9.7 mmol) in THF (2 mL), water (2 mL) and methanol (2 mL) was stirred at 60° C. for 3 h. After cooling to room temperature, the reaction mixture was filtered through a plug of Celite and diluted with dichloromethane. The organic phase was separated, washed with brine, dried over sodium sulfate and the solvents were evaporated in vacuo. The crude product was used in the next step without further purification. LCMS calculated for $C_{16}H_{23}FN_3O_2$ (M+H)$^+$: m/z=308.2; Found: 308.2.

Step 4. N-(2-((1R,4R)-2,5-Diazabicyclo[2.2.1]heptan-2-yl)-5-fluorophenyl)-2-(2-fluoro-6-methoxyphenyl)pyrimidine-4-carboxamide HATU (178 mg, 0.468 mmol) was added to a solution of tert-butyl (1R,4R)-5-(2-amino-4-fluorophenyl)-2,5-diazabicyclo[2.2.1]heptane-2-carboxylate (96 mg, 0.312 mmol), 2-(2-fluoro-6-methoxyphenyl)pyrimidine-4-carboxylic acid (from Step 1; 78 mg, 0.312 mmol) and DIPEA (109 µl, 0.625 mmol) in DMF (2 mL). The reaction mixture was stirred at room temperature for 30 min, and then treated with water. The precipitated product was collected by filtration, washed with water and air dried. The solid residue was then re-dissolved in TFA and the solution was stirred at room temperature for 10 min. The mixture was then diluted with acetonitrile and purified with prep-LCMS (XBridge C18 column, eluting with a gradient of acetonitrile/water containing 0.1% TFA, at flow rate of 60 mL/min) to isolate the title compound as the TFA salt. LCMS calculated for $C_{23}H_{22}F_2N_5O_2$ (M+H)+: m/z=438.2; Found: 438.2.

Example 2. (S)—N-(2-(3-Aminopyrrolidin-1-yl)-5-fluorophenyl)-2-(2-fluoro-6-methoxyphenyl)pyrimidine-4-carboxamide

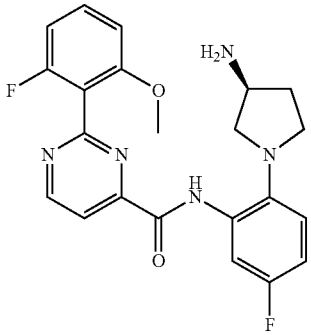 [SMILES: COc1cccc(F)c1-c1nccc(C(=O)Nc2cc(F)ccc2N2CC[C@H](N)C2)n1]

The TFA salt of the title compound was prepared according to the procedures described in Example 1, using (S)-pyrrolidin-3-amine instead of tert-butyl (1R,4R)-2,5-diazabicyclo[2.2.1]heptane-2-carboxylate as starting material. LCMS calculated for $C_{22}H_{22}F_2N_5O_2$ (M+H)+: m/z=426.2; Found: 426.3.

Example 3. (R)—N-(2-(2-(Aminomethyl)pyrrolidin-1-yl)-5-fluorophenyl)-2-(2-fluoro-6-methoxyphenyl)pyrimidine-4-carboxamide

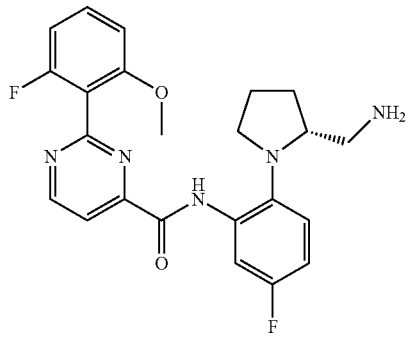 [SMILES: COc1cccc(F)c1-c1nccc(C(=O)Nc2cc(F)ccc2N2CCC[C@@H]2CN)n1]

The TFA salt of the title compound was prepared according to the procedures described in Example 1, using (R)-tert-butyl pyrrolidin-2-ylmethylcarbamate instead of tert-butyl (1R,4R)-2,5-diazabicyclo[2.2.1]heptane-2-carboxylate as starting material. LCMS calculated for $C_{23}H_{24}F_2N_5O_2$ (M+H)+: m/z=440.2; Found: 440.1.

Example 4. (R)—N-(5-Fluoro-2-(2-(hydroxymethyl)pyrrolidin-1-yl)phenyl)-2-(2-fluoro-6-methoxyphenyl)pyrimidine-4-carboxamide

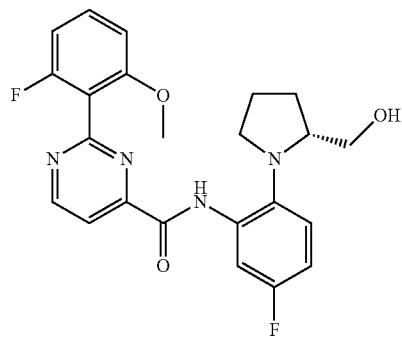 [SMILES: COc1cccc(F)c1-c1nccc(C(=O)Nc2cc(F)ccc2N2CCC[C@@H]2CO)n1]

The TFA salt of the title compound was prepared according to the procedures described in Example 1, using (R)-pyrrolidin-2-ylmethanol instead of tert-butyl (1R,4R)-2,5-diazabicyclo[2.2.1]heptane-2-carboxylate as starting material. LCMS calculated for $C_{23}H_{23}F_2N_4O_3$ (M+H)+: m/z=441.2; Found: 441.1.

Example 5. (R)—N-(5-Fluoro-2-(2-(methoxymethyl)pyrrolidin-1-yl)phenyl)-2-(2-fluoro-6-methoxyphenyl)pyrimidine-4-carboxamide

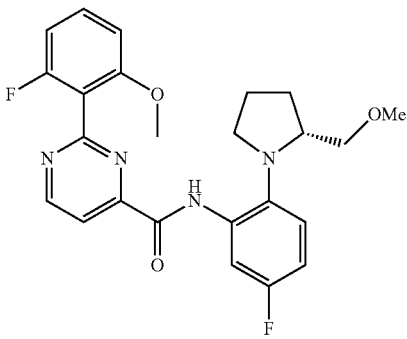 [SMILES: COC[C@H]1CCCN1c1ccc(F)cc1NC(=O)c1ccnc(-c2c(F)cccc2OC)n1]

The TFA salt of the title compound was prepared according to the procedures described in Example 1, using (R)-2-(methoxymethyl)pyrrolidine instead of tert-butyl (1R,4R)-2,5-diazabicyclo[2.2.1]heptane-2-carboxylate as starting material. LCMS calculated for $C_{24}H_{25}F_2N_4O_3$ (M+H)+: m/z=455.2; Found: 455.3.

Example 6. N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide

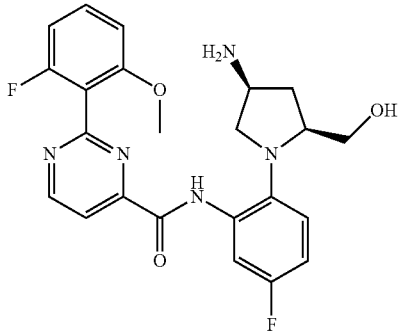 [SMILES: COc1cccc(F)c1-c1nccc(C(=O)Nc2cc(F)ccc2N2C[C@@H](N)C[C@H]2CO)n1]

The free base and TFA salt of the title compound was prepared according to the procedures described in Example 1, (and detailed below) using tert-butyl (3S,5S)-5-(hydroxymethyl)-pyrrolidin-3-ylcarbamate instead of tert-butyl (1R,4R)-2,5-diazabicyclo[2.2.1]heptane-2-carboxylate as starting material.

Step 1. tert-Butyl ((3S,5S)-1-(4-fluoro-2-nitrophenyl)-5-(hydroxymethyl)pyrrolidin-3-yl)carbamate

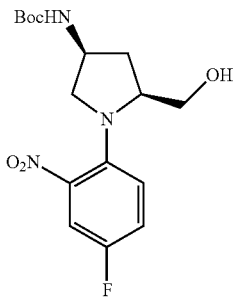 [SMILES: CC(C)(C)OC(=O)N[C@H]1C[C@@H](CO)N(c2ccc(F)cc2[N+](=O)[O-])C1]

A solution of 1,4-difluoro-2-nitrobenzene (68.2 µL, 0.629 mmol) and tert-butyl ((3S,5S)-5-(hydroxymethyl)pyrrolidin-3-yl)carbamate (136 mg, 0.629 mmol) in DMSO (2.5 mL) was treated with triethylamine (131 µL, 0.943 mmol) and the reaction mixture was heated to 80° C. for 3 hrs. After cooling to r.t., the reaction mixture was diluted with DCM, washed with brine, dried over sodium sulfate and the solvent was evaporated under vacuum. The obtained crude product was used in the next step without further purification. LCMS calculated for $C_{12}H_{15}FN_3O_5$ $(M+H-C_4H_8)^+$: m/z=300.1; found 300.1.

Step 2. tert-Butyl ((3S,5S)-1-(2-amino-4-fluorophenyl)-5-(hydroxymethyl)pyrrolidin-3-yl)carbamate A mixture of tert-butyl ((3S,5S)-1-(4-fluoro-2-nitrophenyl)-5-(hydroxymethyl)pyrrolidin-3-yl)carbamate (100 mg, 0.281 mmol), iron (79 mg, 1.407 mmol) and ammonium chloride (90 mg, 1.7 mmol) in THF (2 mL), water (2 mL) and methanol (2 mL) was stirred at 60° C. for 3 hrs. After cooling to r.t., the mixture was filtered through a plug of Celite and diluted with DCM. The organic phase was separated, washed with brine, dried over sodium sulfate and the solvents were evaporated under vacuum. The obtained crude product was used in the next step without further purification. LCMS calculated for $C_{16}H_{25}FN_3O_3$ $(M+H)^+$: m/z=326.2; Found: 326.2.

Step 3. N-(2-((2S,4S)-4-Amino-2-(hydroxymethyl)pyrrolidin-1-yl)-5-fluorophenyl)-2-(2-fluoro-6-methoxyphenyl)pyrimidine-4-carboxamide HATU (175 mg, 0.461 mmol) was added to a solution of tert-butyl ((3S,5S)-1-(2-amino-4-fluorophenyl)-5-(hydroxymethyl)pyrrolidin-3-yl)carbamate (100 mg, 0.307 mmol), 2-(2-fluoro-6-methoxyphenyl)pyrimidine-4-carboxylic acid (the product of Example 1, step 1, 76 mg, 0.307 mmol) and DIPEA (107 µL, 0.615 mmol) in DMF (2 mL). The reaction mixture was stirred at r.t. for 30 mins, then water was added and the precipitated product was collected by filtration, washed with water and air dried. The solid was dissolved in TFA and the resulting solution was stirred at r.t. for 10 mins. The solution was then diluted with acetonitrile and purified with prep-LCMS. LCMS calculated for $C_{23}H_{24}F_2N_5O_3$ $(M+H)^+$: m/z=456.2; Found: 456.3. Prep-LCMS (XBridge C18 column, eluting with a gradient of acetonitrile/water containing 0.1% NH$_4$OH, at flow rate of 60 mL/min). Free base: 1H NMR (600 MHz, DMSO-d$_6$) δ 9.34-9.18 (m, 1H), 8.25-8.19 (m, 1H), 8.18-8.14 (m, 1H), 7.60-7.49 (q, J=7.7 Hz, 1H), 7.49-7.43 (m, 1H), 7.08-7.02 (d, J=8.4 Hz, 1H), 7.02-6.94 (m, 2H), 3.78-3.71 (s, 3H), 3.38-3.30 (t, J=6.4 Hz, 1H), 3.30-3.23 (m, 1H), 3.23-3.17 (m, 1H), 3.17-3.10 (dd, J=11.1, 6.1 Hz, 1H), 2.95-2.88 (t, J=7.4 Hz, 1H), 2.88-2.80 (m, 1H), 2.35-2.25 (dt, J=14.1, 8.0 Hz, 1H), 1.25-1.12 (m, 1H) ppm. Prep-LCMS (XBridge C18 column, eluting with a gradient of acetonitrile/water containing 0.1% TFA, at flow rate of 60 mL/min) TFA salt: 1H NMR (600 MHz, DMSO-d$_6$) δ 10.78-10.58 (s, 1H), 9.32-9.20 (d, J=5.0 Hz, 1H), 8.24-8.08 (m, 2H), 7.93-7.77 (br, J=5.7 Hz, 2H), 7.62-7.53 (td, J=8.4, 6.8 Hz, 1H), 7.53-7.46 (dd, J=8.8, 5.7 Hz, 1H), 7.10-7.02 (m, 2H), 7.02-6.93 (t, J=8.8 Hz, 1H), 3.82-3.73 (s, 3H), 3.75-3.67 (m, 1H), 3.59-3.51 (m, 1H), 3.30-3.15 (m, 4H), 2.44-2.35 (ddd, J=13.6, 9.1, 7.2 Hz, 1H), 1.81-1.71 (dt, J=13.5, 4.3 Hz, 1H) ppm.

Example 7. N-(5-Fluoro-2-((2S,4S)-4-hydroxy-2-methylpyrrolidin-1-yl)phenyl)-2-(2-fluoro-6-methoxyphenyl)pyrimidine-4-carboxamide

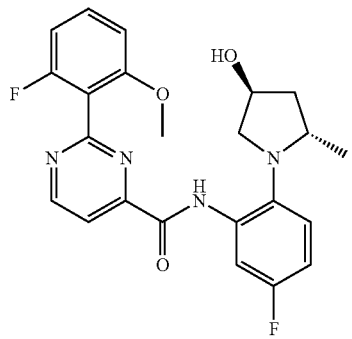 [SMILES: COc1cccc(F)c1-c1nccc(C(=O)Nc2cc(F)ccc2N2C[C@@H](O)C[C@@H]2C)n1]

The TFA salt of the title compound was prepared according to the procedures described in Example 1, using (3S,5S)-5-methylpyrrolidin-3-ol instead of tert-butyl (1R,4R)-2,5-diazabicyclo[2.2.1]heptane-2-carboxylate as starting material. LCMS calculated for $C_{23}H_{23}F_2N_4O_3$ $(M+H)^+$: m/z=441.2; Found: 441.3.

Example 8. N-(5-Fluoro-2-(2-(pyridin-2-yl)pyrrolidin-1-yl)phenyl)-2-(2-fluoro-6-methoxyphenyl)pyrimidine-4-carboxamide

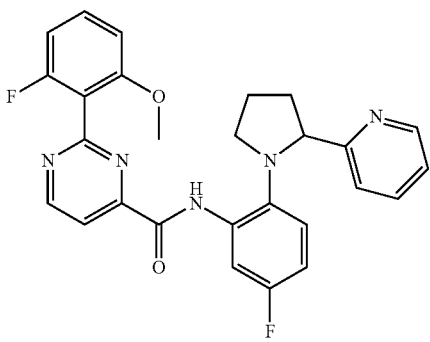 [SMILES: COc1cccc(F)c1-c1nccc(C(=O)Nc2cc(F)ccc2N2CCCC2c2ccccn2)n1]

The TFA salt of the title compound was prepared according to the procedures described in Example 1, using 2-(pyrrolidin-2-yl)pyridine instead of tert-butyl (1R,4R)-2,5-diazabicyclo[2.2.1]heptane-2-carboxylate as starting material. LCMS calculated for $C_{27}H_{24}F_2N_5O_2$ $(M+H)^+$: m/z=488.2; Found: 488.1.

Example 9. N-(5-Fluoro-2-(hexahydropyrrolo[3,4-b]pyrrol-1(2H)-yl)phenyl)-2-(2-fluoro-6-methoxyphenyl)pyrimidine-4-carboxamide

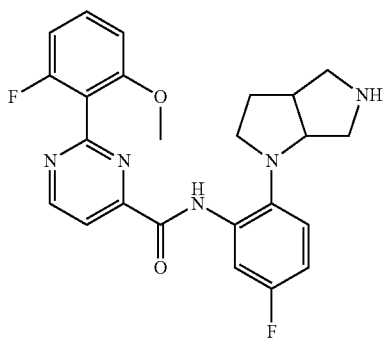 [SMILES: COc1cccc(F)c1-c1nccc(C(=O)Nc2cc(F)ccc2N2CCC3CNCC32)n1]

The TFA salt of the title compound was prepared according to the procedures described in Example 1, using tert-butyl hexahydropyrrolo[3,4-b]pyrrole-5(1H)-carboxylate instead of tert-butyl (1R,4R)-2,5-diazabicyclo[2.2.1]heptane-2-carboxylate as starting material. LCMS calculated for $C_{24}H_{24}F_2N_5O_2$ $(M+H)^+$: m/z=452.2; Found: 452.2.

Example 10. (R)—N-(5-Fluoro-2-(2-methylpiperazin-1-yl)phenyl)-2-(2-fluoro-6-methoxyphenyl)pyrimidine-4-carboxamide

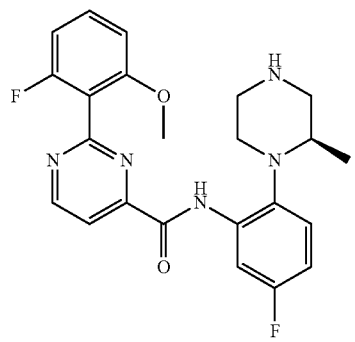 [SMILES: COc1cccc(F)c1-c1nccc(C(=O)Nc2cc(F)ccc2N2CCNC[C@H]2C)n1]

The TFA salt of the title compound was prepared according to the procedures described in Example 1, using (R)-tert-butyl 3-methylpiperazine-1-carboxylate instead of tert-butyl (1R,4R)-2,5-diazabicyclo[2.2.1]heptane-2-carboxylate as starting material. LCMS calculated for $C_{23}H_{24}F_2N_5O_2$ $(M+H)^+$: m/z=440.2; Found: 440.2.

Example 11. (R)—N-(5-Fluoro-2-(2-(hydroxymethyl)piperazin-1-yl)phenyl)-2-(2-fluoro-6-methoxyphenyl)pyrimidine-4-carboxamide

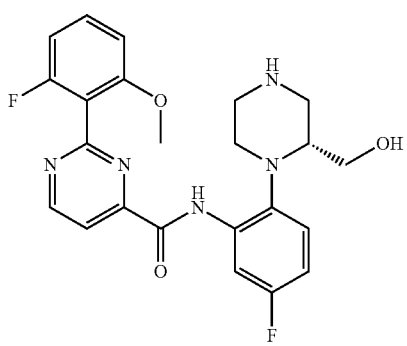 [SMILES: COc1cccc(F)c1-c1nccc(C(=O)Nc2cc(F)ccc2N2CCNC[C@@H]2CO)n1]

The TFA salt of the title compound was prepared according to the procedures described in Example 1, using (R)-tert-butyl 3-(hydroxymethyl)piperazine-1-carboxylate instead of tert-butyl (1R,4R)-2,5-diazabicyclo[2.2.1]heptane-2-carboxylate as starting material. LCMS calculated for $C_{23}H_{24}F_2N_5O_3$ $(M+H)^+$: m/z=456.2; Found: 456.2.

Example 12. N-(5-Fluoro-2-(3-(hydroxymethyl)morpholino)phenyl)-2-(2-fluoro-6-methoxyphenyl)pyrimidine-4-carboxamide

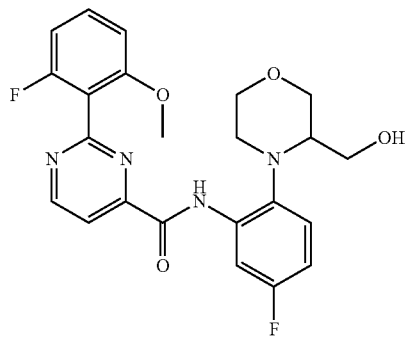 [SMILES: COc1cccc(F)c1-c1nccc(C(=O)Nc2cc(F)ccc2N2CCOCC2CO)n1]

The TFA salt of the title compound was prepared according to the procedures described in Example 1, using morpholin-3-ylmethanol instead of tert-butyl (1R,4R)-2,5-diazabicyclo[2.2.1]heptane-2-carboxylate as starting material. LCMS calculated for $C_{23}H_{23}F_2N_4O_4$ (M+H)$^+$: m/z=457.2; Found: 457.2.

Example 13. N-(2-((1R,4R)-2,5-Diazabicyclo[2.2.1]heptan-2-yl)-3-bromo-5-fluorophenyl)-2-(2-fluoro-6-methoxyphenyl)pyrimidine-4-carboxamide

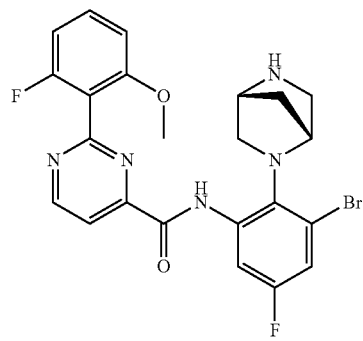 [SMILES: COc1cccc(F)c1-c1nccc(C(=O)Nc2cc(F)cc(Br)c2N2C[C@H]3C[C@@H]2CN3)n1]

The TFA salt of the title compound was prepared according to the procedures described in Example 1, using 1-bromo-2,5-difluoro-3-nitrobenzene instead of 1,4-difluoro-2-nitrobenzene as starting material. LCMS calculated for $C_{23}H_{21}BrF_2N_5O_2$ (M+H)$^+$: m/z=516.1; Found: 516.1.

Example 14. N-(2-((1R,4R)-2,5-Diazabicyclo[2.2.1]heptan-2-yl)-3-cyanophenyl)-2-(2-fluoro-6-methoxyphenyl)pyrimidine-4-carboxamide

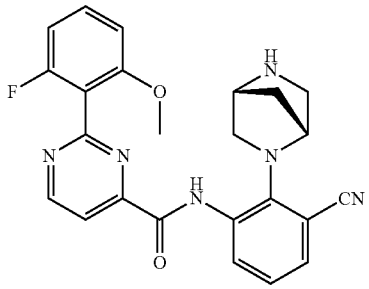 [SMILES: COc1cccc(F)c1-c1nccc(C(=O)Nc2cccc(C#N)c2N2C[C@H]3C[C@@H]2CN3)n1]

The TFA salt of the title compound was prepared according to the procedures described in Example 1, using 2-fluoro-3-nitrobenzonitrile instead of 1,4-difluoro-2-nitrobenzene as starting material. LCMS calculated for $C_{24}H_{22}FN_6O_2$ (M+H)$^+$: m/z=445.2; Found: 445.2.

Example 15. N-(2-((1R,4R)-2,5-Diazabicyclo[2.2.1]heptan-2-yl)-5-fluoro-3-(pyridin-3-yl)phenyl)-2-(2-fluoro-6-methoxyphenyl)pyrimidine-4-carboxamide A mixture of tert-butyl (1R,4R)-5-(2-bromo-4-fluoro-6-(2-(2-fluoro-6-methoxyphenyl)pyrimidine-4-carboxamido)phenyl)-2,5-diazabicyclo[2.2.1]heptane-2-carboxylate (from Example 13; 10 mg, 0.016 mmol), pyridin-3-ylboronic acid (4 mg, 0.032 mmol), XPhosPd G2 (1.3 mg, 1.6 µmol) and potassium phosphate, tribasic (6.7 mg, 0.032 mmol) was combined with 1,4-dioxane (1 mL) and water (0.1 mL). The reaction flask was evacuated, back filled with nitrogen, and the mixture was stirred at 80° C. for 1 h. The reaction mixture was cooled to room temperature and the solvents were evaporated in vacuo. The residue was combined with TFA (1 mL) and stirred at room temperature for 10 min. The reaction mixture was diluted with CH$_3$CN and water and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{28}H_{25}F_2N_6O_2$ (M+H)$^+$: m/z=515.2; Found: 515.3.

Example 16. N-(2-((1R,4R)-2,5-Diazabicyclo[2.2.1]heptan-2-yl)-5-fluoro-3-(1-methyl-1H-pyrazol-4-yl)phenyl)-2-(2-fluoro-6-methoxyphenyl)pyrimidine-4-carboxamide

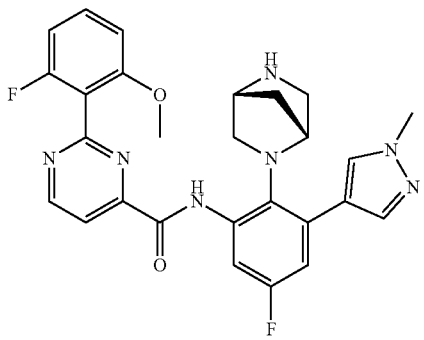 [SMILES: COc1cccc(F)c1-c1nccc(C(=O)Nc2cc(F)cc(-c3cnn(C)c3)c2N2C[C@H]3C[C@@H]2CN3)n1]

The TFA salt of the title compound was prepared according to the procedures described in Example 15, using 1-methyl-4-(4,4,5,5-tetramethyl-1,3,2-dioxaborolan-2-yl)-1H-pyrazole instead of pyridin-3-ylboronic acid as starting material. LCMS calculated for $C_{27}H_{26}F_2N_7O_2$ (M+H)$^+$: m/z=518.2; Found: 518.3.

Example 17. N-(2-((1S,4S)-2,5-Diazabicyclo[2.2.1]heptan-2-yl)-5-fluoro-4-(hydroxymethyl)phenyl)-2-(2-fluoro-6-methoxyphenyl)pyrimidine-4-carboxamide

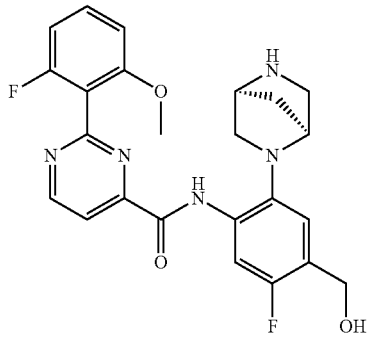 [SMILES: COc1cccc(F)c1-c1nccc(C(=O)Nc2cc(F)c(CO)cc2N2C[C@@H]3C[C@H]2CN3)n1]

The TFA salt of the title compound was prepared according to the procedures described in Example 1, using (2,5-difluoro-4-nitrophenyl)methanol instead of 1,4-difluoro-2-nitrobenzene and tert-butyl (1S,4S)-2,5-diazabicyclo[2.2.1]heptane-2-carboxylate instead of tert-butyl (1R,4R)-2,5-diazabicyclo[2.2.1]heptane-2-carboxylate as starting material. LCMS calculated for $C_{24}H_{24}F_2N_5O_3$ (M+H)$^+$: m/z=468.2; Found: 468.2. $^1$H NMR (600 MHz, DMSO-d$_6$) δ 10.81-10.70 (s, 1H), 9.33-9.25 (d, J=5.0 Hz, 1H), 8.19-8.12 (d, J=5.0 Hz, 1H), 8.12-8.04 (d, J=11.4 Hz, 1H), 7.63-7.52 (q, J=7.9 Hz, 1H), 7.38-7.28 (d, J=7.2 Hz, 1H), 7.13-7.06 (d, J=8.5 Hz, 1H), 7.05-6.95 (t, J=8.8 Hz, 1H), 5.28-5.16 (s, 1H), 4.57-4.42 (s, 2H), 3.82-3.71 (s, 3H), 3.70-3.60 (s, 1H), 3.54-3.46 (s, 1H), 3.26-3.17 (d, J=9.0 Hz, 1H), 3.12-3.04 (d, J=9.0 Hz, 1H), 2.92-2.86 (d, J=10.0 Hz, 1H), 2.67-2.59 (d, J=9.7 Hz, 1H), 1.65-1.59 (d, J=9.3 Hz, 1H), 1.54-1.38 (d, J=9.1 Hz, 1H) ppm.

Example 18. N-(2-((1S,4S)-2,5-Diazabicyclo[2.2.1]heptan-2-yl)-4-bromo-5-fluorophenyl)-2-(2-fluoro-6-methoxyphenyl)pyrimidine-4-carboxamide

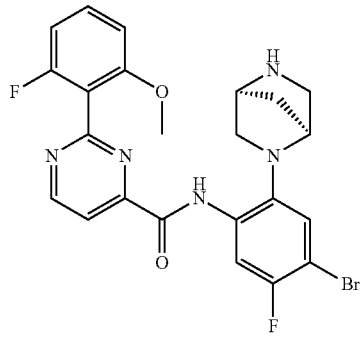 [SMILES: COc1cccc(F)c1-c1nccc(C(=O)Nc2cc(F)c(Br)cc2N2C[C@@H]3C[C@H]2CN3)n1]

The TFA salt of the title compound was prepared according to the procedures described in Example 1, using 1-bromo-2,5-difluoro-4-nitrobenzene instead of 1,4-difluoro-2-nitrobenzene and tert-butyl (1S,4S)-2,5-diazabicyclo[2.2.1]heptane-2-carboxylate instead of tert-butyl (1R,4R)-2,5-diazabicyclo[2.2.1]heptane-2-carboxylate as starting material. LCMS calculated for $C_{23}H_{21}BrF_2N_5O_2$ (M+H)$^+$: m/z=516.1; Found: 516.1.

Example 19. N-(2-((1S,4S)-2,5-Diazabicyclo[2.2.1]heptan-2-yl)-5-fluoro-4-(1-methyl-1H-pyrazol-4-yl)phenyl)-2-(2-fluoro-6-methoxyphenyl)pyrimidine-4-carboxamide

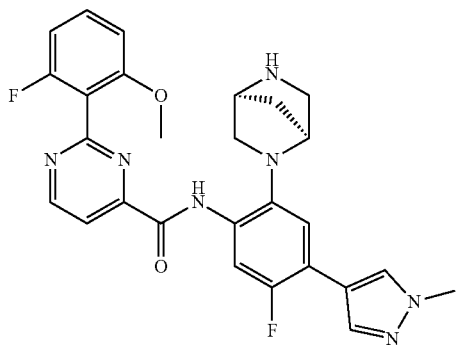 [SMILES: COc1cccc(F)c1-c1nccc(C(=O)Nc2cc(F)c(-c3cnn(C)c3)cc2N2C[C@@H]3C[C@H]2CN3)n1]

A mixture of tert-butyl (1S,4S)-5-(5-bromo-4-fluoro-2-(2-(2-fluoro-6-methoxyphenyl)pyrimidine-4-carboxamido)phenyl)-2,5-diazabicyclo[2.2.1]heptane-2-carboxylate (from Example 18; 10 mg, 0.016 mmol), 1-methyl-4-(4,4,5,5-tetramethyl-1,3,2-dioxaborolan-2-yl)-1H-pyrazole (6.8 mg, 0.032 mmol), XPhosPd G2 (1.3 mg, 1.6 µmol) and potassium phosphate, tribasic (6.7 mg, 0.032 mmol) was combined with 1,4-dioxane (1 mL) and water (0.1 mL). The reaction flask was evacuated, back filled with nitrogen, then stirred at 80° C. for 1 h. The reaction mixture was cooled to room temperature, the solvents were evaporated in vacuo, and TFA (1 mL) was added. The reaction mixture was stirred at room temperature for 10 min, then diluted with CH$_3$CN and water and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{27}H_{26}F_2N_7O_2$ (M+H)$^+$: m/z=518.2; Found: 518.3. $^1$H NMR (600 MHz, DMSO-$d_6$) δ 10.58 (s, 1H), 9.30 (d, J=4.9 Hz, 1H), 8.94 (br, 2H), 8.20-8.15 (m, 2H), 8.14 (s, 1H), 7.94 (s, 1H), 7.67-7.53 (m, 2H), 7.09 (d, J=8.5 Hz, 1H), 7.02 (t, J=8.7 Hz, 1H), 4.41 (s, 1H), 4.04 (s, 1H), 3.91 (s, 3H), 3.78 (s, 3H), 3.51 (d, J=11.0 Hz, 1H), 3.42 (d, J=11.2 Hz, 1H), 3.34-3.20 (m, 1H), 3.03 (s, 1H), 1.91 (d, J=10.6 Hz, 1H), 1.77 (d, J=10.7 Hz, 1H) ppm.

Example 20. N-(2-((1S,4S)-2,5-Diazabicyclo[2.2.1] heptan-2-yl)-5-fluoro-4-(6-(hydroxymethyl)pyridin-3-yl)phenyl)-2-(2-fluoro-6-methoxyphenyl)pyrimidine-4-carboxamide

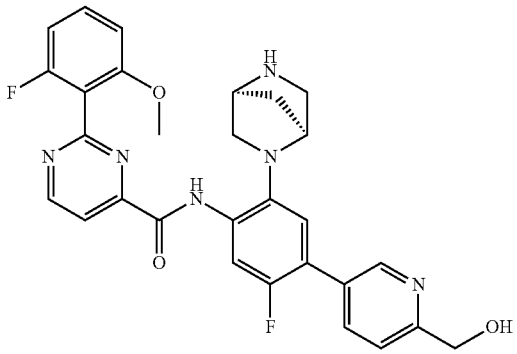 [SMILES: COc1cccc(F)c1-c1nccc(C(=O)Nc2cc(F)c(-c3ccc(CO)nc3)cc2N2C[C@@H]3C[C@H]2CN3)n1]

The TFA salt of the title compound was prepared according to the procedures described in Example 19, using (5-(4,4,5,5-tetramethyl-1,3,2-dioxaborolan-2-yl)pyridin-2-yl)methanol instead of 1-methyl-4-(4,4,5,5-tetramethyl-1,3,2-dioxaborolan-2-yl)-1H-pyrazole as starting material. LCMS calculated for $C_{29}H_{27}F_2N_6O_3$ (M+H)$^+$: m/z=545.2; Found: 545.3.

Example 21. N-(2-((1S,4S)-2,5-Diazabicyclo[2.2.1] heptan-2-yl)-5-fluoro-4-(6-(methylcarbamoyl)pyridin-3-yl)phenyl)-2-(2-fluoro-6-methoxyphenyl)pyrimidine-4-carboxamide

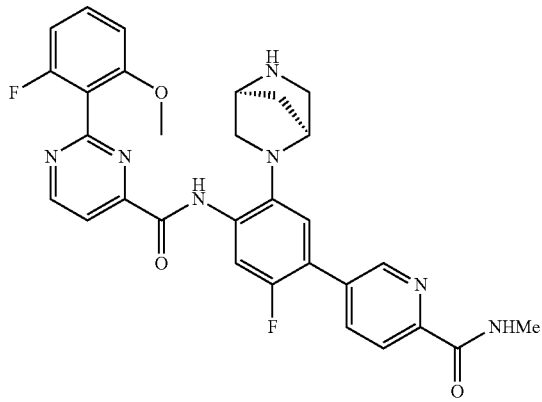 [SMILES: CNC(=O)c1ccc(-c2cc(N3C[C@@H]4C[C@H]3CN4)c(NC(=O)c3ccnc(-c4c(F)cccc4OC)n3)cc2F)cn1]

The TFA salt of the title compound was prepared according to the procedures described in Example 19, using N-methyl-5-(4,4,5,5-tetramethyl-1,3,2-dioxaborolan-2-yl)picolinamide instead of 1-methyl-4-(4,4,5,5-tetramethyl-1,3,2-dioxaborolan-2-yl)-1H-pyrazole as starting material. LCMS calculated for $C_{30}H_{28}F_2N_7O_3$ (M+H)$^+$: m/z=572.2; Found: 572.3.

Example 22. N-(2-((1S,4S)-2,5-Diazabicyclo[2.2.1] heptan-2-yl)-5-fluoro-4-(1-methyl-6-oxo-1,6-dihydropyridin-3-yl)phenyl)-2-(2-fluoro-6-methoxyphenyl)pyrimidine-4-carboxamide

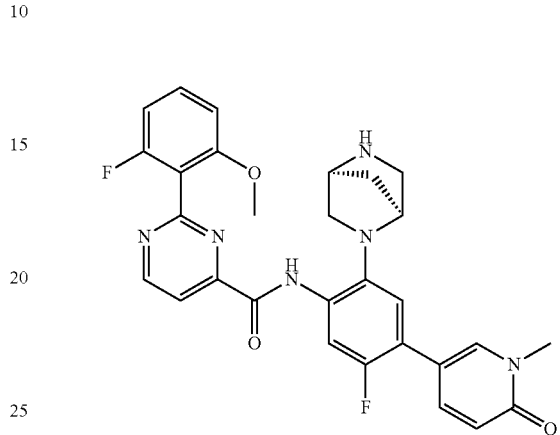

The TFA salt of the title compound was prepared according to the procedures described in Example 19, using 1-methyl-5-(4,4,5,5-tetramethyl-1,3,2-dioxaborolan-2-yl)pyridin-2(1H)-one instead of 1-methyl-4-(4,4,5,5-tetramethyl-1,3,2-dioxaborolan-2-yl)-1H-pyrazole as starting material. LCMS calculated for $C_{29}H_{27}F_2N_6O_3$ (M+H)$^+$: m/z=545.2; Found: 545.3.

Example 23. N-(2-((1S,4S)-2,5-Diazabicyclo[2.2.1] heptan-2-yl)-5-fluoro-4-(2-methylpyridin-3-yl)phenyl)-2-(2-fluoro-6-methoxyphenyl)pyrimidine-4-carboxamide

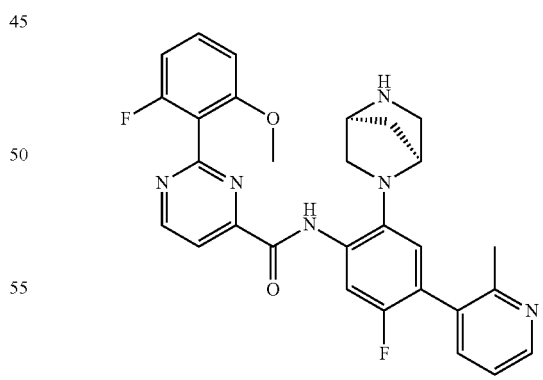

The TFA salt of the title compound was prepared according to the procedures described in Example 19, using 2-methylpyridin-3-ylboronic acid instead of 1-methyl-4-(4,4,5,5-tetramethyl-1,3,2-dioxaborolan-2-yl)-1H-pyrazole as starting material. LCMS calculated for $C_{29}H_{27}F_2N_6O_2$ (M+H)$^+$: m/z=529.2; Found: 529.3.

Example 24. N-(2-((1S,4S)-2,5-Diazabicyclo[2.2.1]heptan-2-yl)-4-(2-methylpyridin-3-yl)phenyl)-2-(2-fluoro-6-methoxyphenyl)pyrimidine-4-carboxamide

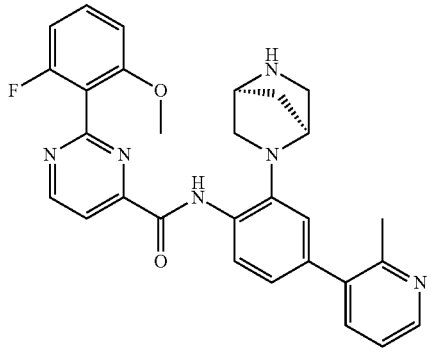 [SMILES: COc1cccc(F)c1-c1nccc(C(=O)Nc2ccc(-c3cccnc3C)cc2N2C[C@@H]3C[C@H]2CN3)n1]

Step 1. (1S,4S)-tert-Butyl 5-(5-bromo-2-(2-(2-fluoro-6-methoxyphenyl)pyrimidine-4-carboxamido)phenyl)-2,5-diazabicyclo[2.2.1]heptane-2-carboxylate

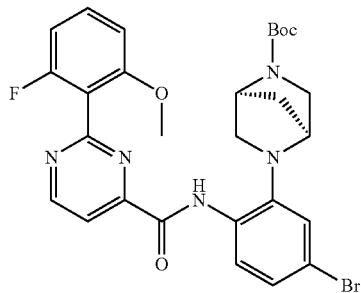 [SMILES: COc1cccc(F)c1-c1nccc(C(=O)Nc2ccc(Br)cc2N2C[C@@H]3C[C@H]2CN3C(=O)OC(C)(C)C)n1]

This compound was prepared according to the procedures described in Example 18, using 4-bromo-2-fluoro-1-nitrobenzene instead of 1-bromo-2,5-difluoro-4-nitrobenzene as starting material. LCMS calculated for $C_{28}H_{30}BrFN_5O_4$ (M+H)$^+$: m/z=598.2; Found: 598.2.

Step 2. N-(2-((1S,4S)-2,5-Diazabicyclo[2.2.1]heptan-2-yl)-4-(2-methylpyridin-3-yl)phenyl)-2-(2-fluoro-6-methoxyphenyl)pyrimidine-4-carboxamide A mixture of tert-butyl (1S,4S)-5-(5-bromo-2-(2-(2-fluoro-6-methoxyphenyl)pyrimidine-4-carboxamido)phenyl)-2,5-diazabicyclo[2.2.1]heptane-2-carboxylate (10 mg, 0.017 mmol), (2-methylpyridin-3-yl)boronic acid (4.6 mg, 0.033 mmol), XPhosPd G2 (1.3 mg, 1.6 µmol) and potassium phosphate, tribasic (6.7 mg, 0.032 mmol) was combined with 1,4-dioxane (1 mL) and water (0.1 mL). The reaction flask was evacuated, back filled with nitrogen, then stirred at 80° C. for 1 h. The reaction mixture was cooled to room temperature, the solvents were evaporated in vacuo and TFA (1 mL) was added. The reaction mixture was stirred at room temperature for 10 min, then diluted with CH$_3$CN and water and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{29}H_{28}FN_6O_2$ (M+H)$^+$: m/z=511.2; Found: 511.2. $^1$H NMR (600 MHz, DMSO-d$_6$) δ 10.54-10.46 (s, 1H), 9.33-9.18 (d, J=5.0 Hz, 1H), 9.06-8.91 (s, 1H), 8.80-8.74 (s, 1H), 8.67-8.63 (dd, J=5.2, 1.8 Hz, 1H), 8.20-8.14 (d, J=5.0 Hz, 1H), 8.14-8.09 (d, J=8.2 Hz, 1H), 8.09-7.98 (d, J=8.1 Hz, 1H), 7.70-7.61 (m, 1H), 7.61-7.55 (td, J=8.4, 6.8 Hz, 1H), 7.31-7.27 (d, J=1.9 Hz, 1H), 7.21-7.15 (dd, J=8.2, 1.8 Hz, 1H), 7.12-7.06 (d, J=8.5 Hz, 1H), 7.06-6.96 (t, J=8.8 Hz, 1H), 4.39-4.30 (s, 1H), 4.28-4.17 (s, 1H), 3.84-3.71 (s, 3H), 3.62-3.52 (m, 1H), 3.39-3.34 (d, J=11.2 Hz, 1H), 3.34-3.28 (m, 1H), 3.15-3.04 (m, 1H), 2.63-2.58 (s, 3H), 1.97-1.90 (dd, J=10.8, 2.5 Hz, 1H), 1.84-1.67 (m, 1H).

Example 25. N-(2-((1S,4S)-2,5-Diazabicyclo[2.2.1]heptan-2-yl)-4-(4-methoxypyridin-3-yl)phenyl)-2-(2-fluoro-6-methoxyphenyl)pyrimidine-4-carboxamide

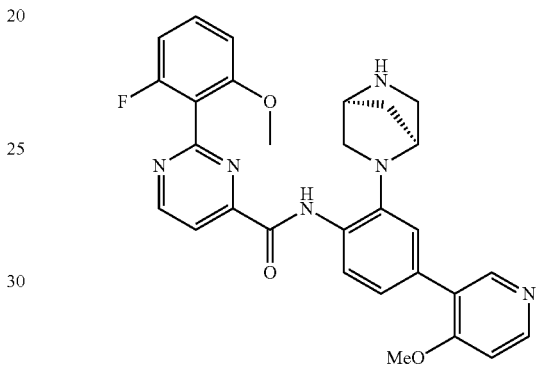

The TFA salt of the title compound was prepared according to the procedures described in Example 24, using 4-methoxypyridin-3-ylboronic acid instead of (2-methylpyridin-3-yl)boronic acid as starting material. LCMS calculated for $C_{29}H_{28}FN_6O_3$ (M+H)$^+$: m/z=527.2; Found: 527.2.

Example 26. N-(2-((1S,4S)-2,5-Diazabicyclo[2.2.1]heptan-2-yl)-4-(4-cyanopyridin-3-yl)phenyl)-2-(2-fluoro-6-methoxyphenyl)pyrimidine-4-carboxamide

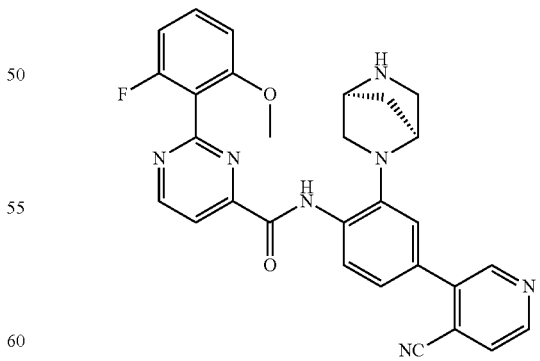

The TFA salt of the title compound was prepared according to the procedures described in Example 24, (and detailed below) using 3-(4,4,5,5-tetramethyl-1,3,2-dioxaborolan-2-yl)isonicotinonitrile instead of (2-methylpyridin-3-yl)boronic acid as starting material.

Step 1. tert-Butyl (1S,4S)-5-(5-bromo-2-nitrophenyl)-2,5-diazabicyclo[2.2.1]heptane-2-carboxylate

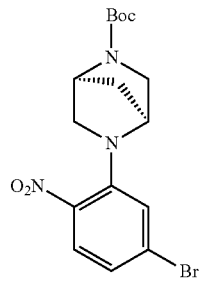

To a solution of 4-bromo-2-fluoro-1-nitrobenzene (500 mg, 2.3 mmol) and tert-butyl (1S,4S)-2,5-diazabicyclo[2.2.1]heptane-2-carboxylate (451 mg, 2.3 mmol) in DMSO (8 mL) was added triethylamine (475 µl, 3.41 mmol) and the reaction mixture was heated to 80° C. for 2 hr. After cooling to r.t., water was added and the precipitated product was collected by filtration, washed with water and air dried. It was used in the next step without further purification. LCMS calculated for $C_{16}H_{21}BrN_3O_4$ (M+H)$^+$: m/z=398.1/400.1; found 398.1/400.1.

Step 2. tert-Butyl (1S,4S)-5-(2-amino-5-bromophenyl)-2,5-diazabicyclo[2.2.1]heptane-2-carboxylate

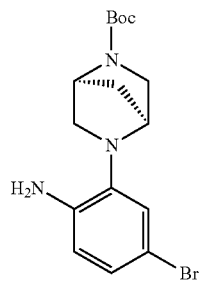

A mixture of tert-butyl (1S,4S)-5-(5-bromo-2-nitrophenyl)-2,5-diazabicyclo[2.2.1]heptane-2-carboxylate (914 mg, 2.295 mmol), iron (684 mg, 12.25 mmol) and ammonium chloride (786 mg, 14.70 mmol) in THF (5 mL), water (5 mL) and methanol (5 mL) was stirred at 60° C. for 3 hrs. After cooling to r.t., it was filtered through a plug of Celite and diluted with DCM. The organic phase was separated, washed with brine, dried over sodium sulfated and the solvents were evaporated in vacuo. The obtained crude product was used in the next step without further purification. LCMS calculated for $C_{16}H_{23}BrN_3O_2$ (M+H)$^+$: m/z=368.1/370.1; Found: 368.1/370.1.

Step 3. tert-Butyl (1S,4S)-5-(5-bromo-2-(2-(2-fluoro-6-methoxyphenyl)pyrimidine-4-carboxamido)phenyl)-2,5-diazabicyclo[2.2.1]heptane-2-carboxylate

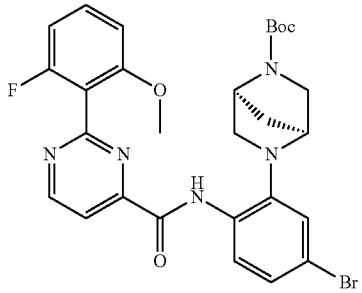 [SMILES: COc1cccc(F)c1-c1nccc(C(=O)Nc2ccc(Br)cc2N2C[C@@H]3C[C@H]2CN3C(=O)OC(C)(C)C)n1]

A solution of tert-butyl (1S,4S)-5-(2-amino-5-bromophenyl)-2,5-diazabicyclo[2.2.1]heptane-2-carboxylate (845 mg, 2.294 mmol), 2-(2-fluoro-6-methoxyphenyl)pyrimidine-4-carboxylic acid (the product of Example 1, Step 1, 570 mg, 2.3 mmol) and DIPEA (800 µl, 4.6 mmol) in DMF (5 mL) was treated with HATU (1.3 g, 3.4 mmol). The reaction mixture was stirred at r.t. for 30 mins, then water was added and the precipitated product was collected by filtration, washed with water and air dried. The crude product was used in the next step without further purification. LCMS calculated for $C_{28}H_{30}BrFN_5O_4$ (M+H)$^+$: m/z=598.2/600.2; Found: 598.2/600.2.

Step 4. N-(2-((1S,4S)-2,5-Diazabicyclo[2.2.1]heptan-2-yl)-4-(4-cyanopyridin-3-yl)phenyl)-2-(2-fluoro-6-methoxyphenyl)pyrimidine-4-carboxamide A mixture of tert-butyl (1S,4S)-5-(5-bromo-2-(2-(2-fluoro-6-methoxyphenyl)pyrimidine-4-carboxamido)phenyl)-2,5-diazabicyclo[2.2.1]heptane-2-carboxylate (10 mg, 0.017 mmol), 3-(4,4,5,5-tetramethyl-1,3,2-dioxaborolan-2-yl)isonicotinonitrile (9.8 mg, 0.043 mmol), Xphos Pd G2 (1.3 mg, 1.6 µmol) and potassium phosphate, tribasic (6.7 mg, 0.032 mmol) in 1,4-dioxane (1 mL) and water (0.1 mL) was degassed by evacuation and back filling with nitrogen. The reaction mixture was stirred at 80° C. for 1 hr, cooled to r.t. and the solvents were evaporated in vacuo. TFA (1 mL) was added to the residue and the reaction mixture was stirred at r.t. for 10 min, then diluted with CH$_3$CN and water and purified with prep-LCMS (XBridge C18 column, eluting with a gradient of acetonitrile/water containing 0.1% TFA, at flow rate of 60 mL/min). LCMS calculated for $C_{29}H_{25}FN_7O_2$ (M+H)$^+$: m/z=522.2; Found: 522.3. $^1$H NMR (600 MHz, DMSO-d$_6$) δ 10.60-10.51 (s, 1H), 9.33-9.22 (d, J=4.9 Hz, 1H), 9.08-9.00 (m, 1H), 9.01-8.95 (s, 1H), 8.88-8.80 (d, J=4.9 Hz, 1H), 8.81-8.70 (m, 1H), 8.21-8.15 (d, J=4.9 Hz, 1H), 8.15-8.10 (d, J=8.2 Hz, 1H), 8.06-8.00 (d, J=5.0 Hz, 1H), 7.60-7.53 (q, J=7.9 Hz, 1H), 7.53-7.49 (s, 1H), 7.40-7.32 (d, J=8.1 Hz, 1H), 7.13-7.07 (d, J=8.5 Hz, 1H), 7.05-6.95 (t, J=8.8 Hz, 1H), 4.42-4.35 (s, 1H), 4.32-4.24 (s, 1H), 3.84-3.76 (s, 3H), 3.67-3.58 (d, J=11.0 Hz, 1H), 3.46-3.35 (d, J=10.9 Hz, 2H), 3.15-3.04 (dd, J=11.6, 8.2 Hz, 1H), 1.99-1.92 (d, J=10.8 Hz, 1H), 1.89-1.75 (d, J=10.7 Hz, 1H).

Example 27. N-(2-((1S,4S)-2,5-Diazabicyclo[2.2.1]heptan-2-yl)-4-(1,3,5-trimethyl-1H-pyrazol-4-yl)phenyl)-2-(2-fluoro-6-methoxyphenyl)pyrimidine-4-carboxamide

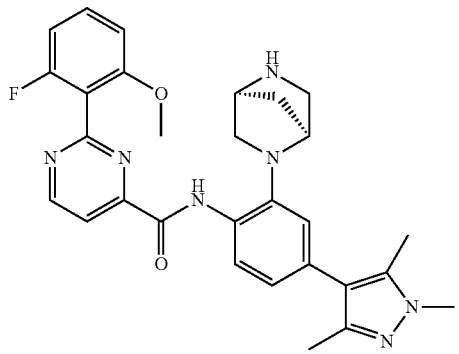 [SMILES: COc1cccc(F)c1-c1nccc(C(=O)Nc2ccc(-c3c(C)nn(C)c3C)cc2N2C[C@@H]3C[C@H]2CN3)n1]

The TFA salt of the title compound was prepared according to the procedures described in Example 24, using 1,3,5-trimethyl-4-(4,4,5,5-tetramethyl-1,3,2-dioxaborolan-2-yl)-1H-pyrazole instead of (2-methylpyridin-3-yl)boronic acid as starting material. LCMS calculated for $C_{29}H_{31}FN_7O_2$ $(M+H)^+$: m/z=528.2; Found: 528.2.

Example 28. N-(2-((1S,4S)-2,5-Diazabicyclo[2.2.1]heptan-2-yl)-5-fluoro-4-morpholinophenyl)-2-(2-fluoro-6-methoxyphenyl)pyrimidine-4-carboxamide

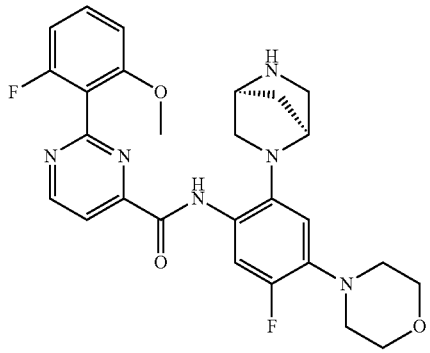 [SMILES: COc1cccc(F)c1-c1nccc(C(=O)Nc2cc(F)c(N3CCOCC3)cc2N2C[C@@H]3C[C@H]2CN3)n1]

A mixture of tert-butyl (1S,4S)-5-(5-bromo-4-fluoro-2-(2-(2-fluoro-6-methoxyphenyl)pyrimidine-4-carboxamido)phenyl)-2,5-diazabicyclo[2.2.1]heptane-2-carboxylate (from Example 18, 10 mg, 0.016 mmol), morpholine (1.4 mg, 0.016 mmol), RuPhosPd G2 (1.2 mg, 1.6 µmol) and cesium carbonate (10.6 mg, 0.032 mmol) was combined with 1,4-dioxane (1 mL). The reaction flask was evacuated, back filled with nitrogen, and stirred at 100° C. for 3 h. The reaction mixture was cooled to room temperature, the solvents were evaporated in vacuo and TFA (1 mL) was added. The reaction mixture was stirred at room temperature for 10 min, then diluted with $CH_3CN$ and water and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{27}H_{29}F_2N_6O_3$ $(M+H)^+$: m/z=523.2; Found: 523.2.

Example 29. N-(4-(Azetidin-1-yl)-2-((1S,4S)-2,5-diazabicyclo[2.2.1]heptan-2-yl)-5-fluorophenyl)-2-(2-fluoro-6-methoxyphenyl)pyrimidine-4-carboxamide

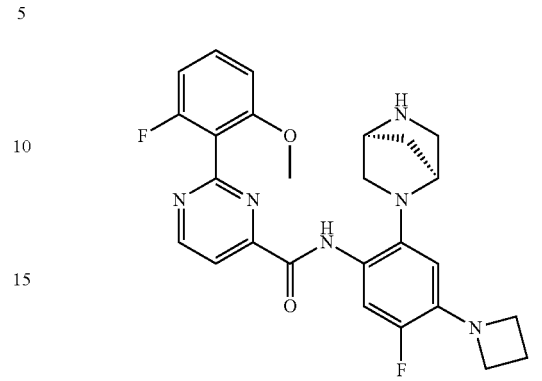

The TFA salt of the title compound was prepared according to the procedures described in Example 28, using azetidine instead of morpholine as starting material. LCMS calculated for $C_{26}H_{27}F_2N_6O_2$ $(M+H)^+$: m/z=493.2; Found: 493.2.

Example 30. N-(2-((1S,4S)-2,5-Diazabicyclo[2.2.1]heptan-2-yl)-5-fluoro-4-(morpholinomethyl)phenyl)-2-(2-fluoro-6-methoxyphenyl)pyrimidine-4-carboxamide

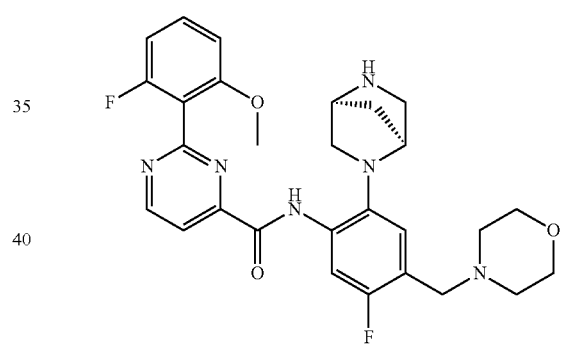

Step 1. (1S,4S)-tert-Butyl 5-(4-fluoro-2-(2-(2-fluoro-6-methoxyphenyl)pyrimidine-4-carboxamido)-5-formylphenyl)-2,5-diazabicyclo[2.2.1]heptane-2-carboxylate

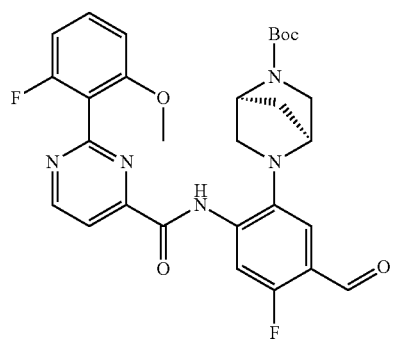 [SMILES: COc1cccc(F)c1-c1nccc(C(=O)Nc2cc(F)c(C=O)cc2N2C[C@@H]3C[C@H]2CN3C(=O)OC(C)(C)C)n1]

Dess-Martin periodinane (269 mg, 0.634 mmol) was added to a solution of tert-butyl (1S,4S)-5-(4-fluoro-2-(2-(2-fluoro-6-methoxyphenyl)pyrimidine-4-carboxamido)-5-(hydroxymethyl)phenyl)-2,5-diazabicyclo[2.2.1]heptane-2-carboxylate (Example 17, 300 mg, 0.529 mmol) and pyridine (51.0 µl, 0.63 mmol) in dichloromethane (5 mL). After stirring at room temperature for 1 h, the solvent was evaporated in vacuo and the crude product was purified by BiotageIsolera™. LCMS calculated for $C_{29}H_{30}F_2N_5O_5$ (M+H)⁺ m/z=566.2; found 566.3.

Step 2. N-(2-((1S,4S)-2,5-Diazabicyclo[2.2.1]heptan-2-yl)-5-fluoro-4-(morpholinomethyl)phenyl)-2-(2-fluoro-6-methoxyphenyl)pyrimidine-4-carboxamide Sodium triacetoxyborohydride (7.5 mg, 0.035 mmol) was added to a solution of morpholine (1.5 mg, 0.018 mmol), acetic acid (2 µl, 0.035 mmol) and tert-butyl (1S,4S)-5-(4-fluoro-2-(2-(2-fluoro-6-methoxyphenyl)pyrimidine-4-carboxamido)-5-formylphenyl)-2,5-diazabicyclo[2.2.1]heptane-2-carboxylate (10 mg, 0.018 mmol) in dichloroethane (1 mL). The reaction mixture was stirred at room temperature for 2 h, and then treated with water. The aqueous phase was extracted with ethyl acetate, and the combined organic phases were washed with brine, dried over sodium sulfate and concentrated. The crude residue was taken up in TFA (1 mL) and the reaction was stirred at room temperature for 30 min. The reaction mixture was then diluted with acetonitrile and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{28}H_{31}F_2N_6O_3$ (M+H)⁺: m/z=537.2; Found: 537.3.

Example 31. N-(2-((1S,4S)-2,5-Diazabicyclo[2.2.1]heptan-2-yl)-4-((cyclobutylamino)methyl)-5-fluorophenyl)-2-(2-fluoro-6-methoxyphenyl)pyrimidine-4-carboxamide

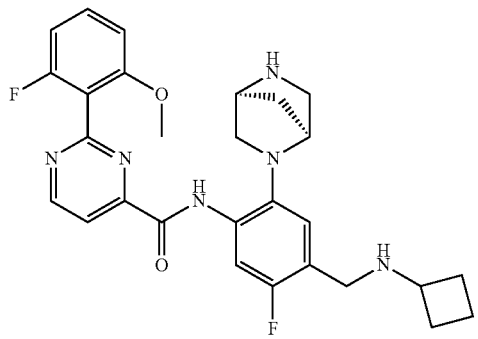 [SMILES: COc1cccc(F)c1-c1nccc(C(=O)Nc2cc(F)c(CNC3CCC3)cc2N2C[C@@H]3C[C@H]2CN3)n1]

The TFA salt of the title compound was prepared according to the procedures described in Example 30, using cyclobutanamine instead of morpholine as starting material. LCMS calculated for $C_{28}H_{31}F_2N_6O_2$ (M+H)⁺: m/z=521.2; Found: 521.2.

Example 32. N-(2-((1R,4R)-5-Ethyl-2,5-diazabicyclo[2.2.1]heptan-2-yl)-5-fluorophenyl)-2-(2-fluoro-6-methoxyphenyl)pyrimidine-4-carboxamide

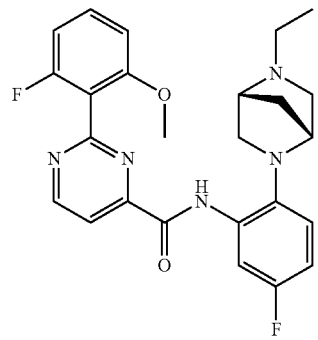 [SMILES: CCN1C[C@H]2C[C@@H]1CN2c1ccc(F)cc1NC(=O)c1ccnc(-c2c(F)cccc2OC)n1]

Sodium triacetoxyborohydride (10 mg, 0.046 mmol) was added to a solution of acetaldehyde (1 mg, 0.023 mmol), acetic acid (2 µl, 0.035 mmol) and N-(2-((1R,4R)-2,5-diazabicyclo[2.2.1]heptan-2-yl)-5-fluorophenyl)-2-(2-fluoro-6-methoxyphenyl)pyrimidine-4-carboxamide (from Example 1; 10 mg, 0.023 mmol) in dichloroethane (1 mL). After the reaction mixture was stirred at room temperature for 2 h, it was diluted with acetonitrile and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{25}H_{26}F_2N_5O_2$ (M+H)⁺: m/z=466.2; Found: 466.3.

Example 33. N-(5-Fluoro-2-((1R,4R)-5-(2-hydroxyethyl)-2,5-diazabicyclo[2.2.1]heptan-2-yl)phenyl)-2-(2-fluoro-6-methoxyphenyl)pyrimidine-4-carboxamide

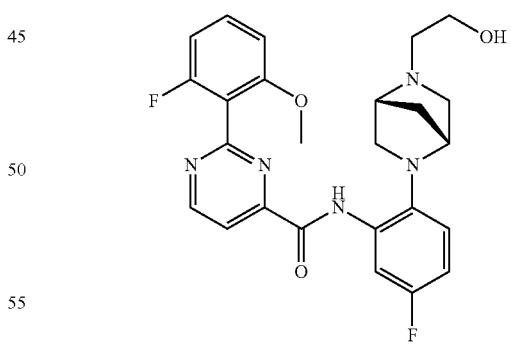

Sodium triacetoxyborohydride (10 mg, 0.046 mmol) was added to a solution of 2-((tert-butyldimethylsilyl)oxy)acetaldehyde (3.98 mg, 0.023 mmol), acetic acid (2 µl, 0.035 mmol) and N-(2-((1R,4R)-2,5-diazabicyclo[2.2.1]heptan-2-yl)-5-fluorophenyl)-2-(2-fluoro-6-methoxyphenyl)pyrimidine-4-carboxamide (from Example 1; 10 mg, 0.023 mmol) in dichloroethane (1 mL). After the reaction mixture was stirred at room temperature for 2 h, the solvent was evaporated in vacuo and 4 M HCl solution in dioxane (1 mL) was added to the residue. After additional stirring at room temperature for 1 h, the reaction mixture was diluted with acetonitrile and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{25}H_{26}F_2N_5O_3$ (M+H)$^+$: m/z=482.2; Found: 482.2.

Example 34. (1R,4R)-5-(4-Fluoro-2-(2-(2-fluoro-6-methoxyphenyl)pyrimidine-4-carboxamido)phenyl)-N-propyl-2,5-diazabicyclo[2.2.1]heptane-2-carboxamide

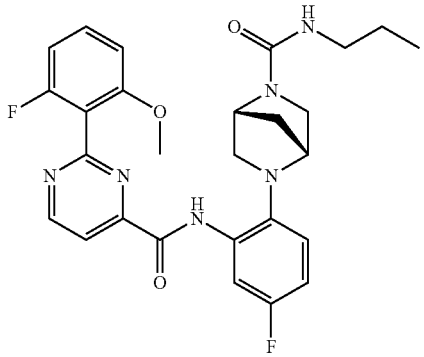 [SMILES: CCCNC(=O)N1C[C@H]2C[C@@H]1CN2c1ccc(F)cc1NC(=O)c1ccnc(-c2c(F)cccc2OC)n1]

Triphosgene (4.1 mg, 0.014 mmol) was added to a solution of N-(2-((1R,4R)-2,5-diazabicyclo[2.2.1]heptan-2-yl)-5-fluorophenyl)-2-(2-fluoro-6-methoxyphenyl)pyrimidine-4-carboxamide (from Example 1, 6 mg, 0.014 mmol) and triethylamine (4 µl, 0.027 mmol) in THF (1 mL). After the reaction mixture was stirred at room temperature for 30 min, propan-1-amine (1.2 mg, 0.021 mmol) was added and the mixture was stirred at room temperature for an additional 30 min. The reaction mixture was then diluted with acetonitrile and purified with prep-LCMS (XBridge C18 column, eluting with a gradient of acetonitrile/water containing 0.1% TFA, at flow rate of 60 mL/min) to provide the TFA salt of the title compound. LCMS calculated for $C_{27}H_{29}F_2N_6O_3$ (M+H)$^+$: m/z=523.2; Found: 523.3.

Example 35. N-(2-((1R,4R)-2,5-Diazabicyclo[2.2.1]heptan-2-yl)-5-methoxyphenyl)-2-(2-fluoro-6-methoxyphenyl)pyrimidine-4-carboxamide

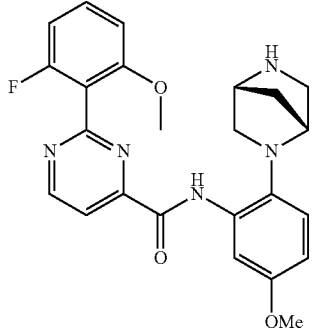 [SMILES: COc1ccc(N2C[C@H]3C[C@@H]2CN3)c(NC(=O)c2ccnc(-c3c(F)cccc3OC)n2)c1]

The TFA salt of the title compound was prepared according to the procedures described in Example 1, using 1-fluoro-4-methoxy-2-nitrobenzene instead of 1,4-difluoro-2-nitrobenzene as starting material. LCMS calculated for $C_{24}H_{25}FN_5O_3$ (M+H)$^+$: m/z=450.2; Found: 450.3.

Example 36. N-(2-((1R,4R)-2,5-Diazabicyclo[2.2.1]heptan-2-yl)-5-(hydroxymethyl)phenyl)-2-(2-fluoro-6-methoxyphenyl)pyrimidine-4-carboxamide

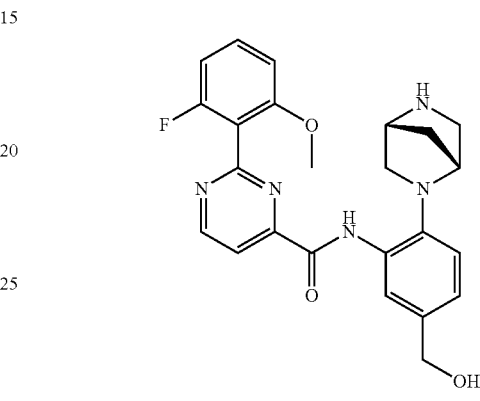

The TFA salt of the title compound was prepared according to the procedures described in Example 1, using (4-fluoro-3-nitrophenyl)methanol instead of 1,4-difluoro-2-nitrobenzene as starting material. LCMS calculated for $C_{24}H_{25}FN_5O_3$ (M+H)$^+$: m/z=450.2; Found: 450.3.

Example 37. N-(2-((1R,4R)-2,5-Diazabicyclo[2.2.1]heptan-2-yl)-5-cyanophenyl)-2-(2-fluoro-6-methoxyphenyl)pyrimidine-4-carboxamide

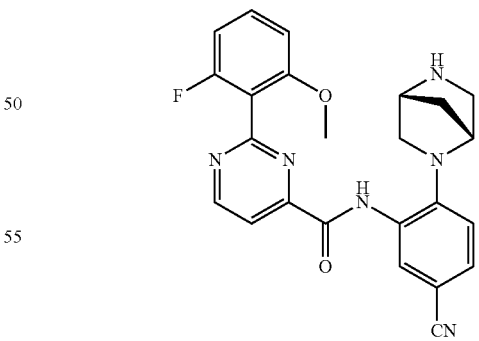

The TFA salt of the title compound was prepared according to the procedures described in Example 1, using 4-fluoro-3-nitrobenzonitrile instead of 1,4-difluoro-2-nitrobenzene as starting material. LCMS calculated for $C_{24}H_{22}FN_6O_2$ (M+H)$^+$: m/z=445.2; Found: 445.1.

Example 38. N-(4-(Azetidin-1-yl)-2-((1S,4S)-2,5-diazabicyclo[2.2.1]heptan-2-yl)phenyl)-2-(2-fluoro-6-methoxyphenyl)pyrimidine-4-carboxamide

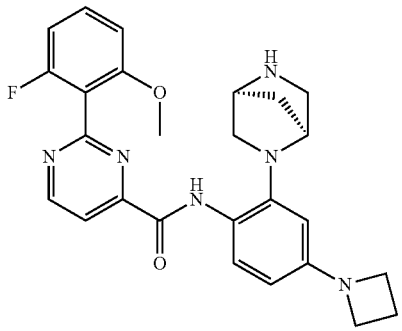 [SMILES: COc1cccc(F)c1-c1nccc(C(=O)Nc2ccc(N3CCC3)cc2N2C[C@@H]3C[C@H]2CN3)n1]

This compound was prepared according to the procedures described in Example 28 and 29, using N-(2-((1S,4S)-2,5-diazabicyclo[2.2.1]heptan-2-yl)-4-bromophenyl)-2-(2-fluoro-6-methoxyphenyl)pyrimidine-4-carboxamide instead of N-(2-((1S,4S)-2,5-diazabicyclo[2.2.1]heptan-2-yl)-4-bromo-5-fluorophenyl)-2-(2-fluoro-6-methoxyphenyl)pyrimidine-4-carboxamide as starting material. LCMS calculated for $C_{26}H_{28}FN_6O_2$ (M+H)$^+$: m/z=475.2; Found: 475.2. $^1$H NMR (500 MHz, DMSO-d$_6$) δ 10.17-10.04 (s, 1H), 9.27-9.16 (d, J=5.0 Hz, 1H), 8.15-8.04 (d, J=5.1 Hz, 1H), 7.83-7.71 (d, J=8.3 Hz, 1H), 7.59-7.48 (td, J=8.4, 6.6 Hz, 1H), 7.10-7.02 (d, J=8.5 Hz, 1H), 7.02-6.96 (t, J=8.8 Hz, 1H), 6.07-5.95 (m, 2H), 3.89-3.83 (s, 1H), 3.81-3.72 (m, 7H), 3.49-3.44 (s, 1H), 3.38-3.25 (m, 1H), 3.00-2.89 (m, 2H), 2.71-2.63 (d, J=9.7 Hz, 1H), 2.34-2.23 (q, J=7.1 Hz, 2H), 1.64-1.57 (m, 1H), 1.52-1.38 (d, J=9.0 Hz, 1H) ppm.

Example 39. N-(2-((1S,4S)-2,5-Diazabicyclo[2.2.1]heptan-2-yl)-4-((S)-2-(methoxymethyl)azetidin-1-yl)phenyl)-2-(2-fluoro-6-methoxyphenyl)pyrimidine-4-carboxamide

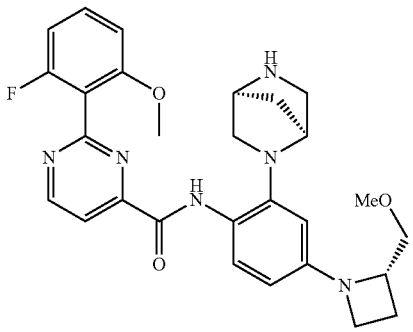 [SMILES: COC[C@@H]1CCN1c1ccc(NC(=O)c2ccnc(-c3c(F)cccc3OC)n2)c(N2C[C@@H]3C[C@H]2CN3)c1]

This compound was prepared according to the procedures described in Example 38, using (S)-2-(methoxymethyl)azetidine instead of azetidine as starting material. LCMS calculated for $C_{28}H_{32}FN_6O_3$ (M+H)$^+$: m/z=519.2; Found: 519.3. $^1$H NMR (500 MHz, DMSO-d$_6$) δ 10.18-9.96 (s, 1H), 9.28-9.11 (d, J=5.0 Hz, 1H), 8.15-8.01 (d, J=5.0 Hz, 1H), 7.79-7.67 (d, J=8.5 Hz, 1H), 7.60-7.37 (td, J=8.4, 6.8 Hz, 1H), 7.10-7.02 (d, J=8.4 Hz, 1H), 7.02-6.91 (m, 1H), 6.41- 6.27 (d, J=2.4 Hz, 1H), 6.19-6.04 (dd, J=8.7, 2.4 Hz, 1H), 4.14-4.05 (dd, J=7.6, 3.6 Hz, 1H), 3.87-3.79 (m, 3H), 3.79-3.74 (s, 3H), 3.67-3.58 (dd, J=10.3, 6.7 Hz, 1H), 3.58-3.46 (m, 3H), 3.40-3.27 (m, 4H), 3.04-2.90 (m, 2H), 2.74-2.60 (dd, J=9.7, 2.2 Hz, 1H), 2.32-2.21 (m, 1H), 2.17-2.05 (dq, J=10.8, 8.3 Hz, 1H), 1.68-1.57 (d, J=9.1 Hz, 1H), 1.56-1.47 (m, 1H) ppm.

Example 40. N-(2-((1S,4S)-2,5-Diazabicyclo[2.2.1]heptan-2-yl)-4-(3-cyanopyridin-4-yl)-3-fluorophenyl)-2-(2-fluoro-6-methoxyphenyl)pyrimidine-4-carboxamide

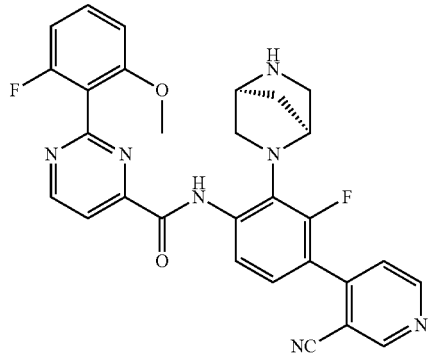 [SMILES: COc1cccc(F)c1-c1nccc(C(=O)Nc2ccc(-c3ccncc3C#N)c(F)c2N2C[C@@H]3C[C@H]2CN3)n1]

Step 1. (1S,4S)-tert-Butyl 5-(3-bromo-2-fluoro-6-(2-(2-fluoro-6-methoxyphenyl)pyrimidine-4-carboxamido)phenyl)-2,5-diazabicyclo[2.2.1]heptane-2-carboxylate

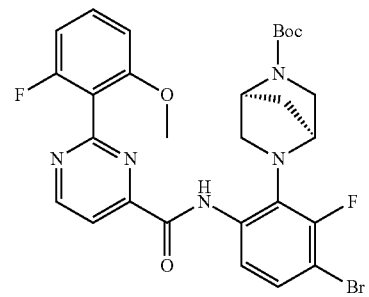 [SMILES: COc1cccc(F)c1-c1nccc(C(=O)Nc2ccc(Br)c(F)c2N2C[C@@H]3C[C@H]2CN3C(=O)OC(C)(C)C)n1]

This compound was prepared according to the procedures described in Example 18, using 1-bromo-2,3-difluoro-4-nitrobenzene instead of 1-bromo-2,5-difluoro-4-nitrobenzene as starting material. LCMS calculated for $C_{28}H_{29}BrF_2N_5O_4$ (M+H)$^+$: m/z=616.1; Found: 616.1.

Step 2. N-(2-((1S,4S)-2,5-Diazabicyclo[2.2.1]heptan-2-yl)-4-(3-cyanopyridin-4-yl)-3-fluorophenyl)-2-(2-fluoro-6-methoxyphenyl)pyrimidine-4-carboxamide A mixture of tert-butyl (1S,4S)-5-(3-bromo-2-fluoro-6-(2-(2-fluoro-6-methoxyphenyl)pyrimidine-4-carboxamido)phenyl)-2,5-diazabicyclo[2.2.1]heptane-2-carboxylate (10 mg, 0.016 mmol), 4-(4,4,5,5-tetramethyl-1,3,2-dioxaborolan-2-yl)nicotinonitrile (10 mg, 0.043 mmol), Xphos Pd G2 (1.3 mg, 1.6 μmol) and potassium phosphate, tribasic (6.7 mg, 0.032 mmol) was combined with 1,4-dioxane (1 ml) and water (0.1 ml). The reaction mixture was degassed under vacuum, back filled with nitrogen and then stirred at 80° C. for 1 h. The reaction mixture was cooled to room temperature, the solvents were concentrated and TFA (1 ml) was added. The reaction mixture was stirred at room temperature for 10 min, then diluted with CH$_3$CN and water and purified with prep-LCMS (XBridge C18 column, eluting with a gradient of acetonitrile/water containing 0.1% TFA, at flow rate of 60 mL/min). LCMS calculated for C$_{29}$H$_{24}$F$_2$N$_7$O$_2$ (M+H)$^+$: m/z=540.2; Found: 540.1. $^1$H NMR (500 MHz, DMSO-d$_6$) δ 10.94-10.84 (s, 1H), 9.37-9.27 (d, J=5.0 Hz, 1H), 9.20-9.11 (s, 1H), 9.07-8.99 (br, 1H), 8.98-8.94 (d, J=5.2 Hz, 1H), 8.81-8.72 (br, 1H), 8.44-8.37 (d, J=8.6 Hz, 1H), 8.27-8.16 (d, J=5.0 Hz, 1H), 7.79-7.75 (d, J=5.2 Hz, 1H), 7.62-7.56 (td, J=8.5, 6.9 Hz, 1H), 7.56-7.51 (t, J=8.1 Hz, 1H), 7.12-7.06 (d, J=8.5 Hz, 1H), 7.05-6.97 (m, 1H), 4.46-4.34 (m, 1H), 4.15-4.08 (s, 1H), 3.82-3.74 (s, 3H), 3.62-3.54 (d, J=10.7 Hz, 1H), 3.49-3.41 (m, 1H), 3.41-3.33 (m, 1H), 3.17-3.07 (m, 1H), 1.95-1.88 (d, J=10.6 Hz, 1H), 1.68-1.58 (m, 1H) ppm.

Example 41. N-(2-((2S,4S)-4-Amino-2-(hydroxymethyl)pyrrolidin-1-yl)-4-(3-cyanopyridin-4-yl)phenyl)-2-(2-fluoro-6-methoxyphenyl)pyrimidine-4-carboxamide

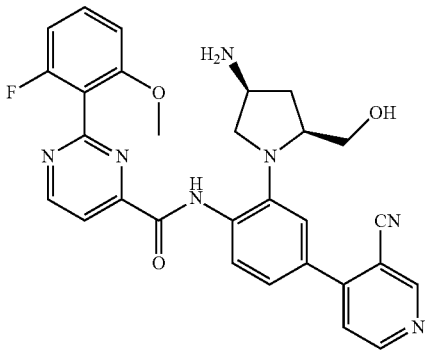

Step 1. tert-Butyl (3S,5S)-1-(5-bromo-2-(2-(2-fluoro-6-methoxyphenyl)pyrimidine-4-carboxamido)phenyl)-5-(hydroxymethyl)pyrrolidin-3-ylcarbamate

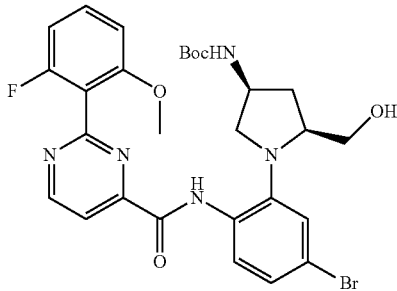 [SMILES: COc1cccc(F)c1-c1nccc(C(=O)Nc2ccc(Br)cc2N2C[C@@H](NC(=O)OC(C)(C)C)C[C@H]2CO)n1]

This compound was prepared according to the procedures described in Example 22 and 1, using tert-butyl (3S,5S)-5-(hydroxymethyl)pyrrolidin-3-ylcarbamate instead of (1S,4S)-tert-butyl 2,5-diazabicyclo[2.2.1]heptane-2-carboxylate as starting material. LCMS calculated for C$_{28}$H$_{32}$BrFN$_5$O$_5$ (M+H)$^+$: m/z=616.2; Found: 616.2.

Step 2. N-(2-((2S,4S)-4-Amino-2-(hydroxymethyl)pyrrolidin-1-yl)-4-(3-cyanopyridin-4-yl)phenyl)-2-(2-fluoro-6-methoxyphenyl)pyrimidine-4-carboxamide A mixture of tert-butyl ((3S,5S)-1-(5-bromo-2-(2-(2-fluoro-6-methoxyphenyl)pyrimidine-4-carboxamido)phenyl)-5-(hydroxymethyl)pyrrolidin-3-yl)carbamate (10 mg, 0.016 mmol), 4-(4,4,5,5-tetramethyl-1,3,2-dioxaborolan-2-yl)nicotinonitrile (9.8 mg, 0.043 mmol), Xphos Pd G2 (1.3 mg, 1.6 µmol) and potassium phosphate, tribasic (6.7 mg, 0.032 mmol) was combined with 1,4-dioxane (1 ml) and water (0.1 ml). The reaction mixture was degassed under vacuum, back filled with nitrogen, then stirred at 80° C. for 1 h. The reaction mixture was cooled to room temperature, the solvents were concentrated and TFA (1 ml) was added. The reaction mixture was stirred at room temperature for 10 min, then diluted with CH$_3$CN and water and purified with prep-LCMS (XBridge C18 column, eluting with a gradient of acetonitrile/water containing 0.1% TFA, at flow rate of 60 mL/min). LCMS calculated for C29H$_{27}$FN$_7$O$_3$ (M+H)$^+$: m/z=540.2; Found: 540.1. $^1$H NMR (600 MHz, DMSO-d$_6$) δ 10.69-10.61 (s, 1H), 9.32-9.25 (d, J=5.0 Hz, 1H), 9.14-9.04 (s, 1H), 8.94-8.86 (d, J=5.3 Hz, 1H), 8.35-8.28 (d, J=8.4 Hz, 1H), 8.22-8.13 (d, J=5.0 Hz, 1H), 7.97-7.85 (d, J=5.5 Hz, 2H), 7.81-7.75 (d, J=5.4 Hz, 1H), 7.73-7.68 (d, J=2.1 Hz, 1H), 7.60-7.53 (td, J=8.4, 6.8 Hz, 1H), 7.53-7.47 (dd, J=8.4, 2.0 Hz, 1H), 7.11-7.05 (d, J=8.5 Hz, 1H), 7.04-6.96 (t, J=8.8 Hz, 1H), 3.89-3.81 (m, 1H), 3.79-3.76 (s, 3H), 3.76-3.68 (m, 1H), 3.44-3.29 (m, 3H), 3.27-3.22 (dd, J=11.1, 2.6 Hz, 1H), 2.43-2.33 (m, 1H), 1.90-1.80 (m, 1H) ppm.

Example 42. N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide

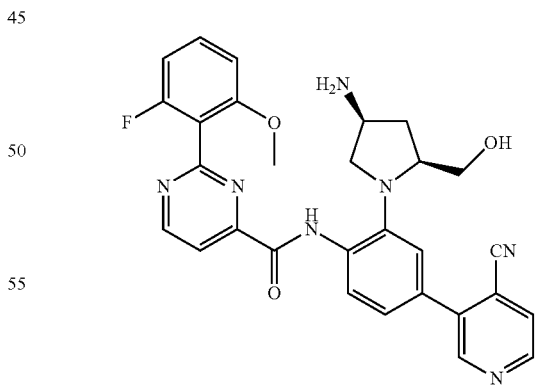

This compound (free base and TFA salt) was prepared according to the procedures described in Example 41 (and detailed below), using 3-(4,4,5,5-tetramethyl-1,3,2-dioxaborolan-2-yl)isonicotinonitrile instead of 4-(4,4,5,5-tetramethyl-1,3,2-dioxaborolan-2-yl)nicotinonitrile as starting material.

Step 1. tert-Butyl ((3S,5S)-1-(5-bromo-2-nitrophenyl)-5-(hydroxymethyl)pyrrolidin-3-yl)carbamate

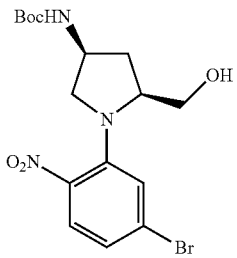 [SMILES: CC(C)(C)OC(=O)N[C@H]1C[C@@H](CO)N(c2cc(Br)ccc2[N+](=O)[O-])C1]

A solution of 4-bromo-2-fluoro-1-nitrobenzene (532 mg, 2.42 mmol) and tert-butyl ((3S,5S)-5-(hydroxymethyl)pyrrolidin-3-yl)carbamate (523 mg, 2.42 mmol) in DMSO (8 mL) was treated with triethylamine (506 μL, 3.63 mmol) and the reaction mixture was heated to 80° C. for 2 hr. After cooling to r.t., water was added and the precipitated product was collected by filtration, washed with water and air dried. It was used in the next step without further purification. LCMS calculated for $C_{12}H_{15}BrN_3O_5$ $(M+H-C_4H_8)^+$: m/z=360.0/362.0; found 360.0/362.0.

Step 2. tert-Butyl ((3S,5S)-1-(2-amino-5-bromophenyl)-5-(hydroxymethyl)pyrrolidin-3-yl)carbamate

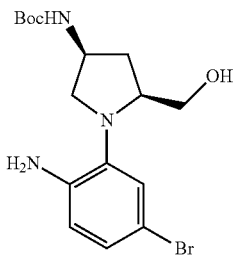

A mixture of tert-butyl ((3S,5S)-1-(5-bromo-2-nitrophenyl)-5-(hydroxymethyl)pyrrolidin-3-yl)carbamate (1 g, 2.45 mmol), iron (684 mg, 12.25 mmol) and ammonium chloride (786 mg, 14.70 mmol) in THF (5 mL), water (5 mL) and methanol (5 mL) was stirred at 60° C. for 3 hrs. After cooling to r.t., it was filtered through a plug of Celite and diluted with DCM. The organic phase was separated, washed with saturated aqueous sodium chloride, dried over sodium sulfate and the solvents were evaporated in vacuo. The obtained crude product was used in the next step without further purification. LCMS calculated for $C_{16}H_{25}BrN_3O_3$ $(M+H)^+$: m/z=386.1/388.1; Found: 386.1/388.1.

Step 3. tert-Butyl ((3S,5S)-1-(5-bromo-2-(2-(2-fluoro-6-methoxyphenyl)pyrimidine-4-carboxamido)phenyl)-5-(hydroxymethyl)pyrrolidin-3-yl)carbamate

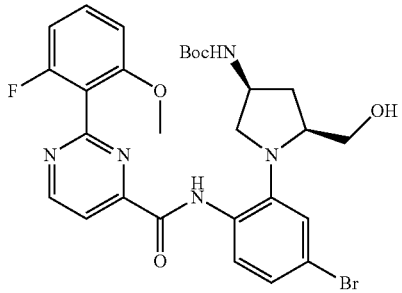

HATU (1196 mg, 3.15 mmol) was added to a solution of tert-butyl ((3S,5S)-1-(2-amino-5-bromophenyl)-5-(hydroxymethyl)pyrrolidin-3-yl)carbamate (810 mg, 2.097 mmol), 2-(2-fluoro-6-methoxyphenyl)pyrimidine-4-carboxylic acid (the product of Example 1, step 1, 520 mg, 2.097 mmol) and DIPEA (732 μl, 4.19 mmol) in DMF (5 mL). The reaction mixture was stirred at r.t. for 30 mins, then water was added and the precipitated product was collected by filtration, washed with water and air dried. The solid was used in the next step without further purification. LCMS calculated for $C_{28}H_{32}BrFN_5O_5$ $(M+H)^+$: m/z=616.2/618.2; Found: 616.2/618.2.

Step 4. N-(2-((2S,4S)-4-Amino-2-(hydroxymethyl)pyrrolidin-1-yl)-4-(4-cyanopyridin-3-yl)phenyl)-2-(2-fluoro-6-methoxyphenyl)pyrimidine-4-carboxamide A mixture of tert-butyl ((3S,5S)-1-(5-bromo-2-(2-(2-fluoro-6-methoxyphenyl)pyrimidine-4-carboxamido)phenyl)-5-(hydroxymethyl)pyrrolidin-3-yl)carbamate (10 mg, 0.016 mmol), 3-(4,4,5,5-tetramethyl-1,3,2-dioxaborolan-2-yl)isonicotinonitrile (9.8 mg, 0.043 mmol), Xphos Pd G2 (1.3 mg, 1.6 μmol) and potassium phosphate, tribasic (6.7 mg, 0.032 mmol) was combined with 1,4-dioxane (1 mL) and water (0.1 mL) and the reaction flask was evacuated, back filled with nitrogen, then stirred at 80° C. for 1 hr. The reaction mixture was cooled to r.t., the solvents were evaporated in vacuo and TFA (1 mL) was added. The reaction mixture was stirred at r.t. for 10 min, then diluted with $CH_3CN$ and water and purified with prep-LCMS. LCMS calculated for $C_{29}H_{27}FN_7O_3$ $(M+H)^+$: m/z=540.2; Found: 540.1. Prep-LCMS (XBridge C18 column, eluting with a gradient of acetonitrile/water containing 0.1% $NH_4OH$, at flow rate of 60 mL/min). Free base: $^1H$ NMR (500 MHz, DMSO-$d_6$) δ 9.33-9.25 (d, J=5.0 Hz, 1H), 8.98-8.93 (s, 1H), 8.84-8.78 (d, J=5.0 Hz, 1H), 8.46-8.39 (d, J=8.4 Hz, 1H), 8.22-8.18 (d, J=5.0 Hz, 1H), 8.00-7.92 (dd, J=5.1, 0.7 Hz, 1H), 7.67-7.64 (m, 1H), 7.59-7.52 (td, J=8.4, 6.8 Hz, 1H), 7.48-7.43 (dd, J=8.3, 2.1 Hz, 1H), 7.11-7.04 (d, J=8.5 Hz, 1H), 7.03-6.90 (t, J=8.8 Hz, 1H), 3.85-3.73 (s, 3H), 3.68-3.56 (m, 1H), 3.39-3.29 (m, 3H), 3.28-3.22 (d, J=4.8 Hz, 1H), 3.06-2.97 (d, J=5.4 Hz, 1H), 2.31-2.18 (dt, J=12.6, 7.5 Hz, 1H), 1.40-1.29 (dt, J=12.7, 6.2 Hz, 1H) ppm. Prep-LCMS (XBridge C18 column, eluting with a gradient of acetonitrile/water containing 0.1% TFA, at flow rate of 60 mL/min). TFA salt: $^1H$ NMR (500 MHz, DMSO-$d_6$) δ

10.66-10.59 (s, 1H), 9.31-9.24 (d, J=5.0 Hz, 1H), 9.03-8.94 (d, J=0.8 Hz, 1H), 8.88-8.78 (d, J=5.0 Hz, 1H), 8.34-8.24 (d, J=8.4 Hz, 1H), 8.24-8.17 (d, J=5.0 Hz, 1H), 8.04-7.95 (dd, J=5.1, 0.8 Hz, 1H), 7.92-7.82 (br, J=5.5 Hz, 2H), 7.73-7.65 (d, J=2.0 Hz, 1H), 7.61-7.54 (td, J=8.5, 6.9 Hz, 1H), 7.50-7.45 (dd, J=8.4, 2.0 Hz, 1H), 7.11-7.05 (d, J=8.5 Hz, 1H), 7.05-6.98 (t, J=8.8 Hz, 1H), 3.89-3.82 (m, 1H), 3.81-3.77 (s, 3H), 3.76-3.69 (m, 1H), 3.42-3.21 (m, 4H), 2.43-2.31 (m, 1H), 1.90-1.77 (dt, J=13.2, 5.3 Hz, 1H) ppm.

Example 43. N-(2-((2S,4S)-4-Amino-2-(hydroxymethyl)pyrrolidin-1-yl)-4-(2-methylpyridin-3-yl)phenyl)-2-(2-fluoro-6-methoxyphenyl)pyrimidine-4-carboxamide

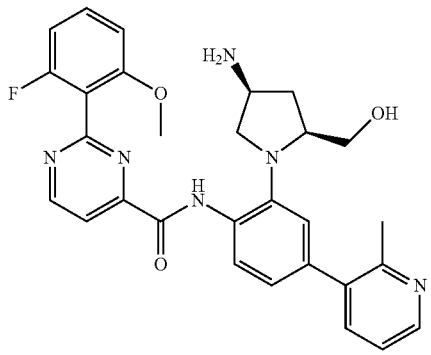 [SMILES: COc1cccc(F)c1-c1nccc(C(=O)Nc2ccc(-c3cccnc3C)cc2N2C[C@@H](N)C[C@H]2CO)n1]

This compound was prepared according to the procedures described in Example 41, using (2-methylpyridin-3-yl)boronic acid instead of 4-(4,4,5,5-tetramethyl-1,3,2-dioxaborolan-2-yl)nicotinonitrile as starting material. LCMS calculated for $C_{29}H_{30}FN_6O_3$ $(M+H)^+$: m/z=529.2; Found: 529.2. $^1$H NMR (500 MHz, DMSO-$d_6$) δ 10.69-10.55 (s, 1H), 9.33-9.17 (d, J=5.0 Hz, 1H), 8.72-8.62 (dd, J=5.4, 1.7 Hz, 1H), 8.31-8.20 (d, J=8.3 Hz, 1H), 8.23-8.15 (d, J=5.0 Hz, 1H), 8.14-8.05 (d, J=7.6 Hz, 1H), 8.05-7.86 (br, J=5.4 Hz, 2H), 7.75-7.64 (dd, J=7.7, 5.4 Hz, 1H), 7.62-7.52 (td, J=8.4, 6.8 Hz, 1H), 7.47-7.41 (d, J=2.0 Hz, 1H), 7.31-7.23 (dd, J=8.3, 1.9 Hz, 1H), 7.11-7.05 (d, J=8.5 Hz, 1H), 7.05-6.95 (t, J=8.8 Hz, 1H), 3.87-3.76 (m, 4H), 3.76-3.66 (m, 1H), 3.42-3.20 (m, 4H), 2.65-2.57 (s, 3H), 2.43-2.32 (dt, J=13.2, 7.9 Hz, 1H), 1.91-1.65 (dt, J=13.3, 5.5 Hz, 1H) ppm.

Example 44. N-(2-((2S,4S)-4-Amino-2-(hydroxymethyl)pyrrolidin-1-yl)-4-(3-methoxypyridin-4-yl)phenyl)-2-(2-fluoro-6-methoxyphenyl)pyrimidine-4-carboxamide

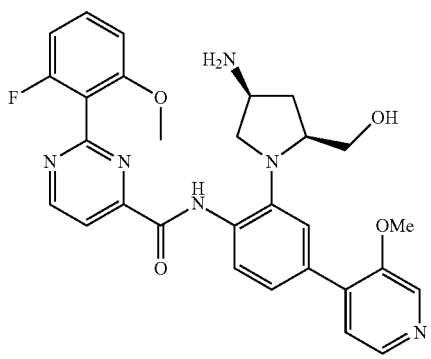 [SMILES: COc1cnccc1-c1ccc(NC(=O)c2ccnc(-c3c(F)cccc3OC)n2)c(N2C[C@@H](N)C[C@H]2CO)c1]

This compound was prepared according to the procedures described in Example 41, using (3-methoxypyridin-4-yl)boronic acid instead of 4-(4,4,5,5-tetramethyl-1,3,2-dioxaborolan-2-yl)nicotinonitrile as starting material. LCMS calculated for $C_{29}H_{30}FN_6O_4$ $(M+H)^+$: m/z=545.2; Found: 545.3. $^1$H NMR (500 MHz, DMSO-$d_6$) δ 10.66-10.59 (s, 1H), 9.30-9.25 (d, J=5.0 Hz, 1H), 8.55-8.48 (s, 1H), 8.39-8.33 (d, J=5.0 Hz, 1H), 8.28-8.21 (d, J=8.4 Hz, 1H), 8.21-8.16 (d, J=5.0 Hz, 1H), 7.92-7.81 (br, 2H), 7.63-7.59 (m, 1H), 7.59-7.55 (m, 1H), 7.55-7.51 (m, 1H), 7.48-7.44 (dd, J=8.4, 1.9 Hz, 1H), 7.14-7.11 (s, 1H), 7.09-7.05 (d, J=8.5 Hz, 1H), 7.01-6.96 (d, J=8.8 Hz, 1H), 3.99-3.90 (s, 3H), 3.83-3.73 (m, 4H), 3.73-3.67 (m, 1H), 3.40-3.19 (m, 4H), 2.44-2.35 (m, 1H), 1.88-1.79 (dt, J=13.3, 5.2 Hz, 1H) ppm.

Example 45. N-(3-((2S,4S)-4-Amino-2-(hydroxymethyl)pyrrolidin-1-yl)-2'-cyano-6'-fluorobiphenyl-4-yl)-2-(2-fluoro-6-methoxyphenyl)pyrimidine-4-carboxamide

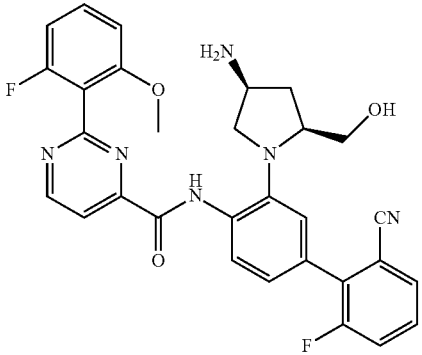 [SMILES: COc1cccc(F)c1-c1nccc(C(=O)Nc2ccc(-c3c(F)cccc3C#N)cc2N2C[C@@H](N)C[C@H]2CO)n1]

This compound was prepared according to the procedures described in Example 41, using 3-fluoro-2-(4,4,5,5-tetramethyl-1,3,2-dioxaborolan-2-yl)benzonitrile instead of 4-(4,4,5,5-tetramethyl-1,3,2-dioxaborolan-2-yl)nicotinonitrile as starting material. LCMS calculated for $C_{30}H_{27}F_2N_6O_3$ $(M+H)^+$: m/z=557.2; Found: 557.1.

Example 46. N-(2-((2S,4S)-4-Amino-2-(hydroxymethyl)pyrrolidin-1-yl)-4-(3-cyanopyridin-2-yl)phenyl)-2-(2-fluoro-6-methoxyphenyl)pyrimidine-4-carboxamide

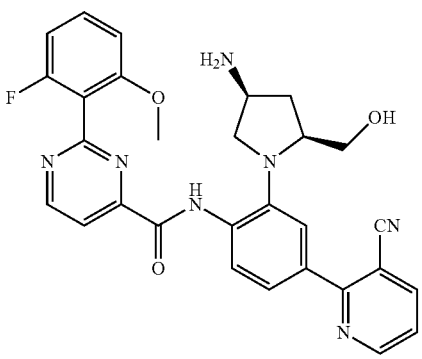 [SMILES: COc1cccc(F)c1-c1nccc(C(=O)Nc2ccc(-c3ncccc3C#N)cc2N2C[C@@H](N)C[C@H]2CO)n1]

Step 1. tert-Butyl (3S,5S)-1-(2-(2-(2-fluoro-6-methoxyphenyl)pyrimidine-4-carboxamido)-5-(4,4,5,5-tetramethyl-1,3,2-dioxaborolan-2-yl)phenyl)-5-(hydroxymethyl)pyrrolidin-3-ylcarbamate

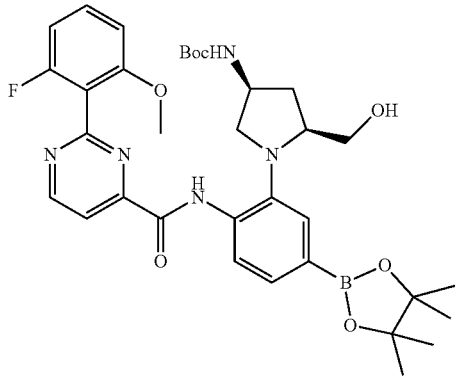 [SMILES: COc1cccc(F)c1-c1nccc(C(=O)Nc2ccc(B3OC(C)(C)C(C)(C)O3)cc2N2C[C@@H](NC(=O)OC(C)(C)C)C[C@H]2CO)n1]

1,4-Dioxane (10 ml) was added to a mixture of 4,4,5,5,4',4',5',5'-octamethyl-[2,2']bi[[1,3,2]dioxaborolanyl] (412 mg, 1.6 mmol), potassium acetate (159 mg, 1.6 mmol), [1,1'-bis(diphenylphosphino)ferrocene]dichloropalladium (II), complexed with dichloromethane (1:1) (66.2 mg, 0.081 mmol) and tert-butyl ((3S,5S)-1-(5-bromo-2-(2-(2-fluoro-6-methoxyphenyl)pyrimidine-4-carboxamido)phenyl)-5-(hydroxymethyl)pyrrolidin-3-yl)carbamate (500 mg, 0.811 mmol). The reaction mixture was degassed under vacuum, back filled with nitrogen, and stirred at 100° C. overnight. The reaction mixture was then cooled to room temperature, filtered through a plug of Celite and the solvent concentrated under vacuum. The crude material was purified by Biotage Isolera to give yellow solid (300 mg, 56%). LCMS calculated for $C_{34}H_{44}BFN_5O_7$ (M+H)$^+$: m/z=664.3; Found: 664.3.

Step 2. N-(2-((2S,4S)-4-Amino-2-(hydroxymethyl)pyrrolidin-1-yl)-4-(3-cyanopyridin-2-yl)phenyl)-2-(2-fluoro-6-methoxyphenyl)pyrimidine-4-carboxamide A mixture of tert-butyl ((3S,5S)-1-(2-(2-(2-fluoro-6-methoxyphenyl)pyrimidine-4-carboxamido)-5-(4,4,5,5-tetramethyl-1,3,2-dioxaborolan-2-yl)phenyl)-5-(hydroxymethyl)pyrrolidin-3-yl)carbamate (10 mg, 0.015 mmol), 2-bromonicotinonitrile (5.52 mg, 0.030 mmol), Xphos Pd G2 (1.3 mg, 1.6 µmol) and potassium phosphate, tribasic (6.7 mg, 0.032 mmol) was combined with 1,4-dioxane (1 ml) and water (0.1 ml). The reaction mixture was degassed under vacuum, back filled with nitrogen and then stirred at 80° C. for 1 h. The reaction mixture was cooled to room temperature, the solvents were concentrated and TFA (1 ml) was added. The reaction mixture was stirred at room temperature for 10 min, then diluted with CH$_3$CN and water and purified with prep-LCMS (XBridge C18 column, eluting with a gradient of acetonitrile/water containing 0.1% TFA, at flow rate of 60 mL/min). LCMS calculated for $C_{29}H_{27}FN_7O_3$ (M+H)$^+$: m/z=540.2; Found: 540.1. $^1$H NMR (500 MHz, DMSO-d$_6$) δ 10.71-10.58 (s, 1H), 9.35-9.21 (d, J=5.0 Hz, 1H), 8.97-8.91 (dd, J=4.8, 1.7 Hz, 1H), 8.49-8.40 (dd, J=7.9, 1.7 Hz, 1H), 8.39-8.30 (d, J=8.4 Hz, 1H), 8.26-8.16 (d, J=5.0 Hz, 1H), 7.96-7.82 (m, 3H), 7.75-7.70 (dd, J=8.4, 2.0 Hz, 1H), 7.66-7.60 (dd, J=7.9, 4.9 Hz, 1H), 7.60-7.52 (td, J=8.4, 6.8 Hz, 1H), 7.11-7.05 (d, J=8.5 Hz, 1H), 7.04-6.97 (t, J=8.8 Hz, 1H), 3.87-3.76 (m, 4H), 3.75-3.69 (m, 1H), 3.46-3.15 (m, 4H), 2.44-2.33 (m, 1H), 1.91-1.76 (m, 1H) ppm.

Example 47. N-(2-((2S,4S)-4-Amino-2-(hydroxymethyl)pyrrolidin-1-yl)-4-(4-cyano-1-methyl-1H-pyrazol-5-yl)phenyl)-2-(2-fluoro-6-methoxyphenyl)pyrimidine-4-carboxamide

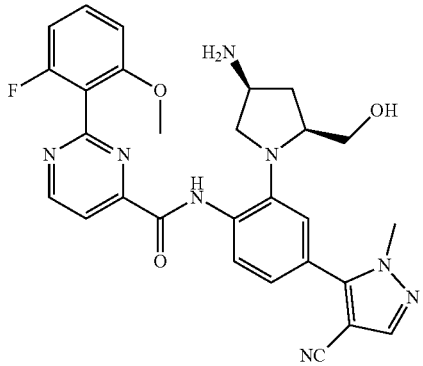 [SMILES: COc1cccc(F)c1-c1nccc(C(=O)Nc2ccc(-c3c(C#N)cnn3C)cc2N2C[C@@H](N)C[C@H]2CO)n1]

This compound was prepared according to the procedures described in Example 46, using 5-bromo-1-methyl-1H-pyrazole-4-carbonitrile instead of 2-bromonicotinonitrile as starting material. LCMS calculated for $C_{28}H_{28}FN_5O_3$ (M+H)$^+$: m/z=543.2; Found: 543.2.

Example 48. N-(2-((2S,4S)-4-Amino-2-(hydroxymethyl)pyrrolidin-1-yl)-4-isopropylphenyl)-2-(2-fluoro-6-methoxyphenyl)pyrimidine-4-carboxamide

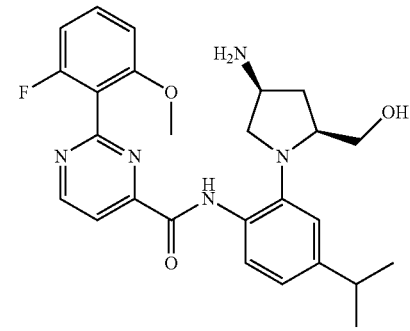 [SMILES: COc1cccc(F)c1-c1nccc(C(=O)Nc2ccc(C(C)C)cc2N2C[C@@H](N)C[C@H]2CO)n1]

Step 1. tert-Butyl (3S,5S)-1-(2-(2-(2-Fluoro-6-methoxyphenyl)pyrimidine-4-carboxamido)-5-(prop-1-en-2-yl)phenyl)-5-(hydroxymethyl)pyrrolidin-3-ylcarbamate

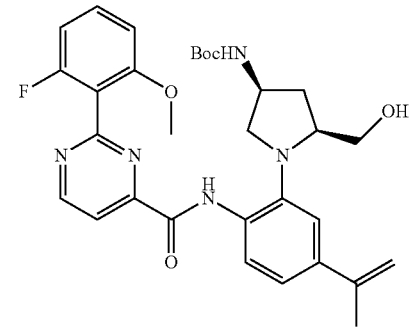 [SMILES: C=C(C)c1ccc(NC(=O)c2ccnc(-c3c(F)cccc3OC)n2)c(N2C[C@@H](NC(=O)OC(C)(C)C)C[C@H]2CO)c1]

This compound was prepared according to the procedures described in Example 41, using 4,4,5,5-tetramethyl-2-(prop-1-en-2-yl)-1,3,2-dioxaborolane instead of 4-(4,4,5,5-tetramethyl-1,3,2-dioxaborolan-2-yl)nicotinonitrile as starting material. LCMS calculated for $C_{31}H_{37}FN_5O_5$ (M+H)$^+$: m/z=578.3; Found: 578.3.

Step 2. N-(2-((2S,4S)-4-Amino-2-(hydroxymethyl)pyrrolidin-1-yl)-4-isopropylphenyl)-2-(2-fluoro-6-methoxyphenyl)pyrimidine-4-carboxamide Palladium on carbon (10w %, 18.42 mg, 0.017 mmol) was added to a solution of tert-butyl ((3S,5S)-1-(2-(2-(2-fluoro-6-methoxyphenyl)pyrimidine-4-carboxamido)-5-(prop-1-en-2-yl)phenyl)-5-(hydroxymethyl)pyrrolidin-3-yl)carbamate (100 mg, 0.173 mmol) in methanol (6 ml). The reaction mixture was stirred at room temperature for 5 h under an atmosphere of hydrogen. The catalyst was filtered off, the solvent was concentrated and TFA (1 ml) was added. The reaction mixture was stirred at room temperature for 10 min, then diluted with CH$_3$CN and water and purified with prep-LCMS (XBridge C18 column, eluting with a gradient of acetonitrile/water containing 0.1% TFA, at flow rate of 60 mL/min). LCMS calculated for $C_{26}H_{31}FN_5O_3$ (M+H)$^+$: m/z=480.2; Found: 480.2. $^1$H NMR (500 MHz, DMSO-d$_6$) δ 10.50-10.37 (s, 1H), 9.33-9.20 (d, J=5.0 Hz, 1H), 8.18-8.07 (d, J=5.0 Hz, 1H), 8.07-8.02 (d, J=8.3 Hz, 1H), 7.88-7.73 (br, J=5.7 Hz, 2H), 7.61-7.47 (td, J=8.4, 6.8 Hz, 1H), 7.27-7.18 (s, 1H), 7.14-7.03 (dd, J=8.4, 1.9 Hz, 2H), 7.03-6.94 (t, J=8.8 Hz, 1H), 3.81-3.73 (s, 3H), 3.75-3.66 (m, 1H), 3.33-3.12 (m, 4H), 2.95-2.81 (p, J=6.9 Hz, 1H), 2.45-2.33 (m, 1H), 1.87-1.67 (dt, J=13.2, 5.0 Hz, 1H), 1.24-1.17 (d, J=6.9 Hz, 6H) ppm.

Example 49. N-(4-(3-Cyanopyridin-4-yl)-2-((2S,4S)-4-hydroxy-2-(hydroxymethyl)pyrrolidin-1-yl)phenyl)-2-(2-fluoro-6-methoxyphenyl)pyrimidine-4-carboxamide

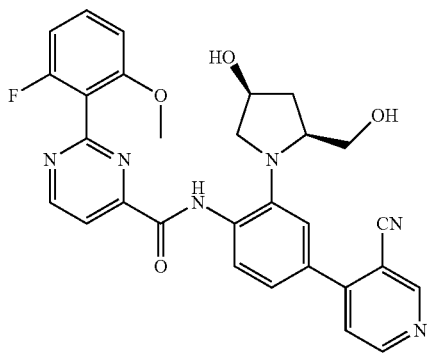

This compound was prepared according to the procedures described in Example 41, using (3S,5S)-5-(hydroxymethyl)pyrrolidin-3-ol instead of tert-butyl (3S,5S)-5-(hydroxymethyl)pyrrolidin-3-ylcarbamate as starting material. LCMS calculated for $C_{29}H_{26}FN_6O_4$ (M+H)$^+$: m/z=541.2; Found: 541.2.

Intermediate 1.
3-(3-Fluoro-4-nitrophenyl)isonicotinonitrile

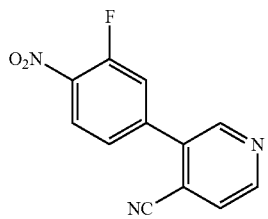 [SMILES: N#Cc1ccncc1-c1ccc([N+](=O)[O-])c(F)c1]

A mixture of 3-(4,4,5,5-tetramethyl-1,3,2-dioxaborolan-2-yl)isonicotinonitrile (1 g, 4.34 mmol), 4-bromo-2-fluoro-1-nitrobenzene (637 mg, 2.90 mmol), XPhos Pd G2 (228 mg, 0.29 mmol), and potassium phosphate, tribasic (1.23 g, 5.79 mmol) was combined with dioxane (88 mL) and water (8.8 mL). The reaction mixture was degassed under vacuum, back filled with nitrogen and then stirred at 80° C. for 16 h. After cooling to room temperature, the mixture was filtered through Celite and washed with ethyl acetate, followed by concentrating under vacuum. The residue was then purified by Biotage Isolera to give 3-(3-fluoro-4-nitrophenyl)isonicotinonitrile as a tan solid (550 mg, 78% yield). LCMS calculated for $C_{12}H_7FN_3O_2$ (M+H)$^+$: m/z=244.0; found 244.0.

Example 50. N-(4-(4-Cyanopyridin-3-yl)-2-((2S,5R)-2-(hydroxymethyl)-5-methylpiperazin-1-yl)phenyl)-2-(2-fluoro-6-methoxyphenyl)pyrimidine-4-carboxamide

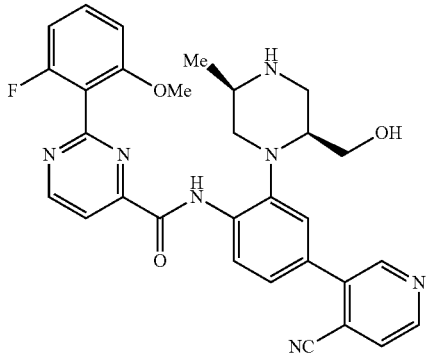 [SMILES: COc1cccc(F)c1-c1nccc(C(=O)Nc2ccc(-c3cnccc3C#N)cc2N2C[C@@H](C)NC[C@H]2CO)n1]

Step 1. (2R,5S)-tert-Butyl 4-(5-(4-cyanopyridin-3-yl)-2-nitrophenyl)-5-(hydroxymethyl)-2-methylpiperazine-1-carboxylate

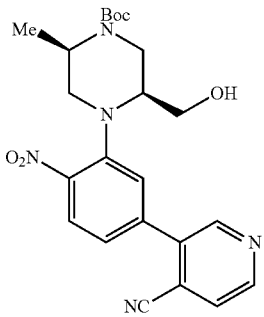

A solution of 3-(3-fluoro-4-nitrophenyl)isonicotinonitrile (Intermediate 1, 52.8 mg, 0.22 mmol) and (2R,5S)-tert-butyl 5-(hydroxymethyl)-2-methylpiperazine-1-carboxylate (50 mg, 0.22 mmol; prepared by an adaptation of the procedure described in: Chessari, G. et al. *J. Med. Chem.* 2015, 58, 6574-6588) in DMSO (724 μL) was treated with triethylamine (45.4 μL, 0.33 mmol) and the reaction mixture was heated to 100° C. for 16 h. After cooling to room temperature, the reaction mixture was diluted with $CH_2Cl_2$, washed with brine, dried over $MgSO_4$, filtered and concentrated under vacuum. The crude product was used in the next reaction without purification. LCMS calculated for $C_{23}H_{28}N_5O_5$ $(M+H)^+$: m/z=454.2; found 454.2.

Step 2. (2R,5S)-tert-Butyl 4-(2-amino-5-(4-cyanopyridin-3-yl)phenyl)-5-(hydroxymethyl)-2-methylpiperazine-1-carboxylate

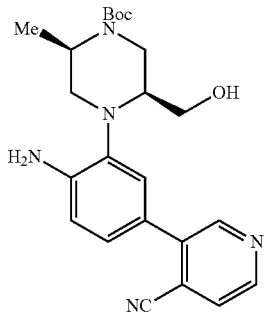 [SMILES: C[C@@H]1CN(c2cc(-c3cnccc3C#N)ccc2[N+](=O)[O-])[C@H](CO)CN1C(=O)OC(C)(C)C]

A mixture of (2R,5S)-tert-butyl 4-(5-(4-cyanopyridin-3-yl)-2-nitrophenyl)-5-(hydroxymethyl)-2-methylpiperazine-1-carboxylate (98 mg, 0.22 mmol), iron (60 mg, 1.08 mmol) and ammonium chloride (69 mg, 1.30 mmol) in THF (2 mL), water (2 mL) and methanol (2 mL) was stirred at 60° C. for 1 h. After cooling to room temperature, the reaction mixture was filtered through a plug of Celite and diluted with $CH_2Cl_2$. The organic phase was separated, washed with brine, dried over $MgSO_4$, filtered and concentrated under vacuum. The crude product was used in the next step without further purification. LCMS calculated for $C_{23}H_{30}N_5O_3$ $(M+H)^+$: m/z=424.2; Found: 424.2.

Step 3. N-(4-(4-Cyanopyridin-3-yl)-2-((2S,5R)-2-(hydroxymethyl)-5-methylpiperazin-1-yl)phenyl)-2-(2-fluoro-6-methoxyphenyl)pyrimidine-4-carboxamide HATU (124 mg, 0.326 mmol) was added to a solution of (2R,5S)-tert-butyl 4-(2-amino-5-(4-cyanopyridin-3-yl)phenyl)-5-(hydroxymethyl)-2-methylpiperazine-1-carboxylate (92 mg, 0.22 mmol), 2-(2-fluoro-6-methoxyphenyl)pyrimidine-4-carboxylic acid (54 mg, 0.22 mmol) and DIPEA (76 μL, 0.43 mmol) in DMF (510 μL). The reaction mixture was stirred at 60° C. for 30 min and then treated with water. The precipitated product was collected by filtration, washed with water and air dried. It was then redissolved in TFA and the solution was stirred at 60° C. for 10 min. After cooling, the solvent was concentrated under vacuum and the crude residue was dissolved in THF (1 mL), MeOH (1 mL), and aq. $NH_4OH$ (1 mL). The reaction mixture was stirred at 60° C. for 30 min in a sealed container. The mixture was cooled, the solvent concentrated under vacuum and the resultant residue was diluted with acetonitrile and purified with prep-LCMS (XBridge C18 column, eluting with a gradient of acetonitrile/water containing 0.1% TFA, at flow rate of 60 mL/min). $C_{30}H_{29}FN_7O_3$ $(M+H)^+$: m/z=554.2; found 554.3.

Example 51. N-(4-(4-Cyanopyridin-3-yl)-2-((2S,5S)-2-(hydroxymethyl)-5-methylpiperazin-1-yl)phenyl)-2-(2-fluoro-6-methoxyphenyl)pyrimidine-4-carboxamide

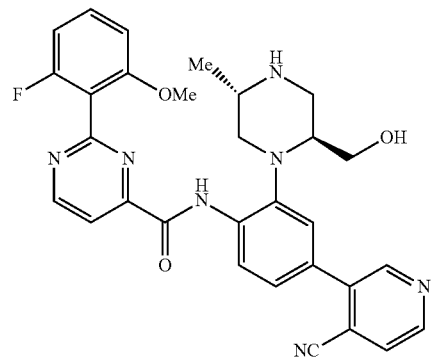 [SMILES: COc1cccc(F)c1-c1nccc(C(=O)Nc2ccc(-c3cnccc3C#N)cc2N2C[C@H](C)NC[C@H]2CO)n1]

This compound was prepared according to the procedures described in Example 50, using (2S,5S)-tert-butyl 5-(hydroxymethyl)-2-methylpiperazine-1-carboxylate instead of (2R,5S)-tert-butyl 5-(hydroxymethyl)-2-methylpiperazine-1-carboxylate as starting material. LCMS calculated for $C_{30}H_{29}FN_7O_3$ $(M+H)^+$: m/z=554.2; Found: 554.1.

Example 52. (S)—N-(4-(4-Cyanopyridin-3-yl)-2-(6-(hydroxymethyl)-4,7-diazaspiro[2.5]octan-7-yl)phenyl)-2-(2-fluoro-6-methoxyphenyl)pyrimidine-4-carboxamide

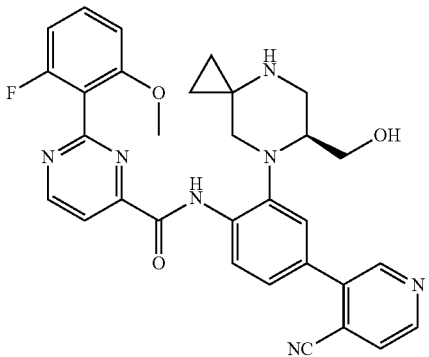 [SMILES: COc1cccc(F)c1-c1nccc(C(=O)Nc2ccc(-c3cnccc3C#N)cc2N2CC3(CC3)NC[C@H]2CO)n1]

This compound was prepared according to the procedures described in Example 50, using (S)-tert-butyl 6-(hydroxymethyl)-4,7-diazaspiro[2.5]octane-4-carboxylate instead of (2R,5S)-tert-butyl 5-(hydroxymethyl)-2-methylpiperazine-1-carboxylate as starting material. LCMS calculated for $C_{31}H_{29}FN_7O_3$ (M+H)$^+$: m/z=566.2; Found: 566.2.

Example 53. N-(2-((2S,4S)-4-Amino-2-(1-hydroxycyclopropyl)pyrrolidin-1-yl)-4-(4-cyanopyridin-3-yl)phenyl)-2-(2-fluoro-6-methoxyphenyl)pyrimidine-4-carboxamide

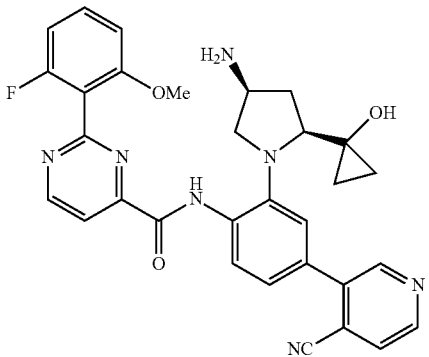 [SMILES: COc1cccc(F)c1-c1nccc(C(=O)Nc2ccc(-c3cnccc3C#N)cc2N2C[C@@H](N)C[C@H]2C2(O)CC2)n1]

Step 1. (2S,4S)-1-Benzyl 2-methyl 4-(tert-butoxycarbonylamino)pyrrolidine-1,2-dicarboxylate

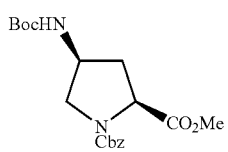 [SMILES: COC(=O)[C@@H]1C[C@H](NC(=O)OC(C)(C)C)CN1C(=O)OCc1ccccc1]

A solution of (2S,4S)-methyl 4-(tert-butoxycarbonylamino)pyrrolidine-2-carboxylate (250 mg, 1.02 mmol) and DIPEA (536 μL, 3.07 mmol) in $CH_2Cl_2$ (6.4 mL) at 0° C. was treated with benzyl chloroformate (175 μL, 1.23 mmol) and the reaction mixture was left to stir for 1 h. The reaction mixture was treated with sat. aq. $NaHCO_3$ and diluted with $CH_2Cl_2$, washed with brine, dried over $MgSO_4$, filtered and concentrated. The crude product was used in the next reaction without purification. LCMS calculated for $C_{19}H_{27}N_2O_6$ (M+H)$^+$: m/z=379.2; found 379.1.

Step 2. (2S,4S)-Benzyl 4-(tert-butoxycarbonylamino)-2-(1-hydroxycyclopropyl)pyrrolidine-1-carboxylate

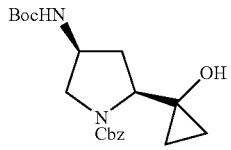

A solution of (2S,4S)-1-benzyl 2-methyl 4-(tert-butoxycarbonylamino)pyrrolidine-1,2-dicarboxylate (100 mg, 0.26 mmol) and titanium isopropoxide (16 μL, 0.053 mmol) in THF (755 μL) at 0° C. was treated with ethylmagnesium bromide (1M in THF, 1.06 mL, 1.06 mmol) and the reaction mixture was stirred at room temperature for 1 h. The reaction mixture was then treated with sat. aq. $NH_4Cl$ and diluted with EtOAc. The separated organic phase was washed with brine, dried over $MgSO_4$, filtered and concentrated. The crude product was used in the next reaction without purification. LCMS calculated for $C_{20}H_{29}N_2O_5$ (M+H)$^+$: m/z=377.2; found 377.1.

Step 3. tert-Butyl (3S,5S)-5-(1-hydroxycyclopropyl)pyrrolidin-3-ylcarbamate

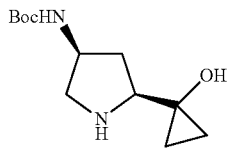 [SMILES: CC(C)(C)OC(=O)N[C@@H]1CN[C@H](C2(O)CC2)C1]

A Parr reaction vessel was charged with (2S,4S)-benzyl 4-(tert-butoxycarbonylamino)-2-(1-hydroxycyclopropyl)pyrrolidine-1-carboxylate (99 mg, 0.26 mmol), Pd/C (10% wetted, Degussa type, 28 mg) followed by MeOH (10.5 mL). The reaction mixture was evacuated and backfilled 3× with nitrogen gas, followed by another evacuation cycle and then pressurized with hydrogen gas to 25 psi. The reaction vessel was agitated overnight. The reaction mixture was then filtered over Celite and the solvent concentrated under vacuum. The crude product was used in the next reaction without purification. LCMS calculated for $C_{12}H_{23}N_2O_3$ (M+H)$^+$: m/z=243.2; found 243.3.

Step 4. tert-Butyl (3S,5S)-1-(5-(4-cyanopyridin-3-yl)-2-nitrophenyl)-5-(1-hydroxycyclopropyl)pyrrolidin-3-ylcarbamate

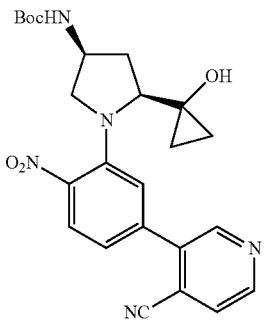

A solution of 3-(3-fluoro-4-nitrophenyl)isonicotinonitrile (Intermediate 1, 64 mg, 0.26 mmol) and tert-butyl (3S,5S)-5-(1-hydroxycyclopropyl)pyrrolidin-3-ylcarbamate (64 mg, 0.26 mmol) in DMSO (880 μL) was treated with triethylamine (55 μL, 0.40 mmol) and the reaction mixture was heated to 100° C. for 16 h. After cooling to room temperature, the reaction mixture was diluted with CH$_2$Cl$_2$, washed with brine, dried over MgSO$_4$, filtered and the solvent concentrated under vacuum. The crude product was used in the next reaction without purification. LCMS calculated for C$_{24}$H$_{28}$N$_5$O$_5$ (M+H)$^+$: m/z=466.2; found 466.3.

Step 5. tert-Butyl (3S,5S)-1-(2-amino-5-(4-cyanopyridin-3-yl)phenyl)-5-(1-hydroxycyclopropyl)pyrrolidin-3-ylcarbamate

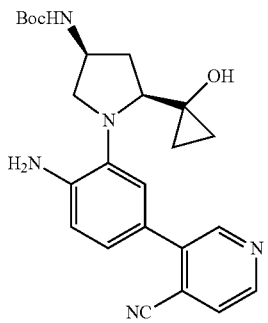 [SMILES: CC(C)(C)OC(=O)N[C@H]1C[C@@H](C2(O)CC2)N(c2cc(-c3cnccc3C#N)ccc2[N+](=O)[O-])C1]

A mixture of tert-butyl (3S,5S)-5-(1-hydroxycyclopropyl)pyrrolidin-3-ylcarbamate (123 mg, 0.26 mmol), iron (74 mg, 1.32 mmol) and ammonium chloride (85 mg, 1.58 mmol) in THF (2 mL), water (2 mL) and methanol (2 mL) was stirred at 60° C. for 1 h. After cooling to room temperature, the mixture was filtered through a plug of Celite and diluted with CH$_2$Cl$_2$. The organic phase was separated, washed with brine, dried over MgSO$_4$, filtered and the solvents concentrated under vacuum. The crude product was used in the next step without further purification. LCMS calculated for C$_{24}$H$_{30}$N$_5$O$_3$ (M+H)$^+$: m/z=436.1; Found: 436.2.

Step 6. N-(2-((2S,4S)-4-Amino-2-(1-hydroxycyclopropyl)pyrrolidin-1-yl)-4-(4-cyanopyridin-3-yl)phenyl)-2-(2-fluoro-6-methoxyphenyl)pyrimidine-4-carboxamide HATU (151 mg, 0.40 mmol) was added to a solution of tert-butyl (3S,5S)-1-(2-amino-5-(4-cyanopyridin-3-yl)phenyl)-5-(1-hydroxycyclopropyl)pyrrolidin-3-ylcarbamate (115 mg, 0.26 mmol), 2-(2-fluoro-6-methoxyphenyl)pyrimidine-4-carboxylic acid (65 mg, 0.26 mmol) and DIPEA (92 μL, 0.53 mmol) in DMF (620 μL). The reaction mixture was stirred at 60° C. for 30 min and then treated with water. The precipitated product was collected by filtration, washed with water and air dried. It was redissolved in TFA and the solution was stirred at 60° C. for 10 min. After cooling, the solvent was concentrated and the crude product was then diluted with CH$_3$CN and purified with prep-LCMS (XBridge C18 column, eluting with a gradient of acetonitrile/water containing 0.1% TFA, at flow rate of 60 mL/min). LCMS calculated for C$_{31}$H$_{29}$FN$_7$O$_3$ (M+H)$^+$: m/z=566.2; Found: 566.3.

Example 54. N-(2-((2S,4S)-4-Amino-2-(2-hydroxypropan-2-yl)pyrrolidin-1-yl)-4-(4-cyanopyridin-3-yl)phenyl)-2-(2-fluoro-6-methoxyphenyl)pyrimidine-4-carboxamide

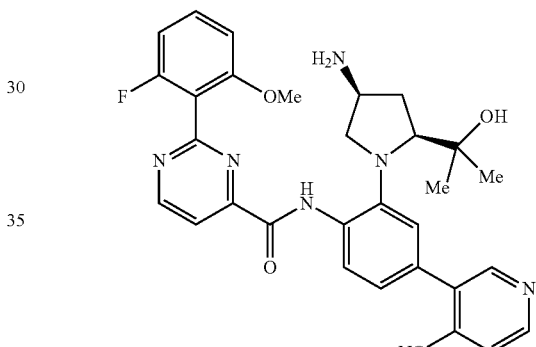

Step 1. tert-Butyl (3S,5S)-5-(2-hydroxypropan-2-yl)pyrrolidin-3-ylcarbamate

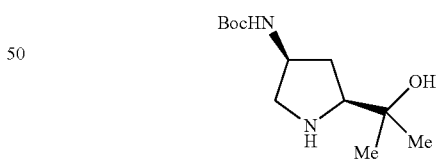

A solution of (2S,4S)-methyl 4-(tert-butoxycarbonylamino)pyrrolidine-2-carboxylate (100 mg, 0.41 mmol) in THF (4.1 mL) at 0° C. was treated with methylmagnesium bromide (3M in THF, 546 μL, 1.64 mmol) and the reaction mixture was stirred at room temperature for 1 h. The reaction mixture was treated with sat. aq. NH$_4$Cl and diluted with EtOAc. The separated organic phase was washed with brine, dried over MgSO$_4$, filtered and concentrated under vacuum. The crude product was used in the next reaction without purification. LCMS calculated for C$_{12}$H$_{25}$N$_2$O$_3$ (M+H)$^+$: m/z=245.2; found 245.2.

Step 2. tert-Butyl (3S,5S)-1-(5-(4-cyanopyridin-3-yl)-2-nitrophenyl)-5-(2-hydroxypropan-2-yl)pyrrolidin-3-ylcarbamate

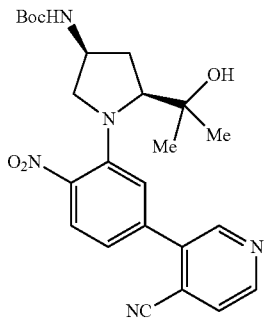 [SMILES: CC(C)(C)OC(=O)N[C@H]1C[C@@H](C(C)(C)O)N(c2cc(-c3cnccc3C#N)ccc2[N+](=O)[O-])C1]

A solution of 3-(3-fluoro-4-nitrophenyl)isonicotinonitrile (Intermediate 1, 50 mg, 0.20 mmol) and tert-butyl (3S,5S)-5-(2-hydroxypropan-2-yl)pyrrolidin-3-ylcarbamate (50 mg, 0.20 mmol) in DMSO (680 μL) was treated with triethylamine (43 μL, 0.31 mmol) and the reaction mixture was heated to 100° C. for 16 h. After cooling to room temperature, the reaction mixture was diluted with CH$_2$Cl$_2$, washed with brine, dried over MgSO$_4$, filtered and concentrated under vacuum. The crude product was used in the next reaction without purification. LCMS calculated for C$_{24}$H$_{30}$N$_5$O$_5$ (M+H)$^+$: m/z=468.2; found 468.1.

Step 3. tert-Butyl (3S,5S)-1-(2-amino-5-(4-cyanopyridin-3-yl)phenyl)-5-(2-hydroxypropan-2-yl)pyrrolidin-3-ylcarbamate

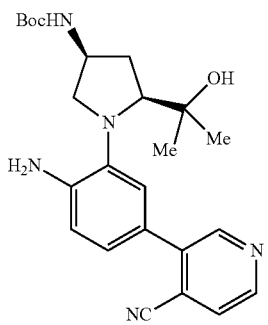

A mixture of tert-butyl (3S,5S)-1-(5-(4-cyanopyridin-3-yl)-2-nitrophenyl)-5-(2-hydroxypropan-2-yl)pyrrolidin-3-ylcarbamate (96 mg, 0.20 mmol), iron (57 mg, 1.03 mmol) and ammonium chloride (66 mg, 1.23 mmol) in THF (2 mL), water (2 mL) and methanol (2 mL) was stirred at 60° C. for 1 h. After cooling to room temperature, the mixture was filtered through a plug of Celite and diluted with CH$_2$Cl$_2$. The organic phase was separated, washed with brine, dried over MgSO$_4$, filtered and the solvents were concentrated under vacuum. The crude product was used in the next step without further purification. LCMS calculated for C$_{24}$H$_{32}$N$_5$O$_3$ (M+H)$^+$: Found: 438.1.

Step 4. N-(2-((2S,4S)-4-Amino-2-(2-hydroxypropan-2-yl)pyrrolidin-1-yl)-4-(4-cyanopyridin-3-yl)phenyl)-2-(2-fluoro-6-methoxyphenyl)pyrimidine-4-carboxamide HATU (117 mg, 0.31 mmol) was added to a solution of tert-butyl (3S,5S)-1-(2-amino-5-(4-cyanopyridin-3-yl)phenyl)-5-(2-hydroxypropan-2-yl)pyrrolidin-3-ylcarbamate (90 mg, 0.21 mmol), 2-(2-fluoro-6-methoxyphenyl)pyrimidine-4-carboxylic acid (51 mg, 0.21 mmol) and DIPEA (72 μL, 0.41 mmol) in DMF (480 μL). The reaction mixture was stirred at 60° C. for 30 min and then treated with water. The precipitated product was collected by filtration, washed with water and air dried. The solid was dissolved in TFA and the resultant solution was stirred at 60° C. for 10 min. The solution was cooled, concentrated and the crude product was diluted with CH$_3$CN and purified with prep-LCMS (XBridge C18 column, eluting with a gradient of acetonitrile/water containing 0.1% TFA, at flow rate of 60 mL/min). LCMS calculated for C$_{31}$H$_{31}$FN$_7$O$_3$ (M+H)$^+$: m/z=568.2; Found: 568.3.

Example 55. N-(2-((2S,4S)-4-Amino-2-(hydroxymethyl-d2)pyrrolidin-1-yl)-4-(4-cyanopyridin-3-yl)phenyl)-2-(2-fluoro-6-methoxyphenyl)pyrimidine-4-carboxamide

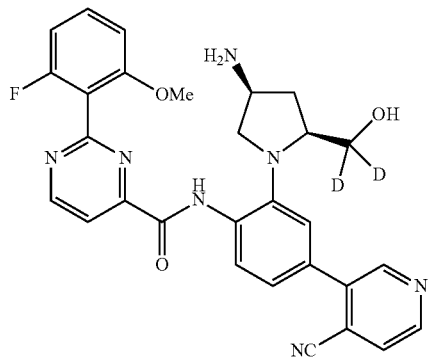

Step 1. tert-Butyl (3S,5S)-5-(hydroxymethyl-d2)pyrrolidin-3-ylcarbamate

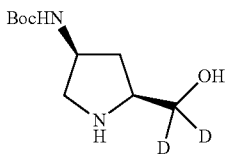 [SMILES: [2H]C([2H])(O)[C@@H]1C[C@H](NC(=O)OC(C)(C)C)CN1]

A solution of (2S,4S)-methyl 4-(tert-butoxycarbonylamino)pyrrolidine-2-carboxylate (100 mg, 0.41 mmol) in THF (4.1 mL) at 0° C. was treated with lithium aluminum deuteride (17 mg, 0.41 mmol) and the reaction mixture was stirred for 1 h, then warmed to room temperature and stirred for an additional 30 min. The reaction mixture was diluted with Et$_2$O, water, and 15% aq. LiOH. The separated organic phase was dried over MgSO$_4$, filtered and the solvent concentrated under vacuum. The crude product was used in the next reaction without purification. LCMS calculated for C$_{10}$H$_{19}$D2N$_2$O$_3$ (M+H)$^+$: m/z=219.2; found 219.1.

Step 2. tert-Butyl (3S,5S)-1-(5-(4-cyanopyridin-3-yl)-2-nitrophenyl)-5-(hydroxymethyl-d2)pyrrolidin-3-ylcarbamate

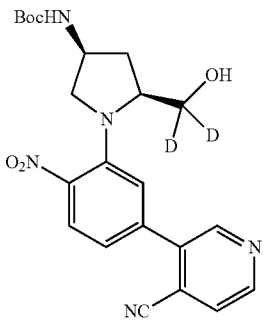 [SMILES: [2H]C([2H])(O)[C@@H]1C[C@H](NC(=O)OC(C)(C)C)CN1c1cc(-c2cnccc2C#N)ccc1[N+](=O)[O-]]

A solution of 3-(3-fluoro-4-nitrophenyl)isonicotinonitrile (Intermediate 1, 99 mg, 0.41 mmol) and tert-butyl (3S,5S)-5-(hydroxymethyl-d2)pyrrolidin-3-ylcarbamate (89 mg, 0.41 mmol) in DMSO (1.36 mL) was treated with triethylamine (85 µL, 0.61 mmol) and the reaction mixture was heated to 100° C. for 16 hrs. After cooling to r.t., the reaction mixture was diluted with CH$_2$Cl$_2$, washed with brine, dried over MgSO$_4$, filtered and the solvent was concentrated. The crude product was used in the next reaction without purification. LCMS calculated for C$_{22}$H$_{24}$D$_2$N$_5$O$_5$ (M+H)$^+$: m/z=442.2; found 442.1.

Step 3. tert-Butyl (3S,5S)-1-(2-amino-5-(4-cyanopyridin-3-yl)phenyl)-5-(hydroxybiusdeuteromethyl)pyrrolidin-3-ylcarbamate

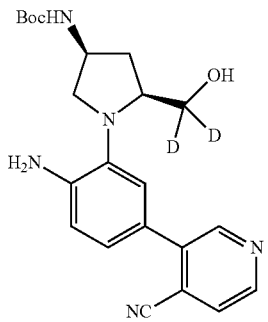

A mixture of tert-butyl (3S,5S)-1-(5-(4-cyanopyridin-3-yl)-2-nitrophenyl)-5-(hydroxymethyl-d2)pyrrolidin-3-ylcarbamate (180 mg, 2.04 mmol), iron (114 mg, 1.03 mmol) and ammonium chloride (131 mg, 2.45 mmol) in THF (2 mL), water (2 mL) and methanol (2 mL) was stirred at 60° C. for 1 h. After cooling to room temperature, the mixture was filtered through a plug of Celite and diluted with CH$_2$Cl$_2$. The organic phase was separated, washed with brine, dried over MgSO$_4$, filtered and the solvents were concentrated. The crude product was used in the next step without further purification. LCMS calculated for C$_{22}$H$_{26}$D2N$_5$O$_3$ (M+H)$^+$: m/z=412.2; Found: 412.2.

Step 4. N-(2-((2S,4S)-4-Amino-2-(hydroxymethyl-d2)pyrrolidin-1-yl)-4-(4-cyanopyridin-3-yl)phenyl)-2-(2-fluoro-6-methoxyphenyl)pyrimidine-4-carboxamide HATU (233 mg, 0.61 mmol) was added to a solution of tert-butyl (3S,5S)-1-(2-amino-5-(4-cyanopyridin-3-yl)phenyl)-5-(hydroxymethyl-d2)pyrrolidin-3-ylcarbamate (168 mg, 0.41 mmol), 2-(2-fluoro-6-methoxyphenyl)pyrimidine-4-carboxylic acid (101 mg, 0.41 mmol) and DIPEA (143 µL, 0.82 mmol) in DMF (956 µL). The reaction mixture was stirred at 60° C. for 30 min and then treated with water. The precipitated product was collected by filtration, washed with water and air dried. The solid was then dissolved in TFA and the solution was stirred at 60° C. for 10 min. After cooling the solution was concentrated and the crude residue was dissolved in THF (1 mL), MeOH (1 mL), and aq. NH$_4$OH (1 mL). The mixture was stirred at 60° C. for 30 min in a sealed container. The mixture was cooled, concentrated under vacuum and the crude product was diluted with CH$_3$CN and purified with prep-LCMS (XBridge C18 column, eluting with a gradient of acetonitrile/water containing 0.1% TFA, at flow rate of 60 mL/min). LCMS calculated for C$_{29}$H$_{25}$D$_2$FN$_7$O$_3$ (M+H)$^+$: m/z=542.2; Found: 542.4. $^1$H NMR (500 MHz, DMSO-d$_6$) δ 10.64 (s, 1H), 9.28 (d, J=5.0 Hz, 1H), 8.97 (s, 1H), 8.82 (d, J=5.0 Hz, 1H), 8.29 (d, J=8.4 Hz, 1H), 8.18 (d, J=5.0 Hz, 1H), 7.99 (d, J=5.0 Hz, 1H), 7.96-7.84 (m, 3H), 7.67 (s, 1H), 7.56 (td, J=8.4, 6.8 Hz, 1H), 7.47 (dd, J=8.4, 2.0 Hz, 1H), 7.06 (d, J=8.5 Hz, 1H), 7.00 (t, J=8.8 Hz, 1H), 4.96 (s, 1H), 3.83 (dd, J=8.6, 5.3 Hz, 1H), 3.78 (s, 3H), 3.74-3.65 (m, 1H), 3.38-3.35 (m, 1H), 3.32-3.29 (m, 1H), 2.38 (dt, J=13.2, 7.8 Hz, 1H), 1.84 (dt, J=13.3, 5.4 Hz, 1H) ppm.

Example 56. N-(4-(4-Cyanopyridin-3-yl)-2-((1S,3R,4S)-3-(hydroxymethyl)-2,5-diazabicyclo[2.2.1]heptan-2-yl)phenyl)-2-(2-fluoro-6-methoxyphenyl)pyrimidine-4-carboxamide

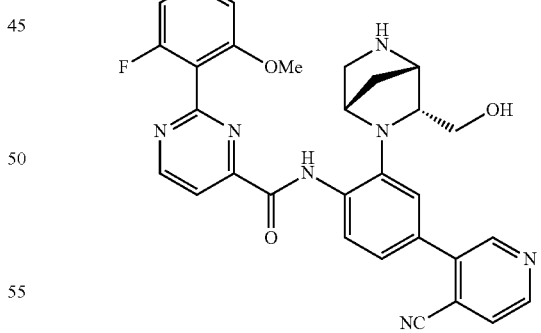

This compound was prepared according to the procedures described in Example 50, using (1S,4S,6R)-tert-butyl 6-(hydroxymethyl)-2,5-diazabicyclo[2.2.1]heptane-2-carboxylate (prepared by an adaptation of the procedure described in: Balog, A. et al. *Bioorg. Med. Chem. Lett.* 2004, 14, 6107-6111) instead of (2R,5S)-tert-butyl 5-(hydroxymethyl)-2-methylpiperazine-1-carboxylate as starting material. LCMS calculated for C$_{30}$H$_{27}$FN$_7$O$_3$ (M+H)$^+$: m/z=552.2; Found: 552.2.

Example 57. N-(4-(4-Cyanopyridin-3-yl)-2-((1S,4S)-1-(hydroxymethyl)-2,5-diazabicyclo[2.2.1]heptan-2-yl)phenyl)-2-(2-fluoro-6-methoxyphenyl)pyrimidine-4-carboxamide

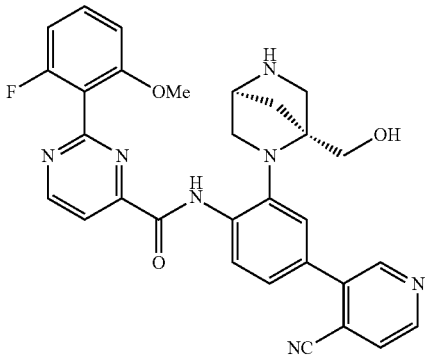 [SMILES: COc1cccc(F)c1-c1nccc(C(=O)Nc2ccc(-c3cnccc3C#N)cc2N2C[C@@H]3C[C@@]2(CO)CN3)n1]

This compound was prepared according to the procedures described in Example 50, using (1S,4S)-tert-butyl 4-(hydroxymethyl)-2,5-diazabicyclo[2.2.1]heptane-2-carboxylate (prepared by an adaptation of the procedure described in: Ivon, Y. et al. *Synthesis* 2015, 47, 1123-1130) instead of (2R,5S)-tert-butyl 5-(hydroxymethyl)-2-methylpiperazine-1-carboxylate as starting material. LCMS calculated for $C_{30}H_{27}FN_7O_3$ (M+H)$^+$: m/z=552.2; Found: 552.3.

Example 58. N-(2-((2S,4S)-4-Amino-2-methylpiperidin-1-yl)-4-(4-cyanopyridin-3-yl)phenyl)-2-(2-fluoro-6-methoxyphenyl)pyrimidine-4-carboxamide

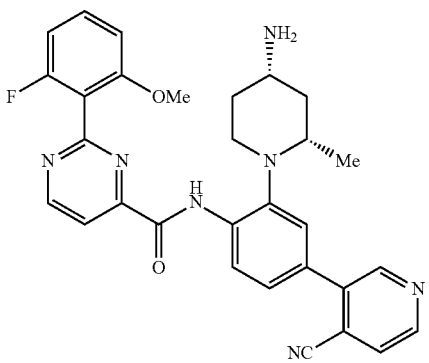 [SMILES: COc1cccc(F)c1-c1nccc(C(=O)Nc2ccc(-c3cnccc3C#N)cc2N2CC[C@H](N)C[C@@H]2C)n1]

Step 1. 2-((2S,4S)-2-Methylpiperidin-4-yl)isoindoline-1,3-dione

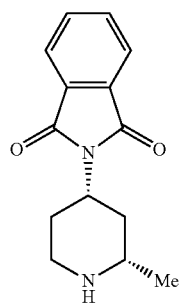 [SMILES: C[C@H]1C[C@@H](N2C(=O)c3ccccc3C2=O)CCN1]

A solution of (2S,4R)-tert-butyl 4-hydroxy-2-methylpiperidine-1-carboxylate (75 mg, 0.35 mmol), phthalimide (62 mg, 0.43 mmoL), and triphenylphosphine (111 mg, 0.43 mmol) in THF (1.7 mL) was treated with DIAD (83 μL, 0.43 mmol) and the mixture was stirred for 1 h at room temperature. The reaction mixture was diluted with MeOH and EtOAc, washed with brine, dried over MgSO$_4$, filtered and the solvent was concentrated. The crude product was then treated with HCl (4M in dioxane, 1 mL) and stirred for 1 h at room temperature. The solvent was concentrated under vacuum and the crude product was used in the next reaction without purification. LCMS calculated for $C_{14}H_{17}N_2O_2$ (M+H)$^+$: m/z=245.1; found 245.1.

Step 2. 3-(3-((2S,4S)-4-(1,3-Dioxoisoindolin-2-yl)-2-methylpiperidin-1-yl)-4-nitrophenyl)isonicotinonitrile

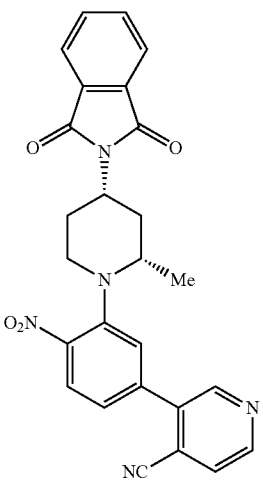 [SMILES: C[C@H]1C[C@@H](N2C(=O)c3ccccc3C2=O)CCN1c1cc(-c2cnccc2C#N)ccc1[N+](=O)[O-]]

A solution of 3-(3-fluoro-4-nitrophenyl)isonicotinonitrile (Intermediate 1, 85 mg, 0.35 mmol) and 2-((2S,4S)-2-methylpiperidin-4-yl)isoindoline-1,3-dione (85 mg, 0.35 mmol) in DMSO (1.2 mL) was treated with triethylamine (73 μL, 0.52 mmol) and the reaction mixture was heated to 100° C. for 16 h. After cooling to room temperature, the reaction mixture was diluted with CH$_2$Cl$_2$, washed with brine, dried over MgSO$_4$, filtered and the solvent concentrated under vacuum. The crude product was used in the next reaction without purification. LCMS calculated for $C_{26}H_{22}N_5O_4$ (M+H)$^+$: m/z=468.2; found 468.1.

Step 3. 3-(4-Amino-3-((2S,4S)-4-(1,3-dioxoisoindolin-2-yl)-2-methylpiperidin-1-yl)phenyl)isonicotinonitrile

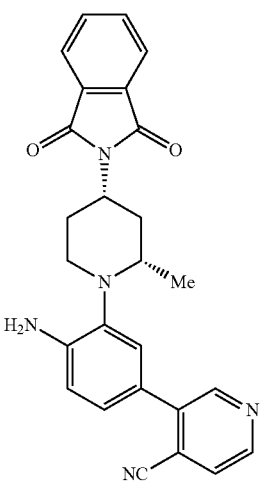

A mixture of 3-(3-((2S,4S)-4-(1,3-dioxoisoindolin-2-yl)-2-methylpiperidin-1-yl)-4-nitrophenyl)isonicotinonitrile (163 mg, 0.35 mmol), iron (97 mg, 1.70 mmol) and ammonium chloride (112 mg, 2.10 mmol) in THF (2 mL), water (2 mL) and methanol (2 mL) was stirred at 60° C. for 1 h. After cooling to room temperature, the mixture was filtered through a plug of Celite and diluted with $CH_2Cl_2$. The organic phase was separated, washed with brine, dried over $MgSO_4$, filtered and the solvents were concentrated. The crude product was used in the next step without further purification. LCMS calculated for $C_{26}H_{24}N_5O_2$ $(M+H)^+$: m/z=438.2; Found: 438.1.

Step 4. N-(2-((2S,4S)-4-Amino-2-methylpiperidin-1-yl)-4-(4-cyanopyridin-3-yl)phenyl)-2-(2-fluoro-6-methoxyphenyl)pyrimidine-4-carboxamide HATU (99 mg, 0.26 mmol) was added to a solution of 3-(4-amino-3-((2S,4S)-4-(1,3-dioxoisoindolin-2-yl)-2-methylpiperidin-1-yl)phenyl)isonicotinonitrile (76 mg, 0.17 mmol), 2-(2-fluoro-6-methoxyphenyl)pyrimidine-4-carboxylic acid (43 mg, 0.17 mmol) and DIPEA (61 μL, 0.35 mmol) in DMF (400 μL). The reaction mixture was stirred at 60° C. for 30 min and then treated with water. The precipitated product was collected by filtration, washed with water and air dried. The solid was then dissolved in EtOH (2 mL) and treated with hydrazine hydrate (aq. 50-60%, 1 mL). The solution was stirred at 60° C. for 16 h, cooled and concentrated. The residue was then diluted with acetonitrile and purified with prep-LCMS (XBridge C18 column, eluting with a gradient of acetonitrile/water containing 0.1% TFA, at flow rate of 60 mL/min). LCMS calculated for $C_{30}H_{29}FN_7O_2$ $(M+H)^+$: m/z=538.2; Found: 538.4.

Example 59. N-(2-((2S,4S)-4-Amino-2-(hydroxymethyl)pyrrolidin-1-yl)-4-(4-cyanopyridin-3-yl)phenyl)-6-(2-fluoro-6-methoxyphenyl)picolinamide

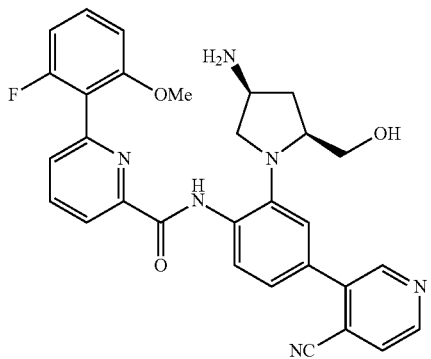 [SMILES: COc1cccc(F)c1-c1cccc(C(=O)Nc2ccc(-c3cnccc3C#N)cc2N2C[C@@H](N)C[C@H]2CO)n1]

Step 1. tert-Butyl (3S,5S)-1-(2-amino-5-(4-cyanopyridin-3-yl)phenyl)-5-(hydroxymethyl)pyrrolidin-3-ylcarbamate

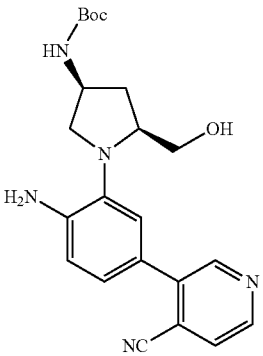 [SMILES: CC(C)(C)OC(=O)N[C@H]1C[C@@H](CO)N(c2cc(-c3cnccc3C#N)ccc2N)C1]

This compound was prepared according to the procedures described in Example 50, Step 2, using tert-butyl (3S,5S)-5-(hydroxymethyl)pyrrolidin-3-ylcarbamate instead of (2R,5S)-tert-butyl 5-(hydroxymethyl)-2-methylpiperazine-1-carboxylate as starting material. LCMS calculated for $C_{22}H_{28}N_5O_3$ $(M+H)^+$: m/z=410.2; Found: 410.1.

Step 2. tert-Butyl (3S,5S)-1-(2-(6-chloropicolinamido)-5-(4-cyanopyridin-3-yl)phenyl)-5-(hydroxymethyl)pyrrolidin-3-ylcarbamate

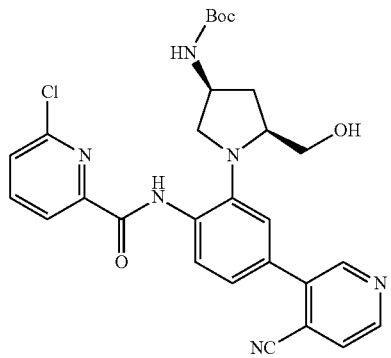 [SMILES: CC(C)(C)OC(=O)N[C@H]1C[C@@H](CO)N(c2cc(-c3cnccc3C#N)ccc2NC(=O)c2cccc(Cl)n2)C1]

HATU (320 mg, 0.843 mmol) was added to a solution of tert-butyl ((3S,5S)-1-(2-amino-5-(4-cyanopyridin-3-yl)phenyl)-5-(hydroxymethyl)pyrrolidin-3-yl)carbamate (230 mg, 0.562 mmol), 6-chloropicolinic acid (88 mg, 0.562 mmol) and DIPEA (0.196 ml, 1.123 mmol) in DMF (1 ml). After stirring at room temperature for 30 min, water (3 mL) was added. The desired product was collected by filtration, washed with water and dried overnight. LCMS calculated for $C_{28}H_{30}ClN_6O_4$ $(M+H)^+$: m/z=549.2; Found: 549.2.

Step 3. N-(2-((2S,4S)-4-Amino-2-(hydroxymethyl)pyrrolidin-1-yl)-4-(4-cyanopyridin-3-yl)phenyl)-6-(2-fluoro-6-methoxyphenyl)picolinamid A mixture of tert-butyl (3S,5S)-1-(2-(6-chloropicolinamido)-5-(4-cyanopyridin-3-yl)phenyl)-5-(hydroxymethyl) pyrrolidin-3-ylcarbamate (20 mg, 0.036 mmol), (2-fluoro-6-methoxyphenyl)boronic acid (6.20 mg, 0.036 mmol), potassium phosphate, tribasic (15.49 mg, 0.073 mmol), XPhos Pd G2 (3.03 mg, 3.65 μmol) in p-dioxane (1 mL) and water (0.2 mL) was stirred at 70° C. for 2 h. The mixture was concentrated under vacuum and dissolved in DCM (1 mL) and TFA (1 mL). The resulting mixture was stirred at room temperature for 15 min. The solvent was concentrated under vacuum and the residue diluted with acetonitrile and purified with prep-LCMS (XBridge C18 column, eluting with a gradient of acetonitrile/water containing 0.1% TFA, at flow rate of 60 mL/min). LCMS calculated for $C_{30}H_{28}FN_6O_3$ (M+H)$^+$: m/z=539.2; Found: 539.1.

Example 60. N-(2-((2S,4S)-4-Amino-2-(hydroxymethyl)pyrrolidin-1-yl)-4-(4-cyanopyridin-3-yl)phenyl)-5-cyano-6-(2-fluoro-6-methoxyphenyl)picolinamide

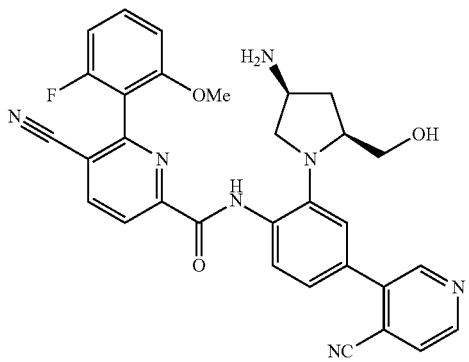 [SMILES: COc1cccc(F)c1-c1nc(C(=O)Nc2ccc(-c3cnccc3C#N)cc2N2C[C@@H](N)C[C@H]2CO)ccc1C#N]

This compound was prepared according to the procedures described in Example 59, using 6-chloro-5-cyanopicolinic acid instead of 6-chloropicolinic acid as starting material. LCMS calculated for $C_{31}H_{27}FN_7O_3$ (M+H)$^+$: m/z=564.2; Found: 564.2.

Example 61. N-(2-((2S,4S)-4-Amino-2-(hydroxymethyl)pyrrolidin-1-yl)-4-(4-cyanopyridin-3-yl)phenyl)-6-(2-fluoro-6-methoxyphenyl)-5-methoxypicolinamide

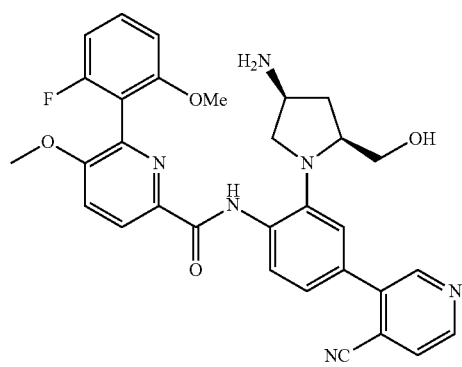 [SMILES: COc1ccc(C(=O)Nc2ccc(-c3cnccc3C#N)cc2N2C[C@@H](N)C[C@H]2CO)nc1-c1c(F)cccc1OC]

This compound was prepared according to the procedures described in Example 59, using 6-chloro-5-methoxypicolinic acid instead of 6-chloropicolinic acid as starting material. LCMS calculated for $C_{31}H_{30}FN_6O_4$ (M+H)$^+$: m/z=569.2; Found: 569.2.

Example 62. N-(2-((2S,4S)-4-Amino-2-(hydroxymethyl)pyrrolidin-1-yl)-4-(4-cyanopyridin-3-yl)phenyl)-2-(2,6-difluorophenyl)pyrimidine-4-carboxamide

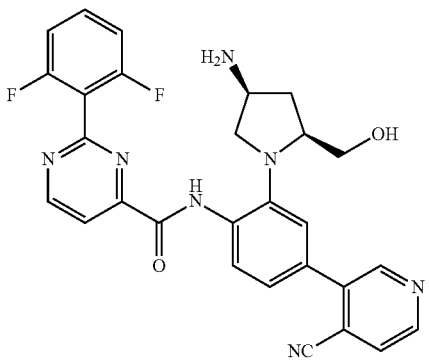 [SMILES: N#Cc1ccncc1-c1ccc(NC(=O)c2ccnc(-c3c(F)cccc3F)n2)c(N2C[C@@H](N)C[C@H]2CO)c1]

Step 1. tert-Butyl (3S,5S)-1-(2-(2-chloropyrimidine-4-carboxamido)-5-(4-cyanopyridin-3-yl)phenyl)-5-(hydroxymethyl)pyrrolidin-3-ylcarbamate

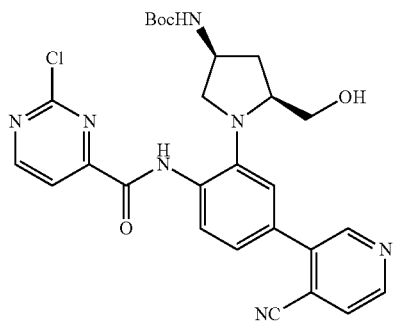 [SMILES: CC(C)(C)OC(=O)N[C@H]1C[C@@H](CO)N(c2cc(-c3cnccc3C#N)ccc2NC(=O)c2ccnc(Cl)n2)C1]

This compound was prepared according to the procedures described in Example 59, Step 2, using 2-chloropyrimidine-4-carboxylic acid instead of 6-chloropicolinic acid as starting material. LCMS calculated for $C_{27}H_{29}ClN_7O_4$ (M+H)$^+$: m/z=550.2; Found: 550.1.

Step 2. N-(2-((2S,4S)-4-Amino-2-(hydroxymethyl)pyrrolidin-1-yl)-4-(4-cyanopyridin-3-yl)phenyl)-2-(2,6-difluorophenyl)pyrimidine-4-carboxamide A mixture of tert-butyl (3S,5S)-1-(2-(2-chloropyrimidine-4-carboxamido)-5-(4-cyanopyridin-3-yl)phenyl)-5-(hydroxymethyl)pyrrolidin-3-ylcarbamate (20 mg, 0.036 mmol), (2,6-difluorophenyl)boronic acid (5.75 mg, 0.036 mmol), potassium phosphate, tribasic (15.46 mg, 0.073 mmol), XPhos Pd G2 (3.02 mg, 3.64 μmol) in p-dioxane (1 mL) and water (0.2 mL) was stirred at 70° C. for 2 h. The mixture was concentrated under vacuum and dissolved in DCM (1 mL) and TFA (1 mL). The resulting mixture was stirred at room temperature for 15 min and then the solvent was concentrated. The residue was diluted with acetonitrile and purified with prep-LCMS (XBridge C18 column, eluting with a gradient of acetonitrile/water containing 0.1% TFA, at flow rate of 60 mL/min). LCMS calculated for $C_{28}H_{24}F_2N_7O_2$ (M+H)$^+$: m/z=528.2; Found: 528.4.

Example 63. N-(2-((2S,4S)-4-Amino-2-(hydroxymethyl)pyrrolidin-1-yl)-4-(4-cyanopyridin-3-yl)phenyl)-2-(2-fluoro-6-methylphenyl)pyrimidine-4-carboxamide

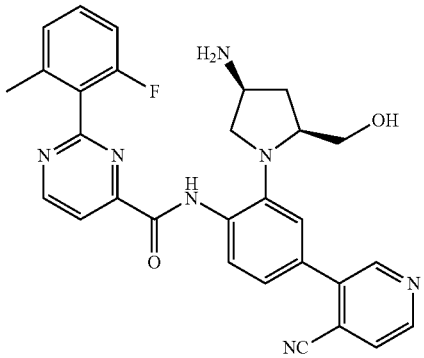 [SMILES: Cc1cccc(F)c1-c1nccc(C(=O)Nc2ccc(-c3cnccc3C#N)cc2N2C[C@@H](N)C[C@H]2CO)n1]

This compound was prepared according to the procedures described in Example 62, using (2-fluoro-6-methylphenyl)boronic acid instead of (2,6-difluorophenyl)boronic acid as starting material. LCMS calculated for $C_{29}H_{27}FN_7O_2$ (M+H)$^+$: m/z=524.2; Found: 524.1.

Example 64. N-(2-((2S,4S)-4-Amino-2-(hydroxymethyl)pyrrolidin-1-yl)-4-(4-cyanopyridin-3-yl)phenyl)-2-(2-chloro-6-fluorophenyl)pyrimidine-4-carboxamide

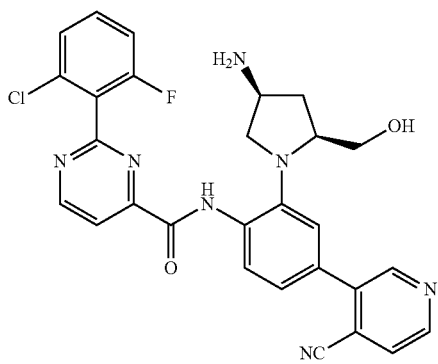 [SMILES: N#Cc1ccncc1-c1ccc(NC(=O)c2ccnc(-c3c(F)cccc3Cl)n2)c(N2C[C@@H](N)C[C@H]2CO)c1]

This compound was prepared according to the procedures described in Example 62, using (2-chloro-6-fluorophenyl)boronic acid instead of (2,6-difluorophenyl)boronic acid as starting material. LCMS calculated for $C_{28}H_{24}ClFN_7O_2$ (M+H)$^+$: m/z=544.2; Found: 544.2.

Example 65. N-(2-((2S,4S)-4-Amino-2-(hydroxymethyl)pyrrolidin-1-yl)-6-(1,3,5-trimethyl-1H-pyrazol-4-yl)pyridin-3-yl)-2-(2-fluoro-6-methoxyphenyl)pyrimidine-4-carboxamide

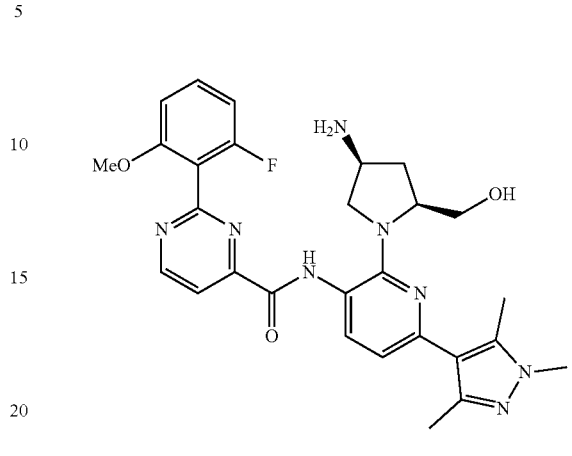

Step 1. tert-Butyl (3S,5S)-1-(6-bromo-3-(2-(2-fluoro-6-methoxyphenyl)pyrimidine-4-carboxamido)pyridin-2-yl)-5-(hydroxymethyl)pyrrolidin-3-ylcarbamate

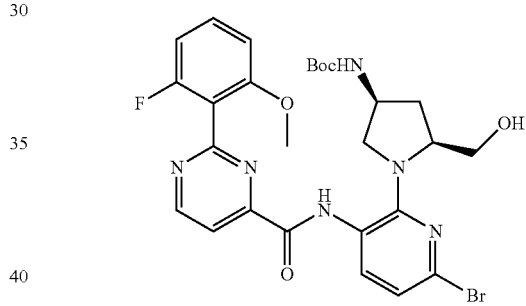

This compound was prepared according to the procedures described in Example 41 and 1, using 6-bromo-2-chloro-3-nitropyridine instead of 4-bromo-2-fluoro-1-nitrobenzene as starting material. LCMS calculated for $C_{27}H_{31}BrFN_6O_5$ (M+H)$^+$: m/z=617.2; Found: 617.2.

Step 2. N-(2-((2S,4S)-4-Amino-2-(hydroxymethyl)pyrrolidin-1-yl)-6-(1,3,5-trimethyl-1H-pyrazol-4-yl)pyridin-3-yl)-2-(2-fluoro-6-methoxyphenyl)pyrimidine-4-carboxamide A mixture of tert-butyl ((3S,5S)-1-(6-bromo-3-(2-(2-fluoro-6-methoxyphenyl)pyrimidine-4-carboxamido)pyridin-2-yl)-5-(hydroxymethyl)pyrrolidin-3-yl)carbamate (35 mg, 0.057 mmol), 1,3,5-trimethyl-4-(4,4,5,5-tetramethyl-1,3,2-dioxaborolan-2-yl)-1H-pyrazole (0.020 g, 0.085 mmol), Xphos Pd G2 (13 mg, 16 μmol) and potassium phosphate, tribasic (67 mg, 0.32 mmol) was combined with 1,4-dioxane (1 ml) and water (0.1 ml). The reaction flask was evacuated, back filled with nitrogen, and then stirred at 80° C. for 1 h. The reaction mixture was cooled to room temperature, the solvents were concentrated under vacuum, and TFA (1 ml) was added. The reaction mixture was stirred at room temperature for 10 min, then diluted with CH$_3$CN and water, and purified with prep-LCMS (XBridge C18 column, eluting with a gradient of acetonitrile/water containing 0.1% TFA, at flow rate of 60 mL/min). LCMS calculated for $C_{28}H_{32}FN_8O_3$ (M+H)+: m/z=547.3; Found: 547.3.

Example 66. N-(2-((2S,4S)-4-Amino-2-(hydroxymethyl)pyrrolidin-1-yl)-5-fluorophenyl)-2-(2,6-difluorophenyl)pyrimidine-4-carboxamide

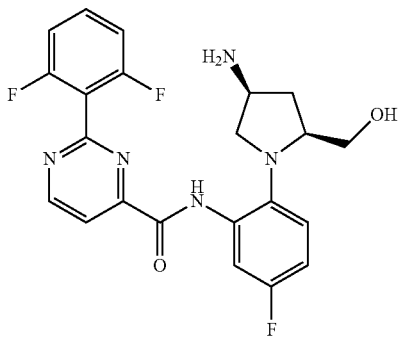 [SMILES: N[C@H]1C[C@@H](CO)N(c2ccc(F)cc2NC(=O)c2ccnc(-c3c(F)cccc3F)n2)C1]

Step 1. tert-Butyl ((3S,5S)-1-(2-amino-4-fluorophenyl)-5-(hydroxymethyl)pyrrolidin-3-yl)carbamate

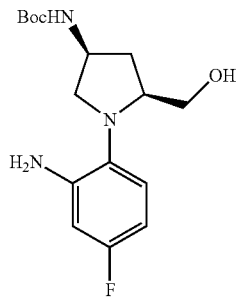

A solution of 1,4-difluoro-2-nitrobenzene (250 mg, 1.57 mmol) and tert-butyl ((3S,5S)-5-(hydroxymethyl)pyrrolidin-3-yl)carbamate (340 mg, 1.57 mmol) in DMSO (5 ml) was treated with Hunig's base (274 µl, 1.57 mmol) and the reaction mixture was heated to 90° C. for 1 hr. The reaction mixture was treated with water and the product was extracted with ethyl acetate. The organic phase was washed with water and saturated aqueous sodium chloride, dried over sodium sulfate and concentrated. The crude product was dissolved in a 1:1:1 mixture of THF/water/MeOH (9 mL) and treated with iron (351 mg, 6.29 mmol) and ammonium chloride (504 mg, 9.43 mmol). The reaction mixture was heated to 60° C. for 1 hr, then diluted with ethyl acetate and filtered through a plug of Celite. The filtrate was washed with water and saturated aqueous sodium chloride, dried over sodium sulfate and concentrated. The crude product was purified by Biotage Isolera™ (30-100% ethyl acetate in hexanes) to provide the desired product as a yellow solid (226 mg, 46%). LCMS calculated for $C_{16}H_{25}FN_3O_3$ (M+H)+: m/z=326.2; Found: 326.2.

Step 2. tert-Butyl ((3S,5S)-1-(2-(2-chloropyrimidine-4-carboxamido)-4-fluorophenyl)-5-(hydroxymethyl)pyrrolidin-3-yl)carbamate

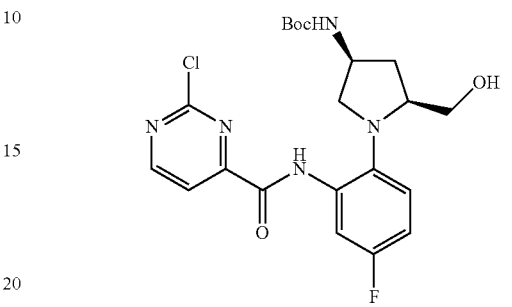

A solution of 2-chloropyrimidine-4-carboxylic acid (87 mg, 0.550 mmol), HATU (230 mg, 0.605 mmol) and tert-butyl ((3S,5S)-1-(2-amino-4-fluorophenyl)-5-(hydroxymethyl)pyrrolidin-3-yl)carbamate (179 mg, 0.550 mmol) in DMF (1834 µl) was treated with Hunig's base (192 µl, 1.100 mmol) and the reaction mixture was stirred at r.t. for 30 mins, then treated with water and the product was extracted with ethyl acetate. The organic phase was washed with water and brine, dried over sodium sulfate and concentrated. The crude product was purified by Biotage Isolera™ (25-100% ethyl acetate in hexane) to provide the desired product (107 mg, 42%). LCMS calculated for $C_{21}H_{26}C_1FN_5O_4$ (M+H)+: m/z=466.2; Found: 466.2.

Step 3. N-(2-((2S,4S)-4-Amino-2-(hydroxymethyl)pyrrolidin-1-yl)-5-fluorophenyl)-2-(2,6-difluorophenyl)pyrimidine-4-carboxamide To a mixture of (2,6-difluorophenyl)boronic acid (15 mg, 0.097 mmol), XPhos Pd G2 (5.07 mg, 6.44 µmol), potassium phosphate (27.5 mg, 0.129 mmol) and tert-butyl ((3S,5S)-1-(2-(2-chloropyrimidine-4-carboxamido)-4-fluorophenyl)-5-(hydroxymethyl)pyrrolidin-3-yl)carbamate (30 mg, 0.064 mmol) were added 1,4-dioxane (530 µl) and water (100 µl) and the flask was evacuated, back filled with nitrogen, then stirred at 90° C. overnight. The reaction was diluted with DCM/water and the phases separated. The organic phase was concentrated and the residue was dissolved in TFA (1 mL) and allowed to stand at r.t. for 30 mins, then diluted with MeOH and purified with prep-LCMS (XBridge C18 column, eluting with a gradient of acetonitrile/water containing 0.1% TFA, at flow rate of 60 mL/min). LCMS calculated for $C_{22}H_{21}F_3N_5O_2$ (M+H)+: m/z=444.2; Found: 444.2.

Example 67. N-(2-((2S,4S)-4-Amino-2-(hydroxymethyl)pyrrolidin-1-yl)-5-fluorophenyl)-2-(3-cyano-2-fluoro-6-methoxyphenyl)pyrimidine-4-carboxamide

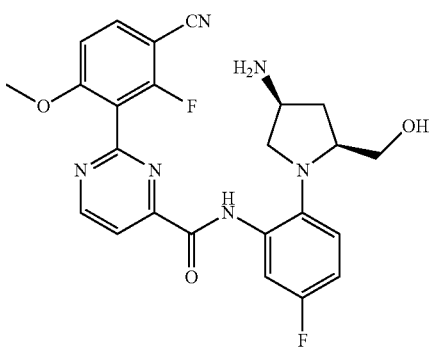 [SMILES: COc1ccc(C#N)c(F)c1-c1nccc(C(=O)Nc2cc(F)ccc2N2C[C@@H](N)C[C@H]2CO)n1]

This compound was prepared in an analogous fashion to Example 66, step 3, using 2-fluoro-4-methoxy-3-(4,4,5,5-tetramethyl-1,3,2-dioxaborolan-2-yl)benzonitrile in place of (2,6-difluorophenyl)boronic acid. LCMS calculated for $C_{24}H_{23}F_2N_6O_3$ (M+H)$^+$: m/z=481.2; Found: 481.2.

Example 68. N-(2-((2S,4S)-4-Amino-2-(hydroxymethyl)pyrrolidin-1-yl)-5-fluorophenyl)-2-(2,3-difluoro-6-methoxyphenyl)pyrimidine-4-carboxamide

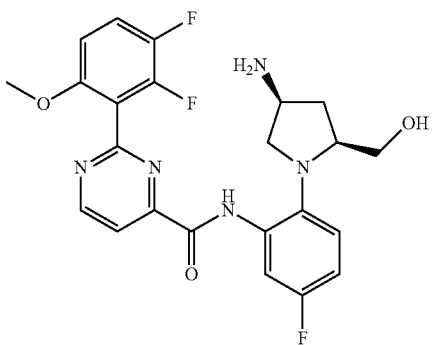 [SMILES: COc1ccc(F)c(F)c1-c1nccc(C(=O)Nc2cc(F)ccc2N2C[C@@H](N)C[C@H]2CO)n1]

This compound was prepared in an analogous fashion to Example 66, step 3, using (2,3-difluoro-6-methoxyphenyl)boronic acid in place of (2,6-difluorophenyl)boronic acid. LCMS calculated for $C_{23}H_{23}F_3N_5O_3$ (M+H)$^+$: m/z=474.2; Found: 474.2. $^1$H NMR (500 MHz, DMSO-d6) δ 10.69 (s, 1H), 9.30 (s, 1H), 8.21 (d, J=5.0 Hz, 1H), 8.18 (d, J=3.0 Hz, 1H), 7.81 (s, 2H), 7.60 (q, J=9.5 Hz, 1H), 7.53 (dd, J=8.9, 5.8 Hz, 1H), 7.13-6.96 (m, 2H), 5.19 (s, 1H), 3.75 (s, 4H), 3.56 (dd, J=8.2, 3.6 Hz, 1H), 3.26-3.17 (m, 4H), 2.46-2.35 (m, 1H), 1.77 (dt, J=13.6, 4.1 Hz, 1H) ppm.

Example 69. N-(2-((2S,4S)-4-Amino-2-(hydroxymethyl)pyrrolidin-1-yl)-5-fluorophenyl)-2-(2-fluoro-6-(methoxy-d3)-3-methylphenyl)pyrimidine-4-carboxamide

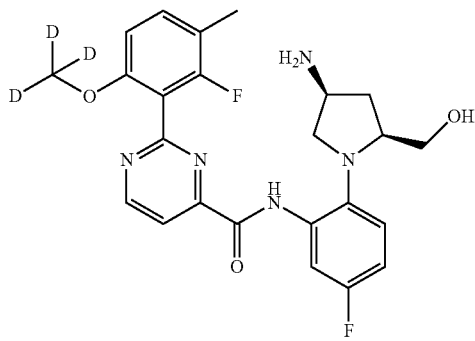 [SMILES: [2H]C([2H])([2H])Oc1ccc(C)c(F)c1-c1nccc(C(=O)Nc2cc(F)ccc2N2C[C@@H](N)C[C@H]2CO)n1]

Step 1. 2-Fluoro-4-(methoxy-d$_3$)-1-methylbenzene

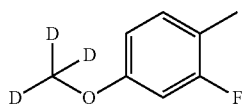

A solution of 3-fluoro-4-methylphenol (1.0 g, 7.93 mmol) in DMF (26.4 ml) was treated with potassium carbonate (1.644 g, 11.89 mmol) and iodomethane-d$_3$ (0.592 ml, 9.51 mmol) and the reaction mixture heated to 80° C. for 1 hr. The reaction mixture was treated with water and extracted with diethyl ether. The organic phase was washed with water and brine, dried over sodium sulfate and concentrated. The crude product was used in the next step without further purification. LCMS calculated for $C_8H_7D_3FO$ (M+H)$^+$: m/z=144.2; Found: 144.2.

Step 2. 2-(2-Fluoro-6-(methoxy-d$_3$)-3-methylphenyl)-4,4,5,5-tetramethyl-1,3,2-dioxaborolane

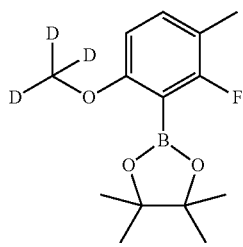 [SMILES: [2H]C([2H])([2H])Oc1ccc(C)c(F)c1B1OC(C)(C)C(C)(C)O1]

A solution of 2-fluoro-4-(methoxy-d$_3$)-1-methylbenzene (1.0 g, 6.98 mmol) and HMPA (1.823 ml, 10.48 mmol) in THF (34.9 ml) at −78° C. was treated with n-BuLi (2.5 M in hexanes, 3.35 ml, 8.38 mmol) dropwise and the reaction mixture stirred at this temperature for 1 hr. 2-isopropoxy-4,4,5,5-tetramethyl-1,3,2-dioxaborolane (2.166 ml, 10.48 mmol) was then added and the reaction mixture stirred at −78° C. for 10 mins, and then warmed up to r.t. by removing the cooling bath. The reaction was treated with aqueous 1N HCl and extracted with ethyl acetate. The organic phase was washed with water and brine, dried over sodium sulfate and concentrated. The crude product was used in the next step without further purification.

Step 3. Methyl 2-(2-fluoro-6-(methoxy-d₃)-3-methylphenyl)pyrimidine-4-carboxylic acid

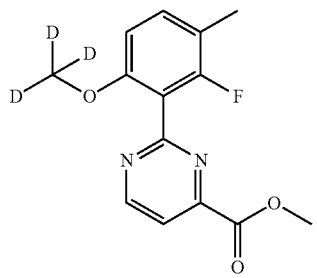 [SMILES: [2H]C([2H])([2H])Oc1ccc(C)c(F)c1-c1nccc(C(=O)OC)n1]

A solution of 2-(2-fluoro-6-(methoxy-d₃)-3-methylphenyl)-4,4,5,5-tetramethyl-1,3,2-dioxaborolane (1.56 g, 5.79 mmol) and Hunig's base (1 ml, 5.79 mmol) in water (1333 µl) and 1,4-dioxane (12 mL) was treated with methyl 2-chloropyrimidine-4-carboxylate (500 mg, 2.90 mmol) and ((t-Bu)₃P)₂Pd (74.0 mg, 0.145 mmol). The reaction flask was evacuated, back filled with nitrogen, and stirred at 80° C. overnight. The reaction mixture was then diluted with DCM and filtered through a plug of Celite. The filtrate was concentrated and the residue purified by Biotage Isolera™ (0-100% ethyl acetate in hexanes) to provide the desired intermediate. LCMS calculated for C₁₄H₁₁D₃FN₂O₃ (M+H)⁺: m/z=280.2; Found: 280.2.

Step 4. 2-(2-Fluoro-6-(methoxy-d₃)-3-methylphenyl)pyrimidine-4-carboxylic acid

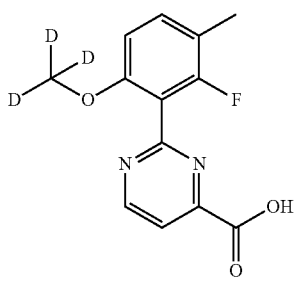 [SMILES: [2H]C([2H])([2H])Oc1ccc(C)c(F)c1-c1nccc(C(=O)O)n1]

The product from the previous step was dissolved in a 1:1 mixture of THF/water (4 mL). Lithium hydroxide (238 mg, 5.79 mmol) was added and the reaction mixture heated to 60° C. for 1 hr, then acidified to pH 1 with 1 N HCl and extracted with ethyl acetate. The organic phase was washed with brine, dried over sodium sulfate and concentrated. The crude product was used in the next step without further purification. LCMS calculated for C₁₃H₉D₃FN₂O₃ (M+H)⁺: m/z=266.2; Found: 266.2.

Step 5. N-(2-((2S,4S)-4-Amino-2-(hydroxymethyl)pyrrolidin-1-yl)-5-fluorophenyl)-2-(2-fluoro-6-(methoxy-d₃)-3-methylphenyl)pyrimidine-4-carboxamide A solution of 2-(2-fluoro-6-(methoxy-d₃)-3-methylphenyl)pyrimidine-4-carboxylic acid (12.27 mg, 0.046 mmol), HATU (21.03 mg, 0.055 mmol) and tert-butyl ((3S,5S)-1-(2-amino-4-fluorophenyl)-5-(hydroxymethyl)pyrrolidin-3-yl)carbamate (Example 66, step 2; 15 mg, 0.046 mmol) in DMF (461 µl) was treated with Hunig's base (16.10 µl, 0.092 mmol) and the reaction mixture stirred at r.t. for 30 mins. The reaction mixture was treated with water and extracted with ethyl acetate. The organic phase was washed with water and brine, dried over sodium sulfate and concentrated. The crude product was dissolved in TFA (1 mL), held at r.t. for 30 mins, then diluted with MeOH and purified with prep-LCMS (XBridge C18 column, eluting with a gradient of acetonitrile/water containing 0.1% TFA, at flow rate of 60 mL/min). LCMS calculated for C₂₄H₂₃D₃F₂N₅O₃ (M+H)⁺: m/z=473.2; Found: 473.2.

Example 70. N-(2-((2S,4S)-4-Amino-2-(hydroxymethyl)pyrrolidin-1-yl)-4-(4-cyanopyridin-3-yl)phenyl)-2-(2-fluoro-6-methoxy-4-methylphenyl)pyrimidine-4-carboxamide

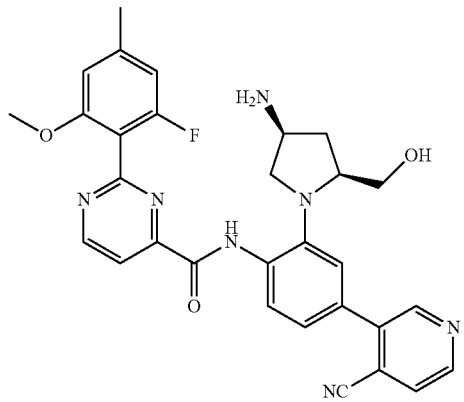 [SMILES: COc1cc(C)cc(F)c1-c1nccc(C(=O)Nc2ccc(-c3cnccc3C#N)cc2N2C[C@@H](N)C[C@H]2CO)n1]

Step 1. 2-(2-Fluoro-6-methoxy-4-methylphenyl)-4,4,5,5-tetramethyl-1,3,2-dioxaborolane

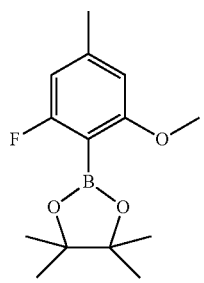 [SMILES: COc1cc(C)cc(F)c1B1OC(C)(C)C(C)(C)O1]

This compound was prepared in an analogous fashion to Example 69, step 1-2 using 3-fluoro-5-methyl phenol instead of 3-fluoro-4-methylphenol.

Step 2. tert-Butyl ((3S,5S)-1-(2-amino-5-bromophenyl)-5-(hydroxymethyl)pyrrolidin-3-yl)carbamate

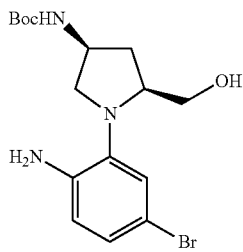 [SMILES: CC(C)(C)OC(=O)N[C@H]1C[C@@H](CO)N(c2cc(Br)ccc2N)C1]

A solution of 4-bromo-2-fluoro-1-nitrobenzene (1.0 g, 4.55 mmol) and tert-butyl ((3S,5S)-5-(hydroxymethyl)pyrrolidin-3-yl)carbamate (0.983 g, 4.55 mmol) in DMF (15.15 ml) was treated with Hunig's base (1.588 ml, 9.09 mmol) and the reaction mixture heated to 80° C. for 1 hr. The reaction mixture was poured into water/ethyl acetate, the phases separated and the organic phase was washed with water and brine, dried over sodium sulfate and concentrated. The residue was dissolved in a 1:1:1 mixture of THF/MeOH/water (15 mL) and treated with iron (1.015 g, 18.18 mmol) and ammonium chloride (1.46 g, 27.3 mmol). The reaction mixture was heated to 60° C. overnight, then diluted with ethyl acetate and filtered through a plug of Celite. The filtrate was washed with water and brine, dried over sodium sulfate and concentrated. The crude product (1.61 g, 92%) was used in the next step without further purification. LCMS calculated for $C_{16}H_{25}BrN_3O_3$ (M+H)$^+$: m/z=386.0/388.0; Found: 386.0/388.0.

Step 3. tert-Butyl ((3S,5S)-1-(2-amino-5-(4-cyanopyridin-3-yl)phenyl)-5-(hydroxymethyl) pyrrolidin-3-yl)carbamate

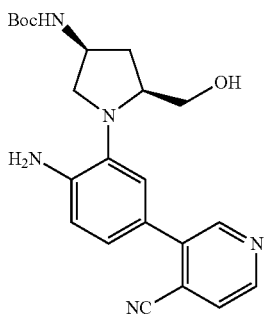 [SMILES: CC(C)(C)OC(=O)N[C@H]1C[C@@H](CO)N(c2cc(-c3cnccc3C#N)ccc2N)C1]

To a mixture of tert-butyl ((3S,5S)-1-(2-amino-5-bromophenyl)-5-(hydroxymethyl)pyrrolidin-3-yl)carbamate (200 mg, 0.518 mmol), XPhos Pd G2 (20.37 mg, 0.026 mmol), 3-(4,4,5,5-tetramethyl-1,3,2-dioxaborolan-2-yl) isonicotinonitrile (155 mg, 0.673 mmol) and potassium phosphate (220 mg, 1.035 mmol) was added 1,4-dioxane (1438 µl) and water (288 µl) and the reaction flask evacuated, back filled with nitrogen, then stirred at 90° C. for 1 hr. The mixture was diluted with ethyl acetate and filtered through a plug of Celite. The filtrate was concentrated and the residue was purified by Biotage Isolera™ (30-100% ethyl acetate in hexanes then 5-20% methanol in ethyl acetate) to provide the desired product as a brown solid (175 mg, 83%). LCMS calculated for $C_{22}H_{28}N_5O_3$ (M+H)$^+$: m/z=410.2; Found: 410.2.

Step 4. tert-Butyl ((3S,5S)-1-(2-(2-chloropyrimidine-4-carboxamido)-5-(4-cyanopyridin-3-yl)phenyl)-5-(hydroxymethyl)pyrrolidin-3-yl)carbamate

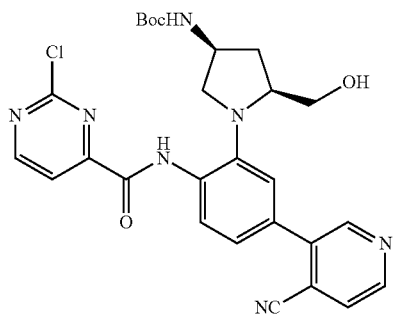 [SMILES: CC(C)(C)OC(=O)N[C@H]1C[C@@H](CO)N(c2cc(-c3cnccc3C#N)ccc2NC(=O)c2ccnc(Cl)n2)C1]

A solution of 2-chloropyrimidine-4-carboxylic acid (119 mg, 0.751 mmol), HATU (314 mg, 0.826 mmol) and tert-butyl ((3S,5S)-1-(2-amino-5-(4-cyanopyridin-3-yl)phenyl)-5-(hydroxymethyl)pyrrolidin-3-yl)carbamate (307 mg, 0.751 mmol) in DMF (3800 µl) was treated with Hunig's base (262 µl, 1.502 mmol) and allowed to stir at r.t. for 30 mins. The reaction mixture was treated with water and extracted with ethyl acetate. The organic phase was washed with water and brine, dried over sodium sulfate and concentrated. The crude product was purified by Biotage Isolera™ (40-100% ethyl acetate in hexanes) to provide the desired product as an orange solid (310 mg, 75%). LCMS calculated for $C_{27}H_{29}ClN_7O_4$ (M+H)$^+$: m/z=550.2; Found: 550.2.

Step 5. N-(2-((2S,4S)-4-Amino-2-(hydroxymethyl) pyrrolidin-1-yl)-4-(4-cyanopyridin-3-yl)phenyl)-2-(2-fluoro-6-methoxy-4-methylphenyl)pyrimidine-4-carboxamide To a mixture of tert-butyl ((3S,5S)-1-(2-(2-chloropyrimidine-4-carboxamido)-5-(4-cyanopyridin-3-yl)phenyl)-5-(hydroxymethyl)pyrrolidin-3-yl)carbamate (15 mg, 0.027 mmol), 2-(2-fluoro-6-methoxy-4-methylphenyl)-4,4,5,5-tetramethyl-1,3,2-dioxaborolane (10.89 mg, 0.041 mmol), XPhos Pd G2 (2.145 mg, 2.73 µmol) and potassium phosphate (12 mg, 0.055 mmol) were added water (54.5 µl) and 1,4-dioxane (218 µl) and the reaction flask was evacuated, back filled with nitrogen, then stirred at 90° C. overnight. The mixture was partitioned between DCM/water and the organic phase concentrated. The residue was allowed to stand in TFA (1 mL) for 30 min, at r.t., then diluted with MeOH and purified with prep-LCMS (XBridge C18 column, eluting with a gradient of acetonitrile/water containing 0.1% TFA, at flow rate of 60 mL/min). LCMS calculated for $C_{30}H_{29}F_2N_7O_3$ (M+H)$^+$: m/z=573.2; Found: 573.2.

Example 71. N-(2-((2S,4S)-4-Amino-2-(hydroxymethyl)pyrrolidin-1-yl)-4-(4-cyanopyridin-3-yl)phenyl)-2-(3,6-difluoro-2-methylphenyl)pyrimidine-4-carboxamide

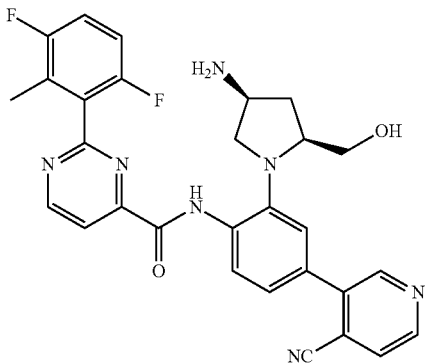 [SMILES: Cc1c(F)ccc(F)c1-c1nccc(C(=O)Nc2ccc(-c3cnccc3C#N)cc2N2C[C@@H](N)C[C@H]2CO)n1]

This compound was prepared in an analogous fashion to Example 70, step 5, using (3,6-difluoro-2-methylphenyl)boronic acid in place of 2-(2-fluoro-6-methoxy-4-methylphenyl)-4,4,5,5-tetramethyl-1,3,2-dioxaborolane. LCMS calculated for $C_{29}H_{26}F_2N_7O_2$ (M+H)$^+$: m/z=542.2; Found: 542.2.

Example 72. N-(2-((2S,4S)-4-Amino-2-(hydroxymethyl)pyrrolidin-1-yl)-4-(4-cyanopyridin-3-yl)phenyl)-2-(2,3-difluoro-6-methoxyphenyl)pyrimidine-4-carboxamide

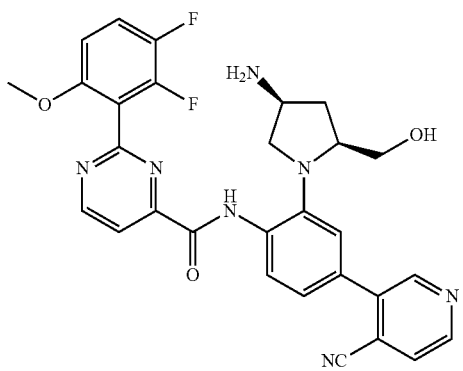 [SMILES: COc1ccc(F)c(F)c1-c1nccc(C(=O)Nc2ccc(-c3cnccc3C#N)cc2N2C[C@@H](N)C[C@H]2CO)n1]

This compound was prepared in an analogous fashion to Example 70, step 5, using (2,3-difluoro-6-methoxyphenyl)boronic acid in place of 2-(2-fluoro-6-methoxy-4-methylphenyl)-4,4,5,5-tetramethyl-1,3,2-dioxaborolane. LCMS calculated for $C_{29}H_{26}F_2N_7O_3$ (M+H)$^+$: m/z=558.2; Found: 558.2.

Example 73. N-(2-((2S,4S)-4-Amino-2-(hydroxymethyl)pyrrolidin-1-yl)-4-(4-cyanopyridin-3-yl)phenyl)-2-(3,6-difluoro-2-methoxyphenyl)pyrimidine-4-carboxamide

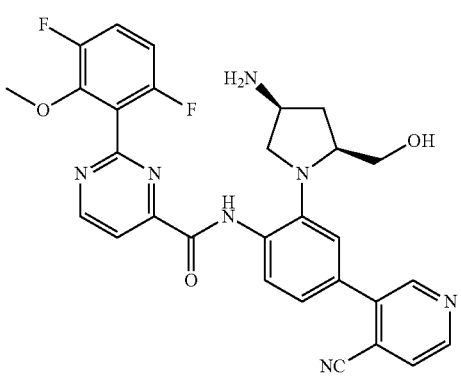 [SMILES: COc1c(F)ccc(F)c1-c1nccc(C(=O)Nc2ccc(-c3cnccc3C#N)cc2N2C[C@@H](N)C[C@H]2CO)n1]

This compound was prepared in an analogous fashion to Example 70, step 5, using (3,6-difluoro-2-methoxyphenyl)boronic acid in place of 2-(2-fluoro-6-methoxy-4-methylphenyl)-4,4,5,5-tetramethyl-1,3,2-dioxaborolane. LCMS calculated for $C_{29}H_{26}F_2N_7O_3$ (M+H)$^+$: m/z=558.2; Found: 558.2.

Example 74. N-(2-((2S,4S)-4-Amino-2-(hydroxymethyl)pyrrolidin-1-yl)-4-(4-cyanopyridin-3-yl)phenyl)-2-(3-cyano-2-fluoro-6-(methoxy-d$_3$)phenyl)pyrimidine-4-carboxamide

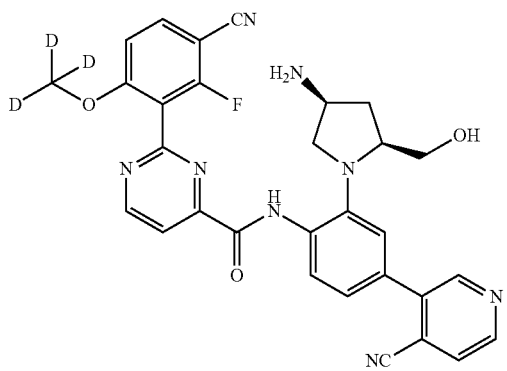 [SMILES: [2H]C([2H])([2H])Oc1ccc(C#N)c(F)c1-c1nccc(C(=O)Nc2ccc(-c3cnccc3C#N)cc2N2C[C@@H](N)C[C@H]2CO)n1]

Step 1. 2-(3-Cyano-2-fluoro-6-(methoxy-d₃)phenyl)pyrimidine-4-carboxylic acid

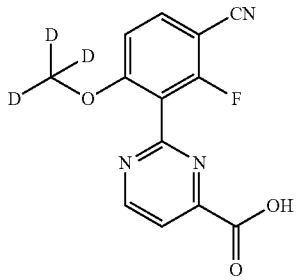 [SMILES: [2H]C([2H])([2H])Oc1ccc(C#N)c(F)c1-c1nccc(C(=O)O)n1]

This compound was prepared in an analogous fashion to Example 69, steps 1-4, starting with 3-fluoro-4-cyanophenol instead of 3-fluoro-4-methylphenol. LCMS calculated for $C_{13}H_6D_3FN_3O_3$ (M+H)⁺: m/z=277.2; Found: 277.2.

Step 2. N-(2-((2S,4S)-4-Amino-2-(hydroxymethyl)pyrrolidin-1-yl)-4-(4-cyanopyridin-3-yl)phenyl)-2-(3-cyano-2-fluoro-6-(methoxy-d₃)phenyl)pyrimidine-4-carboxamide A solution of 2-(3-cyano-2-fluoro-6-(methoxy-d₃)phenyl)pyrimidine-4-carboxylic acid (9.72 mg, 0.037 mmol), HATU (16.71 mg, 0.044 mmol) and tert-butyl ((3S,5S)-1-(2-amino-5-(4-cyanopyridin-3-yl)phenyl)-5-(hydroxymethyl)pyrrolidin-3-yl)carbamate (Example 70, Step 4, 15 mg, 0.037 mmol) in DMF (366 μl) was treated with Hunig's base (12.80 μl, 0.073 mmol) and the reaction mixture allowed to stir at r.t. for 30 mins. The reaction mixture was treated with water and extracted with ethyl acetate. The organic phase was washed with water and brine, dried over sodium sulfate and concentrated. The crude product was dissolved in TFA (1 mL) and allowed to stand at r.t. for 30 mins, then diluted with MeOH and purified with prep-LCMS (XBridge C18 column, eluting with a gradient of acetonitrile/water containing 0.1% TFA, at flow rate of 60 mL/min). LCMS calculated for $C_{30}H_{23}D_3FN_8O_3$ (M+H)⁺: m/z=568.2; Found: 568.2.

Example 75. N-(2-((2S,4S)-4-Amino-2-(hydroxymethyl)pyrrolidin-1-yl)-4-(4-cyanopyridin-3-yl)phenyl)-2-(3,6-difluoro-2-(methoxy-d₃)phenyl)pyrimidine-4-carboxamide

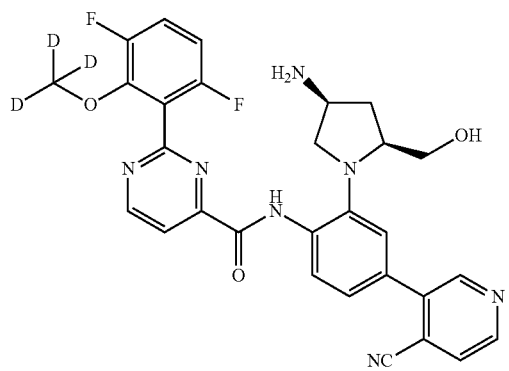 [SMILES: [2H]C([2H])([2H])Oc1c(F)ccc(F)c1-c1nccc(C(=O)Nc2ccc(-c3cnccc3C#N)cc2N2C[C@@H](N)C[C@H]2CO)n1]

Step 1. 2-(3,6-Difluoro-2-(methoxy-d₃)phenyl)pyrimidine-4-carboxylic acid

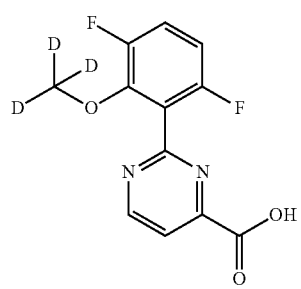 [SMILES: [2H]C([2H])([2H])Oc1c(F)ccc(F)c1-c1nccc(C(=O)O)n1]

This compound was prepared in an analogous fashion to Example 69, steps 1-4, starting with 2,5-difluorophenol instead of 3-fluoro-4-methylphenol. LCMS calculated for $C_{12}H_6D_3F_2N_2O_3$ (M+H)(: m/z=270.2; Found: 270.2.

Step 2. N-(2-((2S,4S)-4-Amino-2-(hydroxymethyl)pyrrolidin-1-yl)-4-(4-cyanopyridin-3-yl)phenyl)-2-(3,6-difluoro-2-(methoxy-d₃)phenyl)pyrimidine-4-carboxamide This compound was prepared in an analogous fashion to Example 74, step 2, using 2-(3,6-difluoro-2-(methoxy-d₃)phenyl)pyrimidine-4-carboxylic acid as the coupling partner. LCMS calculated for $C_{29}H_{23}D_3F_2N_7O_3$ (M+H)⁺: m/z=561.2; Found: 561.2.

Example 76. N-(2-((2S,4S)-4-Amino-2-(hydroxymethyl)pyrrolidin-1-yl)-4-(4-cyanopyridin-3-yl)phenyl)-2-(2,3-difluoro-6-(methoxy-d₃)phenyl)pyrimidine-4-carboxamide

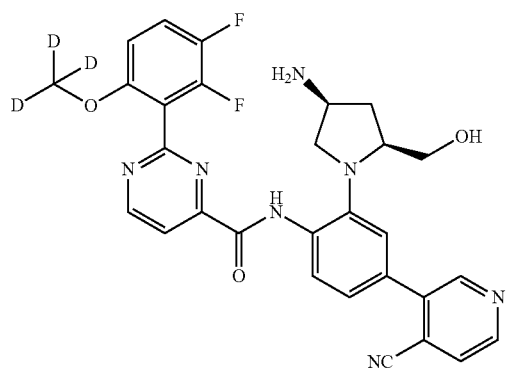 [SMILES: [2H]C([2H])([2H])Oc1ccc(F)c(F)c1-c1nccc(C(=O)Nc2ccc(-c3cnccc3C#N)cc2N2C[C@@H](N)C[C@H]2CO)n1]

This compound was prepared in an analogous fashion to Example 75, steps 1-2 using 4,5-difluorophenol as starting material. LCMS calculated for $C_{29}H_{23}D_3F_2N_7O_3$ (M+H)⁺: m/z=561.2; Found: 561.2.

Example 77. N-(2-((2S,4S)-4-Amino-2-(hydroxymethyl)pyrrolidin-1-yl)-4-(4-cyanopyridin-3-yl)phenyl)-2-(2-fluoro-6-(methoxy-$d_3$)phenyl-5-d)pyrimidine-4-carboxamide

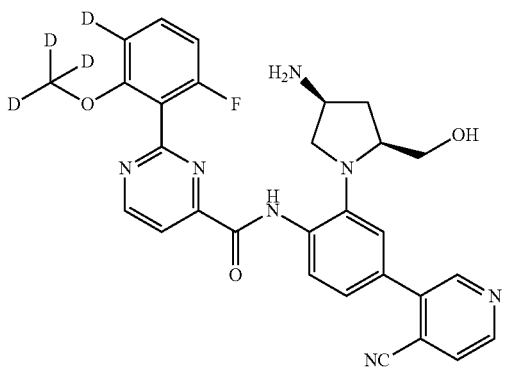 [SMILES: [2H]c1ccc(F)c(-c2nccc(C(=O)Nc3ccc(-c4cnccc4C#N)cc3N3C[C@@H](N)C[C@H]3CO)n2)c1OC([2H])([2H])[2H]]

Step 1. 1-Bromo-4-fluoro-2-(methoxy-$d_3$)benzene

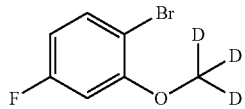

A solution of 2-bromo-5-fluorophenol (1.0 g, 5.24 mmol) in DMF (17.45 ml) was treated with potassium carbonate (1.085 g, 7.85 mmol) and iodomethane-$d_3$ (0.414 ml, 6.28 mmol). The reaction mixture was heated to 60° C. overnight, then treated with water and extracted with ethyl acetate. The organic phase was washed with water and brine, dried over sodium sulfate and concentrated. The crude product was used in the next step without further purification. LCMS calculated for $C_7H_4D_3BrFO$ (M+H)$^+$: m/z=208.0/210.0; Found: 208.0/210.0.

Step 2. 2-(2-Fluoro-6-(methoxy-$d_3$)phenyl-5-d)-4,4,5,5-tetramethyl-1,3,2-dioxaborolane

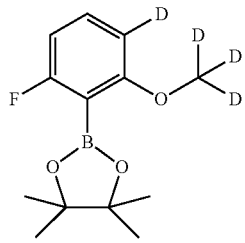 [SMILES: [2H]c1ccc(F)c(B2OC(C)(C)C(C)(C)O2)c1OC([2H])([2H])[2H]]

Magnesium (92 mg, 3.78 mmol) in THF (2 mL) was treated with iodine (23.97 mg, 0.094 mmol) followed by a solution of 1-bromo-4-fluoro-2-(methoxy-$d_3$)benzene (393 mg, 1.889 mmol) in THF (8 mL) dropwise. The mixture was heated to 60° C. for 1 hr, then the reaction mixture was cooled to r.t. and treated by the addition of methanol-$d_4$ (382 µl, 9.45 mmol). After stirring at r.t. for 15 mins, the mixture was further treated with 1N HCl to destroy the remaining magnesium. The mixture was then extracted with diethyl ether. The organic phase was washed with water and brine, dried over sodium sulfate and concentrated. To the crude intermediate was added THF (10 mL) and the mixture cooled to −78° C. n-BuLi (1.6M in hexanes, 907 µl, 2.267 mmol) was added dropwise and the reaction mixture stirred at −78° C. for 1 hr. 2-isopropoxy-4,4,5,5-tetramethyl-1,3,2-dioxaborolane (586 µl, 2.83 mmol) was added. The mixture was stirred at −78° C. for 10 mins, then warmed to r.t. After 1 hr, the reaction was treated with saturated aqueous ammonium chloride and extracted with ethyl acetate. The organic phase was washed with water and brine, dried over sodium sulfate and concentrated. The crude product was used in the next step without further purification.

Step 3. N-(2-((2S,4S)-4-amino-2-(hydroxymethyl)pyrrolidin-1-yl)-4-(4-cyanopyridin-3-yl)phenyl)-2-(2-fluoro-6-(methoxy-$d_3$)phenyl-5-d)pyrimidine-4-carboxamide This compound was prepared in an analogous fashion to Example 70, step 5, using the pinacol boronate prepared in Step 2 in place of 2-(2-fluoro-6-methoxy-4-methylphenyl)-4,4,5,5-tetramethyl-1,3,2-dioxaborolane. LCMS calculated for $C_{29}H_{23}D_4FN_7O_3$ (M+H)$^+$: m/z=544.2; Found: 544.2. $^1$H NMR (600 MHz, DMSO-$d_6$) δ 10.65 (s, 1H), 9.29 (d, J=5.0 Hz, 1H), 8.98 (s, 1H), 8.83 (d, J=5.0 Hz, 1H), 8.30 (d, J=8.4 Hz, 1H), 8.19 (d, J=5.0 Hz, 1H), 7.99 (d, J=5.0 Hz, 1H), 7.93 (s, 2H), 7.68 (s, 1H), 7.60-7.53 (m, 1H), 7.48 (d, J=9.9 Hz, 1H), 7.01 (t, J=8.8 Hz, 1H), 3.88-3.80 (m, 1H), 3.73-3.68 (m, 1H), 3.41-3.29 (m, 3H), 3.26 (d, J=8.9 Hz, 1H), 2.39 (dt, J=15.7, 8.0 Hz, 1H), 1.86 (dt, J=11.2, 5.4 Hz, 1H) ppm.

Example 78. 2-(2-Fluoro-6-methoxyphenyl)-N-(2-(piperidin-4-yl)phenyl)pyrimidine-4-carboxamide

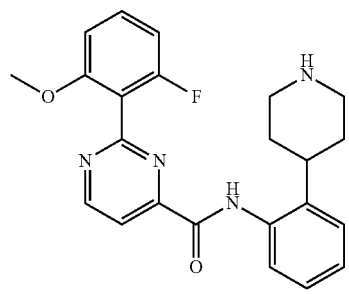 [SMILES: COc1cccc(F)c1-c1nccc(C(=O)Nc2ccccc2C2CCNCC2)n1]

Step 1. tert-Butyl 4-(2-aminophenyl)piperidine-1-carboxylate

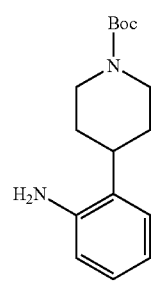 [SMILES: CC(C)(C)OC(=O)N1CCC(c2ccccc2N)CC1]

To a mixture of tert-butyl 4-(4,4,5,5-tetramethyl-1,3,2-dioxaborolan-2-yl)-3,6-dihydropyridine-1(2H)-carboxylate (230 mg, 0.743 mmol), 1-bromo-2-nitrobenzene (100 mg, 0.495 mmol), XPhos Pd G2 (38.9 mg, 0.050 mmol) and potassium phosphate, tribasic (210 mg, 0.990 mmol) were added 1,4-dioxane (1320 µl) and water (330 µl) and the reaction mixture evacuated, back filled with nitrogen, then heated to 90° C. for 1 hr. The mixture was diluted with DCM and filtered through a plug of Celite. The filtrate was concentrated and the residue purified by Biotage Isolera™ (0-70% ethyl acetate in hexanes). To the purified product was added MeOH (4 mL) followed by palladium hydroxide on carbon (20% w/w, 69.5 mg, 0.099 mmol). The reaction flask was evacuated, back filled with hydrogen gas from a balloon, then heated to 60° C. overnight. The mixture was then filtered through a plug of Celite and the filtrate concentrated. The crude product (130 mg, 95%) was used in the next step without further purification. LCMS calculated for $C_{16}H_{25}N_2O_2$ (M+H)$^+$: m/z=277.2; Found: 277.2.

Step 2. 2-(2-Fluoro-6-methoxyphenyl)-N-(2-(piperidin-4-yl)phenyl)pyrimidine-4-carboxamide A solution of 2-(2-fluoro-6-methoxyphenyl)pyrimidine-4-carboxylic acid (93 mg, 0.376 mmol), HATU (215 mg, 0.564 mmol) and tert-butyl 4-(2-aminophenyl)piperidine-1-carboxylate (130 mg, 0.470 mmol) in DMF (2352 µl) was treated with Hunig's base (164 µl, 0.941 mmol) and the reaction mixture was stirred at r.t. for 30 mins. The reaction mixture was treated with water and extracted with ethyl acetate. The organic phase was washed with water and brine, dried over sodium sulfate and concentrated. The residue was dissolved in TFA (1 mL) and allowed to stand for 30 mins, then diluted with methanol and purified with prep-LCMS (XBridge C18 column, eluting with a gradient of acetonitrile/water containing 0.1% TFA, at flow rate of 60 mL/min). LCMS calculated for $C_{23}H_{24}FN_4O_2$ (M+H)$^+$: m/z=407.2; Found: 407.2.

Example 79. N-(2-(cis)4-Aminocyclohexyl)phenyl)-2-(2-fluoro-6-methoxyphenyl) pyrimidine-4-carboxamide and N-(2-(trans)4-Aminocyclohexyl)phenyl)-2-(2-fluoro-6-methoxyphenyl)pyrimidine-4-carboxamide

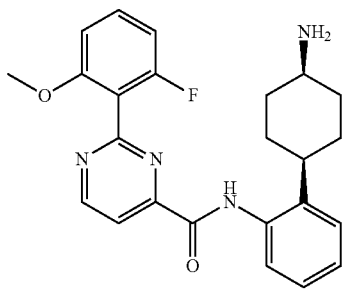

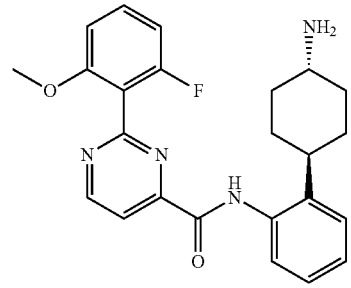

These compounds were prepared in an analogous fashion to Example 78, steps 1-2 starting with tert-butyl (4-(4,4,5,5-tetramethyl-1,3,2-dioxaborolan-2-yl)cyclohex-3-en-1-yl)carbamate. Purification by prep-LCMS provided the cis and trans isomers. LCMS calculated for $C_{24}H_{26}FN_4O_2$ (M+H)$^+$: m/z=421.2; Found: 421.2.

Example 80. N-(2-(3-Aminocyclohexyl)phenyl)-2-(2-fluoro-6-methoxyphenyl)pyrimidine-4-carboxamide

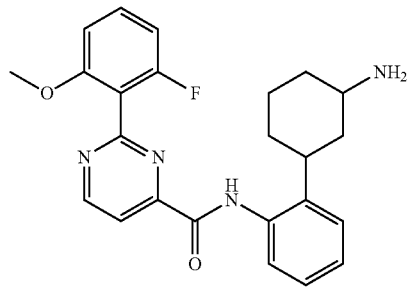 [SMILES: COc1cccc(F)c1-c1nccc(C(=O)Nc2ccccc2C2CCCC(N)C2)n1]

This compound was prepared in an analogous fashion to Example 78, steps 1-2 starting with tert-butyl (3-(4,4,5,5-tetramethyl-1,3,2-dioxaborolan-2-yl)cyclohex-2-en-1-yl)carbamate. LCMS calculated for $C_{24}H_{26}FN_4O_2$ (M+H)$^+$: m/z=421.2; Found: 421.2.

Example 81. N-(2-(3-aminocyclopentyl)phenyl)-2-(2-fluoro-6-methoxyphenyl)pyrimidine-4-carboxamide

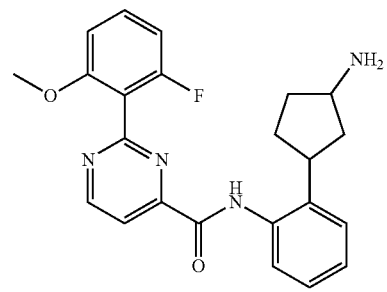 [SMILES: COc1cccc(F)c1-c1nccc(C(=O)Nc2ccccc2C2CCC(N)C2)n1]

This compound was prepared in an analogous fashion to Example 78, steps 1-2 starting with tert-butyl (3-(4,4,5,5-tetramethyl-1,3,2-dioxaborolan-2-yl)cyclopent-3-en-1-yl)carbamate. LCMS calculated for $C_{23}H_{24}FN_4O_2$ (M+H)$^+$: m/z=407.2; Found: 407.2.

Example 82. N-(2-((cis)-4-Aminocyclohexyl)-4-(4-cyanopyridin-3-yl)phenyl)-2-(2-fluoro-6-methoxyphenyl)pyrimidine-4-carboxamide and N-(2-((trans)-4-Aminocyclohexyl)-4-(4-cyanopyridin-3-yl)phenyl)-2-(2-fluoro-6-methoxyphenyl)pyrimidine-4-carboxamide

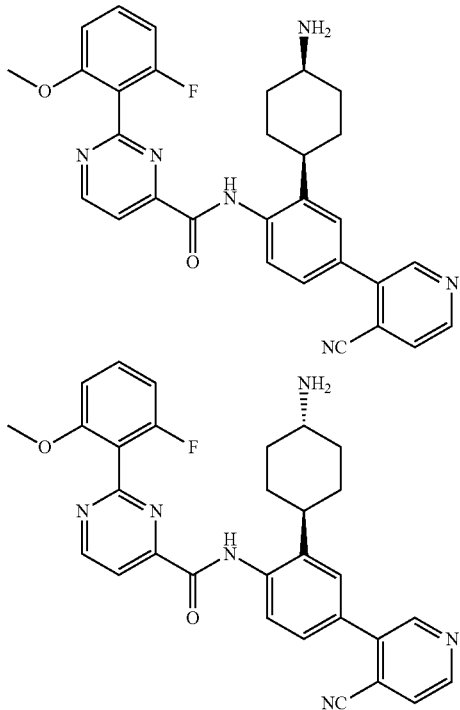

Step 1. tert-Butyl (4-(2-amino-5-hydroxyphenyl)cyclohexyl)carbamate

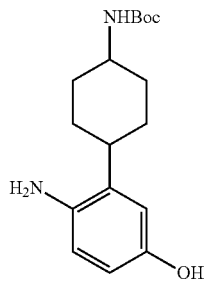

To a mixture of tert-butyl (4-(4,4,5,5-tetramethyl-1,3-dioxolan-2-yl)cyclohex-3-en-1-yl)carbamate (308 mg, 0.947 mmol), 4-chloro-2-iodoaniline (200 mg, 0.789 mmol), DPPF—PdCl$_2$ (64.4 mg, 0.079 mmol) and potassium carbonate (218 mg, 1.578 mmol) were added 1,4-dioxane (3156 µl) and water (789 µl). The reaction flask was evacuated, back filled with nitrogen, then stirred at 90° C. for 2 hr. The mixture was diluted with DCM and filtered through a plug of Celite. The filtrate was concentrated and the residue purified by Biotage Isolera™ (0-100% ethyl acetate in hexanes). The crude material was dissolved in EtOH (4 mL) and palladium hydroxide on carbon (20% w/w, 111 mg, 0.158 mmol) was added. The reaction flask was evacuated, back filed with hydrogen gas from a balloon, then stirred at 60° C. for 2 hr. The reaction mixture was then diluted with ethyl acetate and filtered through a plug of Celite. The filtrate was concentrated and the crude product used in the next step without further purification. LCMS calculated for C$_{17}$H$_{27}$N$_2$O$_3$ (M+H)$^+$: m/z=307.2; Found: 307.2.

Step 2. 3-(4-((tert-Butoxycarbonyl)amino)cyclohexyl)-4-(2-(2-fluoro-6-methoxyphenyl) pyrimidine-4-carboxamido)phenyl trifluoromethanesulfonate

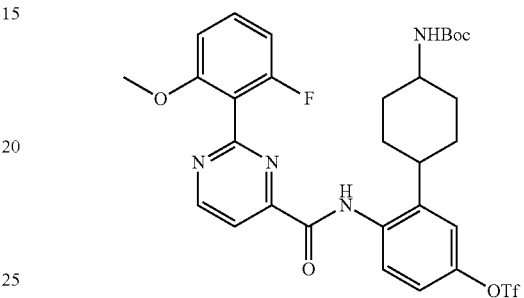

A solution of 2-(2-fluoro-6-methoxyphenyl)pyrimidine-4-carboxylic acid (64.0 mg, 0.258 mmol), HATU (118 mg, 0.309 mmol) and tert-butyl (4-(2-amino-5-hydroxyphenyl)cyclohexyl)carbamate (79 mg, 0.258 mmol) in DMF (1289 µl) was treated with Hunig's base (90 µl, 0.516 mmol) and the reaction mixture was stirred at r.t. for 30 mins. The reaction mixture was diluted with water and extracted with ethyl acetate. The organic phase was washed with water and brine, dried over sodium sulfate and concentrated. The crude product was purified by Biotage Isolera™ (20-100% ethyl acetate in hexanes). The intermediate was dissolved in DCM (3 mL) and triethylamine (71.9 µl, 0.516 mmol) was added. The reaction mixture was cooled to 0° C. and N-phenyltrifluoromethanesulfonimide (92 mg, 0.258 mmol) in DCM (0.5 mL) was added dropwise. The reaction mixture was then warmed to r.t. and stirred for 2 hr, and then treated with saturated sodium bicarbonate. The phases were separated and the organic phase dried over sodium sulfate and concentrated. The crude product was purified by Biotage Isolera™ (20-100% ethyl acetate in hexanes) to provide the desired product as a white solid (68 mg, 40%). LCMS calculated for C$_{30}$H$_{33}$F$_4$N$_4$O$_7$S (M+H)$^+$: m/z=669.2; Found: 669.2.

Step 3. N-(2-((cis)-4-Aminocyclohexyl)-4-(4-cyanopyridin-3-yl)phenyl)-2-(2-fluoro-6-methoxyphenyl)pyrimidine-4-carboxamide and N-(2-((trans)-4-aminocyclohexyl)-4-(4-cyanopyridin-3-yl)phenyl)-2-(2-fluoro-6-methoxyphenyl)pyrimidine-4-carboxamide To a solution of 3-(4,4,5,5-tetramethyl-1,3,2-dioxaborolan-2-yl)isonicotinonitrile (35.1 mg, 0.153 mmol), DPPF—PdCl$_2$ (8.30 mg, 10.17 µmol), cesium carbonate (66.3 mg, 0.203 mmol) and 3-(4-((tert-butoxycarbonyl)amino)cyclohexyl)-4-(2-(2-fluoro-6-methoxyphenyl)pyrimidine-4-carboxamido)phenyl trifluoromethanesulfonate (68 mg, 0.102 mmol) was added 1,4-dioxane (915 µl) and water (102 µl) and the reaction flask was evacuated, back filled with nitrogen, then heated to 90° C. overnight. The mixture was then diluted with water and DCM and the phases separated. The organic phase was concentrated. The residue was allowed to stand in TFA (1 mL) for 30 mins at r.t., then diluted with MeOH and purified with prep-LCMS (XBridge C18 column, eluting with a gradient of acetonitrile/water containing 0.1% TFA, at flow rate of 60 mL/min). The two isomers were successfully separated by prep-LCMS. LCMS calculated for $C_{30}H_{28}FN_6O_2$ (M+H)$^+$: m/z=523.2; Found: 523.2.

Example 83. N-(2-((cis)-4-Aminocyclohexyl)-4-(4-cyano-1-methyl-1H-pyrazol-5-yl)phenyl)-2-(2-fluoro-6-methoxyphenyl)pyrimidine-4-carboxamide and N-(2-((trans)-4-aminocyclohexyl)-4-(4-cyano-1-methyl-1H-pyrazol-5-yl)phenyl)-2-(2-fluoro-6-methoxyphenyl)pyrimidine-4-carboxamide

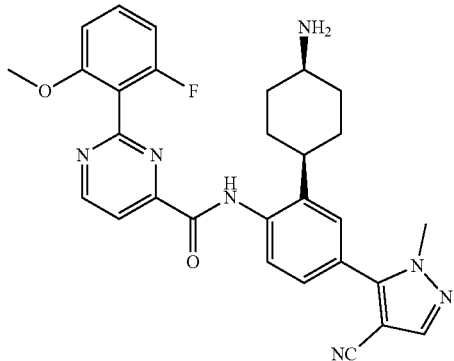

This compound was prepared in an analogous fashion to Example 82, step 2 using 1-methyl-5-(4,4,5,5-tetramethyl-1,3,2-dioxaborolan-2-yl)-1H-pyrazole-4-carbonitrile as coupling partner. LCMS calculated for $C_{29}H_{29}FN_7O_2$ (M+H)$^+$: m/z=526.2; Found: 526.2.

Example 84. N-(2-((cis)-4-Aminocyclohexyl)-4-(1,3,5-trimethyl-1H-pyrazol-4-yl)phenyl)-2-(2-fluoro-6-methoxyphenyl)pyrimidine-4-carboxamide

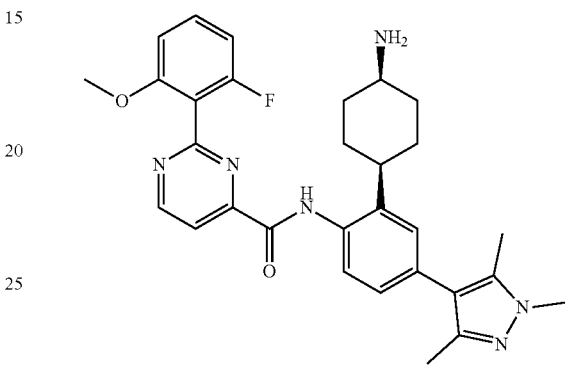

This compound was prepared in an analogous fashion to Example 82, step 2 using 1,3,5-trimethyl-4-(4,4,5,5-tetramethyl-1,3,2-dioxaborolan-2-yl)-1H-pyrazole as coupling partner. LCMS calculated for $C_{30}H_{34}FN_6O_2$ (M+H)$^+$: m/z=529.2; Found: 529.2. $^1$H NMR (500 MHz, DMSO-d6) δ 10.42 (s, 1H), 9.25 (d, J=5.0 Hz, 1H), 8.13 (d, J=5.0 Hz, 1H), 7.75 (s, 2H), 7.54 (q, J=8.1 Hz, 1H), 7.47 (d, J=8.1 Hz, 1H), 7.20 (s, 1H), 7.15 (d, J=8.2 Hz, 1H), 7.07 (d, J=8.5 Hz, 3H), 7.01 (t, J=8.8 Hz, 1H), 3.80 (s, 3H), 3.71 (s, 3H), 3.08 (s, 1H), 2.64 (t, J=11.9 Hz, 1H), 2.25 (s, 3H), 2.16 (s, 3H), 1.98 (d, J=11.6 Hz, 2H), 1.87 (d, J=12.3 Hz, 2H), 1.56 (q, J=12.5 Hz, 2H), 1.30 (q, J=12.0, 11.4 Hz, 2H) ppm.

Example 85. N-(2-((2S,4S)-4-Amino-2-(hydroxymethyl)pyrrolidin-1-yl)-4-(methylsulfonyl)phenyl)-2-(2-fluoro-6-methoxyphenyl)pyrimidine-4-carboxamide

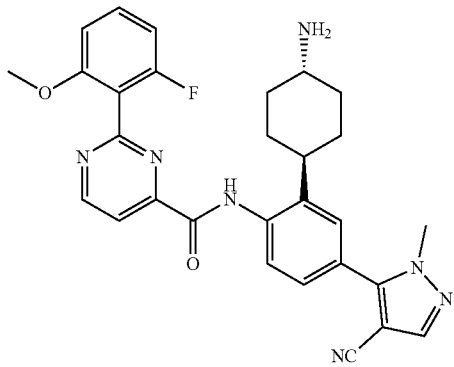

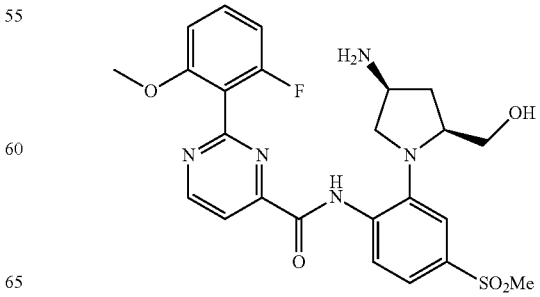

Step 1. tert-Butyl ((3S,5S)-1-(2-amino-5-(methyl-sulfonyl)phenyl)-5-(hydroxymethyl)pyrrolidin-3-yl)carbamate

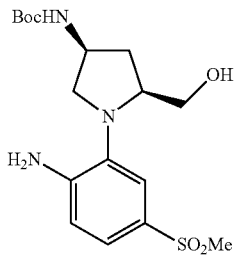 [SMILES: CC(C)(C)OC(=O)N[C@H]1C[C@@H](CO)N(c2cc(S(C)(=O)=O)ccc2N)C1]

A mixture of 2-fluoro-4-(methylsulfonyl)-1-nitrobenzene (100 mg, 0.456 mmol) and tert-butyl ((3S,5S)-5-(hydroxymethyl)pyrrolidin-3-yl)carbamate (118 mg, 0.547 mmol) in DMSO (1521 μl) was treated with Hunig's base (159 μl, 0.912 mmol) and the reaction mixture stirred at 90° C. for 1 hr, then treated with water and extracted with ethyl acetate. The organic phase was washed with water and brine, dried over sodium sulfate and concentrated. The residue was dissolved in a 1:1:1 mixture of THF/water/MeOH (3 mL) and treated with iron (102 mg, 1.825 mmol) and ammonium chloride (146 mg, 2.74 mmol). The reaction mixture was stirred at 60° C. for 1 hr, then diluted with ethyl acetate and filtered through a plug of Celite. The filtrate was washed with water and brine, dried over sodium sulfate and concentrated. The crude solid was used in the next step without further purification. LCMS calculated for $C_{17}H_{28}N_3O_5S$ (M+H)$^+$: m/z=386.2; Found: 386.2.

Step 2. N-(2-((2S,4S)-4-Amino-2-(hydroxymethyl)pyrrolidin-1-yl)-4-(methylsulfonyl)phenyl)-2-(2-fluoro-6-methoxyphenyl)pyrimidine-4-carboxamide A solution of tert-butyl ((3S,5S)-1-(2-amino-5-(methyl-sulfonyl)phenyl)-5-(hydroxymethyl) pyrrolidin-3-yl)carbamate (55 mg, 0.143 mmol) in DMF (476 μl) was treated with 2-(2-fluoro-6-methoxyphenyl)pyrimidine-4-carboxylic acid (31.9 mg, 0.128 mmol), HATU (65.1 mg, 0.171 mmol), and Hunig's base (49.8 μl, 0.285 mmol). The reaction mixture was stirred at r.t. for 30 mins, then treated with water and extracted with ethyl acetate. The organic phase was washed with water and brine, dried over sodium sulfate and concentrated. To the crude residue was added 4N HCl in dioxane and MeOH (2 mL, 1:1) and the reaction mixture heated to 60° C. for 1 hr, then diluted with MeOH and purified with prep-LCMS (XBridge C18 column, eluting with a gradient of acetonitrile/water containing 0.1% TFA, at flow rate of 60 mL/min). LCMS calculated for $C_{24}H_{27}FN_5O_5S$ (M+H)$^+$: m/z=516.2; Found: 516.2.

Example 86. N-(2-((2S,4S)-4-Amino-2-(hydroxymethyl)pyrrolidin-1-yl)phenyl)-2-(2-fluoro-6-methoxyphenyl)pyrimidine-4-carboxamide

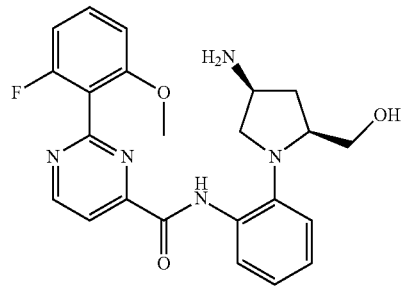 [SMILES: COc1cccc(F)c1-c1nccc(C(=O)Nc2ccccc2N2C[C@@H](N)C[C@H]2CO)n1]

Step 1. tert-Butyl ((3S,5S)-5-(hydroxymethyl)-1-(2-nitrophenyl)pyrrolidin-3-yl)carbamate

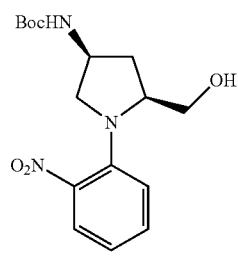

A solution of 1-fluoro-2-nitrobenzene (30 μl, 0.283 mmol) and tert-butyl ((3S,5S)-5-(hydroxymethyl)pyrrolidin-3-yl)carbamate (61.3 mg, 0.283 mmol) in DMSO (1.5 ml) was treated with triethylamine (59.3 μl, 0.425 mmol) and the reaction mixture was heated to 80° C. for 3 hrs. After cooling to r.t., the reaction mixture was diluted with DCM, washed with brine, dried over sodium sulfate and the solvent was evaporated in vacuo. The obtained crude product was used in the next step without further purification. LCMS calculated for $C_{12}H_{16}N_3O_5$ (M+H–$C_4H_8$)$^+$: m/z=282.1; found 282.2.

Step 2. tert-Butyl ((3S,5S)-1-(2-aminophenyl)-5-(hydroxymethyl)pyrrolidin-3-yl)carbamate

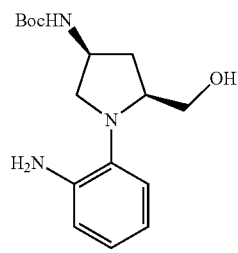 [SMILES: CC(C)(C)OC(=O)N[C@H]1C[C@@H](CO)N(c2ccccc2[N+](=O)[O-])C1]

A mixture of tert-butyl ((3S,5S)-5-(hydroxymethyl)-1-(2-nitrophenyl)pyrrolidin-3-yl)carbamate (70 mg, 0.207 mmol), iron (57.9 mg, 1.037 mmol) and ammonium chloride (67 mg, 1.25 mmol) in THF (2 ml), water (2 ml) and methanol (2 ml) was stirred at 60° C. for 3 hrs. After cooling to r.t., it was filtered through a plug of Celite and diluted with DCM. The organic phase was separated, washed with brine, dried over sodium sulfate and the solvents were evaporated in vacuo. The obtained crude product was used in the next step without further purification. LCMS calculated for $C_{16}H_{26}N_3O_3$ (M+H)$^+$: m/z=308.2; Found: 308.2.

Step 3. N-(2-((2S,4S)-4-Amino-2-(hydroxymethyl) pyrrolidin-1-yl)phenyl)-2-(2-fluoro-6-methoxyphenyl)pyrimidine-4-carboxamide HATU (74.2 mg, 0.195 mmol) was added to a solution of tert-butyl ((3S,5S)-1-(2-aminophenyl)-5-(hydroxymethyl) pyrrolidin-3-yl)carbamate (40 mg, 0.130 mmol), 2-(2-fluoro-6-methoxyphenyl)pyrimidine-4-carboxylic acid (the product of Example 1, step 1, 32.3 mg, 0.130 mmol) and DIPEA (45.5 µl, 0.260 mmol) in DMF (1 ml). The reaction mixture was stirred at r.t. for 30 mins, then water was added and the precipitated product was collected by filtration, washed with water and air dried. The solid was dissolved in TFA and the resultant solution was stirred at r.t. for 10 mins. It was then diluted with acetonitrile and purified with prep-LCMS (XBridge C18 column, eluting with a gradient of acetonitrile/water containing 0.1% TFA, at flow rate of 60 mL/min). LCMS calculated for $C_{23}H_{25}FN_5O_3$ (M+H)$^+$: m/z=438.2; Found: 438.2. $^1$H NMR (500 MHz, DMSO-d6) δ 10.61-10.48 (s, 1H), 9.34-9.19 (d, J=5.0 Hz, 1H), 8.21-8.11 (m, 2H), 7.95-7.80 (br, 2H), 7.60-7.49 (td, J=8.4, 6.8 Hz, 1H), 7.41-7.33 (dd, J=6.7, 2.5 Hz, 1H), 7.25-7.15 (m, 2H), 7.11-7.03 (d, J=8.5 Hz, 1H), 7.03-6.93 (t, J=8.8 Hz, 1H), 3.79-3.74 (s, 3H), 3.75-3.62 (m, 2H), 3.37-3.16 (m, 4H), 2.43-2.31 (m, 1H), 1.87-1.74 (dt, J=13.4, 5.1 Hz, 1H) ppm.

Example 87. N-(2-((2S,4S)-4-Amino-2-(hydroxymethyl)pyrrolidin-1-yl)-5-methylphenyl)-2-(2-fluoro-6-methoxyphenyl)pyrimidine-4-carboxamide

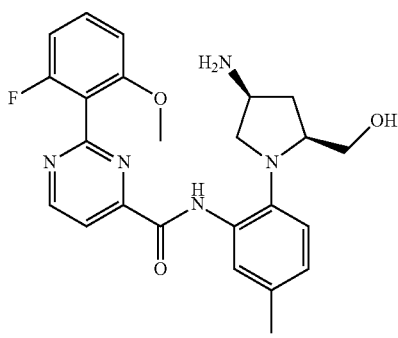 [SMILES: COc1cccc(F)c1-c1nccc(C(=O)Nc2cc(C)ccc2N2C[C@@H](N)C[C@H]2CO)n1]

This compound was prepared according to the procedures described in Example 6, using 1-fluoro-4-methyl-2-nitrobenzene instead of 1,4-difluoro-2-nitrobenzene as starting material. LCMS calculated for $C_{24}H_{27}FN_5O_3$ (M+H)$^+$: m/z=452.2; Found: 452.2.

Example 88. N-(2-((2S,4S)-4-(Dimethylamino)-2-(hydroxymethyl)pyrrolidin-1-yl)-5-fluorophenyl)-2-(2-fluoro-6-methoxyphenyl)pyrimidine-4-carboxamide

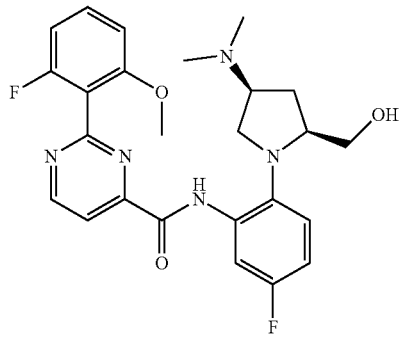 [SMILES: COc1cccc(F)c1-c1nccc(C(=O)Nc2cc(F)ccc2N2C[C@@H](N(C)C)C[C@H]2CO)n1]

Sodium triacetoxyborohydride (9 mg, 0.044 mmol) was added to a solution of formaldehyde (1.4 mg, 0.044 mmol), acetic acid (2.51 µl, 0.044 mmol) and N-(2-((2S,4S)-4-amino-2-(hydroxymethyl)pyrrolidin-1-yl)-5-fluorophenyl)-2-(2-fluoro-6-methoxyphenyl)pyrimidine-4-carboxamide (Example 6, 10 mg, 0.022 mmol) in DCM (1 ml). After stirring at r.t. for 1h, the solvent was evaporated, the reaction mixture was diluted with CH$_3$CN and purified with prep-LCMS (XBridge C18 column, eluting with a gradient of acetonitrile/water containing 0.1% TFA, at flow rate of 60 mL/min). LCMS calculated for $C_{25}H_{28}F_2N_5O_3$ (M+H)$^+$: m/z=484.2; Found: 484.2.

Example 89. N-(5-Fluoro-2-((2S,4S)-2-(hydroxymethyl)-4-(isopropylamino)pyrrolidin-1-yl)phenyl)-2-(2-fluoro-6-methoxyphenyl)pyrimidine-4-carboxamide

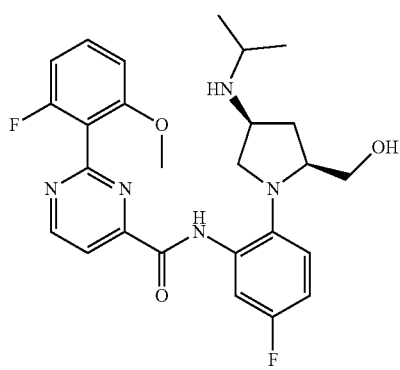 [SMILES: COc1cccc(F)c1-c1nccc(C(=O)Nc2cc(F)ccc2N2C[C@@H](NC(C)C)C[C@H]2CO)n1]

This compound was prepared according to the procedures described in Example 88, using acetone instead of formaldehyde as starting material. LCMS calculated for $C_{26}H_{30}F_2N_5O_3$ (M+H)$^+$: m/z=498.2; Found: 498.1.

Example 90. N-(2-((2S,4S)-4-Amino-2-(hydroxymethyl)pyrrolidin-1-yl)-4-(tetrahydro-2H-pyran-4-yl)phenyl)-2-(2-fluoro-6-methoxyphenyl)pyrimidine-4-carboxamide

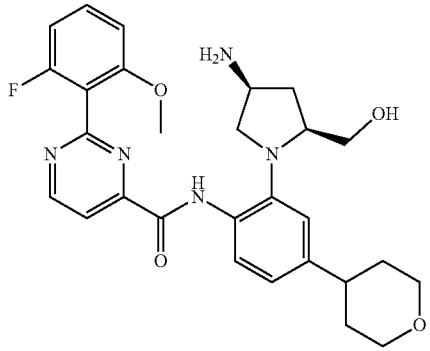 [SMILES: COc1cccc(F)c1-c1nccc(C(=O)Nc2ccc(C3CCOCC3)cc2N2C[C@@H](N)C[C@H]2CO)n1]

This compound was prepared according to the procedures described in Example 49, using 2-(3,6-dihydro-2H-pyran-4-yl)-4,4,5,5-tetramethyl-1,3,2-dioxaborolane instead of 4,4,5,5-tetramethyl-2-(prop-1-en-2-yl)-1,3,2-dioxaborolane as starting material. LCMS calculated for $C_{28}H_{33}FN_5O_4$ (M+H)$^+$: m/z=522.2; Found: 522.2.

Example 91. N-(2-((2S,4S)-4-Amino-2-(hydroxymethyl)pyrrolidin-1-yl)-4-chlorophenyl)-2-(2-fluoro-6-methoxyphenyl)pyrimidine-4-carboxamide

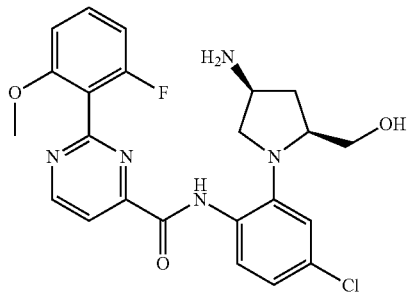 [SMILES: COc1cccc(F)c1-c1nccc(C(=O)Nc2ccc(Cl)cc2N2C[C@@H](N)C[C@H]2CO)n1]

This compound was prepared according to the procedures described in Example 6, using 4-chloro-2-fluoro-1-nitrobenzene instead of 1,4-difluoro-2-nitrobenzene as starting material. LCMS calculated for $C_{23}H_{24}ClFN_5O_3$ (M+H)$^+$: m/z=472.2; Found: 472.3.

Example 92. N-(2-((2S,4S)-4-Amino-2-(hydroxymethyl)pyrrolidin-1-yl)-4-fluorophenyl)-2-(2-fluoro-6-methoxyphenyl)pyrimidine-4-carboxamide

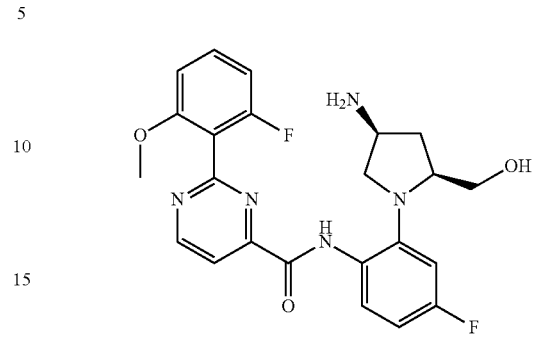

This compound was prepared according to the procedures described in Example 6, using 2,4-difluoro-1-nitrobenzene instead of 1,4-difluoro-2-nitrobenzene as starting material. LCMS calculated for $C_{23}H_{24}F_2N_5O_3$ (M+H)$^+$: m/z=456.2; Found: 456.3.

Example 93. N-(2-((2S,4S)-4-Amino-2-(hydroxymethyl)pyrrolidin-1-yl)-4-(5-cyano-2-(pyrrolidin-1-yl)pyridin-4-yl)phenyl)-2-(2,6-difluorophenyl)pyrimidine-4-carboxamide

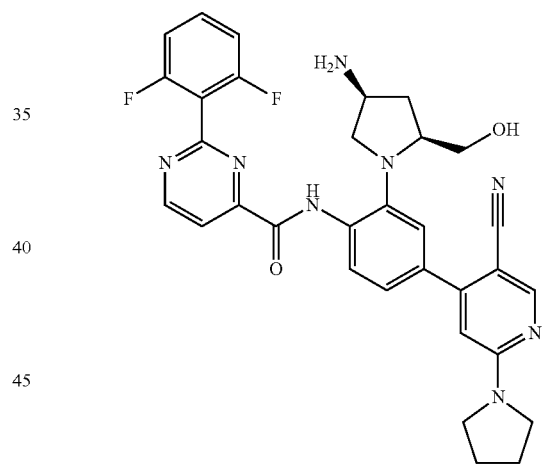

Step 1. 4-Bromo-6-(pyrrolidin-1-yl)nicotinonitrile

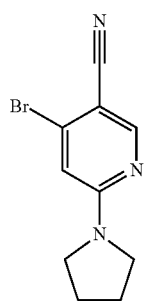 [SMILES: N#Cc1cnc(N2CCCC2)cc1Br]

A solution of 4-bromo-6-chloronicotinonitrile (200 mg, 0.920 mmol) and pyrrolidine (327 mg, 4.60 mmol) in 2-propanol (2 mL) was stirred at 100° C. for 12 h. Then the solvent was evaporated in vacuo. The obtained crude product was used in the next step without further purification. LCMS calculated for $C_{10}H_{11}BrN_3$ (M+H)$^+$: m/z=252.0; Found: 252.0.

Step 2. tert-Butyl ((3S,5S)-1-(2-(2-(2,6-difluorophenyl)pyrimidine-4-carboxamido)-5-(4,4,5,5-tetramethyl-1,3,2-dioxaborolan-2-yl)phenyl)-5-(hydroxymethyl)pyrrolidin-3-yl)carbamate

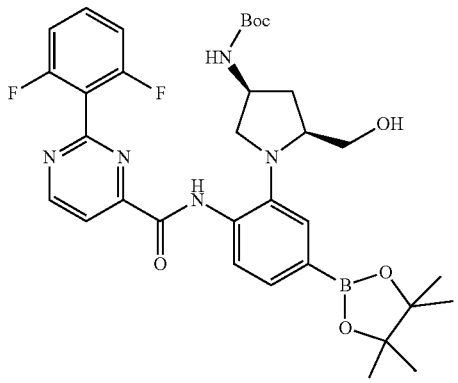 [SMILES: CC(C)(C)OC(=O)N[C@H]1C[C@@H](CO)N(c2cc(B3OC(C)(C)C(C)(C)O3)ccc2NC(=O)c2ccnc(-c3c(F)cccc3F)n2)C1]

This compound was prepared according to the procedures described in Example 46 and 41 using (2,6-difluorophenyl) boronic acid instead of (2-fluoro-6-methoxyphenyl)boronic acid as starting material. LCMS calculated for $C_{33}H_{41}BF_2N_5O_6$ (M+H)$^+$: m/z=652.3; Found: 652.2.

Step 3. N-(2-((2S,4S)-4-Amino-2-(hydroxymethyl) pyrrolidin-1-yl)-4-(5-cyano-2-(pyrrolidin-1-yl)pyridin-4-yl)phenyl)-2-(2,6-difluorophenyl)pyrimidine-4-carboxamide This compound was prepared according to the procedures described in Example 46, Step 2, using 4-bromo-6-(pyrrolidin-1-yl)nicotinonitrile instead of 2-bromonicotinonitrile and tert-butyl ((3S,5S)-1-(2-(2-(2,6-difluorophenyl)pyrimidine-4-carboxamido)-5-(4,4,5,5-tetramethyl-1,3,2-dioxaborolan-2-yl)phenyl)-5-(hydroxymethyl)pyrrolidin-3-yl) carbamate instead of tert-butyl ((3S,5S)-1-(2-(2-(2-fluoro-6-methoxyphenyl)pyrimidine-4-carboxamido)-5-(4,4,5,5-tetramethyl-1,3,2-dioxaborolan-2-yl)phenyl)-5-(hydroxymethyl)pyrrolidin-3-yl)carbamate as starting material. LCMS calculated for $C_{32}H_{31}F_2N_8O_2$ (M+H)$^+$: m/z=597.3; Found: 597.2.

Example 94. N-(2-((2S,4S)-4-Amino-2-(hydroxymethyl)pyrrolidin-1-yl)-4-(1-cyanocyclopropyl)phenyl)-2-(2,6-difluorophenyl)pyrimidine-4-carboxamide

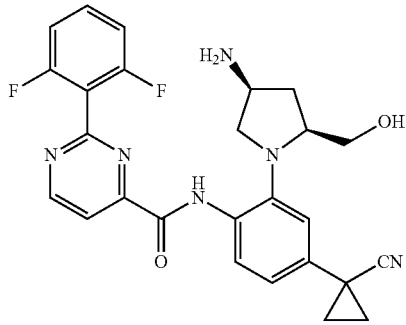 [SMILES: N#CC1(c2ccc(NC(=O)c3ccnc(-c4c(F)cccc4F)n3)c(N3C[C@@H](N)C[C@H]3CO)c2)CC1]

Step 1. tert-Butyl ((3S,5S)-1-(5-(cyanomethyl)-2-nitrophenyl)-5-(hydroxymethyl)pyrrolidin-3-yl)carbamate

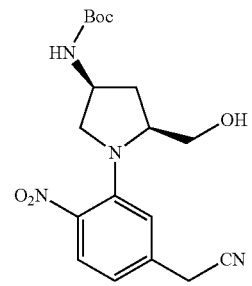 [SMILES: CC(C)(C)OC(=O)N[C@H]1C[C@@H](CO)N(c2cc(CC#N)ccc2[N+](=O)[O-])C1]

This compound was prepared according to the procedures described in Example 6, using 2-(3-fluoro-4-nitrophenyl) acetonitrile instead of 1,4-difluoro-2-nitrobenzene as starting material. LCMS calculated for $C_{14}H_{17}N_4O_5$ (M−$C_4H_8$+H)$^+$: m/z=321.1; Found: 321.1.

Step 2. tert-Butyl ((3S,5S)-5-(((tert-butyldimethylsilyl)oxy)methyl)-1-(5-(cyanomethyl)-2-nitrophenyl) pyrrolidin-3-yl)carbamate

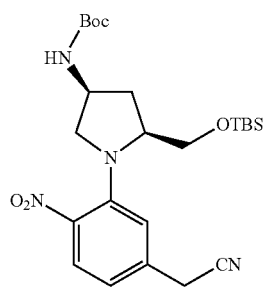 [SMILES: CC(C)(C)OC(=O)N[C@H]1C[C@@H](CO[Si](C)(C)C(C)(C)C)N(c2cc(CC#N)ccc2[N+](=O)[O-])C1]

tert-Butylchlorodimethylsilane (0.054 g, 0.359 mmol) was added to a solution of 1H-imidazole (0.024 g, 0.359 mmol) and tert-butyl ((3S,5S)-1-(5-(cyanomethyl)-2-nitrophenyl)-5-(hydroxymethyl)pyrrolidin-3-yl)carbamate (0.090 g, 0.239 mmol) in 1 mL of DCM. After the reaction mixture was stirred at r.t. for 2 h, water was added and product was extracted with DCM. The combined organic phases were washed with water and brine, dried over sodium sulfate and the solvent was evaporated in vacuo. The obtained crude product was used in the next step without further purification. LCMS calculated for $C_{20}H_{31}N_4O_5Si$ $(M-C_4H_8+H)^+$: m/z=435.2; Found: 435.2.

Step 3. tert-Butyl ((3S,5S)-5-(((tert-butyldimethylsilyl)oxy)methyl)-1-(5-(1-cyanocyclopropyl)-2-nitrophenyl)pyrrolidin-3-yl)carbamate

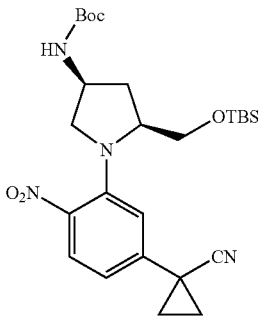 [SMILES: CC(C)(C)OC(=O)N[C@H]1C[C@@H](CO[Si](C)(C)C(C)(C)C)N(c2cc(C3(C#N)CC3)ccc2[N+](=O)[O-])C1]

A solution of tert-Butyl ((3S,5S)-5-(((tert-butyldimethylsilyl)oxy)methyl)-1-(5-(cyanomethyl)-2-nitrophenyl)pyrrolidin-3-yl)carbamate (0.120 g, 0.245 mmol) in 1 mL of DMF was treated with 1,2-dibromoethane (0.046 g, 0.245 mmol). The mixture was stirred at r.t. and then treated with sodium hydride (0.120 g, 5.00 mmol). The mixture was further stirred at r.t. overnight. Then water was added and precipitated product was collected by filtration, washed with water and air dried. It was used in the next step without further purification. LCMS calculated for $C_{22}H_{33}N_4O_5Si$ $(M-C_4H_8+H)^+$: m/z=461.2; Found: 461.2.

Step 4. N-(2-((2S,4S)-4-Amino-2-(hydroxymethyl)pyrrolidin-1-yl)-4-(1-cyanocyclopropyl)phenyl)-2-(2,6-difluorophenyl)pyrimidine-4-carboxamide This compound was prepared according to the procedures described in Example 1, using (2,6-difluorophenyl)boronic acid instead of (2-fluoro-6-methoxyphenyl)boronic acid and tert-butyl ((3S,5S)-5-(((tert-butyldimethylsilyl)oxy)methyl)-1-(5-(1-cyanocyclopropyl)-2-nitrophenyl)pyrrolidin-3-yl)carbamate instead of (1R,4R)-tert-butyl 5-(4-fluoro-2-nitrophenyl)-2,5-diazabicyclo[2.2.1]heptane-2-carboxylate as starting material. LCMS calculated for $C_{26}H_{25}F_2N_6O_2$ $(M+H)^+$: m/z=491.2; Found: 491.1.

Example 95. N-(2-((2S,4S)-4-Amino-2-(hydroxymethyl)pyrrolidin-1-yl)-4-(4-cyanopyridin-3-yl)phenyl)-2-(2-(difluoromethoxy)-6-fluorophenyl)pyrimidine-4-carboxamide

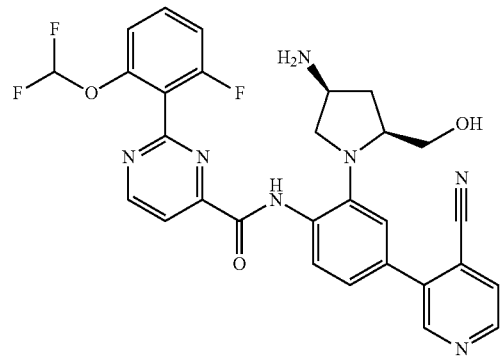 [SMILES: N#Cc1ccncc1-c1ccc(NC(=O)c2ccnc(-c3c(F)cccc3OC(F)F)n2)c(N2C[C@@H](N)C[C@H]2CO)c1]

Step 1.
2-Bromo-1-(difluoromethoxy)-3-fluorobenzene

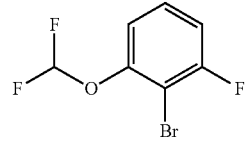 [SMILES: Fc1cccc(OC(F)F)c1Br]

A mixture of 2-bromo-3-fluorophenol (0.865 g, 4.53 mmol), sodium chlorodifluoroacetate (4.14 g, 27.2 mmol) and cesium carbonate (4.43 g, 13.59 mmol) in DMF (10 mL) was stirred at 100° C. for 4 h. After cooling to room temperature, the mixture was concentrated in vacuo. The obtained crude product was purified by Biotage Isolera™ to give the desired product.

Step 2. 2-(2-(Difluoromethoxy)-6-fluorophenyl)-4,4,5,5-tetramethyl-1,3,2-dioxaborolane

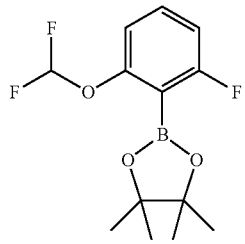 [SMILES: CC1(C)OB(c2c(F)cccc2OC(F)F)OC1(C)C]

A solution of 2-bromo-1-(difluoromethoxy)-3-fluorobenzene (400 mg, 1.660 mmol) in THF (10 mL) was treated with nBuLi 1.6 M (1.72 mL, 4.32 mmol) at −78° C. After stirring for 1 h, 2-isopropoxy-4,4,5,5-tetramethyl-1,3,2-dioxaborolane (1.02 mL, 4.98 mmol) was added, and then the mixture was slowly warmed to rt over 6 h. To the mixture was added EtOAc (50 mL) and water (30 mL). The organic phase was separated, washed with brine, dried over MgSO₄, filtered and the solvents were evaporated in vacuo. The obtained crude product was used in the next step without further purification.

Step 3. N-(2-((2S,4S)-4-Amino-2-(hydroxymethyl) pyrrolidin-1-yl)-4-(4-cyanopyridin-3-yl)phenyl)-2-(2-(difluoromethoxy)-6-fluorophenyl)pyrimidine-4-carboxamide This compound was prepared according to the procedures described in Example 63, using 2-(2-(difluoromethoxy)-6-fluorophenyl)-4,4,5,5-tetramethyl-1,3,2-dioxaborolane instead of (2,6-difluorophenyl)boronic acid as starting material. LCMS calculated for $C_{29}H_{25}F_3N_7O_3$ (M+H)$^+$: m/z=576.2; Found: 576.3.

Example 96. N-(2-((2S,4S)-4-Amino-2-(hydroxymethyl)pyrrolidin-1-yl)-4-(4-cyanopyridin-3-yl)phenyl)-2-(2-fluoro-6-(methoxy-d$_3$)phenyl)pyrimidine-4-carboxamide

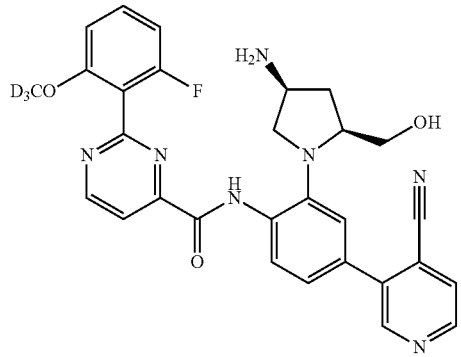

Step 1. 2-(2-Fluoro-6-(methoxy-d3)phenyl)-4,4,5,5-tetramethyl-1,3,2-dioxaborolane

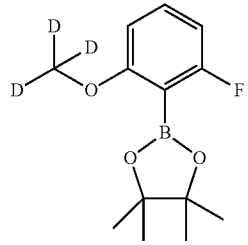 [SMILES: [2H]C([2H])([2H])Oc1cccc(F)c1B1OC(C)(C)C(C)(C)O1]

This compound was prepared in an analogous fashion to Example 69, starting with 3-fluorophenol instead of 3-fluoro-4-methylphenol. LCMS calculated for $C_{13}H_{16}D_3BFO_3$ (M+H)$^+$: m/z=256.2; Found: 256.2.

Step 2. N-(2-((2S,4S)-4-Amino-2-(hydroxymethyl) pyrrolidin-1-yl)-4-(4-cyanopyridin-3-yl)phenyl)-2-(2-fluoro-6-(methoxy-d3)phenyl)pyrimidine-4-carboxamide This compound was prepared according to the procedures described in Example 63, using 2-(2-fluoro-6-(methoxy-d$_3$) phenyl)-4,4,5,5-tetramethyl-1,3,2-dioxaborolane instead of (2,6-difluorophenyl)boronic acid as starting material. LCMS calculated for $C_{29}H_{24}D_3FN_7O_3$ (M+H)$^+$: m/z=543.2; Found: 543.3.

Example 97. N-(2-((2S,4S)-4-Amino-2-(hydroxymethyl)pyrrolidin-1-yl)-4-(4-cyanopyridin-3-yl)phenyl)-2-(2-cyclopropyl-6-fluorophenyl)pyrimidine-4-carboxamide

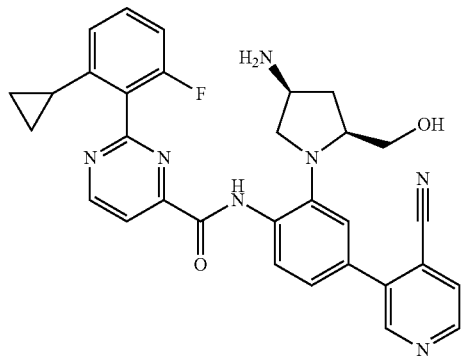 [SMILES: N#Cc1ccncc1-c1ccc(NC(=O)c2ccnc(-c3c(F)cccc3C3CC3)n2)c(N2C[C@@H](N)C[C@H]2CO)c1]

This compound was prepared according to the procedures described in Example 63, using 2-(2-cyclopropyl-6-fluorophenyl)-4,4,5,5-tetramethyl-1,3,2-dioxaborolane instead of (2,6-difluorophenyl)boronic acid as starting material. LCMS calculated for $C_{31}H_{29}FN_7O_2$ (M+H)$^+$: m/z=550.2; Found: 550.3.

Example 98. N-(2-((2S,4S)-4-Amino-2-(hydroxymethyl)pyrrolidin-1-yl)-4-(4-cyanopyridin-3-yl)phenyl)-2-(2-ethoxy-6-fluorophenyl)pyrimidine-4-carboxamide

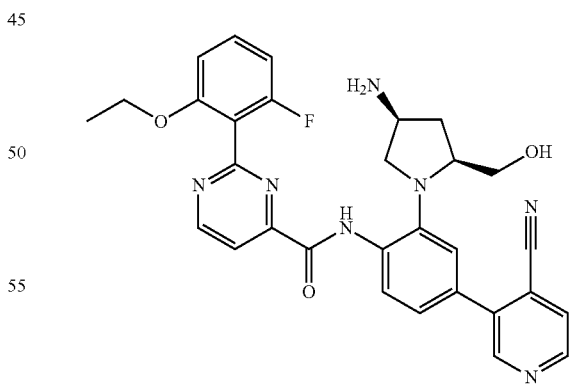

This compound was prepared according to the procedures described in Example 63, using (2-ethoxy-6-fluorophenyl) boronic acid instead of (2,6-difluorophenyl)boronic acid as starting material. LCMS calculated for $C_{30}H_{29}FN_7O_3$ (M+H)$^+$: m/z=554.2; Found: 554.3.

Example 99. N-(4-(4-Cyanopyridin-3-yl)-2-((1S, 4S)-4-(hydroxymethyl)-5-methyl-2,5-diazabicyclo [2.2.1]heptan-2-yl)phenyl)-2-(2-fluoro-6-methoxyphenyl)pyrimidine-4-carboxamide

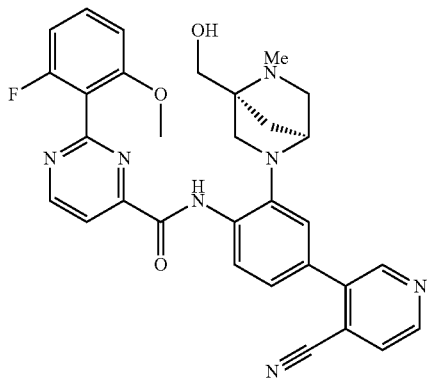 [SMILES: COc1cccc(F)c1-c1nccc(C(=O)Nc2ccc(-c3cnccc3C#N)cc2N2C[C@]3(CO)C[C@H]2CN3C)n1]

Step 1. tert-Butyl (1S,4S)-4-(hydroxymethyl)-2,5-diazabicyclo[2.2.1]heptane-2-carboxylate

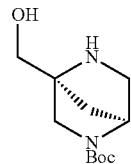

A Parr reaction vessel were charged with tert-butyl (1S, 4S)-4-(hydroxymethyl)-5-(4-methoxybenzyl)-2,5-diazabicyclo[2.2.1]heptane-2-carboxylate (prepared by an adaption of the procedure described in Ivon, Y. et. al. Synthesis 2015, 47, 1123-1130) (25 mg, 0.072 mmol), Pd/C (10% wetted, Degussa type, 7.7 mg) followed by MeOH (7.2 mL) and the reaction mixture was evacuated and backfilled 3 times with nitrogen gas, followed by another evacuation cycle and then pressurized with hydrogen gas to 25 psi. The vessel was shook for 6 hrs under hydrogen pressure, upon which time the solution was filtered over Celite and the solvent was evaporated in vacuo. The obtained crude product was used in the next reaction without purification. LCMS calculated for $C_{11}H_{21}N_2O_3$ (M+H)$^+$: m/z=229.2; found 229.2.

Step 2. tert-Butyl (1S,4S)-4-(hydroxymethyl)-5-methyl-2,5-diazabicyclo[2.2.1]heptane-2-carboxylate

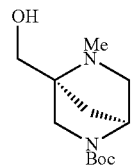

A solution of tert-butyl (1S,4S)-4-(hydroxymethyl)-2,5-diazabicyclo[2.2.1]heptane-2-carboxylate (16.5 mg, 0.072 mmol) in CH$_3$CN (200 μL) and H$_2$O (50 μL) were treated with formaldehyde (37 wt. % in H$_2$O, 16.1 μL, 0.217 mmol) and sodium triacetoxyborohydride (31 mg, 0.145 mmol) and the reaction mixture was stirred at r.t. for 2 hrs. The reaction mixture was then diluted with CH$_2$Cl$_2$, washed with sat. aq. NaHCO$_3$, dried over MgSO$_4$, filtered and the solvent was evaporated in vacuo. The obtained crude product was used in the next reaction without purification. LCMS calculated for $C_{12}H_{23}N_2O_3$ (M+H)$^+$: m/z=243.2; found 243.2.

Step 3. 3-(3-((1S,4S)-4-(Hydroxymethyl)-5-methyl-2,5-diazabicyclo[2.2.1]heptan-2-yl)-4-nitrophenyl) isonicotinonitrile

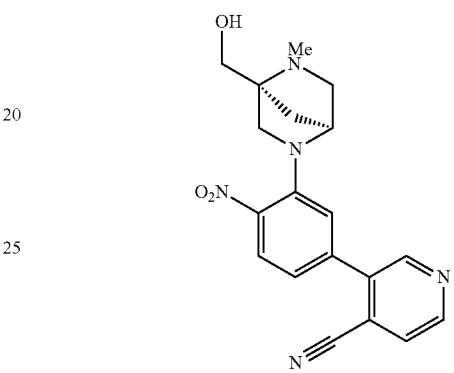

A mixture of tert-butyl (1S,4S)-4-(hydroxymethyl)-5-methyl-2,5-diazabicyclo[2.2.1]heptane-2-carboxylate (17 mg, 0.070 mmol) and 4M HCl/dioxane (1 mL) was stirred at r.t. for 1 hr before the solvent was evaporated in vacuo. The residue was then treated with 3-(3-fluoro-4-nitrophenyl) isonicotinonitrile (Intermediate 1 described between Example 49 and 50, 17.1 mg, 0.070 mmol), DMSO (300 μL), triethylamine (14.7 μL, 0.943 mmol) and the reaction mixture was heated to 100° C. overnight. After cooling to r.t., the reaction mixture was diluted with DCM, washed with brine, dried over sodium sulfate and the solvent was evaporated in vacuo. The obtained crude product was used in the next step without further purification. LCMS calculated for $C_{19}H_{20}N_5O_3$ (M+H)$^+$: m/z=366.2; found 366.1.

Step 4. 3-(4-Amino-3-((1S,4S)-4-(hydroxymethyl)-5-methyl-2,5-diazabicyclo[2.2.1]heptan-2-yl)phenyl) isonicotinonitrile

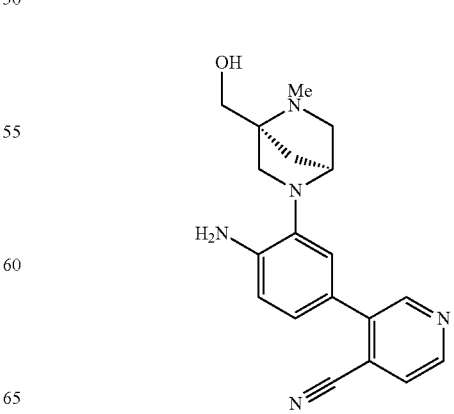

A mixture of 3-(3-((1S,4S)-4-(hydroxymethyl)-5-methyl-2,5-diazabicyclo[2.2.1]heptan-2-yl)-4-nitrophenyl)isonicotinonitrile (26 mg, 0.071 mmol), iron (20.0 mg, 0.356 mmol) and ammonium chloride (22.9 mg, 0.427 mmol) in THF (1 mL), H$_2$O (1 mL) and methanol (1 mL) was stirred at 60° C. for 1 hr. After cooling to r.t., it was filtered through a plug of Celite and diluted with CH$_2$Cl$_2$. The organic phase was separated, washed with brine, dried over MgSO$_4$, filtered and the solvents were evaporated in vacuo. The obtained crude product was used in the next step without further purification. LCMS calculated for C$_{19}$H$_{22}$N$_5$O (M+H)$^+$: m/z=336.2; Found: 336.2.

Step 5. N-(4-(4-Cyanopyridin-3-yl)-2-((1S,4S)-4-(hydroxymethyl)-5-methyl-2,5-diazabicyclo[2.2.1]heptan-2-yl)phenyl)-2-(2-fluoro-6-methoxyphenyl)pyrimidine-4-carboxamide HATU (20.4 mg, 0.054 mmol) was added to a solution of 3-(4-amino-3-((1S,4S)-4-(hydroxymethyl)-5-methyl-2,5-diazabicyclo[2.2.1]heptan-2-yl)phenyl)isonicotinonitrile (13 mg, 0.036 mmol), 2-(2-fluoro-6-methoxyphenyl)pyrimidine-4-carboxylic acid (8.9 mg, 0.036 mmol) and DIPEA (12.5 μL, 0.072 mmol) in DMF (300 μL). The reaction mixture was stirred at 60° C. for 30 min, then water was added and the precipitated product was collected by filtration, washed with water and air dried. The solid was dissolved in TFA and the resultant solution was stirred at 60° C. for 10 min before solvent was evaporated in vacuo. The crude residue was then dissolved in THF (1 mL), MeOH (1 mL), and aq. NH$_4$OH (1 mL), sealed and the solution was stirred at 60° C. for 30 min before solvent was evaporated in vacuo. The obtained crude product was then diluted with CH$_3$CN and purified with prep-LCMS (XBridge C18 column, eluting with a gradient of acetonitrile/water containing 0.1% TFA, at flow rate of 60 mL/min). LCMS calculated for C$_{31}$H$_{29}$FN$_7$O$_3$ (M+H)$^+$: m/z=566.2; Found: 566.2.

Example 100. (S)—N-(4-(4-Cyanopyridin-3-yl)-2-(2-(hydroxymethyl)morpholino)phenyl)-2-(2-fluoro-6-methoxyphenyl)pyrimidine-4-carboxamide

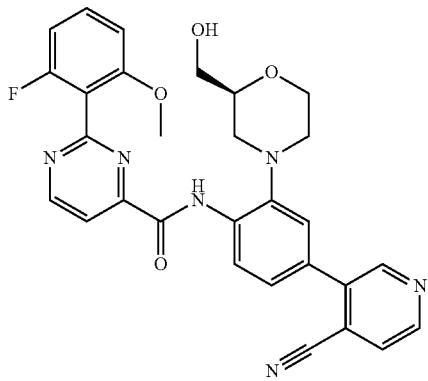 [SMILES: COc1cccc(F)c1-c1nccc(C(=O)Nc2ccc(-c3cnccc3C#N)cc2N2CCO[C@H](CO)C2)n1]

This compound was prepared according to the procedures described in Example 51, using (S)-morpholin-2-ylmethanol instead of (2R,5S)-tert-butyl 5-(hydroxymethyl)-2-methylpiperazine-1-carboxylate as starting material. LCMS calculated for C$_{29}$H$_{26}$FN$_6$O$_4$ (M+H)$^+$: m/z=541.2; Found: 541.3.

Example 101. (S)—N-(4-(4-Cyanopyridin-3-yl)-2-(2-((dimethylamino)methyl)morpholino)phenyl)-2-(2-fluoro-6-methoxyphenyl)pyrimidine-4-carboxamide

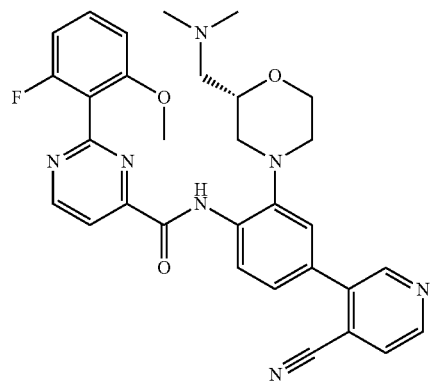 [SMILES: COc1cccc(F)c1-c1nccc(C(=O)Nc2ccc(-c3cnccc3C#N)cc2N2CCO[C@@H](CN(C)C)C2)n1]

Step 1. (R)—N-(4-(4-Cyanopyridin-3-yl)-2-(2-(hydroxymethyl)morpholino)phenyl)-2-(2-fluoro-6-methoxyphenyl)pyrimidine-4-carboxamide

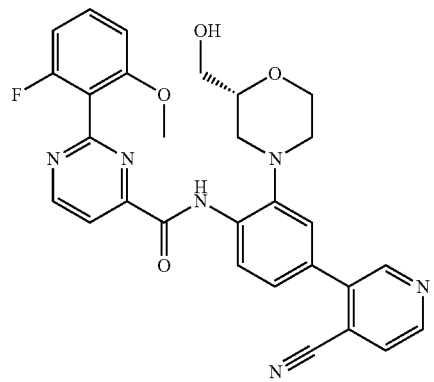 [SMILES: COc1cccc(F)c1-c1nccc(C(=O)Nc2ccc(-c3cnccc3C#N)cc2N2CCO[C@@H](CO)C2)n1]

This compound was prepared in an analogous fashion to Example 51, steps 1-3, starting with (R)-morpholin-2-ylmethanol instead of (2R,5S)-tert-butyl 5-(hydroxymethyl)-2-methylpiperazine-1-carboxylate as starting material. LCMS calculated for C$_{29}$H$_{26}$FN$_6$O$_4$ (M+H)$^+$: m/z=541.2; Found: 541.3.

Step 2. (R)-(4-(5-(4-Cyanopyridin-3-yl)-2-(2-(2-fluoro-6-methoxyphenyl)pyrimidine-4-carboxamido)phenyl)morpholin-2-yl)methyl 4-methylbenzenesulfonate

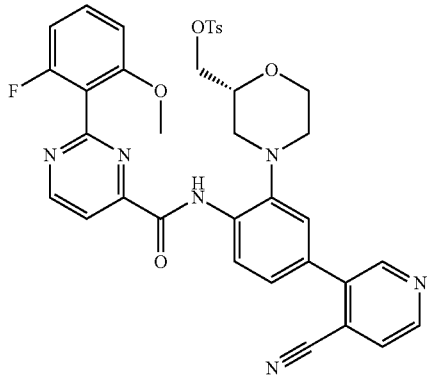 [SMILES: COc1cccc(F)c1-c1nccc(C(=O)Nc2ccc(-c3cnccc3C#N)cc2N2CCO[C@@H](COS(=O)(=O)c3ccc(C)cc3)C2)n1]

A solution of (R)—N-(4-(4-cyanopyridin-3-yl)-2-(2-(hydroxymethyl)morpholino)phenyl)-2-(2-fluoro-6-methoxyphenyl)pyrimidine-4-carboxamide (100 mg, 0.185 mmol) in $CH_2Cl_2$ (740 μL) was treated with DMAP (2.3 mg, 0.018 mmol), triethylamine (77 μL, 0.555 mmol), and TsCl (42.3 mg, 0.222 mmol) and the reaction mixture was stirred at r.t. overnight. The reaction mixture was then diluted with EtOAc, washed with 10% aq. citric acid, sat. aq. $NaHCO_3$, dried over $MgSO_4$, filtered and the solvent was evaporated in vacuo. The obtained crude product was used in the next reaction without purification. LCMS calculated for $C_{36}H_{32}FN_6O_6S$ $(M+H)^+$: m/z=695.2; found 695.3.

Step 3. (S)—N-(4-(4-Cyanopyridin-3-yl)-2-(2-((dimethylamino)methyl)morpholino)phenyl)-2-(2-fluoro-6-methoxyphenyl)pyrimidine-4-carboxamide A solution of (R)-(4-(5-(4-cyanopyridin-3-yl)-2-(2-(2-fluoro-6-methoxyphenyl)pyrimidine-4-carboxamido)phenyl)morpholin-2-yl)methyl 4-methylbenzenesulfonate (20 mg, 0.029 mmol) in EtOH (480 μL) was treated with dimethylamine (461 μL, 0.921 mmol). The reaction mixture was stirred at 100° C. overnight. The solvent was evaporated in vacuo, and the resulting residue was diluted with acetonitrile and purified with prep-LCMS (XBridge C18 column, eluting with a gradient of acetonitrile/water containing 0.1% TFA, at flow rate of 60 mL/min). $C_{31}H_{31}FN_7O_3$ $(M+H)^+$: m/z=568.2; found 568.3.

Example 102. (R)—N-(2-(2-(Cyanomethyl)morpholino)-4-(4-cyanopyridin-3-yl)phenyl)-2-(2-fluoro-6-methoxyphenyl)pyrimidine-4-carboxamide

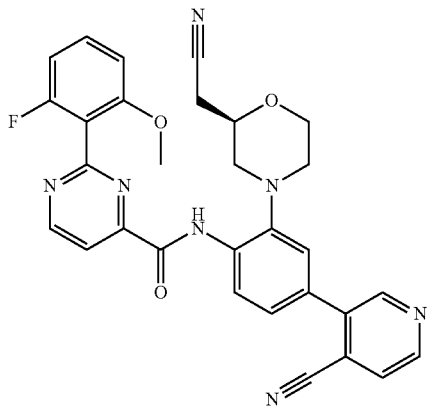 [SMILES: COc1cccc(F)c1-c1nccc(C(=O)Nc2ccc(-c3cnccc3C#N)cc2N2CCO[C@H](CC#N)C2)n1]

A solution of (R)-(4-(5-(4-cyanopyridin-3-yl)-2-(2-(2-fluoro-6-methoxyphenyl)pyrimidine-4-carboxamido)phenyl)morpholin-2-yl)methyl 4-methylbenzenesulfonate (20 mg, 0.029 mmol) in EtOH (480 μL) was treated with potassium cyanide (5.6 mg, 0.086 mmol). The reaction mixture was stirred at 100° C. for 6 hrs. The solvent was evaporated in vacuo, and the resulting residue was diluted with acetonitrile and purified with prep-LCMS (XBridge C18 column, eluting with a gradient of acetonitrile/water containing 0.1% TFA, at flow rate of 60 mL/min). $C_{30}H_{25}FN_7O_3$ $(M+H)^+$: m/z=550.2; found 550.2.

Example 103. (R)—N-(4-(4-Cyanopyridin-3-yl)-2-(3-oxotetrahydro-3H-oxazolo[3,4-a]pyrazin-7(1H)-yl)phenyl)-2-(2-fluoro-6-methoxyphenyl)pyrimidine-4-carboxamide

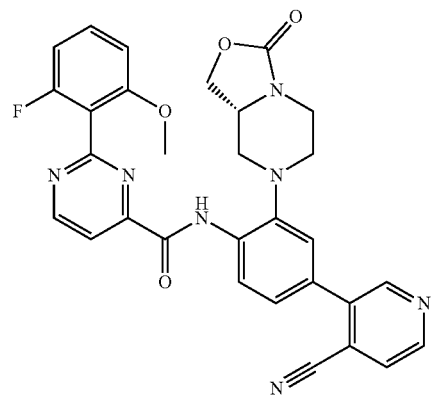 [SMILES: COc1cccc(F)c1-c1nccc(C(=O)Nc2ccc(-c3cnccc3C#N)cc2N2CCN3C(=O)OC[C@H]3C2)n1]

Step 1. tert-Butyl (R)-4-(5-(4-cyanopyridin-3-yl)-2-(2-(2-fluoro-6-methoxyphenyl)pyrimidine-4-carboxamido)phenyl)-2-(hydroxymethyl)piperazine-1-carboxylate

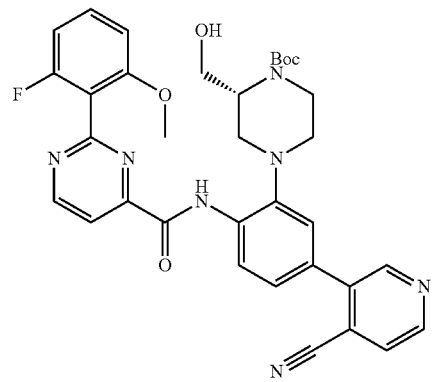 [SMILES: COc1cccc(F)c1-c1nccc(C(=O)Nc2ccc(-c3cnccc3C#N)cc2N2CCN(C(=O)OC(C)(C)C)[C@@H](CO)C2)n1]

This compound was prepared in an analogous fashion to Example 51, steps 1-3, starting with tert-butyl (R)-2-(hydroxymethyl)piperazine-1-carboxylate instead of (2R,5S)-tert-butyl 5-(hydroxymethyl)-2-methylpiperazine-1-carboxylate as starting material. LCMS calculated for $C_{34}H_{35}FN_7O_5$ $(M+H)^+$: m/z=640.3; Found: 640.2.

Step 2. tert-Butyl (R)-4-(5-(4-cyanopyridin-3-yl)-2-(2-(2-fluoro-6-methoxyphenyl)pyrimidine-4-carboxamido)phenyl)-2-(((methylsulfonyl)oxy)methyl)piperazine-1-carboxylate

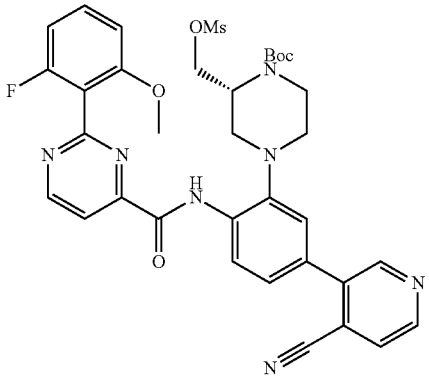 [SMILES: COc1cccc(F)c1-c1nccc(C(=O)Nc2ccc(-c3cnccc3C#N)cc2N2CCN(C(=O)OC(C)(C)C)[C@@H](COS(C)(=O)=O)C2)n1]

A solution of tert-butyl (R)-4-(5-(4-cyanopyridin-3-yl)-2-(2-(2-fluoro-6-methoxyphenyl)pyrimidine-4-carboxamido)phenyl)-2-(hydroxymethyl)piperazine-1-carboxylate (30 mg, 0.047 mmol) in CH$_2$Cl$_2$ (470 μL) was treated with triethylamine (13.1 μL, 0.094 mmol), and MsCl (5.5 μL, 0.070 mmol) and the reaction mixture was stirred at r.t. for 1 hr. The solvent was evaporated in vacuo. The obtained crude product was used in the next reaction without purification. LCMS calculated for C$_{35}$H$_{37}$FN$_7$O$_7$S (M+H)$^+$: m/z=718.2; found 718.2.

Step 3. (R)—N-(4-(4-Cyanopyridin-3-yl)-2-(3-oxotetrahydro-3H-oxazolo[3,4-a]pyrazin-7(1H)-yl)phenyl)-2-(2-fluoro-6-methoxyphenyl)pyrimidine-4-carboxamide Potassium cyanide (9.2 mg, 0.142 mmol) was added to a solution of tert-butyl (R)-4-(5-(4-cyanopyridin-3-yl)-2-(2-(2-fluoro-6-methoxyphenyl)pyrimidine-4-carboxamido)phenyl)-2-(((methylsulfonyl)oxy)methyl)piperazine-1-carboxylate (34 mg, 0.047 mmol) in DMSO (475 μL). The reaction mixture was stirred at 80° C. for 1 hr. After cooling to r.t., the resulting solution was diluted with acetonitrile and purified with prep-LCMS (XBridge C18 column, eluting with a gradient of acetonitrile/water containing 0.1% TFA, at flow rate of 60 mL/min). C$_{30}$H$_{25}$FN$_7$O$_4$ (M+H)$^+$: m/z=566.2; found 566.3.

Example 104. (S)—N-(5-Fluoro-2-(3-(hydroxymethyl)piperazin-1-yl)phenyl)-2-(2-fluoro-6-methoxyphenyl)pyrimidine-4-carboxamide

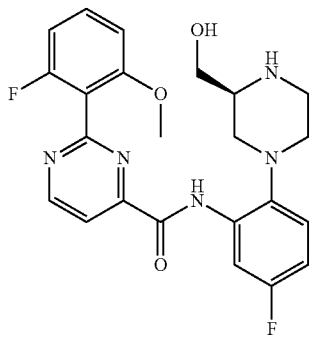 [SMILES: COc1cccc(F)c1-c1nccc(C(=O)Nc2cc(F)ccc2N2CCN[C@H](CO)C2)n1]

This compound was prepared in an analogous fashion to Example 6, starting with tert-butyl (S)-2-(hydroxymethyl)piperazine-1-carboxylate in place of tert-butyl ((3S,5S)-5-(hydroxymethyl)pyrrolidin-3-yl)carbamate as starting material. LCMS calculated for C$_{23}$H$_{24}$F$_2$N$_5$O$_3$ (M+H)$^+$: m/z=456.2; Found: 456.3. $^1$H NMR (400 MHz, DMSO) δ 11.03-10.69 (s, 1H), 9.48-9.26 (d, J=5.0 Hz, 1H), 8.38-8.21 (dd, J=10.8, 3.0 Hz, 1H), 8.20-8.09 (d, J=5.0 Hz, 1H), 7.68-7.51 (td, J=8.4, 6.9 Hz, 1H), 7.42-7.31 (dd, J=8.8, 5.6 Hz, 1H), 7.13-6.96 (m, 3H), 3.83-3.71 (s, 3H), 3.59-3.18 (m, 6H), 3.15-2.79 (m, 4H), 2.81-2.69 (s, 1H).

Example 105. N-(4-(4-Cyanopyridin-3-yl)-2-(3-(methoxymethyl)azetidin-1-yl)phenyl)-2-(2-fluoro-6-methoxyphenyl)pyrimidine-4-carboxamide

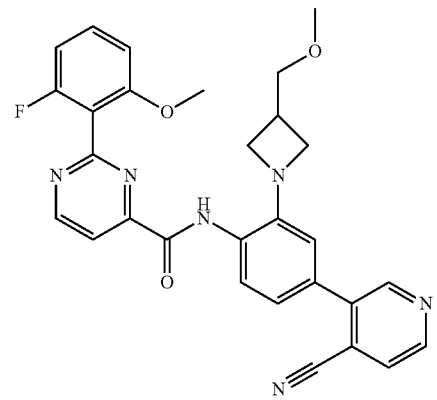 [SMILES: COCC1CN(c2cc(-c3cnccc3C#N)ccc2NC(=O)c2ccnc(-c3c(F)cccc3OC)n2)C1]

This compound was prepared in an analogous fashion to Example 51, starting with 3-(methoxymethyl)azetidine in place of (2R,5S)-tert-butyl 5-(hydroxymethyl)-2-methylpiperazine-1-carboxylate as starting material. LCMS calculated for C$_{29}$H$_{26}$FN$_6$O$_3$ (M+H)$^+$: m/z=525.2; Found: 525.2.

Example 106. (S)—N-(4-(4-Cyanopyridin-3-yl)-2-(2-(hydroxymethyl)azetidin-1-yl)phenyl)-2-(2-fluoro-6-methoxyphenyl)pyrimidine-4-carboxamide

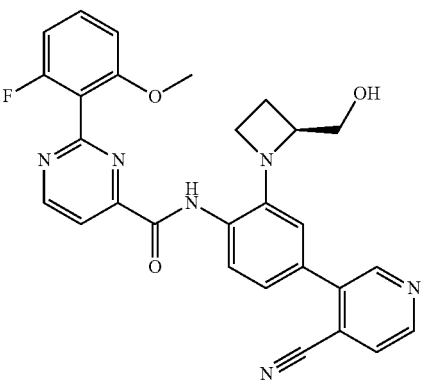 [SMILES: COc1cccc(F)c1-c1nccc(C(=O)Nc2ccc(-c3cnccc3C#N)cc2N2CC[C@H]2CO)n1]

This compound was prepared in an analogous fashion to Example 51, starting with (S)-azetidin-2-ylmethanol in place of (2R,5S)-tert-butyl 5-(hydroxymethyl)-2-methylpiperazine-1-carboxylate as starting material. LCMS calculated for C$_{28}$H$_{24}$FN$_6$O$_3$ (M+H)$^+$: m/z=511.2; Found: 511.2.

Example 107. (R)—N-(4-(4-Cyanopyridin-3-yl)-2-(2-((dimethylamino)methyl)azetidin-1-yl)phenyl)-2-(2-fluoro-6-methoxyphenyl)pyrimidine-4-carboxamide

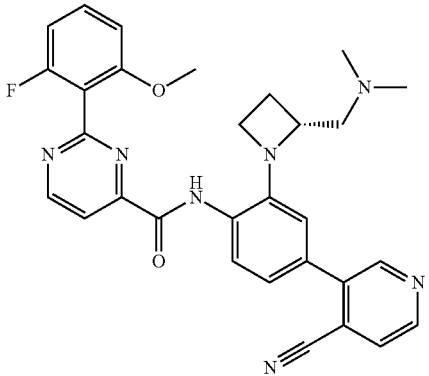 [SMILES: COc1cccc(F)c1-c1nccc(C(=O)Nc2ccc(-c3cnccc3C#N)cc2N2CC[C@@H]2CN(C)C)n1]

Step 1. (R)—N-(4-(4-Cyanopyridin-3-yl)-2-(2-(hydroxymethyl)azetidin-1-yl)phenyl)-2-(2-fluoro-6-methoxyphenyl)pyrimidine-4-carboxamide

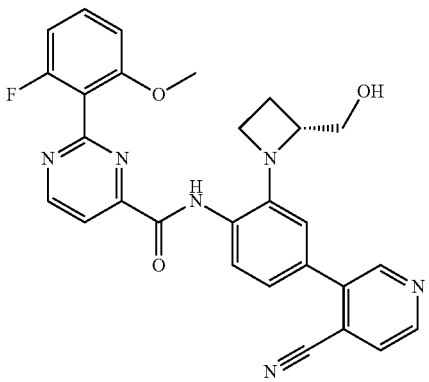 [SMILES: COc1cccc(F)c1-c1nccc(C(=O)Nc2ccc(-c3cnccc3C#N)cc2N2CC[C@@H]2CO)n1]

This compound was prepared in an analogous fashion to Example 51, starting with (R)-azetidin-2-ylmethanol in place of (2R,5S)-tert-butyl 5-(hydroxymethyl)-2-methylpiperazine-1-carboxylate as starting material. LCMS calculated for $C_{28}H_{24}FN_6O_3$ (M+H)$^+$: m/z=511.2; Found: 511.2.

Step 2. (R)-(1-(5-(4-Cyanopyridin-3-yl)-2-(2-(2-fluoro-6-methoxyphenyl)pyrimidine-4-carboxamido)phenyl)azetidin-2-yl)methyl methanesulfonate

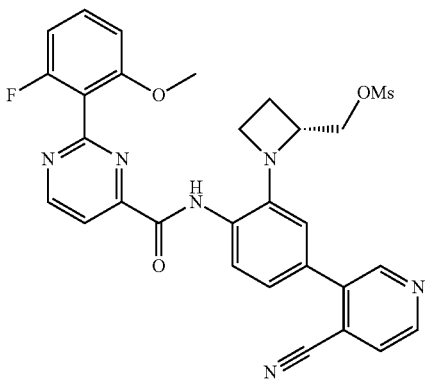 [SMILES: COc1cccc(F)c1-c1nccc(C(=O)Nc2ccc(-c3cnccc3C#N)cc2N2CC[C@@H]2COS(C)(=O)=O)n1]

A solution of (R)—N-(4-(4-cyanopyridin-3-yl)-2-(2-(hydroxymethyl)azetidin-1-yl)phenyl)-2-(2-fluoro-6-methoxyphenyl)pyrimidine-4-carboxamide (50 mg, 0.098 mmol) in $CH_2Cl_2$ (980 μL) was treated with triethylamine (27 μL, 0.196 mmol), and MsCl (11.4 μL, 0.147 mmol) and the reaction mixture was stirred at r.t. for 2 hrs. The solvent was evaporated in vacuo. The obtained crude product was used in the next reaction without purification. LCMS calculated for $C_{29}H_{26}FN_6O_5S$ (M+H)$^+$: m/z=589.2; found 589.3.

Step 3. (R)—N-(4-(4-Cyanopyridin-3-yl)-2-(2-((dimethylamino)methyl)azetidin-1-yl)phenyl)-2-(2-fluoro-6-methoxyphenyl)pyrimidine-4-carboxamide A solution of (R)-(1-(5-(4-cyanopyridin-3-yl)-2-(2-(2-fluoro-6-methoxyphenyl)pyrimidine-4-carboxamido)phenyl)azetidin-2-yl)methyl methanesulfonate (20 mg, 0.034 mmol) in EtOH (570 μL) was treated with dimethylamine (544 μL, 1.09 mmol). The reaction mixture was stirred at 100° C. overnight. After cooling to r.t., the solvent was evaporated in vacuo, and the resulting residue was diluted with acetonitrile and purified with prep-LCMS (XBridge C18 column, eluting with a gradient of acetonitrile/water containing 0.1% TFA, at flow rate of 60 mL/min). $C_{30}H_{29}FN_7O_2$ (M+H)$^+$: m/z=538.2; found 538.2.

Example 108. N-(4-(4-Cyanopyridin-3-yl)-2-(4-methylpiperazin-1-yl)phenyl)-2-(2-fluoro-6-methoxyphenyl)pyrimidine-4-carboxamide

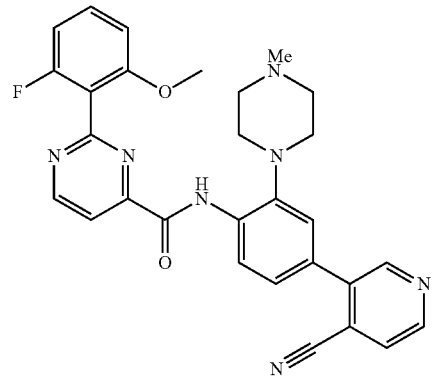 [SMILES: COc1cccc(F)c1-c1nccc(C(=O)Nc2ccc(-c3cnccc3C#N)cc2N2CCNCC2)n1]

Step 1. N-(4-(4-Cyanopyridin-3-yl)-2-(piperazin-1-yl)phenyl)-2-(2-fluoro-6-methoxyphenyl)pyrimidine-4-carboxamide

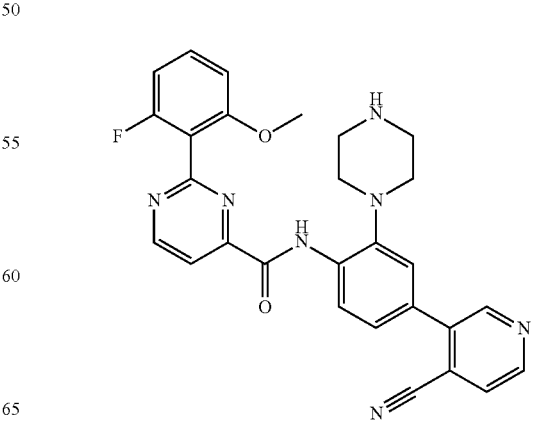

This compound was prepared in an analogous fashion to Example 51, starting with tert-butyl piperazine-1-carboxylate in place of (2R,5S)-tert-butyl 5-(hydroxymethyl)-2-methylpiperazine-1-carboxylate as starting material. LCMS calculated for $C_{28}H_{25}FN_7O_2$ (M+H)$^+$: m/z=510.2; Found: 510.2.

Step 2. N-(4-(4-Cyanopyridin-3-yl)-2-(4-methylpiperazin-1-yl)phenyl)-2-(2-fluoro-6-methoxyphenyl)pyrimidine-4-carboxamide

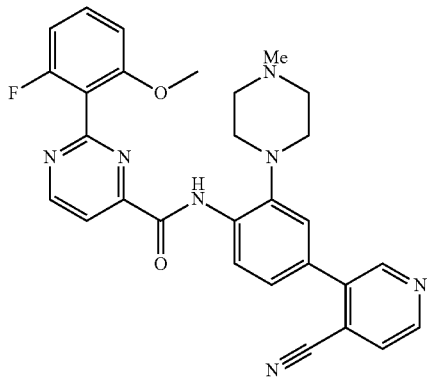

A solution of N-(4-(4-cyanopyridin-3-yl)-2-(piperazin-1-yl)phenyl)-2-(2-fluoro-6-methoxyphenyl)pyrimidine-4-carboxamide (15 mg, 0.029 mmol) in THF (980 µL) was treated with formaldehyde (37 wt. % in H$_2$O, 110 µL, 1.47 mmol), acetic acid (8.4 µL, 0.147 mmol), and sodium triacetoxyborohydride (12.5 mg, 0.059 mmol) and the reaction mixture was stirred at r.t. for 1 h. The solvent was then evaporated in vacuo, and the resulting residue was diluted with acetonitrile and purified with prep-LCMS (XBridge C18 column, eluting with a gradient of acetonitrile/water containing 0.1% TFA, at flow rate of 60 mL/min). $C_{29}H_{27}FN_7O_2$ (M+H)$^+$: m/z=524.2; found 524.2.

Example 109. N-(4-(4-Cyanopyridin-3-yl)-2-(4-(2-hydroxyethyl)piperazin-1-yl)phenyl)-2-(2-fluoro-6-methoxyphenyl)pyrimidine-4-carboxamide

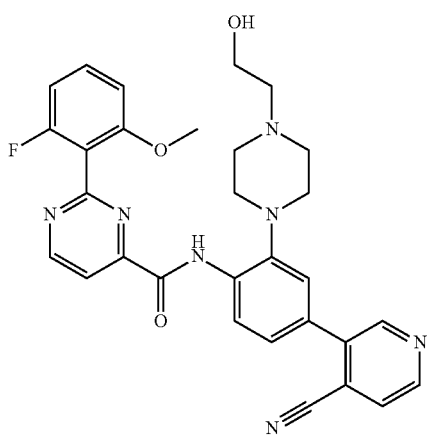 [SMILES: COc1cccc(F)c1-c1nccc(C(=O)Nc2ccc(-c3cnccc3C#N)cc2N2CCN(CCO)CC2)n1]

A solution of N-(4-(4-cyanopyridin-3-yl)-2-(piperazin-1-yl)phenyl)-2-(2-fluoro-6-methoxyphenyl)pyrimidine-4-carboxamide (15 mg, 0.029 mmol) in THF (980 µL) was treated with 2-((tert-butyldimethylsilyl)oxy)acetaldehyde (34 µL, 0.177 mmol), acetic acid (5.0 µL, 0.088 mmol), and sodium triacetoxyborohydride (12.5 mg, 0.059 mmol) and the reaction mixture was stirred at r.t. for 1 h. Upon completion, 4M HCl/dioxane (1 mL) was added and the reaction was left to stir for 30 min. The solvent was then evaporated in vacuo and the resulting residue was diluted with acetonitrile and purified with prep-LCMS (XBridge C18 column, eluting with a gradient of acetonitrile/water containing 0.1% TFA, at flow rate of 60 mL/min). $C_{30}H_{29}FN_7O_3$ (M+H)$^+$: m/z=554.2; found 554.4.

Example 110. (S)—N-(5-Fluoro-2-(3-(hydroxymethyl)piperazin-1-yl)-4-isopropylphenyl)-2-(2-fluoro-6-methoxyphenyl)pyrimidine-4-carboxamide

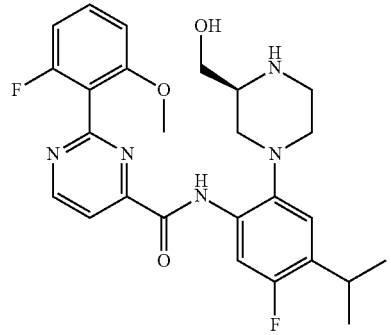 [SMILES: COc1cccc(F)c1-c1nccc(C(=O)Nc2cc(F)c(C(C)C)cc2N2CCN[C@H](CO)C2)n1]

Step 1. tert-Butyl (S)-4-(5-chloro-4-fluoro-2-(2-(2-fluoro-6-methoxyphenyl)pyrimidine-4-carboxamido)phenyl)-2-(hydroxymethyl)piperazine-1-carboxylate

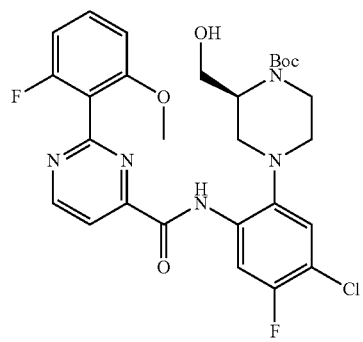 [SMILES: COc1cccc(F)c1-c1nccc(C(=O)Nc2cc(F)c(Cl)cc2N2CCN(C(=O)OC(C)(C)C)[C@H](CO)C2)n1]

This compound was prepared according to the procedures described in Example 41, using 1-chloro-2,5-difluoro-4-nitrobenzene in place of 3-(3-fluoro-4-nitrophenyl)isonicotinonitrile as starting material. LCMS calculated for $C_{28}H_{31}ClF_2N_5O_5$ (M+H)$^+$: m/z=590.2; Found: 590.2.

Step 2. tert-Butyl (S)-4-(4-fluoro-2-(2-(2-fluoro-6-methoxyphenyl)pyrimidine-4-carboxamido)-5-(prop-1-en-2-yl)phenyl)-2-(hydroxymethyl)piperazine-1-carboxylate

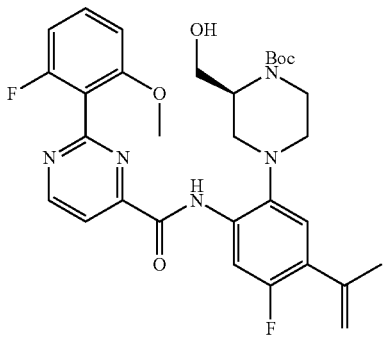 [SMILES: C=C(C)c1cc(N2CCN(C(=O)OC(C)(C)C)[C@H](CO)C2)c(NC(=O)c2ccnc(-c3c(F)cccc3OC)n2)cc1F]

To a mixture of tert-butyl (S)-4-(5-chloro-4-fluoro-2-(2-(2-fluoro-6-methoxyphenyl)pyrimidine-4-carboxamido)phenyl)-2-(hydroxymethyl)piperazine-1-carboxylate (20 mg, 0.034 mmol), 4,4,5,5-tetramethyl-2-(prop-1-en-2-yl)-1,3,2-dioxaborolane (9.6 μL, 0.051 mmol), Xphos Pd G2 (2.7 mg, 3.4 μmol) and potassium phosphate, tribasic (14.4 mg, 0.068 mmol) were added 1,4-dioxane (500 μL) and H$_2$O (100 μL) and the reaction flask was evacuated, back filled with nitrogen, then stirred at 80° C. for 1 hr. The reaction mixture was cooled to r.t., the solvents were evaporated in vacuo and the crude product was purified by Biotage Isolera™ (0-100% ethyl acetate in hexanes) to provide the desired product. LCMS calculated for C$_{31}$H$_{36}$F$_2$N$_5$O$_5$ (M+H)$^+$: m/z=596.3; Found: 596.3.

Step 3. (S)—N-(5-Fluoro-2-(3-(hydroxymethyl)piperazin-1-yl)-4-isopropylphenyl)-2-(2-fluoro-6-methoxyphenyl)pyrimidine-4-carboxamide Palladium on carbon (10% wetted, Degussa type, 3.6 mg) was added to a solution of tert-butyl (S)-4-(4-fluoro-2-(2-(2-fluoro-6-methoxyphenyl)pyrimidine-4-carboxamido)-5-(prop-1-en-2-yl)phenyl)-2-(hydroxymethyl)piperazine-1-carboxylate (20 mg, 0.034 mmol) in methanol (1.1 ml). The reaction flask was connected to a balloon with hydrogen and the reaction mixture was stirred at r.t. for 2 hrs. The catalyst was then filtered off, the solvent was evaporated in vacuo and TFA (2 mL) was added. The reaction mixture was stirred at r.t. for 15 min, then diluted with CH$_3$CN and water and purified with prep-LCMS (XBridge C18 column, eluting with a gradient of acetonitrile/water containing 0.1% TFA, at flow rate of 60 mL/min). LCMS calculated for C$_{26}$H$_{30}$F$_2$N$_5$O$_3$ (M+H)$^+$: m/z=498.2; Found: 498.3.

Example A. HPK1 Kinase Binding Assay

A stock solution of 1 mM test compound was prepared in DMSO. The compound plate was prepared by 3-fold and 11-point serial dilutions. 0.1 μL of the compound in DMSO was transferred from the compound plate to the white 384 well polystyrene plates. The assay buffer contained 50 mM HEPES, pH 7.5, 0.01% Tween-20, 5 mM MgCl$_2$, 0.01% BSA, and 5 mM DTT. 5 μL of 4 nM active HPK1 (Signal-Chem M23-11G) prepared in the buffer was added to the plate. The enzyme concentration given was based on the given stock concentration reported by the vender. 5 μl of 18 nM tracer 222 (ThermoFisher PV6121) and 4 nM LanthaScreen Eu-Anti GST antibody (ThermoFisher PV5595) were added. After one hour incubation at 25° C., the plates were read on a PHERAstar FS plate reader (BMG Labtech). K$_i$ values were determined.

Compounds of the present disclosure, as exemplified in Examples, showed the K$_i$ values in the following ranges: +=K$_i$≤100 nM; ++=100 nM<K$_i$≤500 nM; +++=500 nM<K$_i$≤5000 nM.

TABLE 1

| Example | Ki, nM |
|---|---|
| 1 | + |
| 2 | + |
| 3 | + |
| 4 | + |
| 5 | ++ |
| 6 | + |
| 7 | + |
| 8 | +++ |
| 9 | +++ |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | ++ |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | ++ |
| 62 | + |
| 63 | + |
| 64 | + |
| 65 | + |
| 66 | + |

TABLE 1-continued

| Example | Ki, nM |
|---|---|
| 67 | + |
| 68 | + |
| 69 | + |
| 70 | + |
| 71 | + |
| 72 | + |
| 73 | + |
| 74 | + |
| 75 | + |
| 76 | + |
| 77 | + |
| 78 | ++ |
| 79, peak 1 | + |
| 79, peak 2 | + |
| 80 | + |
| 81 | + |
| 82, peak 1 | + |
| 82, peak 2 | + |
| 83, peak 1 | + |
| 83, peak 2 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |

Example B. p-SLP76S376 HTRF Assay

One or more compounds of the invention can be tested using the p-SLP76S376 HTRF assay described as follows. Jurkat cells (cultured in RPMI1640 media with 10% FBS) are collected and centrifuged, followed by resuspension in appropriate media at $3 \times 10^6$ cells/mL. The Jurkat cells (35 µL) are dispensed into each well in a 384 well plate. Test compounds are diluted with cell culture media for 40-fold dilution (adding 39 µL cell culture media into 1 µL compound). The Jurkat cells in the well plate are treated with the test compounds at various concentrations (adding 5 ul diluted compound into 35 µL Jurkat cells and starting from 3 uM with 1:3 dilution) for 1 hour at 37° C., 5% $CO_2$), followed by treatment with anti-CD3 (5 µg/mL, OKT3 clone) for 30 min. A 1:25 dilution of 100× blocking reagent (from p-SLP76 ser376HTRF kit) with 4×Lysis Buffer(LB) is prepared and 15 µL of the 4×LB buffer with blocking reagent is added into each well and incubated at room temperature for 45 min with gentle shaking. The cell lysate (16 µL) is added into a Greiner white plate, treated with p-SLP76 ser376HTRF reagents (2 µL donor, 2 ul acceptor) and incubated at 4° C. for overnight. The homogeneous time resolved fluorescence (HTRF) is measured on a PHERAstar plate reader the next day. $IC_{50}$ determination is performed by fitting the curve of percent inhibition versus the log of the inhibitor concentration using the GraphPad Prism 5.0 software.

Example C. Isolation of CD4+ or CD8+ T Cells and Cytokine Measurement

Blood samples are collected from healthy donors. CD4+ or CD8+ T cells are isolated by negative selection using CD4+ or CD8+ enrichment kits (lifetech, USA). The purity of the isolated CD4+ or CD8+ T cells is determined by flow cytometry and is routinely >80%. Cells are cultured in RPMI 1640 supplemented with 10% FCS, glutamine and antibiotics (Invitrogen Life Technologies, USA). For cytokine measurement, Jurkat cells or primary CD4+ or CD8+ T cells are plated at 200 k cells/well and are stimulated for 24 h with anti-CD3/anti-CD28 beads in the presence or absence of testing compounds at various concentrations. 16 µL of supernatants are then transferred to a white detection plate and analyzed using the human IL2 or IFNγ assay kits (Cisbio).

Example D. Treg Assay

One or more compounds can be tested using the Regulatory T-cell proliferation assay described as following. Primary CD4+/CD25− T-cells and CD4+/CD25+ regulatory T-cells are isolated from human donated Peripheral Blood Mononuclear Cells, using an isolated kit from Thermo Fisher Scientific (11363D). CD4+/CD25− T-cells are labeled with CFSE (Thermo Fisher Scientific, C34554) following the protocol provided by the vendor. CFSE labeled T-cells and CD4+/CD25+ regulatory T-cells are re-suspended at the concentration of 1×106 cells/mL in RPMI-1640 medium. 100 µL of CFSE-labeled T-cells are mixed with or without 50 µL of CD4+/CD25+ regulatory T-cells, treated with 5 µl of anti-CD3/CD28 beads (Thermo Fisher Scientific, 11132D) and various concentrations of compounds diluted in 50 µl of RPMI-1640 medium. Mixed populations of cells are cultured for 5 days (37° C., 5% $CO_2$) and proliferation of CFSE-labeled T-cells is analyzed by BD LSRFortessa X-20 using FITC channel on the 5th day.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound, which is N-(2-((2S,4S)-4-amino-2-(hydroxymethyl)pyrrolidin-1-yl)-5-fluorophenyl)-2-(2-fluoro-6-methoxyphenyl)pyrimidine-4-carboxamide, or a pharmaceutically acceptable salt thereof.

2. A pharmaceutical composition comprising the compound of claim 1, or a pharmaceutically acceptable salt thereof, and at least one pharmaceutically acceptable carrier or excipient.

3. A compound, which is N-(2-((2S,4S)-4-amino-2-(hydroxymethyl)pyrrolidin-1-yl)-5-fluorophenyl)-2-(2-fluoro-6-methoxyphenyl)pyrimidine-4-carboxamide.

4. A pharmaceutical composition comprising the compound of claim 3 and at least one pharmaceutically acceptable carrier or excipient.

5. A compound, which is N-(2-(1S,4S)-2,5-diazabicyclo[2.2.1]heptan-2-yl)-4-(4-cyanopyridin-3-yl)phenyl)-2-(2-fluoro-6-methoxyphenyl)pyrimidine-4-carboxamide, or a pharmaceutically acceptable salt thereof.

6. A pharmaceutical composition comprising the compound of claim 5, or a pharmaceutically acceptable salt thereof, and at least one pharmaceutically acceptable carrier or excipient.

7. A compound, which is N-(2-(1S,4S)-2,5-diazabicyclo[2.2.1]heptan-2-yl)-4-(4-cyanopyridin-3-yl)phenyl)-2-(2-fluoro-6-methoxyphenyl)pyrimidine-4-carboxamide.

8. A pharmaceutical composition comprising the compound of claim 7 and at least one pharmaceutically acceptable carrier or excipient.

9. A compound, which is N-(2-((2S,4S)-4-amino-2-(hydroxymethyl)pyrrolidin-1-yl)-4-(4-cyanopyridin-3-yl)phenyl)-2-(2-fluoro-6-methoxyphenyl)pyrimidine-4-carboxamide, or a pharmaceutically acceptable salt thereof.

10. A pharmaceutical composition comprising the compound of claim 9, or a pharmaceutically acceptable salt thereof, and at least one pharmaceutically acceptable carrier or excipient.

11. A compound, which is N-(2-((2S,4S)-4-amino-2-(hydroxymethyl)pyrrolidin-1-yl)-4-(4-cyanopyridin-3-yl)phenyl)-2-(2-fluoro-6-methoxyphenyl)pyrimidine-4-carboxamide.

12. A pharmaceutical composition comprising the compound of claim 11 and at least one pharmaceutically acceptable carrier or excipient.

\* \* \* \* \*